US011421023B2

(12) United States Patent
Tu et al.

(10) Patent No.: US 11,421,023 B2
(45) Date of Patent: *Aug. 23, 2022

(54) ANTI-GP73 MONOCLONAL ANTIBODIES AND METHODS OF OBTAINING THE SAME

(71) Applicant: ABBOTT LABORATORIES, Abbott Park, IL (US)

(72) Inventors: Bailin Tu, Libertyville, IL (US); Robert N. Ziemann, Palatine, IL (US); Bryan C. Tieman, Elmhurst, IL (US); Philip M. Hemken, Pleasant Prairie, IL (US); Carol S. Ramsay, Arlington Heights, IL (US); Carolyn J. Strobel, Waukegan, IL (US); David J. Hawksworth, Lake Villa, IL (US); Larry G. Birkenmeyer, Glenview, IL (US); Cheng Zhao, Buffalo Grove, IL (US); Susan E. Brophy, Lindenhurst, IL (US); Barry L. Dowell, Mundelein, IL (US); Anthony S. Muerhoff, Kenosha, WI (US)

(73) Assignee: ABBOTT LABORATORIES, Abbott Park, IL (US)

( * ) Notice: Subject to any disclaimer, the term of this patent is extended or adjusted under 35 U.S.C. 154(b) by 599 days.

This patent is subject to a terminal disclaimer.

(21) Appl. No.: 16/387,282

(22) Filed: Apr. 17, 2019

(65) Prior Publication Data
US 2019/0315844 A1 Oct. 17, 2019

Related U.S. Application Data

(60) Division of application No. 15/290,762, filed on Oct. 11, 2016, now Pat. No. 10,308,709, which is a continuation of application No. 13/836,229, filed on Mar. 15, 2013, now Pat. No. 9,469,686.

(51) Int. Cl.
*G01N 33/53* (2006.01)
*C07K 16/18* (2006.01)
*G01N 33/574* (2006.01)
*G01N 33/68* (2006.01)

(52) U.S. Cl.
CPC ....... *C07K 16/18* (2013.01); *G01N 33/57438* (2013.01); *G01N 33/6893* (2013.01); *C07K 2317/21* (2013.01); *C07K 2317/33* (2013.01); *C07K 2317/34* (2013.01); *C07K 2317/56* (2013.01); *C07K 2317/565* (2013.01); *C07K 2317/92* (2013.01); *G01N 2333/47* (2013.01); *G01N 2800/085* (2013.01); *G01N 2800/50* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,554,101 A | 11/1985 | Hopp |
| 4,704,692 A | 11/1987 | Ladner |
| 4,816,567 A | 3/1989 | Cabilly et al. |
| 4,873,316 A | 10/1989 | Meade et al. |
| 4,880,078 A | 11/1989 | Inoue et al. |
| 4,946,778 A | 8/1990 | Ladner et al. |
| 4,980,286 A | 12/1990 | Morgan et al. |
| 5,063,081 A | 11/1991 | Cozzette et al. |
| 5,128,326 A | 7/1992 | Balazs et al. |
| 5,223,409 A | 6/1993 | Ladner et al. |
| 5,225,539 A | 7/1993 | Winter |
| 5,241,070 A | 8/1993 | Law |
| 5,258,498 A | 11/1993 | Huston et al. |
| 5,290,540 A | 3/1994 | Prince et al. |
| 5,294,404 A | 3/1994 | Grandone et al. |
| 5,304,489 A | 4/1994 | Rosen |
| 5,352,803 A | 10/1994 | Mattingly |
| 5,359,093 A | 10/1994 | Adamczyk et al. |
| 5,403,484 A | 4/1995 | Ladner et al. |
| 5,427,908 A | 6/1995 | Dower et al. |
| 5,468,646 A | 11/1995 | Mattingly et al. |
| 5,480,792 A | 1/1996 | Buechler et al. |
| 5,496,925 A | 3/1996 | Mattingly |
| 5,516,637 A | 5/1996 | Huang et al. |
| 5,525,524 A | 6/1996 | Buechler et al. |
| 5,530,101 A | 6/1996 | Queen et al. |
| 5,543,524 A | 8/1996 | Mattingly et al. |
| 5,565,362 A | 10/1996 | Rosen |
| 5,571,698 A | 11/1996 | Ladner et al. |
| 5,573,904 A | 11/1996 | Mattingly |
| 5,580,717 A | 12/1996 | Dower et al. |
| 5,585,089 A | 12/1996 | Queen et al. |

(Continued)

FOREIGN PATENT DOCUMENTS

| | | |
|---|---|---|
| CN | 101328214 | 12/2008 |
| CN | 101407544 | 4/2009 |

(Continued)

OTHER PUBLICATIONS

Adamczyk M., et al., "Chemiluminescence Quenching of Pteroic Acid-N-sulfonyl-acridinium-9-carboxamide Conjugates by Folate Binding Protein," Bioorganic and Medicinal Chemistry Letters, 2004, vol. 14 (9), pp. 2313-2317.

Adamczyk M., et al., "Chemiluminescent Acridinium-9-Carboxamide Boronic Acid Probes: Application to a Homogeneous Glycated Hemoglobin Assay," Bioorganic & Medicinal Chemistry Letters, 2006, vol. 16 (5), pp. 1324-1328.

(Continued)

*Primary Examiner* — Michael D Pak
(74) *Attorney, Agent, or Firm* — Casimir Jones SC; Lisa Mueller

(57) ABSTRACT

Disclosed herein are antibodies and methods of using said antibodies to detect Golgi protein 73 (GP73) and fucosylated GP73 in a sample.

5 Claims, 21 Drawing Sheets

Specification includes a Sequence Listing.

(56) References Cited

U.S. PATENT DOCUMENTS

| | | |
|---|---|---|
| 5,593,896 A | 1/1997 | Adamczyk et al. |
| 5,627,052 A | 5/1997 | Schrader |
| 5,658,727 A | 8/1997 | Barbas et al. |
| 5,679,377 A | 10/1997 | Bernstein et al. |
| 5,679,526 A | 10/1997 | Buechler et al. |
| 5,693,762 A | 12/1997 | Queen et al. |
| 5,698,426 A | 12/1997 | Huse |
| 5,714,352 A | 2/1998 | Jakobovits |
| 5,723,323 A | 3/1998 | Kauffman et al. |
| 5,733,743 A | 3/1998 | Johnson et al. |
| 5,750,753 A | 5/1998 | Kimae et al. |
| 5,763,192 A | 6/1998 | Kauffman et al. |
| 5,766,886 A | 6/1998 | Studnicka et al. |
| 5,770,429 A | 6/1998 | Lonberg et al. |
| 5,780,225 A | 7/1998 | Wigler et al. |
| 5,783,699 A | 7/1998 | Mattingly et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,824,799 A | 10/1998 | Buechler et al. |
| 5,827,690 A | 10/1998 | Meade et al. |
| 5,833,985 A | 11/1998 | Ball et al. |
| 5,837,243 A | 11/1998 | Deo et al. |
| 5,849,992 A | 12/1998 | Meade et al. |
| 5,851,776 A | 12/1998 | Valkirs |
| 5,855,913 A | 1/1999 | Hanes et al. |
| 5,874,064 A | 2/1999 | Edwards et al. |
| 5,885,527 A | 3/1999 | Buechler |
| 5,912,015 A | 6/1999 | Bernstein et al. |
| 5,916,597 A | 6/1999 | Lee et al. |
| 5,916,771 A | 6/1999 | Hori et al. |
| 5,922,615 A | 7/1999 | Nowakowski et al. |
| 5,922,845 A | 7/1999 | Deo et al. |
| 5,934,272 A | 8/1999 | Lloyd et al. |
| 5,939,598 A | 8/1999 | Kucherlapati et al. |
| 5,947,124 A | 9/1999 | Buechler et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,579 A | 11/1999 | Buechler et al. |
| 5,985,615 A | 11/1999 | Jakobovits et al. |
| 5,989,463 A | 11/1999 | Tracy et al. |
| 5,994,616 A | 11/1999 | Rosen |
| 5,998,209 A | 12/1999 | Jokobovits et al. |
| 6,017,517 A | 1/2000 | Park |
| 6,019,944 A | 2/2000 | Buechler |
| 6,019,968 A | 2/2000 | Platz et al. |
| 6,075,181 A | 6/2000 | Kucherlapati et al. |
| 6,091,001 A | 7/2000 | Jakobovits et al. |
| 6,096,311 A | 8/2000 | Fanger et al. |
| 6,111,166 A | 8/2000 | Van De Winkel |
| 6,113,855 A | 9/2000 | Buechler |
| 6,114,598 A | 9/2000 | Kucherlapati et al. |
| 6,130,364 A | 10/2000 | Jakobovits et al. |
| 6,143,576 A | 11/2000 | Buechler |
| 6,180,370 B1 | 1/2001 | Queen et al. |
| 6,204,023 B1 | 3/2001 | Robinson et al. |
| 6,270,765 B1 | 8/2001 | Deo et al. |
| 6,303,755 B1 | 10/2001 | Deo et al. |
| 6,365,116 B1 | 4/2002 | Barham et al. |
| 6,410,690 B1 | 6/2002 | Deo et al. |
| 6,632,926 B2 | 10/2003 | Chen et al. |
| 6,682,928 B2 | 1/2004 | Keler et al. |
| 6,699,658 B1 | 3/2004 | Wittrup et al. |
| 6,914,128 B1 | 7/2005 | Salfeld et al. |
| 6,984,720 B1 | 1/2006 | Korman et al. |
| 7,612,181 B2 | 11/2009 | Wu et al. |
| 7,776,550 B2 | 8/2010 | Block et al. |
| 7,906,293 B2 | 3/2011 | Mattingly et al. |
| 2003/0170881 A1 | 9/2003 | Davis et al. |
| 2003/0186374 A1 | 10/2003 | Hufton et al. |
| 2004/0018577 A1 | 1/2004 | Emerson et al. |
| 2005/0042664 A1 | 2/2005 | Wu et al. |
| 2005/0054078 A1 | 3/2005 | Miller et al. |
| 2005/0112711 A1 | 5/2005 | Romano et al. |
| 2006/0104968 A1 | 5/2006 | Bookbinder et al. |
| 2006/0160164 A1 | 7/2006 | Miller et al. |
| 2006/0211017 A1 | 9/2006 | Chinnaiyan et al. |
| 2007/0037221 A1 | 2/2007 | Block et al. |
| 2008/0166738 A1 | 7/2008 | Norman et al. |
| 2014/0147437 A1 | 5/2014 | Ma |

FOREIGN PATENT DOCUMENTS

| | | |
|---|---|---|
| CN | 101555282 | 10/2009 |
| CN | 101735319 | 6/2010 |
| CN | 101988926 | 3/2011 |
| EP | 0404097 | 12/1990 |
| WO | WO 9002809 A1 | 3/1990 |
| WO | WO 9105548 A1 | 5/1991 |
| WO | WO 9110737 A1 | 7/1991 |
| WO | WO 9117271 A1 | 11/1991 |
| WO | WO 9201047 A1 | 1/1992 |
| WO | WO 9202551 A1 | 2/1992 |
| WO | WO 9209690 A2 | 6/1992 |
| WO | WO 9215679 A1 | 9/1992 |
| WO | WO 9218619 A1 | 10/1992 |
| WO | WO 9219244 A2 | 11/1992 |
| WO | WO 9220791 A1 | 11/1992 |
| WO | WO 9222324 A1 | 12/1992 |
| WO | WO 9301288 A1 | 1/1993 |
| WO | WO 9311161 A1 | 6/1993 |
| WO | WO 9311236 A1 | 6/1993 |
| WO | WO 9402602 A1 | 2/1994 |
| WO | WO 9515982 A2 | 6/1995 |
| WO | WO 9520401 A1 | 8/1995 |
| WO | WO 9620698 A2 | 7/1996 |
| WO | WO 9633735 A1 | 10/1996 |
| WO | WO 9634096 A1 | 10/1996 |
| WO | WO 9729131 A1 | 8/1997 |
| WO | WO 9732572 A2 | 9/1997 |
| WO | WO 9744013 A1 | 11/1997 |
| WO | WO 9816654 A1 | 4/1998 |
| WO | WO 9824893 A2 | 6/1998 |
| WO | WO 9831346 A1 | 7/1998 |
| WO | WO 9831700 A1 | 7/1998 |
| WO | WO 9850433 A2 | 11/1998 |
| WO | WO 9915154 A1 | 4/1999 |
| WO | WO 9920253 A1 | 4/1999 |
| WO | WO 9945031 A2 | 9/1999 |
| WO | WO 9953049 A1 | 10/1999 |
| WO | WO 9966903 A2 | 12/1999 |
| WO | WO 0009560 A2 | 2/2000 |
| WO | WO 00037504 A2 | 6/2000 |
| WO | WO 0056772 A1 | 9/2000 |
| WO | WO 0158956 A2 | 8/2001 |
| WO | WO 0202773 A1 | 1/2002 |
| WO | WO 2004078140 A2 | 9/2004 |
| WO | WO 2006121892 | 11/2006 |
| WO | WO 2007024715 A2 | 3/2007 |
| WO | WO 2012112798 | 8/2012 |

OTHER PUBLICATIONS

Adamczyk M., et al., "Intrinsic Factor-Mediated Modulation of Cyanocobalamin-N-sulfonyl-acridinium-9-carboxamide Chemiluminescence," Bioorganic and Medicinal Chemistry Letters, 2004, vol. 14 (15), pp. 3917-3921.

Adamczyk M., et al., "Linker-Mediated Modulation of the Chemiluminescent Signal from N10-(3-Sulfopropyl)-N-Sulfonylacridinium-9-carboxamide Tracers," Bioconjugate Chemistry, 2000, vol. 11 (5), pp. 714-724.

Adamczyk M., et al., "Modulation of the Chemiluminescent Signal from N10-(3-Sulfopropyl)-N-Sulfonylacridinium-9-carboxamides," Tetrahedron, 1999, vol. 55, pp. 10899-10914.

Adamczyk M., et al., "Neopentyl 3-Triflyloxypropanesulfonate A Reactive Sulfopropylation Reagent for the Preparation of Chemiluminescent Labels," Journal of Organic Chemistry, 1998, vol. 63, pp. 5636-5639.

(56) References Cited

OTHER PUBLICATIONS

Adamczyk M., et al., "Regiodependent Luminescence Quenching of Biotinylated N-Sulfonyl-acridinium-9-carboxamides by Avidin," Organic Letters, 2003, vol. 5 (21), pp. 3779-3782.

Adamczyk M., et al., "Synthesis of a Chemiluminescent Acridinium Hydroxylamine (AHA) for the Direct Detection of Abasic Sites in DNA," Organic Letters, 1999, vol. 1 (5), pp. 779-781.

Ames R.S., et al., "Conversion of Murine Fabs Isolated from a Combinatorial Phage Display Library to Full Length Immunoglobulins," Journal of Immunological Methods, 1995, vol. 184, pp. 177-186.

Babcook J.S., et al., "A Novel Strategy for Generating Monoclonal Antibodies from Single, Isolated Lymphocytes Producing Antibodies of Defined Specificities," Proceedings of the National Academy of Sciences, 1996, vol. 93 (15), pp. 7843-7848.

Barbas C.F., et al., "Assembly of Combinatorial Antibody Libraries on Phage Surfaces: The Gene III Site," The Proceedings of the National Academy of Sciences of the United States of America, 1991, vol. 88, pp. 7978-7982.

Barbas C.F., et al., "In Vitro Evolution of a Neutralizing Human Antibody to Human Immunodeficiency Virus Type 1 to Enhance Affinity and Broaden Strain Cross-Reactivity," Proceedings of the National Academy of Sciences of the United States of America, 1994, vol. 91 (9), pp. 3809-3813.

Bendig M., "Humanization of Rodent Monoclonal Antibodies by CDR Grafting," Methods: A Companion to Methods in Enzymology 8, 83-93 (1995).

Better M., et al., "*Escherichia coli* Secretion of an Active Chimeric Antibody Fragment," Science, 1988, vol. 240, pp. 1041-1043.

Bird R.E., et al., "Single-Chain Antigen-Binding Proteins," Science, 1988, vol. 242 (4877), pp. 423-426.

Brinkmann U., et al., "Phage Display of Disulfide-stabilized Fv Fragments," Journal of Immunological Methods, 1995, vol. 182, pp. 41-50.

Buchwald H., et al., "Long-term, Continuous Intravenous Heparin Administration by an Implantable Infusion Pump in Ambulatory Patients with Recurrent Venous Thrombosis," Surgery, 1980, vol. 88, pp. 507-516.

Burton D.R., et al., "Human Antibodies from Combinatorial Libraries," Advances in Immunology, 1994, vol. 57, pp. 191-280.

Chen, W. et al., "Value of Golgi protein 73 monoclonal antibody in diagnosis of hepatocellular carcinoma," ACTA Academiae Medicinae Sinicae Feb. 28, 2011 Chinese Academy of Medical Sciences (2011) 33(1):39-44.

Chothia C., et al., "Canonical Structures for the Hypervariable Regions of Immunoglobulins," Journal of Molecular Biology, 1987, vol. 196 (4), pp. 901-917.

Chothia C., et al., "Conformations of Immunoglobulin Hypervariable Regions," Nature, 1989, vol. 342 (6252), pp. 877-883.

Clackson T., et al., "Making Antibody Fragments Using Phage Display Libraries," Nature, 1991, vol. 352, pp. 624-628.

Cleek R.L., et al., "Biodegradable Polymeric Carriers for a bFGF Antibody for Cardiovascular Application," Proc. Intl. Symp. Control. Rel. Bioact. Mater., 1997, vol. 24, pp. 853-854.

Comunale M.A., et al., "Identification and Development of Fucosylated Glycoproteins as Biomarkers of Primary Hepatocellular Carcinoma," Journal of Proteome Research, 2009, vol. 8 (2), pp. 595-602.

Conrad U., et al., "Compartment-Specific Accumulation of Recombinant Immunoglobulins in Plant Cells: An Essential Tool for Antibody Production and Immunomodulation of Physiological Functions and Pathogen Activity," Plant Molecular Biology, 1998, vol. 38 (1-2), pp. 101-109.

Cramer C.L., et al., "Transgenic Plants for Therapeutic Proteins: Linking Upstream and Downstream Strategies," Current Topics in Microbiology and Immunology, 1999, vol. 240, pp. 95-118.

During M. J., et al., "Controlled Release of Dopamine from a Polymeric Brain Implant: In Vivo Characterization," Annals of Neurology, 1989, vol. 25 (4), pp. 351-356.

Eren R.R., et al., "Human Monoclonal Antibodies Specific to Hepatitis B Virus Generated in a Human/mouse Radiation Chimera: the Trimera System," Immunology, 1998, vol. 93 (2), pp. 154-161.

European Extended Search Report for Application No. 16179039.9 dated Dec. 22, 2016.

European Patent Office Action for Application No. 14721654.3 dated Apr. 7, 2017 (5 pages).

Fuchs P., et al., "Targeting Recombinant Antibodies to the Surface of *Escherichia coli*: Fusion to a Peptidoglycan Associated Lipoprotein," BioTechnology, 1991, vol. 9 (12), pp. 1369-1372.

Funaro A., et al., "Generation of Potent Neutralizing Human Monoclonal Antibodies against Cytomegalovirus Infection from Immune B Cells," BMC Biotechnology, 2008, vol. 8, p. 85.

Garrard L.J., et al., "Fab Assembly and Enrichment in a Monovalent Phage Display System," BioTechnology, 1991, vol. 9 (12), pp. 1373-1377.

Goodson, "Medical Applications of Controlled Release," Langer and Wise, Eds., 1984, 2, 115-138.

Gram H., et al., "In Vitro Selection and Affinity Maturation of Antibodies from a Naive Combinatorial Immunoglobulin Library," Proceedings of the National Academy of Sciences, 1992, vol. 89 (8), pp. 3576-3580.

Gray F., et al., "Secretion Capture and Report Web: Use of Affinity Derivatized Agarose Microdroplets for the Selection of Hybridoma Cells," Journal of Immunological Methods, 1995, vol. 182 (2), pp. 155-163.

Green L. L., et al., "Regulation of B Cell Development by Variable Gene Complexity in Mice Reconstituted with Human Immunoglobulin Yeast Artificial Chromosomes," Journal of Experimental Medicine, 1998, vol. 188 (3), pp. 483-495.

Green L.L., et al., "Antigen-Specific Human Monoclonal Antibodies from Mice Engineered with Human Ig Heavy and Light Chain YACs," Nature Genetics, 1994, vol. 7 (1), pp. 13-21.

Griffiths A.D., et al., "Human Anti-Self Antibodies with High Specificity from Phage Display Libraries," European Molecular Biology Organization, 1993, vol. 12 (2), pp. 725-734.

Gu, Y. et al., "Quantitative analysis of elevated serum Golgi protein-73 expression in patients with liver diseases," Annals of Clin. Biochem. (2009) 46(1):38-43.

Hanes J., et al., "In Vitro Selection and Evolution of Functional Proteins by Using Ribosome Display," Proceedings of the National Academy of Sciences, 1997, vol. 94 (10), pp. 4937-4942.

Hanes J., et al., "Ribosome Display Efficiently Selects and Evolves High-Affinity Antibodies in Vitro from Immune Libraries," Proceedings of the National Academy of Sciences, 1998, vol. 95 (24), pp. 14130-14135.

Hawkins R.E., et al., "Selection of Phage Antibodies by Binding Affinity Mimicking Affinity Maturation," Journal of Molecular Biology, 1992, vol. 226 (3), pp. 889-896.

Hay B.N., et al., "Bacteriophage Cloning and *Escherichia coli* Expression of a Human IgM Fab," Human Antibodies and Hybridomas, 1992, vol. 3 (2), pp. 81-85.

Holliger P., et al., ""Diabodies": Small Bivalent and Bispecific Antibody Fragments," Proceedings of the National Academy of Sciences, 1993, vol. 90 (14), pp. 6444-6448.

Hood E.E., et al., "Molecular Farming of Industrial Proteins from Transgenic Maize," Advances in Experimental Medicine and Biology, 1999, vol. 464, pp. 127-147.

Hoogenboom H.R., et al., "Multi-Subunit Proteins on the Surface of Filamentous Phage: Methodologies for Displaying Antibody (Fab) Heavy and Light Chains," Nucleic Acids Research, 1991, vol. 19 (15), pp. 4133-4137.

Howard M.A., et al., "Intracerebral Drug Delivery in Rats with Lesion-Induced Memory Deficits," Journal of Neurosurgery, 1989, vol. 71 (1), pp. 105-112.

Huse W.D., et al., "Generation of a Large Combinatorial Library of the Immunoglobulin Repertoire in Phage Lambda," Science, 1989, vol. 246 (4935), pp. 1275-1281.

Huston J.S., et al., "Protein Engineering of Antibody Binding Sites: Recovery of Specific Activity in an Anti-Digoxin Single-Chain Fv Analogue Produced in *Escherichia coli*," Proceedings of the National Academy of Sciences of the USA, 1988, vol. 85 (16), pp. 5879-5883.

(56) References Cited

OTHER PUBLICATIONS

Huston J.S., et al., "Protein Engineering of Single-Chain Fv Analogs and Fusion Proteins," Methods in Enzymology, 1991, vol. 203, pp. 46-88.
Iftikhar R., et al., "Disease- and Cell-Specific Expression of GP73 in Human Liver Disease," American Journal of Gastroenterology, 2004, vol. 99 (6), pp. 1087-1095.
International Search Report for Application No. PCT/US2014/028725 dated Dec. 15, 2014.
Jackson J.R., et al., "In Vitro Antibody Maturation Improvement of a High Affinity, Neutralizing Antibody Against IL-1β," The Journal of Immunology, 1995, vol. 154 (7), pp. 3310-3319.
Jia W., et al., "A Strategy for Precise and Large Scale Identification of Core Fucosylated Glycoproteins," Molecular & Cellular Proteomics, 2009, vol. 8 (5), pp. 913-923.
Joliot A., et al., "Antennapedia Homeobox Peptide Regulates Neural Morphogenesis," Proceedings of the National Academy of Sciences, 1991, vol. 88 (5), pp. 1864-1868.
Kaufman R.J., et al., "Amplification and Expression of Sequences Cotransfected with a Modular Dihydrofolate Reductase Complementary DNA Gene," Journal of Molecular Biology, 1982, vol. 159 (4), pp. 601-621.
Kenney J.S., et al., "Production of Monoclonal Antibodies Using a Secretion Capture Report Web," Biotechnology, 1995, vol. 13 (8), pp. 787-790.
Kettleborough C.A., et al., "Isolation of Tumor Cell-specific Single-chain Fv from Immunized Mice using Phage-antibody Libraries and the Re-construction of Whole Antibodies from these Antibody Fragments," European Journal of Immunology, 1994, vol. 24 (4), pp. 952-958.
Kladney R., et al., "Expression of Gp73, A Resident Golgi Membrane Protein, In Viral And Nonviral Liver Disease," Hepatology, 2002, vol. 35 (6), 1431-1440.
Lam X.M., et al., "Microencapsulation of Recombinant Humanized Monoclonal Antibody for Local Delivery," Proceedings of the 24th International Symposium on Controlled Release of Bioactive Materials, 1997, vol. 24, pp. 759-760.
Langer R., "New Methods of Drug Delivery," Science, 1990, vol. 249 (4976), pp. 1527-1533.
Levy R.D., et al., "Inhibition of Calcification of Bioprosthetic Heart Valves by Local Controlled-Release Diphosphonate," Science, 1985, vol. 228 (4696), pp. 190-192.
Li, F. et al., "Construction and development of a mammalian cell-based full-length antibody display library for targeting hepatocellular carcinoma," Appl. Microbiol. Biotech. (2012) 96(5):1233-1241.
MacCallum R., et al., "Antibody-antigen Interactions: Contact Analysis and Binding Site Topography," J. Mol. Biol., 1998, 262, 732-745.
MacCallum R.M., et al., "Antibody-Antigen Interactions: Contact Analysis and Binding Site Topography," Journal of Molecular Biology, 1996, vol. 262 (5), pp. 732-745.
Marks J.D., et al., "By-Passing Immunization: Building High Affinity Human Antibodies by Chain Shuffling," Biotechnology, 1992, vol. 10 (7), pp. 779-783.
Marrero, et al., "GP73, a resident Golgi glycoprotein, is a novel serum marker for hepatocellular carcinoma," J Hepatol, 2005, vol. 43 (6), 1007-12.
Mattingly P.G., "Chemiluminescent 10-Methyl-Acridinium-9(N-Sulphonylcarboxamide) Salts. Synthesis and Kinetics of Light Emission," Journal of Bioluminescence and Chemiluminescence, 1991, vol. 6 (2), pp. 107-114.
Mattingly P.G., et al., "Instruments and Applications Luminescence" In: Biotechnology, Dyke K.V., Edition, CRC Press, 2002, pp. 77-115.
McCafferty J., et al., "Phage Antibodies: Filamentous Phage Displaying Antibody Variable Domains," Nature, 1990, vol. 348 (6301), pp. 552-554.

McCapra F., et al., "Chemiluminescence Involving Peroxide Decompositions ," Photochemistry and Photobiology, 1965, vol. 4, pp. 1111-1121.
Mendez M.J., et al., "Functional Transplant of Megabase Human Immunoglobulin Loci Recapitulates Human Antibody Response in Mice," Nature Genetics, 1997, vol. 15 (2), pp. 146-156.
Milstein C., et al, "Hybrid Hybridomas and their use in Immunohistochemistry," Nature, 1983, vol. 305 (5934), pp. 537-540.
Miyoshi E., et al., "Biological Function of Fucosylation in Cancer Biology," The Journal of Biochemistry, 2008, vol. 143 (6), pp. 725-729.
Morota, K. et al., "A comparative evaluation of Golgi protein-73, fucosylated hemopexin, alpha-fetoprotein, and PIVKA-II in the serum of patients with chronic hepatitis, cirrhosis, and hepatocellular carcinoma," Clin. Chem. and Laboratory Medicine (2011) 49(4):711-718.
Mullinax R.L., et al., "Expressoin of a Heterodimeric Fab Antibody Protein in One Cloning Step," BioTechniques, 1992, vol. 12 (6), pp. 864-869.
Nguyen H.H., et al., "Production of Human Monoclonal Antibodies in Scid Mouse," Microbiology and Immunology, 1997, vol. 41 (12), pp. 901-907.
Ning S., et al., "Intratumoral Radioimmunotherapy of a Human Colon Cancer Xenograft Using a Sustained-Release Gel," Radiotherapy & Oncology: The Journal of the European Society for Therapeutic Radiology and Oncology, 1996, vol. 39 (2), pp. 179-189.
Norton P.A., et al., "N-linked Glycosylation of the Liver Cancer Biomarker GP73," Journal of Cellular Biochemistry, 2008, vol. 104 (1), pp. 136-149.
Padlan E.A., et al., "Identification of Specificity-determining Residues in Antibodies," FASEB Journal, 1995, vol. 9 (1), pp. 133-139.
Paul W., "Fundamental Immunology," Third Edition, 1993, pp. 282-295.
Persic L., et al., "An Integrated Vector System for the Eukaryotic Expression of Antibodies or their Fragments After Selection from Phage Display Libraries," Gene, 1997, vol. 187 (1), pp. 9-18.
Powell K.T., et al., "Gel Microdroplets and Flow Cytometry: Rapid Determination of Antibody Secretion by Individual Cells within a Cell Population," Biotechnology, 1990, vol. 8 (4), pp. 333-337.
Ranger et al., Journal of Macromolecular Science—Reviews in Macromolecular Chemistry & Physics, 1983, vol. 23, p. 61.
Razavi Z., et al., "Stable and Versatile Active Acridinium Esters I," Luminescence, 2000, vol. 15 (4), pp. 239-244.
Razavi Z., et al., "Stable and Versatile Active Acridinium Esters II," Luminescence, 2000, vol. 15, pp. 245-249.
Roberts R.W., et al., "RNA-peptide Fusions for the in Vitro Selection of Peptides and Proteins," Proceedings of the National Academy of Sciences, 1997, vol. 94 (23), pp. 12297-12302.
Sandhu J.S., et al., "The use of SCID Mice in Biotechnology and as a Model for Human Disease," Critical Reviews in Biotechnology, 1996, vol. 16 (1), pp. 95-118.
Saudek C.D., et al., "A Preliminary Trial of the Programmable Implantable Medication System for Insulin Delivery," The New England Journal of Medicine, 1989, vol. 321 (9), pp. 574-579.
Sawai H., et al., "Direct Production of the Fab Fragment Derived from the Sperm Immobilizing Antibody using Polymerase Chain Reaction and Cdna Expression Vectors," American Journal of Reproductive Immunology, 1995, vol. 34 (1), pp. 26-34.
Sefton M.V., et al., "Implantable Pumps," Critical Reviews in Biomedical Engineering, 1987, vol. 14 (3), pp. 201-240.
Shu L., et al., "Secretion of a Single-Gene-Encoded Immunoglobulin from Myeloma Cells," Proceedings of the National Academy of Sciences, 1993, vol. 90 (17), pp. 7995-7999.
Skerra A., et al., "Assembly of a Functional Immunoglobulin Fv Fragment in *Escherichia coli*," Science, 1988, vol. 240 (4855), pp. 1038-1041.
Song Y.K., et al., "Antibody Mediated Lung Targeting of Long-Circulating Emulsions," PDA Journal of Pharmaceutical Science & Technology, 1995, vol. 50 (6), pp. 372-377.
Staerz U.D., et al., "Hybrid Antibodies Can Target Sites for Attack by T Cells," Nature, 1985, vol. 314 (6012), pp. 628-631.

(56) References Cited

OTHER PUBLICATIONS

Steenbakkers P.G., et al., "Efficient Generation of Monoclonal Antibodies from Preselected Antigen-Specific B Cells. Efficient Immortalization of Preselected B Cells," Molecular Biology Reports, 1994, vol. 19 (2), pp. 125-134.

Urlaub G., et al., "Isolation of Chinese Hamster Cell Mutants Deficient in Dihydrofolate reductase Activity," Proceedings of the National Academy of Sciences, 1980, vol. 77 (7), pp. 4216-4220.

Wang, et al., "Value of Golgi Protein 73 Monoclonal Antibody in Diagnosis of Heptocellular Carcinoma." Acta Academiae Medicine Sinicae, 2011, 33(1): 39-44.

Wen L., et al., "Limiting Dilution Assay for Human B Cells Based on their Activation by Mutant EI4 Thymoma Cells: Total and Antimalaria Responder B Cell Frequencies," European Journal of Immunology, 1987, vol. 17 (6), pp. 887-892.

Wilbur W.J., et al., "Rapid Similarity Searches of Nucleic Acid and Protein Data Banks," Proceedings of the National Academy of Sciences, 1983, vol. 80 (3), pp. 726-730.

Written Opinion for Application No. PCT/US2014/028725 dated Dec. 15, 2014.

Wu C., et al., "Simultaneous Targeting of Multiple Disease Mediators by a Dual-Variable-Domain Immunoglobulin," Nature Biotechnology, 2007, vol. 25 (11), pp. 1290-1297.

Wu G.Y., et al., "Receptor-mediated in Vitro Gene Transformation by a Soluble DNA Carrier System," Journal of Biological Chemistry, 1987, vol. 262 (10), pp. 4429-4432.

Yelton D.E., et al., "Affinity Maturation of the BR96 Anti-Carcinoma Antibody by Codon-Based Mutagenesis," The Journal of Immunology, 1995, vol. 155 (4), pp. 1994-2004.

Zapata G., et al., "Engineering Linear F(ab')2 Fragments for Efficient Production in *Escherichia coli* and Enhanced Antiproliferative Activity," Protein Engineering, 1995, vol. 8 (10), pp. 1057-1062.

Zhang, A. et al., "Generation and characterization of an anti-GP73 monoclonal antibody for immunoblotting and sandwich ELISA," J. Biomed. Res. (2012) 26(6):467-473.

Zhang, F. et al., "Up-regulated Golgi phosphoprotein 2 (GOLPH2) expression in lung adenocarcinoma tissue," Clin. Biochem. (2010) 43(12):983-991.

E. coli GP73 Construct

MELKKNEELKKNEFQGELEKQREQLDKIQSSHNFQLESVNKLYQKEDAVLVNNITTGE
RLIRVLQDQLKTLQRNYGRLQQDVLQFQKNQTNLERKFSYDLSQCINQMKEVKEQCEE
RIEEVTKKGNEAVASRDLSENNDQRQQLQALSEPQPRLQAAGLPHTEVPQGKGNVLGN
SKSQTPAPSSEVVLDSKRQVEKEETNEIQVVNEEQRDRLPQEPGREQVVEDRPVGGRG
FGGAGELGQTPQVQAALSVSQENPEMEGPERDQLVIPDGQEEEQEAAGEGRNQQKLRG
EDDYNMDENEAESETDKQAALAGNDRNIDVFNVEDQKRDTINLLDQREKRNHTL<u>SG</u>*HH
HHHH* (SEQ ID NO:98)

Bold M indicates the start codon (Methionine).
Bold and underlined letters indicate repeat of first 6 amino acids of
GP73 amino acids 63-400 fragment.
<u>Underlined</u> letters indicate the linker.
*Italicized* letters indicate poly histidine tag.

FIG.1

CHO and HEK GP73-hFc Construct

ELKKNEFQGELEKQREQLDKIQSSHNFQLESVNKLYQDEKAVLVNNITTGERLIRVLQD
QLKTLQRNYGRLQQDVLQFQKNQTNLERKFSYDLSQCINQMKEVKEQCEERIEEVTKK
GNEAVASRDLSENNDQRQQLQALSEPQPRLQAAGLPHTEVPQGKGNVLGNSKSQTPAP
SSEVVLDSKRQVEKEETNEIQVVNEEPQRDRLPQEPGREQVVEDRPVGGRGFGGAGELG
QTPQVQAALSVSQENPEMEGPERDQLVIPDGQEEEQEAAGEGRNQQKLRGEDDYNMDE
NEAESETDKQAALAGNDRNIDVFNVEDQKRDTINLLDQREKRNHTL<u>RSVECPPCPAPPV
AGPSVFLFPPKPKDTLMISRTPEVTCVVVDVSHEDPEVQFNWYVDGMEVHNAKTKPRE
EQFASTFRVVSVLTVVHQDWLNGKEYKCKVSNKGLPAPIEKTISKTKGQPREPQVYTLP
PSREEMTKNQVSLTCLVKGFYPSDIAVEWESNGQPENNYKTTPPMLDSDGSFFLYSKLT
VDKSRWQQGNVFSCSVMHEALHNHYTQKSLSLSPGK</u> (SEQ ID NO:99)

<u>Underlined</u> letters indicate the Human IgG Fc domain.

FIG.2

Anti-GP73 1A-3187 VH sequence

```
(SEQ ID NO: 33) +1    Q G Q L Q Q S G A E L M K P G A S V K I S C K A T G Y
(SEQ ID NO: 81) 1     CAGGGTCAGC TGCAGCAGTC TGGAGCTGAA CTGATGAAGC CTGGGGCCTC AGTGAAGATA TCCTGCAAGG CTACTGGCTA
                      GTCCCAGTCG ACGTCGTCAG ACCTCGACTT GACTACTTCG GACCCCGGAG TCACTTCTAT AGGACGTTCC GATGACCGAT
                                                                                                     CDRH2
(SEQ ID NO: 33) +1    Y T I R   S Y W I E W   V K Q R P G H G L E W I G E I L P G
                            CDRH1 (SEQ ID NO: 34)
(SEQ ID NO: 81) 81    CACAATCAGG AGCTACTGGA TAGAGTGGGT AAAGCAGAGG CCTGGACATG GCCTTGAGTG GATTGGAGAG ATTTTACCTG
                      GTGTTAGTCC TCGATGACCT ATCTCACCCA TTTCGTCTCC GGACTCACTA CCGGAACTCAC CTAACCTCTC TAAAATGGAC
                                                    CDRH2 (SEQ ID NO: 35)
(SEQ ID NO: 33) +1    G S G N T N Y N E K F K G T A L F I A D T S S N T V Y
(SEQ ID NO: 81) 161   GAAGTGGTAA TACTAATTAT AATGAGAAGT TCAAGGGGAC GGCCCACATTC ACTGCAGATA CATCCTCCAA CACAGTCTAT
                      CTTCACCATT ATGATTAATA TTACTCTTCA AGTTCCCCTG CCGGTGTAAG TGACGTCTAT GTAGGAGGTT GTGTCAGATA
                                                                                                       CDRH3
(SEQ ID NO: 33) +1    L H L S S L T S E D S A V Y Y C A N G R G S Y R Y H W
(SEQ ID NO: 81) 241   TTGCCACCTCA GCAGCCTGAC ATCTGAGGAC TCTGCCGTCT ATTACTGTGC AAACGGGAGG GGCTCCTATA GGTACCACTG
                      AACGTGGAGT CGTCGGACTG TAGACTCCTG AGACGGCAGA TAATGACACG TTTGCCCTCC CCGAGAATAT CCATGGTGAC
                          CDRH3 (SEQ ID NO: 36)
(SEQ ID NO: 33) +1    W F A Y W G Q G T L V T V S P
(SEQ ID NO: 81) 321   GTTTCCTTAC TGGGGCCAAG CGACTCTCGT CACTGTCTCT CCA
                      CAAAGGAATG ACCCCGGTTC CCTGAGACCA GTGACAGAGA GGT
```

FIG. 12A

Anti-GP73 1A-3187 VL sequence

```
                      CDRL1
              ┌─────────────────────────────┐
      D I V L T Q S P A S L A V S L G Q R A T I S C K A S Q
(SEQ ID NO: 37) +1
(SEQ ID NO: 85) 1    GACATTGTGC TGACCCAATC TCCAGCTTCT TTGGCTGTGT CTCTAGGGCA GAGGGCCACC ATCTCCTGCA AGGCCAGCCA
                     CTGTAACACG ACTGGGTTAG AGGTCGAAGA AACCGACACA GAGATCCCGT CTCCCGGTGG TAGAGGACGT TCCGGTCGGT
                                                                                          CDRL2
                                                                                   ┌──────────────
      Q S V D Y D G D S Y M N W Y Q Q K P G Q P P K V L I Y A
(SEQ ID NO: 37) +1
(SEQ ID NO: 85) 81   AAGTGTTGAT TATGATGGTG ATAGTTATAT GAACTGGTAC CAACAGAAAC CAGGACAGCC ACCCAAGGTC CTCATCTATG
                     TTCACAACTA ATACTACCAC TATCAATATA CTTGACCATG GTTGTCTTTG GTCCTGTCGG TGGGTTCCAG GAGTAGATAC
            CDRL2
      ─────────────┐
      A A S N L E S G I P A R F S G S G S G T D F T L N I H
(SEQ ID NO: 37) +1
(SEQ ID NO: 85) 161  CTGCATCCAA TCTAGAATCT CGGAATCCCA GCCAGGTTTAG TGGCAGTGGG TCTGGGACAG ACTTCACCCT CAACATCCAT
                     GACGTAGGTT AGATCTTAGA GCCTTAGGGT CGGTCCAAATC ACCGTCACCC AGACCCTGTC TGAAGTGGGA GTTGTAGGTA
                                                                CDRL3 (SEQ ID NO: 40)
                                                       ┌─────────────────────────────────────
      P V E E E D A A T Y Y C Q Q S N E D P Y T F G G G T K
(SEQ ID NO: 37) +1
(SEQ ID NO: 85) 241  CCTGTGGAGG AGGAAGATGC AGCAACCTAT TACTGTCAGC AAAGTAATGA GGATCCGTAC ACGTTCGGAG GGGGGACCAA
                     GGACACCTCC TCCTTCTACG TCGTTGGATA ATGACAGTCG TTTCATTACT CCTAGGCATG TGCAAGCCTC CCCCCCTGGTT
      K L E M K R
(SEQ ID NO: 37) +1
(SEQ ID NO: 85) 321  GCTGGAAATG AAACGG
                     CGACCTTTAC TTTGCC
```

FIG. 12B

Anti-GP73 1A-4246 VH sequence

```
(SEQ ID NO: 41) +1      E  V  M  L  V  E  S  G  G  G  L  V  K  P  G  G  S  L  K  L  S  C  A  A  S  G  F
(SEQ ID NO: 89)   1   GAAGTGATGC TGGTGGAGTC TGGGGGAGGC TTAGTGAAGC CTGGAGGGTC CCTGAAACTC TCCTGTGCAG CCTCTGGATT
                      CTTCACTCAG ACCACCTCAG ACCCCTCCG AATCACTTCG GACCTCCCAG GGACTTTGAG AGGACACGTC GGAGACCTAA
                                                                                                      CDRH1
(SEQ ID NO: 41) +1      F  T  F  S  S  Y  A  M  S  W  V  R  L  T  P  E  K  R  L  E  W  V  A  T  I  S  S  G
(SEQ ID NO: 89)  81   CACTTTCAGT AGCTATGCCA TGTCTTGGGT TCGCCTGACT CCCGAGAAGA GGCTGGAGTG GGTCGCAACC ATTAGTAGTG
                      GTGAAAGTCA TCGATACGGT ACAGAACCCA AGCGGACTGA GGGCTCTTCT CCGACCTCAC CCAGGGTTGG TAATCATCAC
                                                                                        CDRH2
(SEQ ID NO: 41) +1      G  S  S  Y  T  Y  Y  P  D  S  V  K  G  R  F  T  I  S  R  D  N  V  K  S  T  L  Y
(SEQ ID NO: 89) 161   GTAGCAGTTA CACCTACTAT CCAGACAGTG TGAAGGGGCG ATTCACCATC TCCAGAGACA ATGTCAAGAG CACCCTGTAC
                      CATCGTCAAT GTGGATGATA GGTCTGTCAC ACTTCCCGC TAAGTGGTAG AGGTCTCTGT TACAGTTCTC GTGGGACATG
                                                                                                      CDRH3
(SEQ ID NO: 41) +1      L  Q  M  S  S  L  R  S  E  D  T  A  M  Y  Y  C  A  R  N  W  D  G  E  L  H  Y  Y
(SEQ ID NO: 89) 241   CTGCAAATGA GCAGTCTGAG GTCTGAGGAC ACGGCCATGT ATTACTGTGC AAGGAACTGG GACGGGGAAC TCCATTACTA
                      GACGTTTACT CGTCAGACTC CAGACTCCTG TGCCGGTACA TAATGACACG TTCCTTGACC CTGCCCCTTG AGGTAATGAT
                               CDRH3
(SEQ ID NO: 41) +1      Y  A  M  D  Y  W  G  Q  G  T  S  V  T  V  S  S
(SEQ ID NO: 89) 321   TGCTATGGAC TACTGGGGTC AAGGAACTTC AGTCACCGTC TCCTCA
                      ACGATACCTG ATGACCCCAG TTCCTTGAAG TCAGTGGCAG AGGAGT
```

FIG. 13A

Anti-GP73 1A-4246 VL sequence

```
                              Q  I  V  L  T  Q  S  P  A  I  M  S  A  S  L  G  E  R  V  T  M  T  C  T  A  S  S
(SEQ ID NO: 45) +1
(SEQ ID NO: 93) 1    CAAATTGTTC TCACCCAGTC TCCAGCAATC ATGTCTGCAT CTCTAGGGGA ACGGGTCACC ATGACCTGCA CTGCCAGCTC
                                                                                                  ─────────
                                                                                                    CDRL1
                      S  S  V  S  S  Y  L  H  W  Y  Q  Q  K  P  G  S  S  P  K  L  W  V  Y  S  T  S  S
                     ─────────────
                     CTTTAACAAG AGTGGTCAC AGTCCGTTAC TACACAGCTA GAGATCCCT TGCCCAGTGG TACTGGACGT GACGGTCGAG    (SEQ ID NO: 46)
(SEQ ID NO: 45) +1
(SEQ ID NO: 93) 81   AAGTGTAAGT TCCAGTTACT TGCACTGGTA CCAGCAGAAG CCAGGATCCT CCCCCAAACT CTGGGTTTAT AGCACATCCA
                                                                                                  ─────────
                                                                                                    CDRL2
                      S  L  A  S  G  V  P  A  R  F  S  G  S  G  S  G  T  S  Y  S  L  T  I  N  N  M  E
                     ─────
                     TCCACATTCA AGTCAATCA ACGTGACCAT GGTCGTCTTC GGTCCTAGGA GACCCAAATA TCGTGTAGGT    (SEQ ID NO: 47)
(SEQ ID NO: 45) +1
(SEQ ID NO: 93) 161  GCCTGGCTTC TGGAGTCCCA GCTCGCTTCA GTGGCAGTGG GTCTGGGACC TCTTACTCTC TCACAATCAA CAACATGGAG
                                                                                                  ─────────
                                                                                                    CDRL3
                      A  E  D  A  A  T  Y  F  C  H  Q  Y  H  R  S  P  Y  T  F  G  G  G  T  K  L  E  I
(SEQ ID NO: 45) +1
(SEQ ID NO: 93) 241  GCTGAAGATG CTGCCACTTA TTTCTGCCAC CAGTATCATC GTTCCCCGTA CACGTTCGGA GGGGGGACCA AGCTGGAAAT    (SEQ ID NO: 48)

I  K  R
(SEQ ID NO: 45) +1
(SEQ ID NO: 93) 321  AAAACGG
                     TTTTGCC
```

FIG. 13B

Anti-GP73 1B-3246 VH sequence

```
(SEQ ID NO: 17) +1    D  V  K  L  V  E  S  G  G  G  L  V  K  P  G  G  S  L  K  L  S  C  A  A  S  G  F
(SEQ ID NO: 65)  1   GACGTGAAGC TGGTGGAGTC TGGGGGAGGC TTAGTGAAGC CTGGAGGGTC CCTGAAACTC TCCTGTGCAG CCTCTGGATT
                     CTGCACTTCG ACCAGCTCAG ACCCCCTCCG AATCACTTCG GACCTCCCAG GGACTTTGAG AGGACACGTC GGAGACCTAA
                                                                                                      CDRH2
(SEQ ID NO: 17) +1    F  T  F  S  S  Y  T  M  S  W  V  R  Q  T  P  E  K  R  L  E  W  V  A  T  I  S  R  G
(SEQ ID NO: 65) 81   CACTTTCAGT AGTATACCA TGTCTTGGGT TCGCCAGACT CCGGAGAAGA GACTGGAGTG GGTCGCAACC ATTAGTCGTG
                     GTGAAAGTCA TCGATATGGT ACAGAACCCA AGCGGTCTGA GGCCTCTTCT CTGACCTCAC CCAGCGTTGG TAATCAGCAC
                                       CDRH1 (SEQ ID NO: 18)                              CDRH2 (SEQ ID NO: 19)
(SEQ ID NO: 17) +1    G  G  T  Y  Y  I  Y  Y  P  D  S  V  K  G  R  F  T  I  S  R  D  N  A  K  N  T  L  Y
(SEQ ID NO: 65) 161  GTGTACTTA CATCTACTAT CCAGACAGTG TGAAGGGCCG ATTCACCATC TCCAGAGACA ATGCCAAGAA CACCCTGTAC
                     CACATGAAT GTAGATGATA GGTCTGTCAC ACTTCCCGGC TAAGTGGTAG AGGTCTCTGT TACGGTTCTT GTGGGACATG
                                                                                                       CDRH3
(SEQ ID NO: 17) +1    L  Q  M  S  S  L  K  S  E  D  T  A  I  Y  Y  C  T  R  E  Y  F  S  G  D  T  Y  D
(SEQ ID NO: 65) 241  CTGCAAATGA GCAGCCTGAA GTCTGAGGAC ACAGCCATAT ATTACTGTAC AAGAGAATAT TTCTCCGGTG ATACCTACGA
                     GACGTTTACT CGTCGGACTT CAGACTCCTG TGTCGGTATA TAATGACATG TTCTCTTATA AAGAGGCCAC TATGGATGCT
(SEQ ID NO: 17) +1    D  Y  F  D  Y  W  G  Q  G  T  T  L  T  V  S  S
(SEQ ID NO: 65) 321  CTACTTTGAC TATTGGGGCC AAGGCACCAC TCTCACAGTC TCCTCA
                     GATGAAACTG ATAACCCCGG TTCCGTGGTG AGAGTGTCAG AGGAGT
                           CDRH3 (SEQ ID NO: 20)
```

FIG. 14A

Anti-GP73 1B-3246 VL sequence

```
                                                                                                    CDRL1
(SEQ ID NO: 21) +1     E  I  V  M  T  Q  A  A  F  A  N  P  V  T  L  G  T  S  V  S  I  S  C  R  S  S  K
(SEQ ID NO: 69) 1      GAGATTGTGA TGACCCAGGC TGCATTCGCC AATCCAGTCA CTCTTGGAAC ATCCGTCAGT ATCTCCTGCA GGTCTAGTAA
                       CTCTAACACT ACTGGTCCG AGTAAGCGG TTAGGTCAGT GAGAACCTTG TAGGTCAGTA CCAGACTAAA

CDRL1 (SEQ ID NO: 22)
(SEQ ID NO: 21) +1     K  S  L  L  H  S  N  G  I  T  Y  L  Y  W  Y  L  Q  K  P  G  Q  S  P  Q  L  L  I  Y
(SEQ ID NO: 69) 81     GAGTCTCCTA CATAGTAATG GCATCACTTA TTTGTACTGG TATCTGCAGA AGCCAGGCCA GTCTCCTCAG CTCCTGATTT
                       CTCAGAGGAT GTATCATTAC AAACATGACC ATAGACGTCT TCGGTCCGGT CAGAGAGTC GAGGACTAAA

CDRL2 (SEQ ID NO: 23)
(SEQ ID NO: 21) +1     Y  Q  M  S  N  L  A  S  G  V  P  D  R  F  S  S  S  G  S  G  T  D  F  T  L  R  I
(SEQ ID NO: 69) 161    ATCAGATGTC CAACCTTGCC TCAGGAGTCC CAGACAGGTT CAGTAGCAGT GGGTCAGGGA CTGATTTCAC ACTGAGAATC
                       TAGTCTACAG GTTGGAACGG AGTCCTCAGG GTCTGTCCAA GTCATCGTCA CCCAGTCCT GACTAAAGTG TGACTCTTAG

CDRL3 (SEQ ID NO: 24)
(SEQ ID NO: 21) +1     S  R  V  E  A  E  D  V  G  I  Y  Y  C  A  Q  N  L  E  L  Y  T  F  G  G  G  T  K
(SEQ ID NO: 69) 241    AGCCAGAGTG AGGCTGAGGA TGTGGGTATT TACTACTGTG CTCAAAATCT AGAACTTTAC ACGTTCGGAG GGGGGACCAA
                       TCGGTCTCAC TCCGACTCCT ACACCCATAA ATGATGACAC GAGTTTTAGA TCTTGAAATG TGCAAGCCTC CCCCCTGGTT (SEQ ID NO: 21) +1     K  L  E  I  K  R
(SEQ ID NO: 69) 321    GCTGGAAATA AAACGG
                       CGACCTTTAT TTTGCC
```

FIG. 14B

Anti-GP73 1B-3440 VH sequence

```
(SEQ ID NO: 1)  +1        E  V  Q  L  V  E  T  G  G  G  L  V  Q  P  K  G  S  L  K  L  S  C  A  A  S  G  F
(SEQ ID NO: 49)  1   GAGGTGCAGC TTGTTGAGAC TGGTGGAGGA TTGGTGCAGC CTAAAGGGTC ATTGAAACTC TCATGTGCAG CCTCTGGATT
                                                                                           CDRH1 (SEQ ID NO: 2)
                     CTCCAGTCG AACAACTCTG ACCACCTCCT AACAACTCG GATTCCCAG TAACTTGAG AGTACACGTC GGAGACCTAA
                                                                                                CDRH2
(SEQ ID NO: 1)  +1        F  T  F  N  T  N  A  M  N  W  V  R  Q  A  P  G  K  G  L  E  W  V  A  R  I  R  T  K
(SEQ ID NO: 49)  81  CACCTTCAAT ACCAATGCCA TGAACTGGGT CCGCCAGGCT CCAGGAAAGG GTTGGAATG GTTGGCTCGC ATAAGGACTA
                     GTGGAAGTTA TGGTTACGGT ACTTGACCCA GGCGGTCCGA GGTCCTTTCC CAAACCTTAC CCAACGAGCG TATTCCTGAT
                                                                                                CDRH2 (SEQ ID NO: 3)
(SEQ ID NO: 1)  +1        K  R  Y  N  Y  T  T  F  Y  A  D  S  V  K  D  R  F  T  I  S  R  D  D  S  Q  S  M
(SEQ ID NO: 49)  161 AACGTTATAA TTATACAACA TTTTATGCCG ATCAGTGTGA AGGATCGG TTCACCATCCA GAGATGATTC TCAAAGCATG
                     TTGCAATATT AATATGTTGT AAAATACGGC TAGTCACACTT TCTGTCCAAG TGGTAGAGGT CTCTACTAAG AGTTTCGTAC
                                                                                                CDRH3
(SEQ ID NO: 1)  +1        L  F  L  Q  M  N  N  L  K  T  E  D  T  A  M  Y  Y  C  V  T  G  G  T  G  T  F  Q
(SEQ ID NO: 49)  241 CTCTTTCTGC AAATGAACAA CTTGAAAACT GAGGACACAG CCATGTATTA CTGTGTCACA GGGGGACTG GGACGTTTGA
                     GAGAAAGACG TTTACTTGTT GAACTTTTGA CTCCTGTGTC GGTACATAAT GACACACAGT CCCCCCTGAC CCTGCAAACT
                     CDRH3 (SEQ ID NO: 4)
(SEQ ID NO: 1)  +1        D  Y  W  G  Q  G  T  T  L  T  V  S  S
(SEQ ID NO: 49)  321 CTACTGGGGC CAAGGCACCA CTCTCACAGT CTCCTCA
                     GATGACCCCG GTTCCGTGGT GAGAGTGTCA GAGGAGT
```

FIG. 15A

Anti-GP73 1B-3440 VL sequence

```
(SEQ ID NO: 5)  +1        E  I  V  L  T  Q  S  P  T  T   M  P  A  S  P  G  E  K  V  T   F  T  C  S  A  S  S
(SEQ ID NO: 53)  1   GAAATTGTAC TCACCCAGTC TCCAACCACC ATGCCTGCAT CTCCCGGGGA GAAGGTCACT TTCACCTGCA GTGCCAGCTC
                     CTTTAACATG AGTGGGTCAG AGGTTGGTGG TACGGACGTA TCCCAGTGA CTTCCAGTGA AAGTGGACGT CACGGTCGAG
                                                                                                    CDRL1
(SEQ ID NO: 5)  +1    S  G  I  S  S  N  Y  L  H  W   Y  Q  L  K  P  G  F  S  P   K  L  L  I  Y  R  T  S  N
(SEQ ID NO: 53) 81   AGTATAAGT TCCAATTACT TGCATTGGTA TCAGCTGAAG CCAGGATTCT CCCCTAAACT CTTGATTTAT AGGACATCCA
                     TCCATATTCA AGGTTAATGA ACGTAACCAT AGTCGACTTC GGTCCTAAGA GGGGATTTGA GAACTAAATA TCCTGTAGGT
                                                                      CDRL2
(SEQ ID NO: 5)  +1    N  L  A   S  G  V  P  A  R  F  S  G  G  G  S  G  T  S  Y  S  L  T  I  G  T  M  E
(SEQ ID NO: 53) 161  ATCTGGCCTTC TGAGTCCCA GCTCCCTCA GTGGCGGTGG GTCTGGGACC TCTTACTCTC TCACAATTGG CACCATGGAG
                     TAGACCGGAAG ACTCAGGGT CGAGGGAGT CACCGCCACC CAGACCCTGG AGAATGAGAG AGTGTTAACC GTGGTACCTC
                                                                                                   CDRL3
(SEQ ID NO: 5)  +1   A  E  D  V   A  T  Y  Y  C  Q  Q   G  F  S  I  P  L  T  F  G   A  G  T  K  L  E  L
(SEQ ID NO: 53) 241  GCTGAAGATG TTGCCACTTA CTATTGCCAG CAGGGTTTTA GTATACCGCT CACGTTCGGT GCTGGGACCA AGCTGGAGCT
                     CGACTTCTAC AACGGTGAAT GATAACGGTC GTCCCAAAAT CATATGGCGA GTGCAAGCCA CGACCCTGGT TCGACCTCGA
(SEQ ID NO: 5)  +1    L  K  R
(SEQ ID NO: 53) 321  GAAACCG
                     CTTTGGC
```

FIG. 15B

Anti-GP73 1B-4863 VH sequence

| | | |
|---|---|---|
| (SEQ ID NO: 25) +1 | Q V Q L K E S G P G L V A P S Q S L S I T C T V S G F | |
| (SEQ ID NO: 73) 1 | CAGGTGCAGC TGAAGGAGTC AGGACCTGGC CTGGTGGCGC CCTCACAGAG CCTGTCCATC ACTTGCACTG TCTCTGGGTT | |
| | | CDRH1 (SEQ ID NO: 26) |
| (SEQ ID NO: 25) +1 | F S L T S Y G V H W V R Q S P G K G L E W L G V I W T G | |
| (SEQ ID NO: 73) 81 | TTCATTAACC AGCTATGGTG TACACTGGGT TCGCCAGTCT CCAGGAAAGG GTCTGGAGTG GCTGGGAGTA ATATGGACTG | |
| | CDRH2 (SEQ ID NO: 27) | CDRH2 |
| (SEQ ID NO: 25) +1 | G G S T N Y N S A L M S R L S I S K D N S E S Q V F L | |
| (SEQ ID NO: 73) 161 | GTGGAAGCAC AAATTATAAT TCCGCTCTCA TGTCCAGACT GAGCATTAGT AAAGACAACT CCGAGAGCCA AGTTTTCTTA | |
| (SEQ ID NO: 25) +1 | K V N S L Q T D D T G M Y Y C A R D P G T D Y F D Y W | |
| (SEQ ID NO: 73) 241 | AAAGTGAATA GTCTGCAAAC TGATGACACA GGCATGTACT ACTGTGCCAG AGATCCTGGG ACGGACTACT TTGACTACTG | |
| | | CDRH3 (SEQ ID NO: 28) |
| (SEQ ID NO: 25) +1 | W G Q G T T L T V S S | |
| (SEQ ID NO: 73) 321 | GGGCCAAGGC ACCACTCTCA CAGTCTCCTC A | |

FIG. 16A

Anti-GP73 1B-4863 VL sequence

```
                    D  I  V  M  T  Q  S  H  K  F  M  S  T  S  I  G  D  R  V  S  I  S  C  K  A  S  Q
(SEQ ID NO: 29) +1
(SEQ ID NO: 77) 1   GACATTGTGA TGACCCAGTC TCACAAATTC ATGTCCACAT CAATAGGAGA CAGGGTCAGC ATCTCCTGCA AGGCCAGTCA
                                                                                    └─── CDRL1 ───
                    CTGTAACACT ACTGGGTCAG AGTGTTTAAG TACAGGTGTA GTTCCTCCT GTCCCAGTCG TAGAGGACGT TCCGGTCAGT

Q  D  V  S  I  D  V  S  W  Y  Q  Q  K  P  G  Q  S  P  T  L  L  I  Y  S  A  S  Y  R
(SEQ ID NO: 29) +1
(SEQ ID NO: 77) 81  GCAATGTCAGT ATTGATGTGT CCTGGTATCA ACAGAAACCA GGACAGTCTC CTACACTTCT GATTTACTCG GCATCCTACC
                    ─ CDRL1 (SEQ ID NO: 30) ──┘                                         └──── CDRL2
                    CCTACACTCA TAACTACACA GGACCATAGT TGTCTTTGGT CCTGTCAGAG GATGTGAAGA CTAAATGAGC CGTAGGATGG

R  Y  I  G  V  P  D  R  F  T  G  S  G  S  G  T  A  F  T  F  T  I  S  S  V  Q  A
(SEQ ID NO: 29) +1
(SEQ ID NO: 77) 161 GGTACATTGG AGTCCCTGAT CGCTTCACTG GCAGTGGATC TGGGACGGCT TTCACTTTCA CCATCAGCAG TGTCCAGGCT
                    ─── CDRL2 (SEQ ID NO: 31) ─┘
                    CCATGTAACC TCAGGGACTA CCGAAGTGAC CGTCACCTAG ACCCTGCCGA AAGTGAAAGT GGTAGTCGTC ACAGGTCCGA

E  D  L  A  I  Y  Y  C  Q  Q  H  F  T  T  P  L  T  F  G  A  G  T  K  L  E  L  K
(SEQ ID NO: 29) +1
(SEQ ID NO: 77) 241 GAAGACCTGG CAATTTATTA CTGTCAGCAA CATTTTACTA CTCCTCTCAC GTTCGGTGCT GGGACCAAGC TGGAGCTGAA
                                              └──────── CDRL3 ────────┘
                    CTTCTGGACC GTTAAATAAT GACAGTCGTT GTAAAATGAT GAGGAGAGTG CAAGCCACGA CCCTGGTTCG ACCTCGACTT
                                                                        └ CDRL3 (SEQ ID NO: 32)

K  R
(SEQ ID NO: 29) +1
(SEQ ID NO: 77) 321 ACGG
                    TGCC
```

FIG.16B

Anti-GP73 1B-4971 VH sequence (SEQ ID NO: 9) +1    Q  V  Q  L  Q  Q  S  G  P  A  L  V  K  P  G  A  S  V  K  M  S  C  K  A  S  G  Y
(SEQ ID NO: 57) 1    CAGGTCCAGC TGCAGCAGTC TGGACCTGCG CTGGTAAAGC CTGGGGCTTC AGTGAAGATG TCCTGCAAGG CTTCTGGATA
                     GTCCAGGTCG AGGTCGTCAG ACCTGGACGC GACCATTTCG GACCCCGAAG TCACTTCTAC AGGAGACGTT GAAGACCTAT
                                                                                              CDRH1 (SEQ ID NO: 10)                           CDRH2

(SEQ ID NO: 9) +1    Y  T  F  T  N  Y  V  I  H  W  V  K  Q  K  P  G  Q  G  L  E  R  I  G  Y  I  W  P  Y
(SEQ ID NO: 57) 81   CACATTCACT AACTATGTTA TACACTGGGT GAAACAGAAA CCTGGGCAGG GCCTTGAGCG GATTGGATAT ATTTGGCCTT
                     GTGTAAGTGA TTGATACAAT ATGTGACCCA CTTTGTCTTT GGACCCGTCC CGGAACTCGC CTAACCTATA TAAACCGGAA
                                                                                              CDRH2 (SEQ ID NO: 11)

(SEQ ID NO: 9) +1    Y  N  D  G  T  K  F  N  E  K  F  K  G  K  A  T  L  T  S  D  K  S  S  S  T  A  Y
(SEQ ID NO: 57) 161  ACAATGATGG TACTAAGTTC AATGAGAAAT TCAAAGGCAA GGCCACACTG ACTTCAGACA AATCCTCCAG CACAGCCTAC
                     TGTTACTACC ATGATTCAAG TTACTCTTTA AGTTTCCGTT CCGGTGTGAC TGAAGTCTGT TTAGGAGGTC GTGTCGGATG
                                                                                              CDRH3 (SEQ ID NO: 12)

(SEQ ID NO: 9) +1    M  E  L  S  S  L  T  S  E  D  S  A  V  Y  Y  C  S  S  S  Q  L  A  Y  W  G  Q  G
(SEQ ID NO: 57) 241  ATGGAGCTCA GCAGCCTGAC CTCTGAGGAC TCTGCAGTCT ATTACTGTTC AAGTCAACAG CTCGCCTACT GGGGCCAAGG
                     TACCTCGAGT CGTCGGACTG GAGACTCCTG AGACGTCAGA TAATGACAAG TTCAGTTGTC GAGCGGATGA CCCCGGTTCC (SEQ ID NO: 9) +1    G  T  T  L  T  V  S  S
(SEQ ID NO: 57) 321  CACCACTCTC ACAGTCTCCT CA
                     GTGGTGAGAG TGTCAGAGGA GT

FIG. 17A

Anti-GP73 1B-4971 VL sequence

```
                      D   V   V   M   T   Q   T   P   L   T   L   S   V   T   I   L   G   Q   P   A   S   I   S   C   K   S   S   Q
(SEQ ID NO: 13) +1
(SEQ ID NO: 61) 1     GATGTTGTGA TGACCCAGAC TCCACTCACT TTGTCGGTTA CCATTGGACA ACCAGCCTCC ATCTCTTGCA AGTCAAGTCA
                      CTACAACACT ACTGGGTCTG AGGTGAGTGA AACAGCCAAT GGTAACCTGT TGGTCGGAGG TAGAGAACGT TCAGTTCAGT
                                                                         CDRL1
                      Q   S   L   L   Y   S   D   G   K   T   Y   L   I   W   L   L   Q   R   P   G   Q   S   P   K   R   L   I   Y
                                    CDRL1 (SEQ ID NO: 14)
(SEQ ID NO: 13) +1
(SEQ ID NO: 61) 81    GAGCCTCTTA TATAGTGATG GAAAGACATA TTTGATTTGG TTGTTACAGA GGCCAGGCCA GTCCCAAAG CGGCTAATCT
                      CTCGGAGAAT ATATCACTAC CTTTCTGTAT AAACTAAACC ACCAATGTCT CCGGTCCCGT CAGAGGTTTC GCCGATTAGA

Y   L   V   S   K   L   D   S   G   V   P   D   R   F   T   G   S   G   S   G   T   D   F   T   L   R   I
                                    CDRL2 (SEQ ID NO: 15)
(SEQ ID NO: 13) +1
(SEQ ID NO: 61) 161   ATCTGGTGTC TAAACTGGAC TCTGGAGTCC CTGACAGGTT CACTGGCAGT GGATCAGGGA CAGATTTCAC ACTGAGAATC
                      TAGACCACAG ATTTGACCTG AGACCTCAGG GACTGTCCAA GTGACCGTCA CCTAGTCCCT GTCTAAAGTG TGACTCTTAG

S   R   V   E   A   E   D   L   G   V   Y   Y   C   W   Q   G   T   H   F   P   Y   T   F   G   G   G   T
                                                                                                  CDRL3 (SEQ ID NO: 16)
(SEQ ID NO: 13) +1
(SEQ ID NO: 61) 241   AGCAGAGTGG AGGCTGAGGA CCTGGGAGTT TATTATTGTT GGCAAGGTAC ACATTTCCG TACCGTTCG GAGGGGGGAC
                      TCGTCTCACC TCCGACTCCT GGACCCTCAA AATAATAACAA CCGTTCCATG TGTAAAAGGC ATGTGCAAGC CTCCCCCTG

T   K   L   E   I   K   R
(SEQ ID NO: 13) +1
(SEQ ID NO: 61) 321   CAAGCTGGAA ATAAAACGG
                      GTTCGACCTT TATTTTGCC
```

FIG. 17B

ELKKNEFQGE LEKQREQLDK IQSSHNFQLE SVNKLYQDEK AVLVNNITTG
ERLIRVLQDQ LKTLQRNYGR LQQDVLQFQK NQTNLERKFS YDLSQCINQM
KEVKEQCEER IEEVTKKGNE AVASRDLSEN NDQRQQLQAL SEPQPRLQAA
GLPHTEVPQG KGNVLGNSKS QTPAPSSEVV LDSKRQVEKE ETNEIQVVNE
EPQRDRLPQE PGREQVVEDR PVGGRGFGGA GELGQTPQVQ AALSVSQENP
EMEGPERDQL VIPDGQEEEQ EAAGEGRNQQ KLRGEDDYNM DENEAESETD
KQAALAGNDR NIDVFNVEDQ KRDTINLLDQ REKRNHTLRS VECPPCPAPP
VAGPSVFLFP PKPKDTLMIS RTPEVTCVVV DVSHEDPEVQ FNWYVDGMEV
HNAKTKPREE QFASTFRVVS VLTVVHQDWL NGKEYKCKVS NKGLPAPIEK
TISKTKGQPR EPQVYTLPPS REEMTKNQVS LTCLVKGFYP SDIAVEWESN
GQPENNYKTT PPMLDSDGSF FLYSKLTVDK SRWQQGNVFS CSVMHEALHN
HYTQKSLSLS PGK (SEQ ID NO:99)

------- Indicates the peptide including epitope for GP73 and anti-GP73 MAb 1A-3187.
········· Indicates the peptide including epitope for GP73 and anti-GP73 MAb 1B-3246.
-·-·-·- Indicates the peptide including epitope for GP73 and anti-GP73 MAb 1B-4971.
– – – – Indicates the peptide including epitope for GP73 and anti-GP73 MAb 1B-3440.
Underlined letters indicate the huIgG.

FIG. 18

```
                        SEQUENCE LISTING

<160> NUMBER OF SEQ ID NOS: 113

<210> SEQ ID NO 1
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Thr Gly Gly Gly Leu Val Gln Pro Lys Gly
1               5                   10                  15

Ser Leu Lys Leu Ser Cys Ala Ala Ser Gly Phe Thr Phe Asn Thr Asn
            20                  25                  30

Ala Met Asn Trp Val Arg Gln Ala Pro Gly Lys Gly Leu Glu Trp Val
        35                  40                  45

Ala Arg Ile Arg Thr Lys Arg Tyr Asn Tyr Thr Thr Phe Tyr Ala Asp
    50                  55                  60

Ser Val Lys Asp Arg Phe Thr Ile Ser Arg Asp Asp Ser Gln Ser Met
65                  70                  75                  80

Leu Phe Leu Gln Met Asn Asn Leu Lys Thr Glu Asp Thr Ala Met Tyr
                85                  90                  95

Tyr Cys Val Thr Gly Gly Thr Gly Thr Phe Asp Tyr Trp Gly Gln Gly
            100                 105                 110

Thr Thr Leu Thr Val Ser Ser
        115
```

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Asn Ala Met Asn
1               5

<210> SEQ ID NO 3
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Arg Ile Arg Thr Lys Arg Tyr Asn Tyr Thr Thr Phe Tyr Ala Asp Ser
1               5                   10                  15

Val Lys Asp

<210> SEQ ID NO 4
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Gly Thr Gly Thr Phe Asp Tyr
1               5

<210> SEQ ID NO 5
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Ile Val Leu Thr Gln Ser Pro Thr Thr Met Pro Ala Ser Pro Gly
1               5                   10                  15

Glu Lys Val Thr Phe Thr Cys Ser Ala Ser Ser Gly Ile Ser Ser Asn
            20                  25                  30

Tyr Leu His Trp Tyr Gln Leu Lys Pro Gly Phe Ser Pro Lys Leu Leu
        35                  40                  45

Ile Tyr Arg Thr Ser Asn Leu Ala Ser Gly Val Pro Ala Arg Phe Ser
    50                  55                  60

Gly Gly Gly Ser Gly Thr Ser Tyr Ser Leu Thr Ile Gly Thr Met Glu
65                  70                  75                  80

Ala Glu Asp Val Ala Thr Tyr Tyr Cys Gln Gln Gly Phe Ser Ile Pro
                85                  90                  95

Leu Thr Phe Gly Ala Gly Thr Lys Leu Glu Leu Lys Arg
            100                 105

<210> SEQ ID NO 6

-continued

```
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ser Ala Ser Ser Gly Ile Ser Ser Asn Tyr Leu His
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Thr Ser Asn Leu Ala Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Gln Gly Phe Ser Ile Pro Leu Thr
1               5

<210> SEQ ID NO 9
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Gln Ser Gly Pro Ala Leu Val Lys Pro Gly Ala
1               5                   10                  15

Ser Val Lys Met Ser Cys Lys Ala Ser Gly Tyr Thr Phe Thr Asn Tyr
            20                  25                  30

Val Ile His Trp Val Lys Gln Lys Pro Gly Gln Gly Leu Glu Arg Ile
        35                  40                  45

Gly Tyr Ile Trp Pro Tyr Asn Asp Gly Thr Lys Phe Asn Glu Lys Phe
    50                  55                  60

Lys Gly Lys Ala Thr Leu Thr Ser Asp Lys Ser Ser Ser Thr Ala Tyr
65                  70                  75                  80

Met Glu Leu Ser Ser Leu Thr Ser Glu Asp Ser Ala Val Tyr Tyr Cys
                85                  90                  95

Ser Ser Gln Gln Leu Ala Tyr Trp Gly Gln Gly Thr Thr Leu Thr Val
            100                 105                 110

Ser Ser

<210> SEQ ID NO 10
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 10

Asn Tyr Val Ile His
1               5

<210> SEQ ID NO 11
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Tyr Ile Trp Pro Tyr Asn Asp Gly Thr Lys Phe Asn Glu Lys Phe Lys
1               5                   10                  15

Gly

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gln Gln Leu Ala Tyr
1               5

<210> SEQ ID NO 13
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Ile Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Arg Ile
65                  70                  75                  80

Ser Arg Val Glu Ala Glu Asp Leu Gly Val Tyr Tyr Cys Trp Gln Gly
                85                  90                  95

Thr His Phe Pro Tyr Thr Phe Gly Gly Gly Thr Lys Leu Glu Ile Lys
            100                 105                 110

Arg

<210> SEQ ID NO 14
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 14

Lys Ser Ser Gln Ser Leu Leu Tyr Ser Asp Gly Lys Thr Tyr Leu Ile
1               5                   10                  15

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Val Ser Lys Leu Asp Ser
1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Trp Gln Gly Thr His Phe Pro Tyr Thr
1               5

<210> SEQ ID NO 17
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Arg Gly Gly Thr Tyr Ile Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Ile Tyr Tyr Cys
                85                  90                  95

Thr Arg Glu Tyr Phe Ser Gly Asp Thr Tyr Asp Tyr Phe Asp Tyr Trp
            100                 105                 110

Gly Gln Gly Thr Thr Leu Thr Val Ser Ser
        115                 120

<210> SEQ ID NO 18
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 18

Ser Tyr Thr Met Ser
1               5

<210> SEQ ID NO 19
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Thr Ile Ser Arg Gly Gly Thr Tyr Ile Tyr Tyr Pro Asp Ser Val Lys
1               5                   10                  15

Gly

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Glu Tyr Phe Ser Gly Asp Thr Tyr Asp Tyr Phe Asp Tyr
1               5                   10

<210> SEQ ID NO 21
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Ile Val Met Thr Gln Ala Ala Phe Ala Asn Pro Val Thr Leu Gly
1               5                   10                  15

Thr Ser Val Ser Ile Ser Cys Arg Ser Ser Lys Ser Leu Leu His Ser
                20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Ile Tyr Tyr Cys Ala Gln Asn
                85                  90                  95

Leu Glu Leu Tyr Thr Phe Gly Gly Gly Thr Lys Leu Glu Ile Lys Arg
            100                 105                 110

<210> SEQ ID NO 22
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22
```

-continued

Arg Ser Ser Lys Ser Leu Leu His Ser Asn Gly Ile Thr Tyr Leu
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Gln Met Ser Asn Leu Ala Ser
1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Ala Gln Asn Leu Glu Leu Tyr Thr
1               5

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Thr Gly Gly Ser Thr Asn Tyr Asn Ser Ala Leu Met
    50                  55                  60

Ser Arg Leu Ser Ile Ser Lys Asp Asn Ser Glu Ser Gln Val Phe Leu
65                  70                  75                  80

Lys Val Asn Ser Leu Gln Thr Asp Asp Thr Gly Met Tyr Tyr Cys Ala
                85                  90                  95

Arg Asp Pro Gly Thr Asp Tyr Phe Asp Tyr Trp Gly Gln Gly Thr Thr
            100                 105                 110

Leu Thr Val Ser Ser
        115

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ser Tyr Gly Val His
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Ile Trp Thr Gly Gly Ser Thr Asn Tyr Asn Ser Ala Leu Met Ser
1               5                   10                  15

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Pro Gly Thr Asp Tyr Phe Asp Tyr
1               5

<210> SEQ ID NO 29
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Asp Ile Val Met Thr Gln Ser His Lys Phe Met Ser Thr Ser Ile Gly
1               5                   10                  15

Asp Arg Val Ser Ile Ser Cys Lys Ala Ser Gln Asp Val Ser Ile Asp
            20                  25                  30

Val Ser Trp Tyr Gln Gln Lys Pro Gly Gln Ser Pro Thr Leu Leu Ile
        35                  40                  45

Tyr Ser Ala Ser Tyr Arg Tyr Ile Gly Val Pro Asp Arg Phe Thr Gly
    50                  55                  60

Ser Gly Ser Gly Thr Ala Phe Thr Phe Thr Ile Ser Ser Val Gln Ala
65                  70                  75                  80

Glu Asp Leu Ala Ile Tyr Tyr Cys Gln Gln His Phe Thr Thr Pro Leu
                85                  90                  95

Thr Phe Gly Ala Gly Thr Lys Leu Glu Leu Lys Arg
            100                 105

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Lys Ala Ser Gln Asp Val Ser Ile Asp Val Ser
1               5                   10

<210> SEQ ID NO 31
<211> LENGTH: 6
<212> TYPE: PRT

```
<213> ORGANISM: Artificial Sequence
<220> FEATURE:
<223> OTHER INFORMATION: Description of Artificial Sequence: Synthetic
      peptide

<400> SEQUENCE: 31

Ser Ala Ser Tyr Arg Tyr
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Gln Gln His Phe Thr Thr Pro Leu Thr
1               5

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Gln Gly Gln Leu Gln Gln Ser Gly Ala Glu Leu Met Lys Pro Gly Ala
1               5                   10                  15

Ser Val Lys Ile Ser Cys Lys Ala Thr Gly Tyr Thr Ile Arg Ser Tyr
            20                  25                  30

Trp Ile Glu Trp Val Lys Gln Arg Pro Gly His Gly Leu Glu Trp Ile
        35                  40                  45

Gly Glu Ile Leu Pro Gly Ser Gly Asn Thr Asn Tyr Asn Glu Lys Phe
    50                  55                  60

Lys Gly Thr Ala Thr Phe Thr Ala Asp Thr Ser Ser Asn Thr Val Tyr
65                  70                  75                  80

Leu His Leu Ser Ser Leu Thr Ser Glu Asp Ser Ala Val Tyr Tyr Cys
                85                  90                  95

Ala Asn Gly Arg Gly Ser Tyr Tyr His Trp Phe Ala Tyr Trp Gly
            100                 105                 110

Gln Gly Thr Leu Val Thr Val Ser Pro
        115                 120

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Ser Tyr Trp Ile Glu
1               5

<210> SEQ ID NO 35
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 35

Glu Ile Leu Pro Gly Ser Gly Asn Thr Asn Tyr Asn Glu Lys Phe Lys
1               5                   10                  15

Gly

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Gly Ser Tyr Arg Tyr His Trp Phe Ala Tyr
1               5                   10

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Tyr Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Tyr Thr Phe Gly Gly Gly Thr Lys Leu Glu Met Lys Arg
            100                 105                 110

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Lys Ala Ser Gln Ser Val Asp Tyr Asp Gly Asp Ser Tyr Met Asn
1               5                   10                  15

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 39

Ala Ala Ser Asn Leu Glu Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Gln Ser Asn Glu Asp Pro Tyr Thr
1               5

<210> SEQ ID NO 41
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Leu Thr Pro Glu Lys Arg Leu Glu Trp Val
        35                  40                  45

Ala Thr Ile Ser Ser Gly Ser Ser Tyr Thr Tyr Tyr Pro Asp Ser Val
    50                  55                  60

Lys Gly Arg Phe Thr Ile Ser Arg Asp Asn Val Lys Ser Thr Leu Tyr
65                  70                  75                  80

Leu Gln Met Ser Ser Leu Arg Ser Glu Asp Thr Ala Met Tyr Tyr Cys
                85                  90                  95

Ala Arg Asn Trp Asp Gly Glu Leu His Tyr Tyr Ala Met Asp Tyr Trp
            100                 105                 110

Gly Gln Gly Thr Ser Val Thr Val Ser Ser
        115                 120

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Ser Tyr Ala Met Ser
1               5

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43
```

```
Thr Ile Ser Ser Gly Ser Ser Tyr Thr Tyr Tyr Pro Asp Ser Val Lys
1               5                   10                  15

Gly

<210> SEQ ID NO 44
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Asp Gly Glu Leu His Tyr Tyr Ala Met Asp Tyr
1               5                   10

<210> SEQ ID NO 45
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Ile Val Leu Thr Gln Ser Pro Ala Ile Met Ser Ala Ser Leu Gly
1               5                   10                  15

Glu Arg Val Thr Met Thr Cys Thr Ala Ser Ser Ser Val Ser Ser Ser
            20                  25                  30

Tyr Leu His Trp Tyr Gln Gln Lys Pro Gly Ser Ser Pro Lys Leu Trp
        35                  40                  45

Val Tyr Ser Thr Ser Ser Leu Ala Ser Gly Val Pro Ala Arg Phe Ser
    50                  55                  60

Gly Ser Gly Ser Gly Thr Ser Tyr Ser Leu Thr Ile Asn Asn Met Glu
65                  70                  75                  80

Ala Glu Asp Ala Ala Thr Tyr Phe Cys His Gln Tyr His Arg Ser Pro
                85                  90                  95

Tyr Thr Phe Gly Gly Gly Thr Lys Leu Glu Ile Lys Arg
            100                 105

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Thr Ala Ser Ser Ser Val Ser Ser Ser Tyr Leu His
1               5                   10

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Ser Thr Ser Ser Leu Ala Ser
1               5
```

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

His Gln Tyr His Arg Ser Pro Tyr Thr
1               5

<210> SEQ ID NO 49
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 49 gag gtg cag ctt gtt gag act ggt gga gga ttg gtg cag cct aaa ggg      48
Glu Val Gln Leu Val Glu Thr Gly Gly Gly Leu Val Gln Pro Lys Gly
1               5                   10                  15 tca ttg aaa ctc tca tgt gca gcc tct gga ttc acc ttc aat acc aat      96
Ser Leu Lys Leu Ser Cys Ala Ala Ser Gly Phe Thr Phe Asn Thr Asn
            20                  25                  30 gcc atg aac tgg gtc cgc cag gct cca gga aag ggt ttg gaa tgg gtt     144
Ala Met Asn Trp Val Arg Gln Ala Pro Gly Lys Gly Leu Glu Trp Val
        35                  40                  45 gct cgc ata agg act aaa cgt tat aat tat aca aca ttt tat gcc gat     192
Ala Arg Ile Arg Thr Lys Arg Tyr Asn Tyr Thr Thr Phe Tyr Ala Asp
    50                  55                  60 tca gtg aaa gac agg ttc acc atc tcc aga gat gat tct caa agc atg     240
Ser Val Lys Asp Arg Phe Thr Ile Ser Arg Asp Asp Ser Gln Ser Met
65                  70                  75                  80 ctc ttt ctg caa atg aac aac ttg aaa act gag gac aca gcc atg tat     288
Leu Phe Leu Gln Met Asn Asn Leu Lys Thr Glu Asp Thr Ala Met Tyr
                85                  90                  95 tac tgt gtg aca ggg ggg act ggg acg ttt gac tac tgg ggc caa ggc     336
Tyr Cys Val Thr Gly Gly Thr Gly Thr Phe Asp Tyr Trp Gly Gln Gly
            100                 105                 110 acc act ctc aca gtc tcc tca                                          357
Thr Thr Leu Thr Val Ser Ser
        115

<210> SEQ ID NO 50
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
accaatgcca tgaac                                                      15

<210> SEQ ID NO 51
<211> LENGTH: 57
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 51
cgcataagga ctaaacgtta taattataca acattttatg ccgattcagt gaaagac       57

<210> SEQ ID NO 52
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 gggggactg ggacgtttga ctac                                            24

<210> SEQ ID NO 53
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(327)

<400> SEQUENCE: 53 gaa att gta ctc acc cag tct cca acc acc atg cct gca tct ccc ggg     48
Glu Ile Val Leu Thr Gln Ser Pro Thr Thr Met Pro Ala Ser Pro Gly
1               5                   10                  15 gag aag gtc act ttc acc tgc agt gcc agc tca ggt ata agt tcc aat     96
Glu Lys Val Thr Phe Thr Cys Ser Ala Ser Ser Gly Ile Ser Ser Asn
            20                  25                  30 tac ttg cat tgg tat cag ctg aag cca gga ttc tcc cct aaa ctc ttg    144
Tyr Leu His Trp Tyr Gln Leu Lys Pro Gly Phe Ser Pro Lys Leu Leu
        35                  40                  45 att tat agg aca tcc aat ctg gct tct gga gtc cca gct cgc ttc agt    192
Ile Tyr Arg Thr Ser Asn Leu Ala Ser Gly Val Pro Ala Arg Phe Ser
    50                  55                  60 ggc ggt ggg tct ggg acc tct tac tct ctc aca att ggc acc atg gag    240
Gly Gly Gly Ser Gly Thr Ser Tyr Ser Leu Thr Ile Gly Thr Met Glu
65                  70                  75                  80 gct gaa gat gtt gcc act tac tat tgc cag cag ggt ttt agt ata ccg    288
Ala Glu Asp Val Ala Thr Tyr Tyr Cys Gln Gln Gly Phe Ser Ile Pro
                85                  90                  95 ctc acg ttc ggt gct ggg acc aag ctg gag ctg aaa cgg                327
Leu Thr Phe Gly Ala Gly Thr Lys Leu Glu Leu Lys Arg
            100                 105

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
agtgccagct caggtataag ttccaattac ttgcat                              36

<210> SEQ ID NO 55
<211> LENGTH: 21
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 55
aggacatcca atctggcttc t                                              21

<210> SEQ ID NO 56
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56
cagcagggtt ttagtatacc gctcacg                                        27

<210> SEQ ID NO 57
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 57 cag gtc cag ctg cag cag tct gga cct gcg ctg gta aag cct ggg gct      48
Gln Val Gln Leu Gln Gln Ser Gly Pro Ala Leu Val Lys Pro Gly Ala
1               5                   10                  15 tca gtg aag atg tcc tgc aag gct tct gga tac aca ttc act aac tat      96
Ser Val Lys Met Ser Cys Lys Ala Ser Gly Tyr Thr Phe Thr Asn Tyr
            20                  25                  30 gtt ata cac tgg gtg aaa cag aag cct ggg cag ggc ctt gag cgg att     144
Val Ile His Trp Val Lys Gln Lys Pro Gly Gln Gly Leu Glu Arg Ile
        35                  40                  45 gga tat att tgg cct tac aat gat ggt act aag ttc aat gag aaa ttc     192
Gly Tyr Ile Trp Pro Tyr Asn Asp Gly Thr Lys Phe Asn Glu Lys Phe
    50                  55                  60 aaa ggc aag gcc aca ctg act tca gac aaa tcc tcc agc aca gcc tac     240
Lys Gly Lys Ala Thr Leu Thr Ser Asp Lys Ser Ser Ser Thr Ala Tyr
65                  70                  75                  80 atg gag ctc agc agc ctg acc tct gag gac tct gca gtc tat tac tgt     288
Met Glu Leu Ser Ser Leu Thr Ser Glu Asp Ser Ala Val Tyr Tyr Cys
                85                  90                  95 tca agt caa cag ctc gcc tac tgg ggc caa ggc acc act ctc aca gtc     336
Ser Ser Gln Gln Leu Ala Tyr Trp Gly Gln Gly Thr Thr Leu Thr Val
            100                 105                 110 tcc tca                                                             342
Ser Ser

<210> SEQ ID NO 58
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 58
aactatgtta tacac                                                     15
```

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 59
tatatttggc cttacaatga tggtactaag ttcaatgaga aattcaaagg c        51

<210> SEQ ID NO 60
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 60
caacagctcg cctac        15

<210> SEQ ID NO 61
<211> LENGTH: 339
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(339)

<400> SEQUENCE: 61

```
gat gtt gtg atg acc cag act cca ctc act ttg tcg gtt acc att gga       48
Asp Val Val Met Thr Gln Thr Pro Leu Thr Leu Ser Val Thr Ile Gly
1               5                   10                  15 caa cca gcc tcc atc tct tgc aag tca agt cag agc ctc tta tat agt       96
Gln Pro Ala Ser Ile Ser Cys Lys Ser Ser Gln Ser Leu Leu Tyr Ser
            20                  25                  30 gat gga aag aca tat ttg att tgg ttg tta cag agg cca ggc cag tct      144
Asp Gly Lys Thr Tyr Leu Ile Trp Leu Leu Gln Arg Pro Gly Gln Ser
        35                  40                  45 cca aag cgc cta atc tat ctg gtg tct aaa ctg gac tct gga gtc cct      192
Pro Lys Arg Leu Ile Tyr Leu Val Ser Lys Leu Asp Ser Gly Val Pro
    50                  55                  60 gac agg ttc act ggc agt gga tca ggg aca gat ttc aca ctg aga atc      240
Asp Arg Phe Thr Gly Ser Gly Ser Gly Thr Asp Phe Thr Leu Arg Ile
65                  70                  75                  80 agc aga gtg gag gct gag gat ttg gga gtt tat tat tgt tgg caa ggt      288
Ser Arg Val Glu Ala Glu Asp Leu Gly Val Tyr Tyr Cys Trp Gln Gly
                85                  90                  95 aca cat ttt ccg tac acg ttc gga ggg ggg acc aag ctg gaa ata aaa      336
Thr His Phe Pro Tyr Thr Phe Gly Gly Gly Thr Lys Leu Glu Ile Lys
            100                 105                 110 cgg                                                                  339
Arg
```

<210> SEQ ID NO 62
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 62
aagtcaagtc agagcctctt atatagtgat ggaaagacat atttgatt                48

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63
ctggtgtcta aactggactc t                                             21

<210> SEQ ID NO 64
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64
tggcaaggta cacattttcc gtacacg                                       27

<210> SEQ ID NO 65
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(366)

<400> SEQUENCE: 65 gac gtg aag ctg gtg gag tct ggg gga ggc tta gtg aag cct gga ggg        48
Asp Val Lys Leu Val Glu Ser Gly Gly Gly Leu Val Lys Pro Gly Gly
1               5                   10                  15 tcc ctg aaa ctc tcc tgt gca gcc tct gga ttc act ttc agt agc tat        96
Ser Leu Lys Leu Ser Cys Ala Ala Ser Gly Phe Thr Phe Ser Ser Tyr
            20                  25                  30 acc atg tct tgg gtt cgc cag act ccg gag aag aga ctg gag tgg gtc       144
Thr Met Ser Trp Val Arg Gln Thr Pro Glu Lys Arg Leu Glu Trp Val
        35                  40                  45 gca acc att agt cgt ggt ggt act tac atc tac tat cca gac agt gtg       192
Ala Thr Ile Ser Arg Gly Gly Thr Tyr Ile Tyr Tyr Pro Asp Ser Val
    50                  55                  60 aag ggc cga ttc acc atc tcc aga gac aat gcc aag aac acc ctg tac       240
Lys Gly Arg Phe Thr Ile Ser Arg Asp Asn Ala Lys Asn Thr Leu Tyr
65                  70                  75                  80 ctg caa atg agc agt ctg aag tct gag gac aca gcc ata tat tac tgt       288
Leu Gln Met Ser Ser Leu Lys Ser Glu Asp Thr Ala Ile Tyr Tyr Cys
                85                  90                  95 aca aga gaa tat ttc tcc ggt gat acc tac gac tac ttt gac tat tgg       336
Thr Arg Glu Tyr Phe Ser Gly Asp Thr Tyr Asp Tyr Phe Asp Tyr Trp
            100                 105                 110 ggc caa ggc acc act ctc aca gtc tcc tca                              366
Gly Gln Gly Thr Thr Leu Thr Val Ser Ser
        115                 120

<210> SEQ ID NO 66
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 66
agctatacca tgtct        15

<210> SEQ ID NO 67
<211> LENGTH: 51
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 67
accattagtc gtggtggtac ttacatctac tatccagaca gtgtgaaggg c        51

<210> SEQ ID NO 68
<211> LENGTH: 39
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 68
gaatatttct ccggtgatac ctacgactac tttgactat        39

<210> SEQ ID NO 69
<211> LENGTH: 336
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (1)..(336)

<400> SEQUENCE: 69

```
gag att gtg atg acg cag gct gca ttc gcc aat cca gtc act ctt gga      48
Glu Ile Val Met Thr Gln Ala Ala Phe Ala Asn Pro Val Thr Leu Gly
1               5                   10                  15 aca tca gtt tcc atc tcc tgc agg tct agt aag agt ctc cta cat agt      96
Thr Ser Val Ser Ile Ser Cys Arg Ser Ser Lys Ser Leu Leu His Ser
            20                  25                  30 aat ggc atc act tat ttg tac tgg tat ctg cag aag cca ggc cag tct     144
Asn Gly Ile Thr Tyr Leu Tyr Trp Tyr Leu Gln Lys Pro Gly Gln Ser
        35                  40                  45 cct cag ctc ctg att tat cag atg tcc aac ctt gcc tca gga gtc cca     192
Pro Gln Leu Leu Ile Tyr Gln Met Ser Asn Leu Ala Ser Gly Val Pro
    50                  55                  60 gac agg ttc agt agc agt ggg tca gga act gat ttc aca ctg aga atc     240
Asp Arg Phe Ser Ser Ser Gly Ser Gly Thr Asp Phe Thr Leu Arg Ile
65                  70                  75                  80 agc aga gtg gag gct gag gat gtg ggt att tac tac tgt gct caa aat     288
Ser Arg Val Glu Ala Glu Asp Val Gly Ile Tyr Tyr Cys Ala Gln Asn
                85                  90                  95 cta gaa ctt tac acg ttc gga ggg ggg acc aag ctg gaa ata aaa cgg     336
Leu Glu Leu Tyr Thr Phe Gly Gly Gly Thr Lys Leu Glu Ile Lys Arg
            100                 105                 110
```

<210> SEQ ID NO 70
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
aggtctagta agagtctcct acatagtaat ggcatcactt atttgtac                48

<210> SEQ ID NO 71
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
cagatgtcca accttgcctc a                                             21

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
gctcaaaatc tagaacttta cacg                                          24

<210> SEQ ID NO 73
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(351)

<400> SEQUENCE: 73 cag gtg cag ctg aag gag tca gga cct ggc ctg gtg gcg ccc tca cag      48
Gln Val Gln Leu Lys Glu Ser Gly Pro Gly Leu Val Ala Pro Ser Gln
1               5                   10                  15 agc ctg tcc atc act tgc act gtc tct ggg ttt tca tta acc agc tat      96
Ser Leu Ser Ile Thr Cys Thr Val Ser Gly Phe Ser Leu Thr Ser Tyr
            20                  25                  30 ggt gta cac tgg gtt cgc cag tct cca gga aag ggt ctg gag tgg ctg     144
Gly Val His Trp Val Arg Gln Ser Pro Gly Lys Gly Leu Glu Trp Leu
        35                  40                  45 gga gta ata tgg act ggt gga agc aca aat tat aat tcg gct ctc atg     192
Gly Val Ile Trp Thr Gly Gly Ser Thr Asn Tyr Asn Ser Ala Leu Met
    50                  55                  60 tcc aga ctg agc att agt aaa gac aac tcc gag agc caa gtt ttc tta     240
Ser Arg Leu Ser Ile Ser Lys Asp Asn Ser Glu Ser Gln Val Phe Leu
65                  70                  75                  80 aaa gtg aat agt ctg caa act gat gac aca ggc atg tac tac tgt gcc     288
Lys Val Asn Ser Leu Gln Thr Asp Asp Thr Gly Met Tyr Tyr Cys Ala
                85                  90                  95 aga gat cct ggg acg gac tac ttt gac tac tgg ggc caa ggc acc act     336

```
                Arg Asp Pro Gly Thr Asp Tyr Phe Asp Tyr Trp Gly Gln Gly Thr Thr
                            100                 105                 110 ctc aca gtc tcc tca                                                          351
Leu Thr Val Ser Ser
        115

<210> SEQ ID NO 74
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
agctatggtg tacac                                                              15

<210> SEQ ID NO 75
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
gtaatatgga ctggtggaag cacaaattat aattcggctc tcatgtcc                          48

<210> SEQ ID NO 76
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gatcctggga cggactactt tgactac                                                 27

<210> SEQ ID NO 77
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(324)

<400> SEQUENCE: 77 gac att gtg atg acc cag tct cac aaa ttc atg tcc aca tca ata gga              48
Asp Ile Val Met Thr Gln Ser His Lys Phe Met Ser Thr Ser Ile Gly
1               5                   10                  15 gac agg gtc agc atc tcc tgc aag gcc agt cag gat gtg agt att gat              96
Asp Arg Val Ser Ile Ser Cys Lys Ala Ser Gln Asp Val Ser Ile Asp
            20                  25                  30 gtg tcc tgg tat caa cag aaa cca gga cag tct cct aca ctt ctg att             144
Val Ser Trp Tyr Gln Gln Lys Pro Gly Gln Ser Pro Thr Leu Leu Ile
        35                  40                  45 tac tcg gca tcc tac cgg tac att gga gtc cct gat cgc ttc act ggc             192
Tyr Ser Ala Ser Tyr Arg Tyr Ile Gly Val Pro Asp Arg Phe Thr Gly
    50                  55                  60 agt gga tct ggg acg gct ttc act ttc acc atc agc agt gtc cag gct             240
Ser Gly Ser Gly Thr Ala Phe Thr Phe Thr Ile Ser Ser Val Gln Ala
65                  70                  75                  80
```

```
gaa gac ctg gca att tat tac tgt cag caa cat ttt act act cct ctc      288
Glu Asp Leu Ala Ile Tyr Tyr Cys Gln Gln His Phe Thr Thr Pro Leu
                85                  90                  95 acg ttc ggt gct ggg acc aag ctg gag ctg aaa cgg                      324
Thr Phe Gly Ala Gly Thr Lys Leu Glu Leu Lys Arg
        100                 105

<210> SEQ ID NO 78
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaggccagtc aggatgtgag tattgatgtg tcc                                  33

<210> SEQ ID NO 79
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 79
tcggcatcct accggtacat t                                               21

<210> SEQ ID NO 80
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
cagcaacatt ttactactcc tctcacg                                         27

<210> SEQ ID NO 81
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(363)

<400> SEQUENCE: 81 cag ggt cag ctg cag cag tct gga gct gaa ctg atg aag cct ggg gcc      48
Gln Gly Gln Leu Gln Gln Ser Gly Ala Glu Leu Met Lys Pro Gly Ala
1               5                   10                  15 tca gtg aag ata tcc tgc aag gct act ggc tac aca atc agg agc tac      96
Ser Val Lys Ile Ser Cys Lys Ala Thr Gly Tyr Thr Ile Arg Ser Tyr
                20                  25                  30 tgg ata gag tgg gta aag cag agg cct gga cat ggc ctt gag tgg att      144
Trp Ile Glu Trp Val Lys Gln Arg Pro Gly His Gly Leu Glu Trp Ile
            35                  40                  45 gga gag att tta cct gga agt ggt aat act aat tat aat gag aag ttc      192
Gly Glu Ile Leu Pro Gly Ser Gly Asn Thr Asn Tyr Asn Glu Lys Phe
        50                  55                  60 aag ggg acg gcc aca ttc act gca gat aca tcc tcc aac aca gtc tat      240
```

```
               Lys Gly Thr Ala Thr Phe Thr Ala Asp Thr Ser Ser Asn Thr Val Tyr
                65                  70                  75                  80 ttg cac ctc agc agc ctg aca tct gag gac tct gcc gtc tat tac tgt              288
Leu His Leu Ser Ser Leu Thr Ser Glu Asp Ser Ala Val Tyr Tyr Cys
                        85                  90                  95 gca aac ggg agg ggc tcc tat agg tac cac tgg ttt gct tac tgg ggc              336
Ala Asn Gly Arg Gly Ser Tyr Arg Tyr His Trp Phe Ala Tyr Trp Gly
                100                 105                 110 caa ggg act ctg gtc act gtc tct cca                                          363
Gln Gly Thr Leu Val Thr Val Ser Pro
            115                 120

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
agctactgga tagag                                                              15

<210> SEQ ID NO 83
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 83
gagattttac ctggaagtgg taatactaat tataatgaga agttcaaggg g                      51

<210> SEQ ID NO 84
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 84
gggaggggct cctataggta ccactggttt gcttac                                       36

<210> SEQ ID NO 85
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 85 gac att gtg ctg acc caa tct cca gct tct ttg gct gtg tct cta ggg               48
Asp Ile Val Leu Thr Gln Ser Pro Ala Ser Leu Ala Val Ser Leu Gly
1               5                   10                  15 cag agg gcc acc atc tcc tgc aag gcc agc caa agt gtt gat tat gat               96
Gln Arg Ala Thr Ile Ser Cys Lys Ala Ser Gln Ser Val Asp Tyr Asp
                20                  25                  30 ggt gat agt tat atg aac tgg tac caa cag aaa cca gga cag cca ccc              144
Gly Asp Ser Tyr Met Asn Trp Tyr Gln Gln Lys Pro Gly Gln Pro Pro
            35                  40                  45
```

```
aaa gtc ctc atc tat gct gca tcc aat cta gaa tct ggg atc cca gcc        192
Lys Val Leu Ile Tyr Ala Ala Ser Asn Leu Glu Ser Gly Ile Pro Ala
    50                  55                  60 agg ttt agt ggc agt ggg tct ggg aca gac ttc acc ctc aac atc cat        240
Arg Phe Ser Gly Ser Gly Ser Gly Thr Asp Phe Thr Leu Asn Ile His
65                  70                  75                  80 cct gtg gag gag gag gat gct gca acc tat tac tgt cag caa agt aat        288
Pro Val Glu Glu Glu Asp Ala Ala Thr Tyr Tyr Cys Gln Gln Ser Asn
                85                  90                  95 gag gat ccg tac acg ttc gga ggg ggg acc aag ctg gaa atg aaa cgg        336
Glu Asp Pro Tyr Thr Phe Gly Gly Gly Thr Lys Leu Glu Met Lys Arg
                100                 105                 110
```

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
aaggccagcc aaagtgttga ttatgatggt gatagttata tgaac                      45

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
gctgcatcca atctagaatc t                                                21

<210> SEQ ID NO 88
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 88
cagcaaagta atgaggatcc gtacacg                                          27

<210> SEQ ID NO 89
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(366)

<400> SEQUENCE: 89

```
gaa gtg atg ctg gtg gag tct ggg gga ggc tta gtg aag cct gga ggg         48
Glu Val Met Leu Val Glu Ser Gly Gly Gly Leu Val Lys Pro Gly Gly
1               5                   10                  15 tcc ctg aaa ctc tcc tgt gca gcc tct gga ttc act ttc agt agc tat         96
Ser Leu Lys Leu Ser Cys Ala Ala Ser Gly Phe Thr Phe Ser Ser Tyr
                20                  25                  30 gcc atg tct tgg gtt cgc ctg act ccg gag aag agg ctg gag tgg gtc        144
```

```
                Ala Met Ser Trp Val Arg Leu Thr Pro Glu Lys Arg Leu Glu Trp Val
                             35                  40                  45 gca acc att agt agt ggt agc agt tac acc tac tat cca gac agt gtg         192
Ala Thr Ile Ser Ser Gly Ser Ser Tyr Thr Tyr Tyr Pro Asp Ser Val
 50                  55                  60 aag ggg cga ttc acc atc tcc aga gac aat gtc aag agc acc ctg tac         240
Lys Gly Arg Phe Thr Ile Ser Arg Asp Asn Val Lys Ser Thr Leu Tyr
 65                  70                  75                  80 ctg caa atg agc agt ctg agg tct gag gac acg gcc atg tat tac tgt         288
Leu Gln Met Ser Ser Leu Arg Ser Glu Asp Thr Ala Met Tyr Tyr Cys
                 85                  90                  95 gca agg aac tgg gac ggg gaa ctc cat tac tat gct atg gac tac tgg         336
Ala Arg Asn Trp Asp Gly Glu Leu His Tyr Tyr Ala Met Asp Tyr Trp
            100                 105                 110 ggt caa gga acc tca gtc acc gtc tcc tca                                 366
Gly Gln Gly Thr Ser Val Thr Val Ser Ser
            115                 120

<210> SEQ ID NO 90
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 90
agctatgcca tgtct                                                         15

<210> SEQ ID NO 91
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
accattagta gtggtagcag ttacacctac tatccagaca gtgtgaaggg g                 51

<210> SEQ ID NO 92
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
aactgggacg gggaactcca ttactatgct atggactac                               39

<210> SEQ ID NO 93
<211> LENGTH: 327
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(327)

<400> SEQUENCE: 93 caa att gtt ctc acc cag tct cca gca atc atg tct gca tct cta ggg          48
Gln Ile Val Leu Thr Gln Ser Pro Ala Ile Met Ser Ala Ser Leu Gly
  1               5                  10                  15
```

-continued

```
gaa cgg gtc acc atg acc tgc act gcc agc tca agt gta agt tcc agt         96
Glu Arg Val Thr Met Thr Cys Thr Ala Ser Ser Ser Val Ser Ser Ser
         20                  25                  30 tac ttg cac tgg tac cag cag aag cca gga tcc tcc ccc aaa ctc tgg        144
Tyr Leu His Trp Tyr Gln Gln Lys Pro Gly Ser Ser Pro Lys Leu Trp
     35                  40                  45 gtt tat agc aca tcc agc ctg gct tct gga gtc cca gct cgc ttc agt        192
Val Tyr Ser Thr Ser Ser Leu Ala Ser Gly Val Pro Ala Arg Phe Ser
 50                  55                  60 ggc agt ggg tct ggg acc tct tac tct ctc aca atc aac aac atg gag        240
Gly Ser Gly Ser Gly Thr Ser Tyr Ser Leu Thr Ile Asn Asn Met Glu
65                  70                  75                  80 gct gaa gat gct gcc act tat ttc tgc cac cag tat cat cgt tcc ccg        288
Ala Glu Asp Ala Ala Thr Tyr Phe Cys His Gln Tyr His Arg Ser Pro
                 85                  90                  95 tac acg ttc gga ggg ggg acc aag ctg gaa ata aaa cgg                    327
Tyr Thr Phe Gly Gly Gly Thr Lys Leu Glu Ile Lys Arg
            100                 105
```

<210> SEQ ID NO 94
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 94
actgccagct caagtgtaag ttccagttac ttgcac                                 36

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 95
agcacatcca gcctggcttc t                                                 21

<210> SEQ ID NO 96
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 96
caccagtatc atcgttcccc gtacacg                                           27

<210> SEQ ID NO 97
<211> LENGTH: 400
<212> TYPE: PRT
<213> ORGANISM: Homo sapiens

<400> SEQUENCE: 97

Met Gly Leu Gly Asn Gly Arg Arg Ser Met Lys Ser Pro Pro Leu Val
1               5                   10                  15

Leu Ala Ala Leu Val Ala Cys Ile Ile Val Leu Gly Phe Asn Tyr Trp
            20                  25                  30

Ile Ala Ser Ser Arg Ser Val Asp Leu Gln Thr Arg Ile Met Glu Leu

```
            35                  40                  45
Glu Gly Arg Val Arg Ala Ala Glu Arg Gly Ala Val Glu Leu
 50                  55                  60

Lys Lys Asn Glu Phe Gln Gly Glu Leu Glu Lys Gln Arg Glu Gln Leu
 65                  70                  75                  80

Asp Lys Ile Gln Ser Ser His Asn Phe Gln Leu Glu Ser Val Asn Lys
                 85                  90                  95

Leu Tyr Gln Asp Glu Lys Ala Val Leu Val Asn Asn Ile Thr Thr Gly
                100                 105                 110

Glu Arg Leu Ile Arg Val Leu Gln Asp Gln Leu Lys Thr Leu Gln Arg
                115                 120                 125

Asn Tyr Gly Arg Leu Gln Gln Asp Val Leu Gln Phe Gln Lys Asn Gln
            130                 135                 140

Thr Asn Leu Glu Arg Lys Phe Ser Tyr Asp Leu Ser Gln Cys Ile Asn
145                 150                 155                 160

Gln Met Lys Glu Val Lys Glu Gln Cys Glu Glu Arg Ile Glu Glu Val
                165                 170                 175

Thr Lys Lys Gly Asn Glu Ala Val Ala Ser Arg Asp Leu Ser Glu Asn
            180                 185                 190

Asn Asp Gln Arg Gln Leu Gln Ala Leu Ser Glu Pro Gln Pro Arg
            195                 200                 205

Leu Gln Ala Ala Gly Leu Pro His Thr Glu Val Pro Gln Gly Lys Gly
            210                 215                 220

Asn Val Leu Gly Asn Ser Lys Ser Gln Thr Pro Ala Pro Ser Ser Glu
225                 230                 235                 240

Val Val Leu Asp Ser Lys Arg Gln Val Glu Lys Glu Thr Asn Glu
                245                 250                 255

Ile Gln Val Val Asn Glu Glu Pro Gln Arg Asp Arg Leu Pro Gln Glu
            260                 265                 270

Pro Gly Arg Glu Gln Val Val Glu Asp Arg Pro Val Gly Gly Arg Gly
            275                 280                 285

Phe Gly Gly Ala Gly Glu Leu Gly Gln Thr Pro Gln Val Gln Ala Ala
            290                 295                 300

Leu Ser Val Ser Gln Glu Asn Pro Glu Met Glu Gly Pro Glu Arg Asp
305                 310                 315                 320

Gln Leu Val Ile Pro Asp Gly Gln Glu Glu Gln Glu Ala Ala Gly
                325                 330                 335

Glu Gly Arg Asn Gln Gln Lys Leu Arg Gly Glu Asp Asp Tyr Asn Met
            340                 345                 350

Asp Glu Asn Glu Ala Glu Ser Glu Thr Asp Lys Gln Ala Ala Leu Ala
            355                 360                 365

Gly Asn Asp Arg Asn Ile Asp Val Phe Asn Val Glu Asp Gln Lys Arg
            370                 375                 380

Asp Thr Ile Asn Leu Leu Asp Gln Arg Glu Lys Arg Asn His Thr Leu
385                 390                 395                 400

<210> SEQ ID NO 98
<211> LENGTH: 353
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98
```

Met Glu Leu Lys Lys Asn Glu Glu Leu Lys Lys Asn Glu Phe Gln Gly
1               5                   10                  15

Glu Leu Glu Lys Gln Arg Glu Gln Leu Asp Lys Ile Gln Ser Ser His
            20                  25                  30

Asn Phe Gln Leu Glu Ser Val Asn Lys Leu Tyr Gln Asp Glu Lys Ala
        35                  40                  45

Val Leu Val Asn Asn Ile Thr Thr Gly Glu Arg Leu Ile Arg Val Leu
    50                  55                  60

Gln Asp Gln Leu Lys Thr Leu Gln Arg Asn Tyr Gly Arg Leu Gln Gln
65                  70                  75                  80

Asp Val Leu Gln Phe Gln Lys Asn Gln Thr Asn Leu Glu Arg Lys Phe
                85                  90                  95

Ser Tyr Asp Leu Ser Gln Cys Ile Asn Gln Met Lys Glu Val Lys Glu
            100                 105                 110

Gln Cys Glu Glu Arg Ile Glu Glu Val Thr Lys Lys Gly Asn Glu Ala
        115                 120                 125

Val Ala Ser Arg Asp Leu Ser Glu Asn Asn Asp Gln Arg Gln Gln Leu
    130                 135                 140

Gln Ala Leu Ser Glu Pro Gln Pro Arg Leu Gln Ala Ala Gly Leu Pro
145                 150                 155                 160

His Thr Glu Val Pro Gln Gly Lys Gly Asn Val Leu Gly Asn Ser Lys
                165                 170                 175

Ser Gln Thr Pro Ala Pro Ser Ser Glu Val Val Leu Asp Ser Lys Arg
            180                 185                 190

Gln Val Glu Lys Glu Glu Thr Asn Glu Ile Gln Val Val Asn Glu Glu
        195                 200                 205

Pro Gln Arg Asp Arg Leu Pro Gln Glu Pro Gly Arg Glu Gln Val Val
    210                 215                 220

Glu Asp Arg Pro Val Gly Gly Arg Gly Phe Gly Gly Ala Gly Glu Leu
225                 230                 235                 240

Gly Gln Thr Pro Gln Val Gln Ala Ala Leu Ser Val Ser Gln Glu Asn
                245                 250                 255

Pro Glu Met Glu Gly Pro Glu Arg Asp Gln Leu Val Ile Pro Asp Gly
            260                 265                 270

Gln Glu Glu Glu Gln Glu Ala Ala Gly Glu Gly Arg Asn Gln Gln Lys
        275                 280                 285

Leu Arg Gly Glu Asp Asp Tyr Asn Met Asp Glu Asn Glu Ala Glu Ser
    290                 295                 300

Glu Thr Asp Lys Gln Ala Ala Leu Ala Gly Asn Asp Arg Asn Ile Asp
305                 310                 315                 320

Val Phe Asn Val Glu Asp Gln Lys Arg Asp Thr Ile Asn Leu Leu Asp
                325                 330                 335

Gln Arg Glu Lys Arg Asn His Thr Leu Ser Gly His His His His His
            340                 345                 350

His

<210> SEQ ID NO 99
<211> LENGTH: 563
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

-continued

```
Glu Leu Lys Lys Asn Glu Phe Gln Gly Glu Leu Lys Gln Arg Glu
 1               5                  10                  15

Gln Leu Asp Lys Ile Gln Ser Ser His Asn Phe Gln Leu Glu Ser Val
             20                  25                  30

Asn Lys Leu Tyr Gln Asp Glu Lys Ala Val Leu Val Asn Asn Ile Thr
             35                  40                  45

Thr Gly Glu Arg Leu Ile Arg Val Leu Gln Asp Gln Leu Lys Thr Leu
 50                  55                  60

Gln Arg Asn Tyr Gly Arg Leu Gln Gln Asp Val Leu Gln Phe Gln Lys
 65                  70                  75                  80

Asn Gln Thr Asn Leu Glu Arg Lys Phe Ser Tyr Asp Leu Ser Gln Cys
             85                  90                  95

Ile Asn Gln Met Lys Glu Val Lys Glu Gln Cys Glu Glu Arg Ile Glu
             100                 105                 110

Glu Val Thr Lys Lys Gly Asn Glu Ala Val Ala Ser Arg Asp Leu Ser
             115                 120                 125

Glu Asn Asn Asp Gln Arg Gln Leu Gln Ala Leu Ser Glu Pro Gln
             130                 135                 140

Pro Arg Leu Gln Ala Ala Gly Leu Pro His Thr Glu Val Pro Gln Gly
 145                 150                 155                 160

Lys Gly Asn Val Leu Gly Asn Ser Lys Ser Gln Thr Pro Ala Pro Ser
             165                 170                 175

Ser Glu Val Val Leu Asp Ser Lys Arg Gln Val Glu Lys Glu Thr
             180                 185                 190

Asn Glu Ile Gln Val Val Asn Glu Glu Pro Gln Arg Asp Arg Leu Pro
             195                 200                 205

Gln Glu Pro Gly Arg Glu Gln Val Val Glu Asp Arg Pro Val Gly Gly
 210                 215                 220

Arg Gly Phe Gly Gly Ala Gly Glu Leu Gly Gln Thr Pro Gln Val Gln
 225                 230                 235                 240

Ala Ala Leu Ser Val Ser Gln Glu Asn Pro Glu Met Glu Gly Pro Glu
             245                 250                 255

Arg Asp Gln Leu Val Ile Pro Asp Gly Gln Glu Glu Glu Gln Glu Ala
             260                 265                 270

Ala Gly Glu Gly Arg Asn Gln Gln Lys Leu Arg Gly Glu Asp Asp Tyr
             275                 280                 285

Asn Met Asp Glu Asn Glu Ala Glu Ser Glu Thr Asp Lys Gln Ala Ala
             290                 295                 300

Leu Ala Gly Asn Asp Arg Asn Ile Asp Val Phe Asn Val Glu Asp Gln
 305                 310                 315                 320

Lys Arg Asp Thr Ile Asn Leu Leu Asp Gln Arg Glu Lys Arg Asn His
             325                 330                 335

Thr Leu Arg Ser Val Glu Cys Pro Pro Cys Pro Ala Pro Val Ala
             340                 345                 350

Gly Pro Ser Val Phe Leu Phe Pro Pro Lys Pro Lys Asp Thr Leu Met
             355                 360                 365

Ile Ser Arg Thr Pro Glu Val Thr Cys Val Val Val Asp Val Ser His
             370                 375                 380

Glu Asp Pro Glu Val Gln Phe Asn Trp Tyr Val Asp Gly Met Glu Val
 385                 390                 395                 400

His Asn Ala Lys Thr Lys Pro Arg Glu Glu Gln Phe Ala Ser Thr Phe
             405                 410                 415

Arg Val Val Ser Val Leu Thr Val Val His Gln Asp Trp Leu Asn Gly
```

```
                420             425             430
Lys Glu Tyr Lys Cys Lys Val Ser Asn Lys Gly Leu Pro Ala Pro Ile
            435             440             445

Glu Lys Thr Ile Ser Lys Thr Lys Gly Gln Pro Arg Glu Pro Gln Val
        450             455             460

Tyr Thr Leu Pro Pro Ser Arg Glu Glu Met Thr Lys Asn Gln Val Ser
465             470             475             480

Leu Thr Cys Leu Val Lys Gly Phe Tyr Pro Ser Asp Ile Ala Val Glu
            485             490             495

Trp Glu Ser Asn Gly Gln Pro Glu Asn Asn Tyr Lys Thr Thr Pro Pro
            500             505             510

Met Leu Asp Ser Asp Gly Ser Phe Phe Leu Tyr Ser Lys Leu Thr Val
            515             520             525

Asp Lys Ser Arg Trp Gln Gln Gly Asn Val Phe Ser Cys Ser Val Met
            530             535             540

His Glu Ala Leu His Asn His Tyr Thr Gln Lys Ser Leu Ser Leu Ser
545             550             555             560

Pro Gly Lys

<210> SEQ ID NO 100
<211> LENGTH: 344
<212> TYPE: PRT
<213> ORGANISM: Homo sapiens

<400> SEQUENCE: 100

Glu Leu Lys Lys Asn Glu Glu Leu Lys Lys Asn Glu Phe Gln Gly Glu
1               5                   10                  15

Leu Glu Lys Gln Arg Glu Gln Leu Asp Lys Ile Gln Ser Ser His Asn
            20                  25                  30

Phe Gln Leu Glu Ser Val Asn Lys Leu Tyr Gln Asp Glu Lys Ala Val
        35                  40                  45

Leu Val Asn Asn Ile Thr Thr Gly Glu Arg Leu Ile Arg Val Leu Gln
    50                  55                  60

Asp Gln Leu Lys Thr Leu Gln Arg Asn Tyr Gly Arg Leu Gln Gln Asp
65                  70                  75                  80

Val Leu Gln Phe Gln Lys Asn Gln Thr Asn Leu Glu Arg Lys Phe Ser
            85                  90                  95

Tyr Asp Leu Ser Gln Cys Ile Asn Gln Met Lys Glu Val Lys Glu Gln
            100                 105                 110

Cys Glu Glu Arg Ile Glu Glu Val Thr Lys Lys Gly Asn Glu Ala Val
        115                 120                 125

Ala Ser Arg Asp Leu Ser Glu Asn Asn Asp Gln Arg Gln Gln Leu Gln
    130                 135                 140

Ala Leu Ser Glu Pro Gln Pro Arg Leu Gln Ala Ala Gly Leu Pro His
145                 150                 155                 160

Thr Glu Val Pro Gln Gly Lys Gly Asn Val Leu Gly Asn Ser Lys Ser
            165                 170                 175

Gln Thr Pro Ala Pro Ser Ser Glu Val Val Leu Asp Ser Lys Arg Gln
        180                 185                 190

Val Glu Lys Glu Glu Thr Asn Glu Ile Gln Val Val Asn Glu Glu Pro
    195                 200                 205

Gln Arg Asp Arg Leu Pro Gln Glu Pro Gly Arg Glu Gln Val Val Glu
    210                 215                 220

Asp Arg Pro Val Gly Gly Arg Gly Phe Gly Gly Ala Gly Glu Leu Gly
```

```
                225                 230                 235                 240
Gln Thr Pro Gln Val Gln Ala Ala Leu Ser Val Ser Gln Glu Asn Pro
                245                 250                 255
Glu Met Glu Gly Pro Glu Arg Asp Gln Leu Val Ile Pro Asp Gly Gln
            260                 265                 270
Glu Glu Glu Gln Glu Ala Ala Gly Gly Arg Asn Gln Gln Lys Leu
        275                 280                 285
Arg Gly Glu Asp Asp Tyr Asn Met Asp Glu Asn Glu Ala Glu Ser Glu
    290                 295                 300
Thr Asp Lys Gln Ala Ala Leu Ala Gly Asn Asp Arg Asn Ile Asp Val
305                 310                 315                 320
Phe Asn Val Glu Asp Gln Lys Arg Asp Thr Ile Asn Leu Leu Asp Gln
                325                 330                 335
Arg Glu Lys Arg Asn His Thr Leu
            340

<210> SEQ ID NO 101
<211> LENGTH: 33
<212> TYPE: PRT
<213> ORGANISM: Homo sapiens

<400> SEQUENCE: 101

Val Ser Gln Glu Asn Pro Glu Met Glu Gly Pro Glu Arg Asp Gln Leu
1               5                   10                  15
Val Ile Pro Asp Gly Gln Glu Glu Gln Glu Ala Ala Gly Glu Gly
            20                  25                  30
Arg

<210> SEQ ID NO 102
<211> LENGTH: 12
<212> TYPE: PRT
<213> ORGANISM: Homo sapiens

<400> SEQUENCE: 102

Glu Gln Val Val Glu Asp Arg Pro Val Gly Gly Arg
1               5                   10

<210> SEQ ID NO 103
<211> LENGTH: 20
<212> TYPE: PRT
<213> ORGANISM: Homo sapiens

<400> SEQUENCE: 103

Leu Arg Gly Glu Asp Asp Tyr Asn Met Asp Glu Asn Glu Ala Glu Ser
1               5                   10                  15
Glu Thr Asp Lys
            20

<210> SEQ ID NO 104
<211> LENGTH: 34
<212> TYPE: PRT
<213> ORGANISM: Homo sapiens

<400> SEQUENCE: 104

Glu Leu Lys Lys Asn Glu Phe Gln Gly Glu Leu Glu Lys Gln Arg Glu
1               5                   10                  15
Gln Leu Asp Lys Ile Gln Ser Ser His Asn Phe Gln Leu Glu Ser Val
            20                  25                  30
Asn Lys
```

```
<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Asp Asp Asp Lys
1               5

<210> SEQ ID NO 107
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Ala Asp Asp Asp Asp Lys
1               5

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ser, Asn or Thr
<220> FEATURE:
<221> NAME/KEY: MOD_RES
<222> LOCATION: (2)..(2)
<223> OTHER INFORMATION: Tyr or Asn
<220> FEATURE:
<221> NAME/KEY: MOD_RES
<222> LOCATION: (3)..(3)
<223> OTHER INFORMATION: Trp, Val, Gly, Ala or Thr
<220> FEATURE:
<221> NAME/KEY: MOD_RES
<222> LOCATION: (4)..(4)
<223> OTHER INFORMATION: Ile, Val or Met
<220> FEATURE:
<221> NAME/KEY: MOD_RES
<222> LOCATION: (5)..(5)
<223> OTHER INFORMATION: Glu, His, Ser or Asn

<400> SEQUENCE: 108

Xaa Xaa Xaa Xaa Xaa
1               5

<210> SEQ ID NO 109
```

```
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Glu, Tyr, Val, Thr or Arg
<220> FEATURE:
<221> NAME/KEY: MOD_RES
<222> LOCATION: (3)..(3)
<223> OTHER INFORMATION: Leu, Trp, Ser or Arg
<220> FEATURE:
<221> NAME/KEY: MOD_RES
<222> LOCATION: (4)..(4)
<223> OTHER INFORMATION: Pro, Ser, Arg or Thr
<220> FEATURE:
<221> NAME/KEY: MOD_RES
<222> LOCATION: (5)..(6)
<223> OTHER INFORMATION: May or may not be present
<220> FEATURE:
<221> NAME/KEY: MOD_RES
<222> LOCATION: (7)..(7)
<223> OTHER INFORMATION: Gly, Thr or Tyr
<220> FEATURE:
<221> NAME/KEY: MOD_RES
<222> LOCATION: (8)..(8)
<223> OTHER INFORMATION: Ser, Gly or Asn
<220> FEATURE:
<221> NAME/KEY: MOD_RES
<222> LOCATION: (9)..(9)
<223> OTHER INFORMATION: Gly, Asp, Ser, Thr or Tyr
<220> FEATURE:
<221> NAME/KEY: MOD_RES
<222> LOCATION: (10)..(10)
<223> OTHER INFORMATION: Asn, Ser, Tyr, Gly or Thr
<220> FEATURE:
<221> NAME/KEY: MOD_RES
<222> LOCATION: (11)..(11)
<223> OTHER INFORMATION: Thr or Ile
<220> FEATURE:
<221> NAME/KEY: MOD_RES
<222> LOCATION: (12)..(12)
<223> OTHER INFORMATION: Asn, Lys, Tyr or Phe
<220> FEATURE:
<221> NAME/KEY: MOD_RES
<222> LOCATION: (13)..(13)
<223> OTHER INFORMATION: Tyr or Phe
<220> FEATURE:
<221> NAME/KEY: MOD_RES
<222> LOCATION: (14)..(14)
<223> OTHER INFORMATION: Asn, Pro or Ala
<220> FEATURE:
<221> NAME/KEY: MOD_RES
<222> LOCATION: (15)..(15)
<223> OTHER INFORMATION: Glu, Ser or Asp
<220> FEATURE:
<221> NAME/KEY: MOD_RES
<222> LOCATION: (16)..(16)
<223> OTHER INFORMATION: Lys, Ala or Ser
<220> FEATURE:
<221> NAME/KEY: MOD_RES
<222> LOCATION: (17)..(17)
<223> OTHER INFORMATION: Phe, Leu or Val
<220> FEATURE:
<221> NAME/KEY: MOD_RES
<222> LOCATION: (18)..(18)
<223> OTHER INFORMATION: Lys or Met
<220> FEATURE:
<221> NAME/KEY: MOD_RES
<222> LOCATION: (19)..(19)
<223> OTHER INFORMATION: Gly, Ser or Asp

<400> SEQUENCE: 109

Xaa Ile Xaa Xaa Lys Arg Xaa Xaa Xaa Xaa Xaa Xaa Xaa Xaa Xaa
1               5                   10                  15
```

Xaa Xaa Xaa

```
<210> SEQ ID NO 110
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gly, Gln, Asp, Glu or Asn
<220> FEATURE:
<221> NAME/KEY: MOD_RES
<222> LOCATION: (2)..(2)
<223> OTHER INFORMATION: Arg, Gln, Pro, Tyr, Trp or Gly
<220> FEATURE:
<221> NAME/KEY: MOD_RES
<222> LOCATION: (3)..(3)
<223> OTHER INFORMATION: Gly, Leu, Phe, Asp or Thr
<220> FEATURE:
<221> NAME/KEY: MOD_RES
<222> LOCATION: (4)..(4)
<223> OTHER INFORMATION: Ser, Thr or Gly
<220> FEATURE:
<221> NAME/KEY: MOD_RES
<222> LOCATION: (5)..(5)
<223> OTHER INFORMATION: Tyr, Asp, Gly, Glu or Thr
<220> FEATURE:
<221> NAME/KEY: MOD_RES
<222> LOCATION: (6)..(6)
<223> OTHER INFORMATION: Arg, Tyr, Asp, Leu or Phe
<220> FEATURE:
<221> NAME/KEY: MOD_RES
<222> LOCATION: (7)..(7)
<223> OTHER INFORMATION: Tyr, Phe, Thr or His
<220> FEATURE:
<221> NAME/KEY: MOD_RES
<222> LOCATION: (8)..(8)
<223> OTHER INFORMATION: His or Tyr
<220> FEATURE:
<221> NAME/KEY: MOD_RES
<222> LOCATION: (9)..(9)
<223> OTHER INFORMATION: Trp, Asp or Tyr
<220> FEATURE:
<221> NAME/KEY: MOD_RES
<222> LOCATION: (10)..(10)
<223> OTHER INFORMATION: Phe, Tyr or Ala
<220> FEATURE:
<221> NAME/KEY: MOD_RES
<222> LOCATION: (11)..(11)
<223> OTHER INFORMATION: Phe, Met or absent
<220> FEATURE:
<221> NAME/KEY: MOD_RES
<222> LOCATION: (12)..(12)
<223> OTHER INFORMATION: Ala or Asp

<400> SEQUENCE: 110

Xaa Xaa Xaa Xaa Xaa Xaa Xaa Xaa Xaa Xaa Xaa Xaa Tyr
1               5                   10

<210> SEQ ID NO 111
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Lys, Thr, Arg or Ser
<220> FEATURE:
<221> NAME/KEY: MOD_RES
```

```
<222> LOCATION: (2)..(2)
<223> OTHER INFORMATION: Ala or Ser
<220> FEATURE:
<221> NAME/KEY: MOD_RES
<222> LOCATION: (4)..(4)
<223> OTHER INFORMATION: Gln, Ser or Lys
<220> FEATURE:
<221> NAME/KEY: MOD_RES
<222> LOCATION: (5)..(5)
<223> OTHER INFORMATION: Ser or Gly
<220> FEATURE:
<221> NAME/KEY: MOD_RES
<222> LOCATION: (6)..(6)
<223> OTHER INFORMATION: Val or Leu
<220> FEATURE:
<221> NAME/KEY: MOD_RES
<222> LOCATION: (7)..(7)
<223> OTHER INFORMATION: Asp or Leu
<220> FEATURE:
<221> NAME/KEY: MOD_RES
<222> LOCATION: (8)..(8)
<223> OTHER INFORMATION: Tyr, Asp or His
<220> FEATURE:
<221> NAME/KEY: MOD_RES
<222> LOCATION: (9)..(9)
<223> OTHER INFORMATION: May or may not be present
<220> FEATURE:
<221> NAME/KEY: MOD_RES
<222> LOCATION: (10)..(10)
<223> OTHER INFORMATION: Asp, Val, Asn or Ile
<220> FEATURE:
<221> NAME/KEY: MOD_RES
<222> LOCATION: (11)..(11)
<223> OTHER INFORMATION: Gly, Val or Ser
<220> FEATURE:
<221> NAME/KEY: MOD_RES
<222> LOCATION: (12)..(12)
<223> OTHER INFORMATION: Asp, Lys, Ser or Ile
<220> FEATURE:
<221> NAME/KEY: MOD_RES
<222> LOCATION: (13)..(13)
<223> OTHER INFORMATION: Ser, Thr, Ile or Asn
<220> FEATURE:
<221> NAME/KEY: MOD_RES
<222> LOCATION: (14)..(14)
<223> OTHER INFORMATION: Tyr or Asp
<220> FEATURE:
<221> NAME/KEY: MOD_RES
<222> LOCATION: (15)..(15)
<223> OTHER INFORMATION: Met, Leu or Val
<220> FEATURE:
<221> NAME/KEY: MOD_RES
<222> LOCATION: (16)..(16)
<223> OTHER INFORMATION: Asn, Ile, Ser, His or Tyr

<400> SEQUENCE: 111

Xaa Xaa Ser Xaa Xaa Xaa Xaa Xaa Ser Xaa Xaa Xaa Xaa Xaa Xaa Xaa
1               5                   10                  15

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ala, Leu, Ser, Gln or Arg
<220> FEATURE:
<221> NAME/KEY: MOD_RES
<222> LOCATION: (2)..(2)
<223> OTHER INFORMATION: Ala, Val, Thr or Met
<220> FEATURE:
<221> NAME/KEY: MOD_RES
<222> LOCATION: (4)..(4)
```

```
<223> OTHER INFORMATION: Asn, Lys, Tyr or Ser
<220> FEATURE:
<221> NAME/KEY: MOD_RES
<222> LOCATION: (5)..(5)
<223> OTHER INFORMATION: Leu or Arg
<220> FEATURE:
<221> NAME/KEY: MOD_RES
<222> LOCATION: (6)..(6)
<223> OTHER INFORMATION: Glu, Asp, Tyr or Ala
<220> FEATURE:
<221> NAME/KEY: MOD_RES
<222> LOCATION: (7)..(7)
<223> OTHER INFORMATION: Ser or Ile

<400> SEQUENCE: 112

Xaa Xaa Ser Xaa Xaa Xaa Xaa
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Trp, His or Ala
<220> FEATURE:
<221> NAME/KEY: MOD_RES
<222> LOCATION: (3)..(3)
<223> OTHER INFORMATION: Ser, Gly, His, Tyr or Asn
<220> FEATURE:
<221> NAME/KEY: MOD_RES
<222> LOCATION: (4)..(4)
<223> OTHER INFORMATION: Asn, Thr, Phe, His or Leu
<220> FEATURE:
<221> NAME/KEY: MOD_RES
<222> LOCATION: (5)..(5)
<223> OTHER INFORMATION: Glu, His, Thr, Arg or Ser
<220> FEATURE:
<221> NAME/KEY: MOD_RES
<222> LOCATION: (6)..(6)
<223> OTHER INFORMATION: Asp, Phe, Thr, Ser, Leu or Ile
<220> FEATURE:
<221> NAME/KEY: MOD_RES
<222> LOCATION: (8)..(8)
<223> OTHER INFORMATION: Tyr or Leu

<400> SEQUENCE: 113

Xaa Gln Xaa Xaa Xaa Xaa Pro Xaa Thr
1               5
```

US 11,421,023 B2

ANTI-GP73 MONOCLONAL ANTIBODIES AND METHODS OF OBTAINING THE SAME

CROSS-REFERENCE TO RELATED APPLICATION(S)

This application is a divisional of copending U.S. application Ser. No. 15/290,762, filed on Oct. 11, 2016, which is a continuation of U.S. application Ser. No. 13/836,229, filed on Mar. 15, 2013, now U.S. Pat. No. 9,469,686, the entire contents of which are fully incorporated herein by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 76,114 Byte ASCII (Text) file named "35942-403-SQL.TXT," created on Dec. 30, 2021.

TECHNICAL FIELD

The present invention relates to GP73, in particular anti-GP73 monoclonal antibodies, an assay involving the use of at least one antibody (e.g., monoclonal antibody), such as an immunoassay, and related amino acid and nucleic acid sequences and vectors and host cells comprising same.

BACKGROUND

Golgi protein 73 ("GP73") is a 73-kd resident Golgi membrane protein. GP73 is a type II transmembrane protein with a single N-terminal transmembrane domain and an extensive C-terminal coiled coil domain located on the lumenal surface of the Golgi apparatus. GP73 has been shown to be up-regulated in hepatocytes in viral and non-viral chronic liver disease, which suggests that the protein may be involved in the cellular disease response of hepatocytes. In addition, GP73 levels are higher in patients with liver cancer than in healthy individuals. Fucosylated glycosylation has been found in three quarters of secreted GP73 from hepatocellular carcinoma (HCC) patients. Early studies suggest that GP73 and fucosylated GP73 may be more reliable biomarkers for the early diagnosis of liver disease than current markers such as alpha-fetoprotein (AFP), which has the disadvantage of producing false positive results since AFP is produced under many circumstances, including other liver diseases. In addition, AFP is not present in all patients with HCC. Furthermore, a previously known anti-GP73 antibody, the 14H4-23 monoclonal antibody (provided by Dr. Anand Mehta, Drexel University School of Medicine), is insensitive to the presence or absence of a fucose sugar moiety on the GP73 molecule.

In view of the foregoing, it is an object of the present disclosure to provide anti-GP73 monoclonal antibodies that may be sensitive to the presence or absence of a fucose sugar moiety on the GP73 molecule and bind to the fucosylated form of GP73, or alternatively, are insensitive to the presence or absence of a fucose sugar moiety on the GP73 molecule but have binding affinities sufficient to be used in immunoassays for detecting GP73 and/or fucosylated GP73. This and other objects and advantages, as well as inventive features, will become apparent from the detailed description provided herein.

SUMMARY

The present invention is directed to an isolated antibody or antibody fragment thereof capable of binding an epitope within the amino acid sequence of VSQENPEMEGPERDQLVIPDGQEEEQEAAGEGR (hGP73 307-339) (SEQ ID NO:101). The isolated antibody or antibody fragment is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The isolated antibody or antibody fragment is human. The isolated antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human IgG3 constant domain, and a human IgA constant domain.

The present invention is directed to an isolated antibody or antibody fragment thereof capable of binding an epitope within the amino acid sequence of: EQVVEDRPVGGR (hGP73 276-287) (SEQ ID NO:102). The isolated antibody or antibody fragment is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The isolated antibody or antibody is human. The isolated antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain.

The present invention is directed to an isolated antibody or antibody fragment thereof capable of binding an epitope within the amino acid sequence of: LRGEDDYNMDENEAESETDK (hGP73 344-363) (SEQ ID NO:103). The antibody is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The antibody or antibody fragment is human. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain.

The present invention is directed to an isolated antibody or antibody fragment thereof capable of binding an epitope within the amino acid sequence of: ELKKNEFQGELEKQREQLDKIQSSHNFQLESVNK (hGP73 63-96) (SEQ ID NO:104). The antibody is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The antibody or antibody fragment is human. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain.

The present invention is directed to an isolated antibody or antibody fragment thereof which immunospecifically binds to Golgi Protein 73 ("GP73"), wherein the binding of the antibody or antibody fragment to GP73 is sensitive to fucosylation of GP73. The antibody is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The antibody or antibody fragment is human. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain.

The present invention is directed to an isolated antibody or antibody fragment thereof which immunospecifically binds to Golgi Protein 73 ("GP73"), wherein the binding of the antibody or antibody fragment to GP73 is insensitive to fucosylation of GP73. The antibody is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The antibody or antibody fragment is human. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain.

The present invention is directed to an isolated antibody or antibody fragment thereof which binds to Golgi Protein 73 ("GP73"), wherein the antibody comprises a domain or region selected from the group consisting of: (a) a variable heavy domain region comprising the amino acid sequence of SEQ ID NO:1, (b) a variable light domain region comprising the amino acid sequence of SEQ ID NO:5, (c) a variable heavy domain region comprising the amino acid sequence of SEQ ID NO:9, (d) a variable light domain region comprising the amino acid sequence of SEQ ID NO:13, (e) a variable heavy domain region comprising the amino acid sequence of SEQ ID NO:17, (f) a variable light domain region comprising the amino acid sequence of SEQ ID NO:21, (g) a variable heavy domain region comprising the amino acid sequence of SEQ ID NO:25, (h) a variable light domain region comprising the amino acid sequence of SEQ ID NO:29, (i) a variable heavy domain region comprising the amino acid sequence of SEQ ID NO:33, (j) a variable light domain region comprising the amino acid sequence of SEQ ID NO:37; (k) a variable heavy domain region comprising the amino acid sequence of SEQ ID NO:41; (l) a variable light domain region comprising the amino acid sequence of SEQ ID NO:45; (m) variable heavy domain comprising the amino acid sequence of SEQ ID NO:1 and a variable light domain region comprising the amino acid sequence of SEQ ID NO:5, (n) a variable heavy domain comprising the amino acid sequence of SEQ ID NO:9 and a variable light domain region comprising the amino acid sequence of SEQ ID NO:13, (o) a variable heavy domain comprising the amino acid sequence of SEQ ID NO:17 and a variable light domain region comprising the amino acid sequence of SEQ ID NO:21, (p) a variable heavy domain comprising the amino acid sequence of SEQ ID NO:25 and a variable light domain region comprising the amino acid sequence of SEQ ID NO:29, (q) a variable heavy domain comprising the amino acid sequence of SEQ ID NO:33 and a variable light domain region comprising the amino acid sequence of SEQ ID NO:37, (r) a variably heavy domain comprising the amino acid sequence of SEQ ID NO:41 and a variable light domain region comprising the amino acid sequence of SEQ ID NO:45, (s) a variable heavy chain comprising a complementarity determining region (CDR)1 comprising the amino acid sequence of SEQ ID NO:2, a CDR2 comprising the amino acid sequence of SEQ ID NO:3, and a CDR3 comprising the amino acid sequence of SEQ ID NO:4, (t) a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8, (u) a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12, (v) a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16, (w) a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20, (x) a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24, (y) a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, (z) a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32, (aa) a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36, (bb) a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40, (cc) a variable heavy chain comprising a CDR1 comprising the amino acid sequence of SEQ ID NO:42, a CDR2 comprising the amino acid sequence of SEQ ID NO:43, and CDR3 comprising the amino acid sequence of SEQ ID NO:44; (dd) a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; (ee) a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8, (ff) a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16, (gg) a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24, (hh) a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32, (ii) a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40, and (jj) a variable heavy domain chain comprising a CDR1 comprising the amino acid sequence of SEQ ID NO:42, a CDR2 comprising the amino acid sequence of SEQ ID NO:43, and a CDR comprising the amino acid sequence of SEQ ID NO:44, and a variable light domain chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48. The antibody is selected from the group consisting of a human antibody, an immunoglobulin molecule, a disulfide linked Fv, a monoclonal antibody, an affinity matured, a scFv, a chimeric antibody, a single domain antibody, a CDR-grafted antibody, a diabody, a humanized antibody, a multispecific antibody, a Fab, a dual specific antibody, a DVD, a TVD, a Fab', a bispecific antibody, a F(ab')2, and a Fv. The antibody or antibody fragment is human. The antibody or antibody fragment comprises a heavy chain immunoglobulin constant domain selected from the group consisting of a human IgM constant domain, a human IgG4 constant domain, a human IgG1 constant domain, a human IgE constant domain, a human IgG2 constant domain, a human igG3 constant domain, and a human IgA constant domain. The antibody or antibody fragment comprises a variable heavy region comprising a sequence selected from the group consisting of SEQ ID NO:1, SEQ ID NO:9, SEQ ID NO:17, SEQ ID NO:25, SEQ ID NO:33, and SEQ ID NO:41. The antibody or antibody fragment comprises a variable light region comprising a sequence selected from the group consisting of SEQ ID NO:5, SEQ ID NO:13, SEQ ID NO:21, SEQ ID NO:29, SEQ ID NO:37, and SEQ ID NO:45. The antibody or antibody fragment comprises variable heavy domain comprising the amino acid sequence of SEQ ID NO:1 and a variable light domain region comprising the amino acid sequence of SEQ ID NO:5. The antibody or antibody fragment comprises a variable heavy domain comprising the amino acid sequence of SEQ ID NO:9 and a variable light domain region comprising the amino acid sequence of SEQ ID NO:13. The antibody or antibody fragment comprises a variable heavy domain comprising the amino acid sequence of SEQ ID NO:17 and a variable light domain region comprising the amino acid sequence of SEQ ID NO:21. The antibody or antibody fragment comprises a variable heavy domain comprising the amino acid sequence of SEQ ID NO:25 and a variable light domain region comprising the amino acid sequence of SEQ ID NO:29. The antibody or antibody fragment comprises a variable heavy domain comprising the amino acid sequence of SEQ ID NO:33 and a variable light domain region comprising the amino acid sequence of SEQ ID NO:37. The antibody or antibody fragment comprises a variably heavy domain comprising the amino acid sequence of SEQ ID NO:41 and a variable light domain region comprising the amino acid sequence of SEQ ID NO:45. The antibody or antibody fragment comprises a variable heavy domain that comprises complementarity-determining region (CDR) residues: SEQ ID NO:2, SEQ ID NO:3, and SEQ ID NO:4; SEQ ID NO:10, SEQ ID NO:11, and SEQ ID NO:12; SEQ ID NO:18, SEQ ID NO:19, and SEQ ID NO:20; SEQ ID NO:26, SEQ ID NO:27, and SEQ ID NO:28; SEQ ID NO:34, SEQ ID NO:35, and SEQ ID NO:36; or SEQ ID NO:42, SEQ ID NO:43, and SEQ ID NO:44. The antibody or antibody fragment comprises a variable light domain that comprises complementarity-determining region (CDR) residues: SEQ ID NO:6, SEQ ID NO:7, and SEQ ID NO:8; SEQ ID NO:14, SEQ ID NO:15, and SEQ ID NO:16; SEQ ID NO:22, SEQ ID NO:23, and SEQ ID NO:24; SEQ ID NO:30, SEQ ID NO:31, and SEQ ID NO:32; SEQ ID NO:38, SEQ ID NO:39, and SEQ ID NO:40; or SEQ ID NO:46, SEQ ID NO:47, and SEQ ID NO:48. The antibody or antibody fragment comprises a variable heavy domain that comprises complementarity-determining region (CDR) residues SEQ ID NO:2, SEQ ID NO:3, and SEQ ID NO:4, and a variable light domain that comprises complementarity-determining region (CDR) residues SEQ ID NO:6, SEQ ID NO:7, and SEQ ID NO:8. The antibody or antibody fragment comprises a variable heavy domain that comprises complementarity-determining region (CDR) residues SEQ ID NO:10, SEQ ID NO:11, and SEQ ID NO:12, and a variable light domain that comprises complementarity-determining region (CDR) residues SEQ ID NO:14, SEQ ID NO:15, and SEQ ID NO:16. The antibody or antibody fragment comprises a variable heavy domain that comprises complementarity-determining region (CDR) residues SEQ ID NO:18, SEQ ID NO:19, and SEQ ID NO:20, and a variable light domain that comprises complementarity-determining region (CDR) residues SEQ ID NO:22, SEQ ID NO:23, and SEQ ID NO:24. The antibody or antibody fragment comprises a variable heavy domain that comprises complementarity-determining region (CDR) residues SEQ ID NO:26, SEQ ID NO:27, and SEQ ID NO:28, and a variable light domain that comprises complementarity-determining region (CDR) residues SEQ ID NO:30, SEQ ID NO:31, and SEQ ID NO:32. The antibody or antibody fragment comprises a variable heavy domain that comprises complementarity-determining region (CDR) residues SEQ ID NO:34, SEQ ID NO:35, and SEQ ID NO:36, and a variable light domain that comprises complementarity-determining region (CDR) residues SEQ ID NO:38, SEQ ID NO:39, and SEQ ID NO:40. The antibody or antibody fragment comprises a variable heavy domain that comprises complementarity-determining region (CDR) residues SEQ ID NO:42, SEQ ID NO:43, and SEQ ID NO:44, and a variable light domain that comprises complementarity-determining region (CDR) residues SEQ ID NO:46, SEQ ID NO:47, and SEQ ID NO:48. The antibody or antibody fragment further comprises an agent selected from the group consisting of: an immunoadhesion molecule, an imaging agent, and a therapeutic agent. The imaging agent is selected from the group consisting of a radiolabel, an enzyme, a fluorescent label, a luminescent label, a bioluminescent label, a magnetic label, and biotin. The radiolabel is selected from the group consisting of 3H, 14C, 35S, 90Y, 99Tc, 111In, 125I, 131I, 177Lu, 166Ho, and 153Sm. The antibody or antibody fragment binds to the GP73 epitope within the amino acid sequence of: VSQEN-PEMEGPERDQLVIPDGQEEEQEAAGEGR (hGP73 307-339) (SEQ ID NO:101). The antibody or antibody fragment comprises: a variable heavy domain region comprising the amino acid sequence of SEQ ID NO:9; a variable light domain region comprising the amino acid sequence of SEQ ID NO:13; a variable heavy domain comprising the amino acid sequence of SEQ ID NO:9 and a variable light domain region comprising the amino acid sequence of SEQ ID NO:13; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; or a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16. The antibody or antibody fragment binds to the GP73 epitope within the amino acid sequence of: EQVVEDRPVGGR (hGP73 276-287) (SEQ ID NO:102). The antibody or antibody fragment comprises: a variable heavy domain region comprising the amino acid sequence of SEQ ID NO:17; a variable light domain region comprising the amino acid sequence of SEQ ID NO:21; a variable heavy domain comprising the amino acid sequence of SEQ ID NO:17 and a variable light domain region comprising the amino acid sequence of SEQ ID NO:21; a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20; a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; or a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24. The antibody or antibody fragment binds to the GP73 epitope within the amino acid sequence of: LRGEDDYNMDENE-AESETDK (hGP73 344-363) (SEQ ID NO:103). The antibody or antibody fragment comprises: a variable heavy domain region comprising the amino acid sequence of SEQ ID NO:1; a variable light domain region comprising the amino acid sequence of SEQ ID NO:5; a variable heavy domain comprising the amino acid sequence of SEQ ID NO:1 and a variable light domain region comprising the amino acid sequence of SEQ ID NO:5; a variable heavy chain comprising a complementarity determining region (CDR)1 comprising the amino acid sequence of SEQ ID NO:2, a CDR2 comprising the amino acid sequence of SEQ ID NO:3, and a CDR3 comprising the amino acid sequence of SEQ ID NO:4; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; or a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8. The antibody or antibody fragment binds to the GP73 epitope within the amino acid sequence of: ELK-KNEFQGELEKQREQLDKIQSSHNFQLESVNK (hGP73 63-96) (SEQ ID NO:104). The antibody or antibody fragment comprises: a variable heavy domain region comprising the amino acid sequence of SEQ ID NO:33; a variable light domain region comprising the amino acid sequence of SEQ ID NO:37; a variable heavy domain comprising the amino acid sequence of SEQ ID NO:33 and a variable light domain region comprising the amino acid sequence of SEQ ID NO:37; a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36; a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40; or a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40. The binding of the antibody or antibody fragment to GP73 is sensitive to the presence or absence of a fucose sugar moiety on GP73. The antibody or antibody fragment comprises: a variable heavy domain region comprising the amino acid sequence of SEQ ID NO:25 or SEQ ID NO:33; a variable light domain region comprising the amino acid sequence of SEQ ID NO:29 or SEQ ID NO:37; a variable heavy domain comprising the amino acid sequence of SEQ ID NO:25 and a variable light domain region comprising the amino acid sequence of SEQ ID NO:29; a variable heavy domain comprising the amino acid sequence of SEQ ID NO:33 and a variable light domain region comprising the amino acid sequence of SEQ ID NO:37; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40; a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40. The binding of the antibody or antibody fragment to GP73 is insensitive to the presence or absence of a fucose sugar moiety on GP73. The antibody or antibody fragment comprises: a variable heavy domain region comprising the amino acid sequence of SEQ ID NO:1, SEQ ID NO:9, SEQ ID NO:17, or SEQ ID NO:41; a variable light domain region comprising the amino acid sequence of SEQ ID NO:5, SEQ ID NO:13, SEQ ID NO:21, or SEQ ID NO:45; a variable heavy domain comprising the amino acid sequence of SEQ ID NO:1 and a variable light domain region comprising the amino acid sequence of SEQ ID NO:5; a variable heavy domain comprising the amino acid sequence of SEQ ID NO:9 and a variable light domain region comprising the amino acid sequence of SEQ ID NO:13; a variable heavy domain comprising the amino acid sequence of SEQ ID NO:17 and a variable light domain region comprising the amino acid sequence of SEQ ID NO:21; a variable heavy domain comprising the amino acid sequence of SEQ ID NO:41 and a variable light domain region comprising the amino acid sequence of SEQ ID NO:45; a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20; a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; or a variable heavy chain comprising a CDR 1 comprising the amino acid sequence of SEQ ID NO:42, a CDR2 comprising the amino acid sequence of SEQ ID NO:43, and a CDR3 comprising the amino acid sequence of SEQ ID NO:44, and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48.

The present invention is directed to an isolated antibody that specifically binds GP-73 and has a CDR-H1 having the formula: $X_5$-$X_6$-$X_7$-$X_8$-$X_9$ (SEQ ID NO:108) a CDR-H2 having the formula: $X_{10}$-I-$X_{11}$-$X_{12}$-$X_{13}$-$X_{14}$-$X_{15}$-$X_{16}$$X_{17}$-$X_{18}$-$X_{19}$-$X_{20}$-$X_{21}$-$X_{22}$-$X_{23}$-$X_{24}$-$X_{25}$-$X_{26}$-$X_{27}$ (SEQ ID NO:109), a CDR-H3 having the formula: $X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-Y (SEQ ID NO:110), a CDR-L1 having the formula: $X_{40}$-$X_{41}$-S-$X_{42}$-$X_{43}$-$X_{44}$-$X_{45}$-$X_{46}$-$X_{47}$-$X_{48}$-$X_{49}$-$X_{50}$-$X_{51}$-$X_{52}$-$X_{53}$-$X_{54}$ (SEQ ID NO:111), a CDR-L2 having the formula: $X_{55}$-$X_{56}$-S-$X_{57}$-$X_{58}$-$X_{59}$-$X_{60}$ (SEQ ID NO:112) and a CDR-L3 having the formula: $X_{61}$-Q-$X_{62}$-$X_{63}$-$X_{64}$-$X_{65}$-P-$X_{66}$-T (SEQ ID NO:113), wherein: $X_5$ is S, N or T; $X_6$ is Y or N; $X_7$ is W, V, G, A or T; $X_8$ is I, V or M; $X_9$ is E, H, S or N; $X_{10}$ is E, Y, V, T or R; $X_{11}$ is L, W, S or R; $X_{12}$ is P, S, R or T; $X_{13}$ is absent or is K; $X_{14}$ is absent or is R; $X_{15}$ is G, T or Y; $X_{16}$ is S, G or N; $X_{17}$ is G, D, S, T or Y; $X_{18}$ is N, S, Y, G or T; $X_{19}$ is T or I; $X_{20}$ is N, K, Y or F; $X_{21}$ is Y or F; $X_{22}$ is N, P or A; $X_{23}$ is E, S or D; $X_{24}$ is K, A or S; $X_{25}$ is F, L or V; $X_{26}$ is K or M; $X_{27}$ is G, S or D; $X_{28}$ is G, Q, D, E or N; $X_{29}$ is R, Q, P, Y, W or G; $X_{30}$ is G, L, F, D or T; $X_{31}$ is S, T, S or G; $X_{32}$ is Y, D, G, E or T; $X_{33}$ is R, Y, D, L or F; $X_{34}$ is Y, F, T or H; $X_{35}$ is H or Y; $X_{36}$ is W, D or Y; $X_{37}$ is F, Y or A; $X_{38}$ is absent or is F or M; $X_{39}$ is A or D; $X_{40}$ is K, T, R or S; $X_{41}$ is A or S; $X_{42}$ is Q, S or K; $X_{43}$ is S or G; $X_{44}$ is V or L; $X_{45}$ is D or L; $X_{46}$ is Y, D or H; $X_{47}$ is absent or S; $X_{48}$ is D, V, N or I; $X_{49}$ is G, V or S; $X_{50}$ is D, K, S or I; $X_{51}$ is S, T, I or N; $X_{52}$ is Y or D; $X_{53}$ is M, L or V; $X_{54}$ is N, I, S, H or Y; $X_{55}$ is A, L, S, Q or R; $X_{56}$ is A, V, T or M; $X_{57}$ is N, K, Y or S; $X_{58}$ is L or R; $X_{59}$ is E, D, Y or A; $X_{60}$ is S or I; $X_{61}$ is Q, W, H or A; $X_{62}$ is S, G, H, Y or N; $X_{63}$ is N, T, F, H or L; $X_{64}$ is E, H, T, R or S; $X_{65}$ is D, F, T, S, L or I; and $X_{66}$ is Y or L.

The present invention is directed to an isolated antibody or antibody fragment thereof which immunospecifically binds to Golgi Protein 73 ("GP73"), wherein said antibody has an equilibrium dissociation constant (KD) of between about $4.0 \times 10^{-9}$ to about $1.8 \times 10^{-12}$.

The present invention is directed to an isolated antibody or antibody fragment thereof which immunospecifically binds to Golgi Protein 73 ("GP73"), wherein said antibody has a dissociation rate (koff) of between about $1.5 \times 10^{-3}$ to about $8.0 \times 10^{-6}$.

The present invention is directed to an isolated antibody or antibody fragment thereof which immunospecifically binds to Golgi Protein 73 ("GP73"), wherein said antibody has an association rate (kon) of between about $1.0 \times 10^{5}$ to about $4.1 \times 10^{6}$.

The present invention is directed to an isolated nucleic acid encoding any one of SEQ ID NO:1-48.

The present invention is directed to an isolated nucleic acid encoding the antibody or antibody fragment of claims 1, 5, 9, 13, 17, 21, 25, 60, 61, 62, or 63.

The present invention is directed to an isolated nucleic acid comprising at least one nucleic acid sequence of SEQ ID NO:49-96.

The present invention is directed to an isolated nucleic acid comprising a nucleotide sequence encoding: the amino acid sequence of (i) SEQ ID NO:1, (ii) SEQ ID NO:5, or (iii) SEQ ID NO:1 and SEQ ID NO:5, optionally as part of a vector; the amino acid sequence of (i) SEQ ID NO:9, (ii) SEQ ID NO:13, or (iii) SEQ ID NO:9 and SEQ ID NO:13, optionally as part of a vector; the amino acid sequence of (i) SEQ ID NO:17, (ii) SEQ ID NO:21, or (iii) SEQ ID NO:17 and SEQ ID NO:21, optionally as part of a vector; the amino acid sequence of (i) SEQ ID NO:25, (ii) SEQ ID NO:29, or (iii) SEQ ID NO:25 and SEQ ID NO:29, optionally as part of a vector; the amino acid sequence of (i) SEQ ID NO:33, (ii) SEQ ID NO:37, or (iii) SEQ ID NO:33 and SEQ ID NO:37, optionally as part of a vector; or the amino acid sequence of (i) SEQ ID NO:41, (ii) SEQ ID NO:45, or (iii) SEQ ID NO:41 and SEQ ID NO:45, optionally as part of a vector. The isolated nucleic acid of claim 67, wherein the nucleic acid comprises: the nucleotide sequence of (i) SEQ ID NO:49, (ii) SEQ ID NO:53, or (iii) SEQ ID NO:49 and SEQ ID NO:53, optionally as part of a vector; the nucleotide sequence of (i) SEQ ID NO:57, (ii) SEQ ID NO:61, or (iii) SEQ ID NO:57 and SEQ ID NO:61, optionally as part of a vector; the nucleotide sequence of (i) SEQ ID NO:65, (ii) SEQ ID NO:69, or (iii) SEQ ID NO:65 and SEQ ID NO:69, optionally as part of a vector; the nucleotide sequence of (i) SEQ ID NO:73, (ii) SEQ ID NO:77, or (iii) SEQ ID NO:73 and SEQ ID NO:77, optionally as part of a vector; the nucleotide sequence of (i) SEQ ID NO:81, (ii) SEQ ID NO:85, or (iii) SEQ ID NO:81 and SEQ ID NO:85, optionally as part of a vector; or the nucleotide sequence of (i) SEQ ID NO:89, (ii) SEQ ID NO:93, or (iii) SEQ ID NO:89 and SEQ ID NO:93, optionally as part of a vector.

The present invention is directed to a host cell comprising and expressing an isolated nucleic acid comprising a nucleotide sequence encoding: the amino acid sequence of (i) SEQ ID NO:1, (ii) SEQ ID NO:5, or (iii) SEQ ID NO:1 and SEQ ID NO:5, optionally as part of a vector; the amino acid sequence of (i) SEQ ID NO:9, (ii) SEQ ID NO:13, or (iii) SEQ ID NO:9 and SEQ ID NO:13, optionally as part of a vector; the amino acid sequence of (i) SEQ ID NO:17, (ii) SEQ ID NO:21, or (iii) SEQ ID NO:17 and SEQ ID NO:21, optionally as part of a vector; the amino acid sequence of (i) SEQ ID NO:25, (ii) SEQ ID NO:29, or (iii) SEQ ID NO:25 and SEQ ID NO:29, optionally as part of a vector; the amino acid sequence of (i) SEQ ID NO:33, (ii) SEQ ID NO:37, or (iii) SEQ ID NO:33 and SEQ ID NO:37, optionally as part of a vector; or the amino acid sequence of (i) SEQ ID NO:41, (ii) SEQ ID NO:45, or (iii) SEQ ID NO:41 and SEQ ID NO:45, optionally as part of a vector.

The present invention is directed to a pharmaceutical composition comprising the antibody, antibody fragment, mixture or derivative thereof of claims 1, 5, 9, 13, 17, 21, 25, 60, 61, 62, or 63. The present invention is directed to a method for determining GP73 concentration in a test sample, the method comprising: contacting the test sample with at least one capture antibody, wherein the capture antibody binds to an epitope on GP73 or a fragment of GP73 to form a capture antibody-GP73 antigen complex; contacting the capture antibody-GP73 antigen complex with at least one detection antibody comprising a detectable label, wherein the detection antibody binds to an epitope on GP73 that is not bound by the capture antibody and forms a capture antibody-GP73 antigen-detection antibody complex; and determining the GP73 concentration in the test sample based on the signal generated by the detectable label in the capture antibody-GP73 antigen-detection antibody complex formed in the previous step; wherein the at least one capture antibody comprises the isolated antibody or antibody fragment of claims 1, 5, 9, 13, 17, 21, 25, 60, 61, 62, or 63 and the at least one detection antibody comprises the isolated antibody or fragment antibody of claims 1, 5, 9, 13, 17, 21, 25, 60, 61, 62, or 63, and wherein the least one capture antibody is different from the at least one detection antibody. The method further comprises comparing the signal generated by the detectable label as a direct or indirect indication of the GP73 concentration in the test sample to a signal generated as a direct or indirect indication of the GP73 concentration in a control or calibrator. The GP73 concentration in the test sample is used to determine or assess whether a subject has or is at risk of developing liver disease. An increased GP73 concentration as compared to the GP73 concentration in a control or calibrator indicates that the subject has liver disease. The liver disease is liver cirrhosis or liver cancer.

The present invention is directed to a method for determining GP73 concentration in a test sample, the method comprising: contacting the test sample with at least one capture antibody, wherein the capture antibody binds to an epitope on GP73 or a fragment of GP73 to form a capture antibody-GP73 antigen complex; contacting the capture antibody-GP73 antigen complex with at least one detection antibody comprising a detectable label, wherein the detection antibody binds to an epitope on GP73 that is not bound by the capture antibody and forms a capture antibody-GP73 antigen-detection antibody complex; and determining the GP73 concentration in the test sample based on the signal generated by the detectable label in the capture antibody-GP73 antigen-detection antibody complex formed in (b); wherein the at least one capture antibody comprises: a variable heavy domain comprising the amino acid sequence of SEQ ID NO:41; a variable light domain comprising the amino acid sequence of SEQ ID NO:45; a variable heavy domain comprising the amino acid sequence of SEQ ID NO:41 and a variable light domain comprising the amino acid sequence of SEQ ID NO:45; a variable heavy chain comprising a complementarity determining region (CDR)1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; or a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44 and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; wherein the at least one detection antibody comprises: a variable heavy domain comprising the amino acid sequence of SEQ ID NO:25; a variable light domain comprising the amino acid sequence of SEQ ID NO:29; a variable heavy domain comprising the amino acid sequence of SEQ ID NO:25 and a variable light domain comprising the amino acid sequence of SEQ ID NO:29; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28 and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32.

The present invention is directed to a method for determining fucosylated GP73 concentration in a test sample, the method comprising: contacting the test sample with at least one capture binding protein, wherein the capture binding protein binds to a region of GP73 or a fragment of GP73 to form a capture binding protein-GP73 complex; contacting the capture binding protein-GP73 complex with at least one detection binding protein comprising a detectable label, wherein the detection binding protein binds to a region of GP73 that is not bound by the capture binding protein and forms a capture binding protein-GP73-detection binding protein complex; and determining the GP73 concentration in the test sample based on the signal generated by the detectable label in the capture binding protein-GP73-detection binding protein complex formed in the previous step; wherein the at least one capture binding protein comprises a protein, antibody or antibody fragment whose binding to GP73 is sensitive to the presence or absence of a fucose sugar moiety on GP73 and the at least one detection binding protein comprises a protein, antibody or antibody fragment whose binding to GP73 is insensitive to the presence or absence of a fucose sugar moiety on GP73.

The present invention is directed to a method for determining fucosylated GP73 concentration in a test sample, the method comprising: contacting the test sample with at least one capture binding protein, wherein the capture binding protein binds to a region of GP73 or a fragment of GP73 to form a capture binding protein-GP73 complex; contacting the capture binding protein-GP73 complex with at least one detection binding protein comprising a detectable label, wherein the detection binding protein binds to a region of GP73 that is not bound by the capture binding protein and forms a capture binding protein-GP73-detection binding protein complex; and determining the GP73 concentration in the test sample based on the signal generated by the detectable label in the capture binding protein-GP73-detection binding protein complex formed in the previous step; wherein the at least one capture binding protein comprises a protein, antibody or antibody fragment whose binding to GP73 is insensitive to the presence or absence of a fucose sugar moiety on GP73 and the at least one detection binding protein comprises a protein, antibody or antibody fragment whose binding to GP73 is sensitive the presence or absence of a fucose sugar moiety on GP73. The protein, antibody or antibody fragment whose binding to GP73 is sensitive to the presence or absence of a fucose sugar moiety on GP73 comprises: Aleuria aurantia lectin (AAL) or a fragment thereof; a variable heavy domain region comprising the amino acid sequence of SEQ ID NO:25 or SEQ ID NO:33; a variable light domain region comprising the amino acid sequence of SEQ ID NO:29 or SEQ ID NO:37; a variable heavy domain comprising the amino acid sequence of SEQ ID NO:25 and a variable light domain region comprising the amino acid sequence of SEQ ID NO:29; a variable heavy domain comprising the amino acid sequence of SEQ ID NO:33 and a variable light domain region comprising the amino acid sequence of SEQ ID NO:37; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40; a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40. The protein, antibody or antibody fragment whose binding to GP73 is insensitive to the presence or absence of a fucose sugar moiety on GP73 comprises: a variable heavy domain region comprising the amino acid sequence of SEQ ID NO:1, SEQ ID NO:9, SEQ ID NO:17, or SEQ ID NO:41; a variable light domain region comprising the amino acid sequence of SEQ ID NO:5, SEQ ID NO:13, SEQ ID NO:21, or SEQ ID NO:45; a variable heavy domain comprising the amino acid sequence of SEQ ID NO:1 and a variable light domain region comprising the amino acid sequence of SEQ ID NO:5; a variable heavy domain comprising the amino acid sequence of SEQ ID NO:9 and a variable light domain region comprising the amino acid sequence of SEQ ID NO:13; a variable heavy domain comprising the amino acid sequence of SEQ ID NO:17 and a variable light domain region comprising the amino acid sequence of SEQ ID NO:21; a variable heavy domain comprising the amino acid sequence of SEQ ID NO:41 and a variable light domain region comprising the amino acid sequence of SEQ ID NO:45; a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20; a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; or a variable heavy chain comprising a CDR 1 comprising the amino acid sequence of SEQ ID NO:42, a CDR2 comprising the amino acid sequence of SEQ ID NO:43, and a CDR3 comprising the amino acid sequence of SEQ ID NO:44, and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48. The method further comprises comparing the signal generated by the detectable label as a direct or indirect indication of the GP73 concentration in the test sample to a signal generated as a direct or indirect indication of the GP73 concentration in a control or calibrator. The GP73 concentration in the test sample is used to determine or assess whether a subject has or is at risk of developing liver disease. An increased GP73 concentration as compared to the GP73 concentration in a control or calibrator indicates that the subject has liver disease. The liver disease is liver cirrhosis or liver cancer.

The present invention is directed to a method of diagnosing and treating liver disease in a subject, the method comprising: obtaining a biological sample comprising blood from the subject; determining the GP73 concentration in the biological sample from the subject using the method of claim 81; comparing the GP73 concentration in the biological sample with the GP73 concentration in a normal control or calibrator; diagnosing the subject as having liver disease if the GP73 concentration in the biological sample is greater than the GP73 concentration in the normal control or calibrator; and administering a liver disease treatment regimen to the subject diagnosed as having liver disease. The biological sample of a subject is selected from a tissue sample, bodily fluid, whole blood, plasma, serum, urine, bronchoalveolar lavage fluid, and a cell culture suspension or fraction thereof. The biological sample of a subject is blood plasma or blood serum. The liver disease is liver cirrhosis or liver cancer. The method further comprises determining the level of at least one additional biomarker of liver disease in the biological sample, and comparing the level of the at least one additional biomarker of liver disease to a reference concentration value for the at least one biomarker of liver disease. The additional biomarker of liver disease is selected from the group consisting of PIVKA-II, AFP, AFP-L3, Fuc-HPX, Fc-Kin and F-AT.

The present invention is directed to a method for determining if a subject is responding to the administration of one or more pharmaceutical compositions, the method comprising: measuring the GP73 concentration in a sample from the subject using the method of claim 81; comparing the GP73 concentration in the sample with the GP73 concentration in a normal control or calibrator, wherein an altered GP73 concentration indicates that the subject is not responding to the administration of one or more pharmaceutical compositions; and adjusting the treatment of the subject if the subject is not responding to the administration of one or more pharmaceutical compositions.

The present invention is directed to a method of diagnosing and treating liver disease in a subject, the method comprising: contacting the test sample with at least one capture antibody, wherein the capture antibody binds to an epitope on GP73 or a fragment of GP73 to form a capture antibody-GP73 antigen complex; contacting the capture antibody-GP73 antigen complex with at least one detection antibody comprising a detectable label, wherein the detection antibody binds to an epitope on GP73 that is not bound by the capture antibody and forms a capture antibody-GP73 antigen-detection antibody complex; determining the GP73 concentration in the test sample based on the signal generated by the detectable label in the capture antibody-GP73 antigen-detection antibody complex formed in (b); comparing the GP73 concentration in the sample with the GP73 concentration in a normal control or calibrator; diagnosing the subject as having liver disease if the GP73 concentration in the biological sample is greater than the GP73 concentration in the normal control or calibrator; and administering a liver disease treatment regimen to the subject diagnosed as having liver disease; wherein the at least one capture antibody comprises: a variable heavy domain comprising the amino acid sequence of SEQ ID NO:41; a variable light domain comprising the amino acid sequence of SEQ ID NO:45; a variable heavy domain comprising the amino acid sequence of SEQ ID NO:41 and a variable light domain comprising the amino acid sequence of SEQ ID NO:45; a variable heavy chain comprising a complementarity determining region (CDR)1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; or a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44 and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; wherein the at least one detection antibody comprises: a variable heavy domain comprising the amino acid sequence of SEQ ID NO:25; a variable light domain comprising the amino acid sequence of SEQ ID NO:29; a variable heavy domain comprising the amino acid sequence of SEQ ID NO:25 and a variable light domain comprising the amino acid sequence of SEQ ID NO:29; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28 and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32. The liver disease is liver cirrhosis or liver cancer.

The present invention is directed to a kit comprising the antibody, antibody fragment, mixture or derivative thereof of claims 1, 5, 9, 13, 17, 21, 25, 60, 61, 62, or 63.

The present invention is directed to a kit comprising an isolated nucleic acid encoding the antibody or antibody fragment of claims 1, 5, 9, 13, 17, 21, 25, 60, 61, 62, or 63.

The present invention is directed to a kit for assaying a test sample for GP73, which kit comprises at least one capture antibody, wherein the capture antibody binds to an epitope on GP73 or a fragment of GP73, at least one detection antibody, wherein the detection antibody binds to an epitope on GP73 that is not bound by the capture antibody, and instructions for assaying the test sample for GP73, wherein the at least one capture antibody comprises the isolated antibody or antibody fragment of claims 1, 5, 9, 13, 17, 21, 25, 60, 61, 62, or 63 and the at least one detection antibody comprises the isolated antibody or antibody fragment of claims 1, 5, 9, 13, 17, 21, 25, 60, 61, 62, or 63, and wherein the least one capture antibody is different from the at least one detection antibody. The kit further comprises a reference standard indicating a GP73 concentration in a control or calibrator.

The present invention is directed to a kit for assaying a test sample for GP73, which kit comprises at least one capture antibody, wherein the capture antibody binds to an epitope on GP73 or a fragment of GP73, at least one detection antibody, wherein the detection antibody binds to an epitope on GP73 that is not bound by the capture antibody, and instructions for assaying the test sample for GP73, wherein the at least one capture antibody comprises: a variable heavy domain comprising the amino acid sequence of SEQ ID NO:41; a variable light domain comprising the amino acid sequence of SEQ ID NO:45; a variable heavy domain comprising the amino acid sequence of SEQ ID NO:41 and a variable light domain comprising the amino acid sequence of SEQ ID NO:45; a variable heavy chain comprising a complementarity determining region (CDR)1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; or a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44 and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; wherein the at least one detection antibody comprises: a variable heavy domain comprising the amino acid sequence of SEQ ID NO:25; a variable light domain comprising the amino acid sequence of SEQ ID NO:29; a variable heavy domain comprising the amino acid sequence of SEQ ID NO:25 and a variable light domain comprising the amino acid sequence of SEQ ID NO:29; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28 and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32, wherein the at least one detection antibody is optionally detectably labeled.

The present invention is directed to a kit for assaying a test sample for fucosylated GP73, which kit comprises at least one capture binding protein, wherein the capture binding protein binds to GP73 or a fragment of GP73, at least one detection binding protein, wherein the detection binding protein binds to GP73 that is not bound by the capture binding protein, and instructions for assaying the test sample for GP73, wherein the at least one capture binding protein comprises a protein, antibody or antibody fragment whose binding to GP73 is insensitive to the presence or absence of a fucose sugar moiety on GP73 and the at least one detection binding protein comprises a protein, antibody or antibody fragment whose binding to GP73 is sensitive to fucosylation of GP73.

The present invention is directed to a kit for assaying a test sample for fucosylated GP73, which kit comprises at least one capture binding protein, wherein the capture binding protein binds to GP73 or a fragment of GP73, at least one detection binding protein, wherein the detection binding protein binds to GP73 that is not bound by the capture binding protein, and instructions for assaying the test sample for GP73, wherein the at least one capture binding protein comprises a protein, antibody or antibody fragment whose binding to GP73 is sensitive to fucosylation of GP73 and the at least one detection binding protein comprises a protein, antibody or antibody fragment whose binding to GP73 is insensitive to fucosylation of GP73. The protein, antibody or antibody fragment whose binding to GP73 is sensitive to fucosylation of GP73 comprises: Aleuria aurantia lectin (AAL) or a fragment thereof; a variable heavy domain region comprising the amino acid sequence of SEQ ID NO:25 or SEQ ID NO:33; a variable light domain region comprising the amino acid sequence of SEQ ID NO:29 or SEQ ID NO:37; a variable heavy domain comprising the amino acid sequence of SEQ ID NO:25 and a variable light domain region comprising the amino acid sequence of SEQ ID NO:29; a variable heavy domain comprising the amino acid sequence of SEQ ID NO:33 and a variable light domain region comprising the amino acid sequence of SEQ ID NO:37; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40; a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40. The protein, antibody or antibody fragment whose binding to GP73 is insensitive to fucosylation of GP73 comprises a variable heavy domain region comprising the amino acid sequence of SEQ ID NO:1, SEQ ID NO:9, SEQ ID NO:17, or SEQ ID NO:41; a variable light domain region comprising the amino acid sequence of SEQ ID NO:5, SEQ ID NO:13, SEQ ID NO:21, or SEQ ID NO:45; a variable heavy domain comprising the amino acid sequence of SEQ ID NO:1 and a variable light domain region comprising the amino acid sequence of SEQ ID NO:5; a variable heavy domain comprising the amino acid sequence of SEQ ID NO:9 and a variable light domain region comprising the amino acid sequence of SEQ ID NO:13; a variable heavy domain comprising the amino acid sequence of SEQ ID NO:17 and a variable light domain region comprising the amino acid sequence of SEQ ID NO:21; a variable heavy domain comprising the amino acid sequence of SEQ ID NO:41 and a variable light domain region comprising the amino acid sequence of SEQ ID NO:45; a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20; a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; or a variable heavy chain comprising a CDR 1 comprising the amino acid sequence of SEQ ID NO:42, a CDR2 comprising the amino acid sequence of SEQ ID NO:43, and a CDR3 comprising the amino acid sequence of SEQ ID NO:44, and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48. The kit further comprises a reference standard indicating a GP73 concentration in a control or calibrator.

BRIEF DESCRIPTION OF THE DRAWINGS

FIG. 1 shows the *E. coli* GP73 construct.

FIG. 2 shows the CHO and HEK GP73-hFc construct.

FIG. 12 shows a diagram and the nucleotide and amino acid sequences of the variable heavy (FIG. 12A) and light chain sequences (FIG. 12B) for mAb 1A-3187.

FIG. 13 shows a diagram and the nucleotide and amino acid sequences of the variable heavy (FIG. 13A) and light chain sequences (FIG. 13B) for mAb 1A-4246.

FIG. 14 shows a diagram and the nucleotide and amino acid sequences of the variable heavy (FIG. 14A) and light chain sequences (FIG. 14B) for mAb 1B-3246.

FIG. 15 shows a diagram and the nucleotide and amino acid sequences of the variable heavy (FIG. 15A) and light chain sequences (FIG. 15B) for mAb 1B-3440.

FIG. 16 shows a diagram and the nucleotide and amino acid sequences of the variable heavy (FIG. 16A) and light chain sequences (FIG. 16B) for mAb 1B-4863.

FIG. 17 shows a diagram and the nucleotide and amino acid sequences of the variable heavy (FIG. 17A) and light chain sequences (FIG. 17B) for mAb 1B-4971.

FIG. 18 shows the epitope peptide map of anti-GP73 mAbs for GP73-hFc.

DETAILED DESCRIPTION

Figure 3:
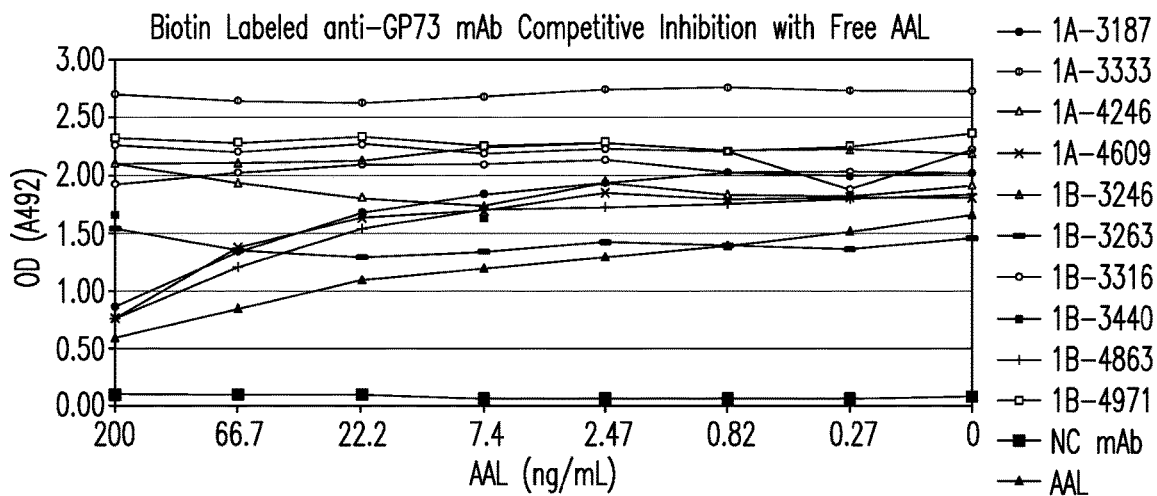
FIG. 3 shows a competitive inhibition assay of the biotin labeled anti-GP73 mAb with free AAL.

The present invention relates to anti-Golgi protein 73 (GP73) antibodies and the use of said antibodies in immunoassays for analyzing the levels of GP73 and fucosylated GP73 to identify, diagnose and treat diseases in subjects in need thereof. The anti-GP73 antibodies of the present invention have higher binding affinities than previously available antibodies. The antibodies of the present invention can be used in immunoassays for detecting GP73 and/or fucosylated GP73 thus providing a unique combination of antibodies to detect GP73 and/or fucosylated GP73 in a sample over a wider range of concentrations. The use of these antibodies in such immunoassays provides a more versatile and sensitive assay. It has also been found that the antibodies of the present invention outperformed a known anti-GP73 antibody by about three-fold in immunoassays.

The increased detectable range of concentration of the disclosed immunoassays provides a more accurate and sensitive assay for diagnosing and distinguishing liver disease and cancer in a patient. Thus, the disclosed immunoassays may be used to detect increased or decreased GP73 concentrations in a sample compared to a control or calibrator sample and thus be used to identify various diseases in a patient, such as liver diseases and cancers. The use of the GP73 immunoassay may provide accurate diagnosing and subsequent treatment of patients with diseases, such as liver disease or cancer.

Section headings as used in this section and the entire disclosure herein are merely for organizational purposes and are not intended to be limiting.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

"14H4-23", "14H4-23 monoclonal antibody" and "monoclonal antibody 14H4-23" as used herein interchangeably refer to a mouse monoclonal antibody which binds to GP73. The 14H4-23 monoclonal antibody was from the lab of Drs. Anand Mehta and Tim Block at Drexel University College of Medicine. The binding of the 14H4-23 monoclonal antibody is not sensitive to presence or absence of a fucose sugar moiety on GP73.

"Affinity Matured Antibody" is used herein to refer to an antibody with one or more alterations in one or more CDRs, which result in an improvement in the affinity (i.e. $K_D$, $k_d$ or $k_a$) of the antibody for a target antigen compared to a parent antibody, which does not possess the alteration(s). Exemplary affinity matured antibodies will have nanomolar or even picomolar affinities for the target antigen. A variety of procedures for producing affinity matured antibodies is known in the art, including the screening of a combinatory antibody library that has been prepared using bio-display. For example, Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); and Hawkins et al, J. Mol. Biol., 226: 889-896 (1992). Selective mutation at selective mutagenesis positions and at contact or hypermutation positions with an activity-enhancing amino acid residue is described in U.S. Pat. No. 6,914,128 B1.

"Aleuria aurantia lectin" and "AAL" as used herein interchangeably refers to a fungal protein composed of two identical 312-amino acid subunits that specifically recognizes fucosylated glycans, and is widely used as a specific probe for fucose. AAL binds preferentially to fucose linked (α-1,6) to N-acetylglucosamine or to fucose linked (α-1,3) to N-acetyllactosamine related structures.

"Antibody" and "antibodies" as used herein refers to monoclonal antibodies, multispecific antibodies, human antibodies, humanized antibodies (fully or partially humanized), animal antibodies such as, but not limited to, a bird (for example, a duck or a goose), a shark, a whale, and a mammal, including a non-primate (for example, a cow, a pig, a camel, a llama, a horse, a goat, a rabbit, a sheep, a hamster, a guinea pig, a cat, a dog, a rat, a mouse, etc.) or a non-human primate (for example, a monkey, a chimpanzee, etc.), recombinant antibodies, chimeric antibodies, single-chain Fvs ("scFv"), single chain antibodies, single domain antibodies, Fab fragments, F(ab') fragments, F(ab')2 fragments, disulfide-linked Fvs ("sdFv"), and anti-idiotypic ("anti-Id") antibodies, dual-domain antibodies, dual variable domain (DVD) or triple variable domain (TVD) antibodies (dual-variable domain immunoglobulins and methods for making them are described in Wu, C., et al., Nature Biotechnology, 25(11):1290-1297 (2007) and PCT International Application WO 2001/058956, the contents of each of which are herein incorporated by reference), and functionally active epitope-binding fragments of any of the above. In particular, antibodies include immunoglobulin molecules and immunologically active fragments of immunoglobulin molecules, namely, molecules that contain an analyte-binding site. Immunoglobulin molecules can be of any type (for example, IgG, IgE, IgM, IgD, IgA, and IgY), class (for example, IgG1, IgG2, IgG3, IgG4, IgA1, and IgA2), or subclass. For simplicity sake, an antibody against an analyte is frequently referred to herein as being either an "anti-analyte antibody" or merely an "analyte antibody" (e.g., an anti-GP73 antibody or a GP73 antibody).

"Antibody fragment" as used herein refers to a portion of an intact antibody comprising the antigen-binding site or variable region. The portion does not include the constant heavy chain domains (i.e. CH2, CH3, or CH4, depending on the antibody isotype) of the Fc region of the intact antibody. Examples of antibody fragments include, but are not limited to, Fab fragments, Fab' fragments, Fab'-SH fragments, F(ab')2 fragments, Fd fragments, Fv fragments, diabodies, single-chain Fv (scFv) molecules, single-chain polypeptides containing only one light chain variable domain, single-chain polypeptides containing the three CDRs of the light-chain variable domain, single-chain polypeptides containing only one heavy chain variable region, and single-chain polypeptides containing the three CDRs of the heavy chain variable region.

The "area under curve" or "AUC" refers to area under a ROC curve. AUC under a ROC curve is a measure of accuracy. An area of 1 represents a perfect test, whereas an area of 0.5 represents an insignificant test. A preferred AUC may be at least approximately 0.700, at least approximately 0.750, at least approximately 0.800, at least approximately 0.850, at least approximately 0.900, at least approximately 0.910, at least approximately 0.920, at least approximately 0.930, at least approximately 0.940, at least approximately 0.950, at least approximately 0.960, at least approximately 0.970, at least approximately 0.980, at least approximately 0.990, or at least approximately 0.995.

"Binding Constants" are described herein. The term "association rate constant," "$k_{on}$" or "$k_a$" as used herein, refers to the value indicating the binding rate of an antibody to its target antigen or the rate of complex formation between an antibody and antigen as shown by the equation below:

Antibody (Ab)+Antigen (Ag)→Ab-Ag.

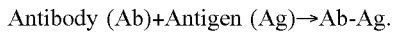

The term "dissociation rate constant," "$k_{off}$" or "$k_d$" as used interchangeably herein, refers to the value indicating the dissociation rate of an antibody form its target antigen or separation of Ab-Ag complex over time into free antibody and antigen as shown by the equation below:

Antibody (Ab)+Antigen (Ag)←Ab-Ag.

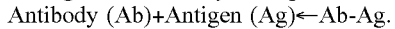

Methods for determining association and dissociation rate constants are well known in the art. Using fluorescence-based techniques offers high sensitivity and the ability to examine samples in physiological buffers at equilibrium. Other experimental approaches and instruments such as a BIAcore® (biomolecular interaction analysis) assay can be used (e.g., instrument available from BIAcore International AB, a GE Healthcare company, Uppsala, Sweden). Additionally, a KinExA® (Kinetic Exclusion Assay) assay, available from Sapidyne Instruments (Boise, Id.) can also be used.

The term "equilibrium dissociation constant", "Kd", "$K_d$" or "$K_D$" as used interchangeably, herein, refers to the value obtained by dividing the dissociation rate (koff) by the association rate (kon). The association rate, the dissociation rate and the equilibrium dissociation constant are used to represent the binding affinity of an antibody to an antigen.

"Binding Protein" is used herein to refer to a monomeric or multimeric protein that binds to and forms a complex with a binding partner, such as, for example, a polypeptide, an antigen, a chemical compound or other molecule, or a substrate of any kind. A binding protein specifically binds a binding partner. Binding proteins include antibodies, as well as antigen-binding fragments thereof and other various forms and derivatives thereof as are known in the art and described herein below, and other molecules comprising one or more antigen-binding domains that bind to an antigen molecule or a particular site (epitope) on the antigen molecule. Accordingly, a binding protein includes, but is not limited to, an antibody a tetrameric immunoglobulin, an IgG molecule, an IgG1 molecule, a monoclonal antibody, a chimeric antibody, a CDR-grafted antibody, a humanized antibody, an affinity matured antibody, and fragments of any such antibodies that retain the ability to bind to an antigen.

"Bispecific antibody" is used herein to refer to a full-length antibody that is generated by quadroma technology (see Milstein et al., Nature, 305(5934): 537-540 (1983)), by chemical conjugation of two different monoclonal antibodies (see, Staerz et al., Nature, 314(6012): 628-631 (1985)), or by knob-into-hole or similar approaches, which introduce mutations in the Fc region (see Holliger et al., Proc. Natl. Acad. Sci. USA, 90(14): 6444-6448 (1993)), resulting in multiple different immunoglobulin species of which only one is the functional bispecific antibody. A bispecific antibody binds one antigen (or epitope) on one of its two binding arms (one pair of HC/LC), and binds a different antigen (or epitope) on its second arm (a different pair of HC/LC). By this definition, a bispecific antibody has two distinct antigen-binding arms (in both specificity and CDR sequences), and is monovalent for each antigen to which it binds to.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"Cancer" as used herein refers to the uncontrolled and unregulated growth of abnormal cells in the body. Cancerous cells are also called malignant cells. Cancer may invade nearby parts of the body and may also spread to more distant parts of the body through the lymphatic system or bloodstream. Cancers include Adrenocortical Carcinoma, Anal Cancer, Bladder Cancer, Brain Tumor, Breast Cancer, Carcinoid Tumor, Gastrointestinal, Carcinoma of Unknown Primary, Cervical Cancer, Colon Cancer, Endometrial Cancer, Esophageal Cancer, Extrahepatic Bile Duct Cancer, Ewings Family of Tumors (PNET), Extracranial Germ Cell Tumor, Intraocular Melanoma Eye Cancer, Gallbladder Cancer, Gastric Cancer (Stomach), Extragonadal Germ Cell Tumor, Gestational Trophoblastic Tumor, Head and Neck Cancer, Hypopharyngeal Cancer, Islet Cell Carcinoma, Kidney Cancer (renal cell cancer), Laryngeal Cancer, Acute Lymphoblastic Leukemia, Leukemia, Acute Myeloid, Chronic Lymphocytic Leukemia, Chronic Myelogenous Leukemia, Hairy Cell Leukemia, Lip and Oral Cavity Cancer, Liver Cancer, Non-Small Cell Lung Cancer, Small Cell Lung Cancer, AIDS-Related Lymphoma, Central Nervous System (Primary) Lymphoma, Cutaneous T-Cell Lymphoma, Hodgkin's Disease Lymphoma, Non-Hodgkin's Disease Lymphoma, Malignant Mesothelioma, Melanoma, Merkel Cell Carcinoma, Metasatic Squamous Neck Cancer with Occult Primary, Multiple Myeloma and Other Plasma Cell Neoplasms, Mycosis Fungoides, Myelodysplastic Syndrome, Myeloproliferative Disorders, Nasopharyngeal Cancer, euroblastoma, Oral Cancer, Oropharyngeal Cancer, Osteosarcoma, Ovarian Epithelial Cancer, Ovarian Germ Cell Tumor, Pancreatic Cancer, Exocrine, Pancreatic Cancer, Islet Cell Carcinoma, Paranasal Sinus and Nasal Cavity Cancer, Parathyroid Cancer, Penile Cancer, Pituitary Cancer, Plasma Cell Neoplasm, Prostate Cancer, Rhabdomyosarcoma, Rectal Cancer, Renal Cell Cancer (cancer of the kidney), Transitional Cell Renal Pelvis and Ureter, Salivary Gland Cancer, Sezary Syndrome, Skin Cancer, Small Intestine Cancer, Soft Tissue Sarcoma, Testicular Cancer, Malignant Thymoma, Thyroid Cancer, Urethral Cancer, Uterine Cancer, Unusual Cancer of Childhood, Vaginal Cancer, Vulvar Cancer, and Wilms' Tumor.

"CDR" is used herein to refer to the "complementarity determining region" within an antibody variable sequence. There are three CDRs in each of the variable regions of the heavy chain and the light chain, which are designated "CDR1", "CDR2", and "CDR3", for each of the variable regions. The term "CDR set" as used herein refers to a group of three CDRs that occur in a single variable region that binds the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as "Kabat CDRs". Chothia and coworkers (Chothia and Lesk, J. Mol. Biol., 196: 901-917 (1987); and Chothia et al., Nature, 342: 877-883 (1989)) found that certain sub-portions within Kabat CDRs adopt nearly identical peptide backbone conformations, despite having great diversity at the level of amino acid sequence. These sub-portions were designated as "L1", "L2", and "L3", or "H1", "H2", and "H3", where the "L" and the "H" designate the light chain and the heavy chain regions, respectively. These regions may be referred to as "Chothia CDRs", which have boundaries that overlap with Kabat CDRs. Other boundaries defining CDRs overlapping with the Kabat CDRs have been described by Padlan, FASEB J., 9: 133-139 (1995), and MacCallum, J. Mol. Biol., 262(5): 732-745 (1996). Still other CDR boundary definitions may not strictly follow one of the herein systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although certain embodiments use Kabat- or Chothia-defined CDRs.

"Component," "components," or "at least one component," refer generally to a capture antibody, a detection or conjugate a calibrator, a control, a sensitivity panel, a container, a buffer, a diluent, a salt, an enzyme, a co-factor for an enzyme, a detection reagent, a pretreatment reagent/solution, a substrate (e.g., as a solution), a stop solution, and the like that can be included in a kit for assay of a test sample, such as a patient urine, serum or plasma sample, in accordance with the methods described herein and other methods known in the art. Some components can be in solution or lyophilized for reconstitution for use in an assay.

"Derivative" of an antibody as used herein may refer to an antibody having one or more modifications to its amino acid sequence when compared to a genuine or parent antibody and exhibit a modified domain structure. The derivative may still be able to adopt the typical domain configuration found in native antibodies, as well as an amino acid sequence, which is able to bind to targets (antigens) with specificity. Typical examples of antibody derivatives are antibodies coupled to other polypeptides, rearranged antibody domains, or fragments of antibodies. The derivative may also comprise at least one further compound, e.g. a protein domain, said protein domain being linked by covalent or non-covalent bonds. The linkage can be based on genetic fusion according to the methods known in the art. The additional domain present in the fusion protein comprising the antibody employed in accordance with the invention may preferably be linked by a flexible linker, advantageously a peptide linker, wherein said peptide linker comprises plural, hydrophilic, peptide-bonded amino acids of a length sufficient to span the distance between the C-terminal end of the further protein domain and the N-terminal end of the antibody or vice versa. The antibody may be linked to an effector molecule having a conformation suitable for biological activity or selective binding to a solid support, a biologically active substance (e.g. a cytokine or growth hormone), a chemical agent, a peptide, a protein, or a drug, for example.

"Dual-specific antibody" is used herein to refer to a full-length antibody that can bind two different antigens (or epitopes) in each of its two binding arms (a pair of HC/LC) (see PCT publication WO 02/02773). Accordingly, a dual-specific binding protein has two identical antigen binding arms, with identical specificity and identical CDR sequences, and is bivalent for each antigen to which it binds.

"Dual variable domain" is used herein to refer to two or more antigen binding sites on a binding protein, which may be divalent (two antigen binding sites), tetravalent (four antigen binding sites), or multivalent binding proteins. DVDs may be monospecific, i.e., capable of binding one antigen (or one specific epitope), or multispecific, i.e., capable of binding two or more antigens (i.e., two or more epitopes of the same target antigen molecule or two or more epitopes of different target antigens). A preferred DVD binding protein comprises two heavy chain DVD polypeptides and two light chain DVD polypeptides and is referred to as a "DVD immunoglobulin" or "DVD-Ig". Such a DVD-Ig binding protein is thus tetrameric and reminiscent of an IgG molecule, but provides more antigen binding sites than an IgG molecule. Thus, each half of a tetrameric DVD-Ig molecule is reminiscent of one half of an IgG molecule and comprises a heavy chain DVD polypeptide and a light chain DVD polypeptide, but unlike a pair of heavy and light chains of an IgG molecule that provides a single antigen binding domain, a pair of heavy and light chains of a DVD-Ig provide two or more antigen binding sites.

Each antigen binding site of a DVD-Ig binding protein may be derived from a donor ("parental") monoclonal antibody and thus comprises a heavy chain variable domain (VH) and a light chain variable domain (VL) with a total of six CDRs involved in antigen binding per antigen binding site. Accordingly, a DVD-Ig binding protein that binds two different epitopes (i.e., two different epitopes of two different antigen molecules or two different epitopes of the same antigen molecule) comprises an antigen binding site derived from a first parental monoclonal antibody and an antigen binding site of a second parental monoclonal antibody.

A description of the design, expression, and characterization of DVD-Ig binding molecules is provided in PCT Publication No. WO 2007/024715, U.S. Pat. No. 7,612,181, and Wu et al., Nature Biotech., 25: 1290-1297 (2007). A preferred example of such DVD-Ig molecules comprises a heavy chain that comprises the structural formula VD1-(X1)n-VD2-C-(X2)n, wherein VD1 is a first heavy chain variable domain, VD2 is a second heavy chain variable domain, C is a heavy chain constant domain, X1 is a linker with the proviso that it is not CH1, X2 is an Fc region, and n is 0 or 1, but preferably 1; and a light chain that comprises the structural formula VD1-(X1)n-VD2-C-(X2)n, wherein VD1 is a first light chain variable domain, VD2 is a second light chain variable domain, C is a light chain constant domain, X1 is a linker with the proviso that it is not CH1, and X2 does not comprise an Fc region; and n is 0 or 1, but preferably 1. Such a DVD-Ig may comprise two such heavy chains and two such light chains, wherein each chain comprises variable domains linked in tandem without an intervening constant region between variable regions, wherein a heavy chain and a light chain associate to form tandem functional antigen binding sites, and a pair of heavy and light chains may associate with another pair of heavy and light chains to form a tetrameric binding protein with four functional antigen binding sites. In another example, a DVD-Ig molecule may comprise heavy and light chains that each comprise three variable domains (VD1, VD2, VD3) linked in tandem without an intervening constant region between variable domains, wherein a pair of heavy and light chains may associate to form three antigen binding sites, and wherein a pair of heavy and light chains may associate with another pair of heavy and light chains to form a tetrameric binding protein with six antigen binding sites.

In a preferred embodiment, a DVD-Ig binding protein according to the invention not only binds the same target molecules bound by its parental monoclonal antibodies, but also possesses one or more desirable properties of one or more of its parental monoclonal antibodies. Preferably, such an additional property is an antibody parameter of one or more of the parental monoclonal antibodies. Antibody parameters that may be contributed to a DVD-Ig binding protein from one or more of its parental monoclonal antibodies include, but are not limited to, antigen specificity, antigen affinity, potency, biological function, epitope recognition, protein stability, protein solubility, production efficiency, immunogenicity, pharmacokinetics, bioavailability, tissue cross reactivity, and orthologous antigen binding.

A DVD-Ig binding protein binds at least one epitope of a GP73. Non-limiting examples of a DVD-Ig binding protein include a DVD-Ig binding protein that binds one or more epitopes of GP73, a DVD-Ig binding protein that binds an epitope of a human GP73 and an epitope of a GP73 of another species (for example, mouse), and a DVD-Ig binding protein that binds an epitope of a human GP73 and an epitope of another target molecule.

"Epitope," or "epitopes," or "epitopes of interest" refer to a site(s) on any molecule that is recognized and can bind to a complementary site(s) on its specific binding partner. The molecule and specific binding partner are part of a specific binding pair. For example, an epitope can be on a polypeptide, a protein, a hapten, a carbohydrate antigen (such as, but not limited to, glycolipids, glycoproteins or lipopolysaccharides), or a polysaccharide. Its specific binding partner can be, but is not limited to, an antibody.

"F(ab')2 fragment" as used herein refers to antibodies generated by pepsin digestion of whole IgG antibodies to remove most of the Fc region while leaving intact some of the hinge region. F(ab')2 fragments have two antigen-binding F(ab) portions linked together by disulfide bonds, and therefore are divalent with a molecular weight of about 110 kDa. Divalent antibody fragments (F(ab')2 fragments) are smaller than whole IgG molecules and enable a better penetration into tissue thus facilitating better antigen recognition in immunohistochemistry. The use of F(ab')2 fragments also avoids unspecific binding to Fc receptor on live cells or to Protein A/G. F(ab')2 fragments can both bind and precipitate antigens.

"Framework" (FR) or "Framework sequence" as used herein may mean the remaining sequences of a variable region minus the CDRs. Because the exact definition of a CDR sequence can be determined by different systems (for example, see above), the meaning of a framework sequence is subject to correspondingly different interpretations. The six CDRs (CDR-L1, -L2, and -L3 of light chain and CDR-H1, -H2, and -H3 of heavy chain) also divide the framework regions on the light chain and the heavy chain into four sub-regions (FR1, FR2, FR3, and FR4) on each chain, in which CDR1 is positioned between FR1 and FR2, CDR2 between FR2 and FR3, and CDR3 between FR3 and FR4. Without specifying the particular sub-regions as FR1, FR2, FR3, or FR4, a framework region, as referred by others, represents the combined FRs within the variable region of a single, naturally occurring immunoglobulin chain. As used herein, a FR represents one of the four sub-regions, and FRs represents two or more of the four sub-regions constituting a framework region.

Human heavy chain and light chain FR sequences are known in the art that can be used as heavy chain and light chain "acceptor" framework sequences (or simply, "acceptor" sequences) to humanize a non-human antibody using techniques known in the art. In one embodiment, human heavy chain and light chain acceptor sequences are selected from the framework sequences listed in publicly available databases such as V-base (hypertext transfer protocol://vbase.mrc-cpe.cam.ac.uk/) or in the international ImMunoGeneTics® (IMGT®) information system (hypertext transfer protocol://imgt.cines.fr/texts/IMGTrepertoire/Locus Genes/).

"Fucosylated GP73" is used herein to describe a Golgi membrane protein 73 which has a fucose sugar moiety added to it.

"Functional antigen binding site" as used herein may mean a site on a binding protein (e.g. an antibody) that is capable of binding a target antigen. The antigen binding affinity of the antigen binding site may not be as strong as the parent binding protein, e.g., parent antibody, from which the antigen binding site is derived, but the ability to bind antigen must be measurable using any one of a variety of methods known for evaluating protein, e.g., antibody, binding to an antigen. Moreover, the antigen binding affinity of each of the antigen binding sites of a multivalent protein, e.g., multivalent antibody, herein need not be quantitatively the same.

"GP73" is used herein to describe Golgi protein 73, also known as Golgi membrane protein 1 (GOLM1) and Golgi phosphoprotein 2 (GOLPH2). GP73 is a protein that is encoded by the GOLM1 gene. It processes protein synthesized in the rough endoplasmic reticulum and assists in the transport of protein cargo through the Golgi apparatus. GP73 is widely expressed in normal epithelial cells from several tissues. Upregulated intracellular GP73 expression enhances its intracellular trafficking through the endosomal pathway, which provides the opportunity for endoproteolytic cleavage of GP73, resulting in the secretion of truncated GP73. GP73 expression is upregulated in response to viral infection but has also been found to be upregulated in hepatocytes from patients with viral and non-viral liver disease. GP73 is overexpressed in prostate cancer and lung adenocarcinoma tissue. Fucosylated glycosylation has been found in three quarters of secreted GP73 from hepatocellular carcinoma patients.

"Humanized antibody" is used herein to describe an antibody that comprises heavy and light chain variable region sequences from a non-human species (e.g. a mouse) but in which at least a portion of the VH and/or VL sequence has been altered to be more "human-like," i.e., more similar to human germline variable sequences. A "humanized antibody" is an antibody or a variant, derivative, analog, or fragment thereof, which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, at least 85%, at least 90%, at least 95%, at least 98%, or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. In an embodiment, a humanized antibody also comprises at least a portion of an immunoglobulin constant region (Fc), typically that of a human immunoglobulin. In some embodiments, a humanized antibody contains the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

A humanized antibody can be selected from any class of immunoglobulins, including IgM, IgG, IgD, IgA, and IgE, and any isotype, including without limitation IgG1, IgG2, IgG3, and IgG4. A humanized antibody may comprise sequences from more than one class or isotype, and particular constant domains may be selected to optimize desired effector functions using techniques well-known in the art.

The framework regions and CDRs of a humanized antibody need not correspond precisely to the parental sequences, e.g., the donor antibody CDR or the consensus framework may be mutagenized by substitution, insertion, and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (see, e.g., Winnaker, From Genes to Clones (Verlagsgesellschaft, Weinheim, 1987)). A "consensus immunoglobulin sequence" may thus comprise a "consensus framework region(s)" and/or a "consensus CDR(s)". In a family of immunoglobulins, each position in the consensus sequence is occupied by the amino acid occurring most frequently at that position in the family. If two amino acids occur equally frequently, either can be included in the consensus sequence.

"Identical" or "identity," as used herein in the context of two or more polypeptide or polynucleotide sequences, can mean that the sequences have a specified percentage of residues that are the same over a specified region. The percentage can be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of the single sequence are included in the denominator but not the numerator of the calculation.

"Isolated polynucleotide" as used herein may mean a polynucleotide (e.g. of genomic, cDNA, or synthetic origin, or a combination thereof) that, by virtue of its origin, the isolated polynucleotide is not associated with all or a portion of a polynucleotide with which the "isolated polynucleotide" is found in nature; is operably linked to a polynucleotide that it is not linked to in nature; or does not occur in nature as part of a larger sequence.

"Label" and "detectable label" as used herein refer to a moiety attached to an antibody or an analyte to render the reaction between the antibody and the analyte detectable, and the antibody or analyte so labeled is referred to as "detectably labeled." A label can produce a signal that is detectable by visual or instrumental means. Various labels include signal-producing substances, such as chromagens, fluorescent compounds, chemiluminescent compounds, radioactive compounds, and the like. Representative examples of labels include moieties that produce light, e.g., acridinium compounds, and moieties that produce fluorescence, e.g., fluorescein. Other labels are described herein. In this regard, the moiety, itself, may not be detectable but may become detectable upon reaction with yet another moiety. Use of the term "detectably labeled" is intended to encompass such labeling.

Any suitable detectable label as is known in the art can be used. For example, the detectable label can be a radioactive label (such as 3H, 14C, 32P, 33P, 35S, 90Y, 99Tc, 111In, 125I, 131I, 177Lu, 166Ho, and 153Sm), an enzymatic label (such as horseradish peroxidase, alkaline peroxidase, glucose 6-phosphate dehydrogenase, and the like), a chemiluminescent label (such as acridinium esters, thioesters, or sulfonamides; luminol, isoluminol, phenanthridinium esters, and the like), a fluorescent label (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label. An introduction to labels, labeling procedures and detection of labels is found in Polak and Van Noorden, Introduction to Immunocytochemistry, 2nd ed., Springer Verlag, N.Y. (1997), and in Haugland, Handbook of Fluorescent Probes and Research Chemicals (1996), which is a combined handbook and catalogue published by Molecular Probes, Inc., Eugene, Oreg. A fluorescent label can be used in FPIA (see, e.g., U.S. Pat. Nos. 5,593,896, 5,573,904, 5,496,925, 5,359,093, and 5,352,803, which are hereby incorporated by reference in their entireties). An acridinium compound can be used as a detectable label in a homogeneous chemiluminescent assay (see, e.g., Adamczyk et al., Bioorg. Med. Chem. Lett. 16: 1324-1328 (2006); Adamczyk et al., Bioorg. Med. Chem. Lett. 4: 2313-2317 (2004); Adamczyk et al., Biorg. Med. Chem. Lett. 14: 3917-3921 (2004); and Adamczyk et al., Org. Lett. 5: 3779-3782 (2003)).

In one aspect, the acridinium compound is an acridinium-9-carboxamide. Methods for preparing acridinium 9-carboxamides are described in Mattingly, J. Biolumin. Chemilumin. 6: 107-114 (1991); Adamczyk et al., J. Org. Chem. 63: 5636-5639 (1998); Adamczyk et al., Tetrahedron 55: 10899-10914 (1999); Adamczyk et al., Org. Lett. 1: 779-781 (1999); Adamczyk et al., Bioconjugate Chem. 11: 714-724 (2000); Mattingly et al., In Luminescence Biotechnology: Instruments and Applications; Dyke, K. V. Ed.; CRC Press: Boca Raton, pp. 77-105 (2002); Adamczyk et al., Org. Lett. 5: 3779-3782 (2003); and U.S. Pat. Nos. 5,468,646, 5,543,524 and 5,783,699 (each of which is incorporated herein by reference in its entirety for its teachings regarding same).

Another example of an acridinium compound is an acridinium-9-carboxylate aryl ester. An example of an acridinium-9-carboxylate aryl ester of formula II is 10-methyl-9-(phenoxycarbonyl)acridinium fluorosulfonate (available from Cayman Chemical, Ann Arbor, Mich.). Methods for preparing acridinium 9-carboxylate aryl esters are described in McCapra et al., Photochem. Photobiol. 4: 1111-21 (1965); Razavi et al., Luminescence 15: 245-249 (2000); Razavi et al., Luminescence 15: 239-244 (2000); and U.S. Pat. No. 5,241,070 (each of which is incorporated herein by reference in its entirety for its teachings regarding same). Such acridinium-9-carboxylate aryl esters are efficient chemiluminescent indicators for hydrogen peroxide produced in the oxidation of an analyte by at least one oxidase in terms of the intensity of the signal and/or the rapidity of the signal. The course of the chemiluminescent emission for the acridinium-9-carboxylate aryl ester is completed rapidly, i.e., in under 1 second, while the acridinium-9-carboxamide chemiluminescent emission extends over 2 seconds. Acridinium-9-carboxylate aryl ester, however, loses its chemiluminescent properties in the presence of protein. Therefore, its use requires the absence of protein during signal generation and detection. Methods for separating or removing proteins in the sample are well-known to those skilled in the art and include, but are not limited to, ultrafiltration, extraction, precipitation, dialysis, chromatography, and/or digestion (see, e.g., Wells, High Throughput Bioanalytical Sample Preparation. Methods and Automation Strategies, Elsevier (2003)). The amount of protein removed or separated from the test sample can be about 40%, about 45%, about 50%, about 55%, about 60%, about 65%, about 70%, about 75%, about 80%, about 85%, about 90%, or about 95%. Further details regarding acridinium-9-carboxylate aryl ester and its use are set forth in U.S. patent application Ser. No. 11/697,835, filed Apr. 9, 2007. Acridinium-9-carboxylate aryl esters can be dissolved in any suitable solvent, such as degassed anhydrous N,N-dimethylformamide (DMF) or aqueous sodium cholate.

"Linking sequence" or "linking peptide sequence" refers to a natural or artificial polypeptide sequence that is connected to one or more polypeptide sequences of interest (e.g., full-length, fragments, etc.). The term "connected" refers to the joining of the linking sequence to the polypeptide sequence of interest. Such polypeptide sequences are preferably joined by one or more peptide bonds. Linking sequences can have a length of from about 4 to about 50 amino acids. Preferably, the length of the linking sequence is from about 6 to about 30 amino acids. Natural linking sequences can be modified by amino acid substitutions, additions, or deletions to create artificial linking sequences. Exemplary linking sequences include, but are not limited to: (i) Histidine (His) tags, such as a 6× His tag, which has an amino acid sequence of HHHHHH (SEQ ID NO:105), are useful as linking sequences to facilitate the isolation and purification of polypeptides and antibodies of interest; (ii) Enterokinase cleavage sites, like His tags, are used in the isolation and purification of proteins and antibodies of interest. Often, enterokinase cleavage sites are used together with His tags in the isolation and purification of proteins and antibodies of interest. Various enterokinase cleavage sites are known in the art. Examples of enterokinase cleavage sites include, but are not limited to, the amino acid sequence of DDDDK (SEQ ID NO:106) and derivatives thereof (e.g., ADDDDK (SEQ ID NO:107), etc.); (iii) Miscellaneous sequences can be used to link or connect the light and/or heavy chain variable regions of single chain variable region fragments. Examples of other linking sequences can be found in Bird et al., Science 242: 423-426 (1988); Huston et al., PNAS USA 85: 5879-5883 (1988); and McCafferty et al., Nature 348: 552-554 (1990). Linking sequences also can be modified for additional functions, such as attachment of drugs or attachment to solid supports. In the context of the present disclosure, the monoclonal antibody, for example, can contain a linking sequence, such as a His tag, an enterokinase cleavage site, or both.

"Liver cancer" as used herein refers to cancer that originates in the liver. Liver cancer includes hepatocellular carcinoma (HCC) and fibrolamellar carcinoma. In most cases, the cause of liver cancer is usually scarring of the liver (i.e., cirrhosis).

"Liver cirrhosis" as used herein refers to the consequence of chronic liver disease characterized by replacement of liver tissue by fibrosis, scar tissue, and regenerative nodules (lumps that occur because of a process in which damaged tissue is regenerated, leading to loss of liver function. The architectural organization of the functional units of the liver become so disrupted that blood flow through the liver and liver function become disrupted. Cirrhosis is most commonly caused by alcoholism, hepatitis B and C, and fatty liver disease, but has many other possible causes. Some cases are idiopathic (i.e., of unknown cause). Once cirrhosis has developed, the serious complications of liver disease may occur including portal hypertension, liver failure, and liver cancer. The risk of liver cancer is greatly increased once cirrhosis develops and cirrhosis should be considered to be a pre-malignant condition. Cirrhosis may be caused by alcohol abuse, autoimmune diseases of the liver, Hepatitis B or C virus infection, inflammation of the liver that is long-term (chronic), and iron overload in the body (hemochromatosis). Patients with hepatitis B or C are at risk for liver cancer, even if they have not developed cirrhosis.

"Liver disease" as used herein refers to damage to or disease of the liver. Symptoms of liver dysfunction include both physical signs and a variety of symptoms related to digestive problems, blood sugar problems, immune disorders, abnormal absorption of fats, and metabolism problems. Liver disease includes liver fibrosis, liver cirrhosis, and liver cancer. All chronic liver diseases can lead to liver fibrosis. Chronic liver disease may be caused by chronic viral hepatitis B and alcoholic liver disease.

"Liver fibrosis" as used herein refers to an excessive accumulation of extracellular matrix proteins including collagen that occurs in most types of chronic liver diseases. Liver fibrosis is the scarring process that represents the liver's response to injury or illness. Liver fibrosis may be cause by infections due hepatitis B and C, parasites, excessive alcohol use and exposure to toxic chemicals, including pharmaceutical drugs and blocked bile ducts. Advanced liver fibrosis results in cirrhosis, liver failure, and portal hypertension and often requires liver transplantation.

"Monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological.

"Multivalent binding protein" is used herein to refer to a binding protein comprising two or more antigen binding sites (also referred to herein as "antigen binding domains"). A multivalent binding protein is preferably engineered to have three or more antigen binding sites, and is generally not a naturally occurring antibody. The term "multispecific binding protein" refers to a binding protein that can bind two or more related or unrelated targets, including a binding protein capable of binding two or more different epitopes of the same target molecule.

"Predetermined cutoff" and "predetermined level" as used herein refer to an assay cutoff value that is used to assess diagnostic, prognostic, or therapeutic efficacy results by comparing the assay results against the predetermined cutoff/level, where the predetermined cutoff/level already has been linked or associated with various clinical parameters (e.g., presence of disease, stage of disease, severity of disease, progression, non-progression, or improvement of disease, etc.). The disclosure provides exemplary predetermined levels. However, it is well-known that cutoff values may vary depending on the nature of the immunoassay (e.g., antibodies employed, reaction conditions, sample purity, etc.). It further is well within the ordinary skill of one in the art to adapt the disclosure herein for other immunoassays to obtain immunoassay-specific cutoff values for those other immunoassays based on the description provided by this disclosure. Whereas the precise value of the predetermined cutoff/level may vary between assays, the correlations as described herein should be generally applicable.

"Pretreatment reagent," e.g., lysis, precipitation and/or solubilization reagent, as used in a diagnostic assay as described herein is one that lyses any cells and/or solubilizes any analyte that is/are present in a test sample. Pretreatment is not necessary for all samples, as described further herein. Among other things, solubilizing the analyte (i.e., GP73, fragments of GP73, variants of GP73 or any combinations thereof) entails release of the analyte from any endogenous binding proteins present in the sample. A pretreatment reagent may be homogeneous (not requiring a separation step) or heterogeneous (requiring a separation step). With use of a heterogeneous pretreatment reagent, there is removal of any precipitated analyte binding proteins from the test sample prior to proceeding to the next step of the assay. The pretreatment reagent optionally can comprise: (a) one or more solvents and salt, (b) one or more solvents, salt and detergent, (c) detergent, (d) detergent and salt, or (e) any reagent or combination of reagents appropriate for cell lysis and/or solubilization of analyte.

"Quality control reagents" in the context of immunoassays and kits described herein, include, but are not limited to, calibrators, controls, and sensitivity panels. A "calibrator" or "standard" typically is used (e.g., one or more, such as a plurality) in order to establish calibration (standard) curves for interpolation of the concentration of an analyte, such as an antibody or an analyte. Alternatively, a single calibrator, which is near a predetermined positive/negative cutoff, can be used. Multiple calibrators (i.e., more than one calibrator or a varying amount of calibrator(s)) can be used in conjunction to comprise a "sensitivity panel."

A "receiver operating characteristic" curve or "ROC" curve refers to a graphical plot that illustrates the performance of a binary classifier system as its discrimination threshold is varied. It is created by plotting the fraction of true positives out of the positives (TPR=true positive rate) vs. the fraction of false positives out of the negatives (FPR=false positive rate), at various threshold settings. TPR is also known as sensitivity, and FPR is one minus the specificity or true negative rate.

"Recombinant antibody" and "recombinant antibodies" refer to antibodies prepared by one or more steps, including cloning nucleic acid sequences encoding all or a part of one or more monoclonal antibodies into an appropriate expression vector by recombinant techniques and subsequently expressing the antibody in an appropriate host cell. The terms include, but are not limited to, recombinantly produced monoclonal antibodies, chimeric antibodies, humanized antibodies (fully or partially humanized), multi-specific or multi-valent structures formed from antibody fragments, bifunctional antibodies, heteroconjugate Abs, DVD-Ig®s, and other antibodies as described in (i) herein. (Dual-variable domain immunoglobulins and methods for making them are described in Wu, C., et al., Nature Biotechnology, 25:1290-1297 (2007)). The term "bifunctional antibody," as used herein, refers to an antibody that comprises a first arm having a specificity for one antigenic site and a second arm having a specificity for a different antigenic site, i.e., the bifunctional antibodies have a dual specificity.

"Risk assessment," "risk classification," "risk identification," or "risk stratification" of subjects (e.g., patients) as used herein refers to the evaluation of factors including biomarkers, to predict the risk of occurrence of future events including disease onset or disease progression, so that treatment decisions regarding the subject may be made on a more informed basis.

"Sample," "test sample," "specimen," "sample from a subject," and "patient sample" as used herein may be used interchangeable and may be a sample of blood, tissue, urine, serum, plasma, amniotic fluid, cerebrospinal fluid, placental cells or tissue, endothelial cells, leukocytes, or monocytes. The sample can be used directly as obtained from a patient or can be pre-treated, such as by filtration, distillation, extraction, concentration, centrifugation, inactivation of interfering components, addition of reagents, and the like, to modify the character of the sample in some manner as discussed herein or otherwise as is known in the art.

Any cell type, tissue, or bodily fluid may be utilized to obtain a sample. Such cell types, tissues, and fluid may include sections of tissues such as biopsy and autopsy samples, frozen sections taken for histologic purposes, blood (such as whole blood), plasma, serum, sputum, stool, tears, mucus, saliva, bronchoalveolar lavage (BAL) fluid, hair, skin, red blood cells, platelets, interstitial fluid, ocular lens fluid, cerebral spinal fluid, sweat, nasal fluid, synovial fluid, menses, amniotic fluid, semen, etc. Cell types and tissues may also include lymph fluid, ascetic fluid, gynecological fluid, urine, peritoneal fluid, cerebrospinal fluid, a fluid collected by vaginal rinsing, or a fluid collected by vaginal flushing. A tissue or cell type may be provided by removing a sample of cells from an animal, but can also be accomplished by using previously isolated cells (e.g., isolated by another person, at another time, and/or for another purpose). Archival tissues, such as those having treatment or outcome history, may also be used. Protein or nucleotide isolation and/or purification may not be necessary.

"Series of calibrating compositions" refers to a plurality of compositions comprising a known concentration of GP73, wherein each of the compositions differs from the other compositions in the series by the concentration of GP73.

"Solid phase" refers to any material that is insoluble, or can be made insoluble by a subsequent reaction. The solid phase can be chosen for its intrinsic ability to attract and immobilize a capture agent. Alternatively, the solid phase can have affixed thereto a linking agent that has the ability to attract and immobilize the capture agent. For example, the linking agent can include a charged substance that is oppositely charged with respect to the capture agent itself or to a charged substance conjugated to the capture agent. In general, the linking agent can be any binding partner (preferably specific) that is immobilized on (attached to) the solid phase and that has the ability to immobilize the capture agent through a binding reaction. The linking agent enables the indirect binding of the capture agent to a solid phase material before the performance of the assay or during the performance of the assay. For examples, the solid phase can be plastic, derivatized plastic, magnetic, or non-magnetic metal, glass or silicon, including, for example, a test tube, microtiter well, sheet, bead, microparticle, chip, and other configurations known to those of ordinary skill in the art.

"Specific binding" or "specifically binding" as used herein may refer to the interaction of an antibody, a protein, or a peptide with a second chemical species, wherein the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

"Specific binding partner" is a member of a specific binding pair. A specific binding pair comprises two different molecules, which specifically bind to each other through chemical or physical means. Therefore, in addition to antigen and antibody specific binding pairs of common immunoassays, other specific binding pairs can include biotin and avidin (or streptavidin), carbohydrates and lectins, complementary nucleotide sequences, effector and receptor molecules, cofactors and enzymes, enzymes and enzyme inhibitors, and the like. Furthermore, specific binding pairs can include members that are analogs of the original specific binding members, for example, an analyte-analog Immunoreactive specific binding members include antigens, antigen fragments, and antibodies, including monoclonal and polyclonal antibodies as well as complexes and fragments thereof, whether isolated or recombinantly produced.

"Subject" and "patient" as used herein interchangeably refers to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous or rhesus monkey, chimpanzee, etc) and a human). In some embodiments, the subject may be a human or a non-human. The subject or patient may be undergoing other forms of treatment.

"Treat", "treating" or "treatment" are each used interchangeably herein to describe reversing, alleviating, or inhibiting the progress of a disease, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of an antibody or pharmaceutical composition of the present invention to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

"Variant" is used herein to describe a peptide or polypeptide that differs in amino acid sequence by the insertion, deletion, or conservative substitution of amino acids, but retain at least one biological activity. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties. "Variant" also can be used to refer to an antigenically reactive fragment of an anti-GP73 antibody that differs from the corresponding fragment of anti-GP73 antibody in amino acid sequence but is still antigenically reactive and can compete with the corresponding fragment of anti-GP73 antibody for binding with GP73. "Variant" also can be used to describe a polypeptide or a fragment thereof that has been differentially processed, such as by proteolysis, phosphorylation, or other post-translational modification, yet retains its antigen reactivity.

"Vector" is used herein to describe a nucleic acid molecule that can transport another nucleic acid to which it has been linked One type of vector is a "plasmid", which refers to a circular double-stranded DNA loop into which additional DNA segments may be ligated. Another type of vector is a viral vector, wherein additional DNA segments may be ligated into the viral genome. Certain vectors can replicate autonomously in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "expression vectors"). In general, expression vectors of utility in recombinant DNA techniques are often in the form of plasmids. "Plasmid" and "vector" may be used interchangeably as the plasmid is the most commonly used form of vector. However, other forms of expression vectors, such as viral vectors (e.g., replication defective retroviruses, adenoviruses and adeno-associated viruses), which serve equivalent functions, can be used. In this regard, RNA versions of vectors (including RNA viral vectors) may also find use in the context of the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event, however of any latent ambiguity, definitions provided herein take precedent over any dictionary or extrinsic definition. Further, unless otherwise required by context, singular terms shall include pluralities and plural terms shall include the singular.

2. GP73 ANTIBODIES

Provided herein are antibodies for use in methods of detecting and treating diseases, such as liver disease and/or cancer. An isolated antibody that specifically binds to Golgi protein 73 ("GP73") (or fragments thereof) is provided herein, and referred to as "GP73 antibody".

a. Golgi Protein 73 (GP73)

Golgi protein 73 (GP73), also known as "Golgi membrane protein 1", "Golgi phosphoprotein 2" and "Golgi membrane protein GP73", is a protein that processes protein synthesized in the rough endoplasmic reticulum and assists in the transport of protein cargo through the Golgi apparatus. Human GP73 is a 400 amino acid protein encoded by the GOLM1 gene. GP73 is widely expressed in normal epithelial cells from several tissues. Upregulated intracellular GP73 expression enhances its intracellular trafficking through the endosomal pathway, which provides the opportunity for endoproteolytic cleavage of GP73, resulting in the secretion of truncated GP73. GP73 expression is upregulated in response to viral infection but has also been found to be upregulated in hepatocytes from patients with viral and non-viral liver disease. GP73 is overexpressed in prostate cancer and lung adenocarcinoma tissue. Human GP73 may have the following amino acid sequence:

```
MGLGNGRRSMKSPPLVLAALVACIIVLGFNYWIASSRSVDLQTRIMELEGR

VRRAAAERGAVELKKNEFQGELEKQREQLDKIQSSHNFQLESVNKLYQDEK

AVLVNNITTGERLIRVLQDQLKTLQRNYGRLQQDVLQFQKNQTNLERKFSY

DLSQCINQMKEVKEQCEERIEEVTKKGNEAVASRDLSENNDQRQQLQALSE

PQPRLQAAGLPHTEVPQGKGNVLGNSKSQTPAPSSEVVLDSKRQVEKEETN

EIQVVNEEPQRDRLPQEPGREQVVEDRPVGGRGFGGAGELGQTPQVQAALS

VSQENPEMEGPERDQLVIPDGQEEEQEAAGEGRNQQKLRGEDDYNMDENEA

ESETDKQAALAGNDRNIDVFNVEDQKRDTINLLDQREKRNHTL (SEQ ID

NO: 97; GenBank Accession NO: AAF44663).
```

The human GP73 may be a fragment or variant of SEQ ID NO:97. The fragment of GP73 may be between 5 and 400 amino acids, between 10 and 400 amino acids, between 50 and 400 amino acids, between 60 and 400 amino acids, between 65 and 400 amino acids, between 100 and 400 amino acids, between 150 and 400 amino acids, between 100 and 300 amino acids, or between 200 and 300 amino acids in length. The fragment may comprise a contiguous number of amino acids from SEQ ID NO:97.

The fragment of human GP73 may have the following amino acid sequence:

```
                                        (SEQ ID NO: 100)
ELKKNEELKKNEFQGELEKQREQLDKIQSSHNFQLESVNKLYQDEKAVLV

NNITTGERLIRVLQDQLKTLQRNYGRLQQDVLQFQKNQTNLERKFSYDL

SQCINQMKEVKEQCEERIEEVTKKGNEAVASRDLSENNDQRQQLQALSE

PQPRLQAAGLPHTEVPQGKGNVLGNSKSQTPAPSSEVVLDSKRQVEKEE

TNEIQVVNEEPQRDRLPQEPGREQVVEDRPVGGRGEGGAGELGQTPQVQ

AALSVSQENPEMEGPERDQLVIPDGQEEEQEAAGEGRNQQKLRGEDDYN

MDENEAESETDKQAALAGNDRNIDVFNVEDQKRDTINLLDQREKRNHT

L, which correspond to amino acids 63-400 of SEQ

ID NO: 97.
``` b. GP73-Recognizing Antibody

The antibody is an antibody that binds to GP73, a fragment thereof, an epitope of GP73, or a variant thereof. The antibody may be a fragment of the anti-GP73 antibody or a variant or a derivative thereof. The antibody may be a polyclonal or monoclonal antibody. The antibody may be a chimeric antibody, a single chain antibody, an affinity matured antibody, a human antibody, a humanized antibody, a fully human antibody or an antibody fragment, such as a Fab fragment, or a mixture thereof. Antibody fragments or derivatives may comprise F(ab')$_2$, Fv or scFv fragments. The antibody derivatives can be produced by peptidomimetics. Further, techniques described for the production of single chain antibodies can be adapted to produce single chain antibodies.

The anti-GP73 antibodies may be a chimeric anti-GP73 or humanized anti-GP73 antibody. In one embodiment, both the humanized antibody and chimeric antibody are monovalent. In one embodiment, both the humanized antibody and chimeric antibody comprise a single Fab region linked to an Fc region.

Human antibodies may be derived from phage-display technology or from transgenic mice that express human immunoglobulin genes. The human antibody may be generated as a result of a human in vivo immune response and isolated. See, for example, Funaro et al., BMC Biotechnology, 2008(8):85. Therefore, the antibody may be a product of the human and not animal repertoire. Because it is of human origin, the risks of reactivity against self-antigens may be minimized. Alternatively, standard yeast display libraries and display technologies may be used to select and isolate human anti-GP73 antibodies. For example, libraries of naïve human single chain variable fragments (scFv) may be used to select human anti-GP73 antibodies. Transgenic animals may be used to express human antibodies.

Humanized antibodies may be antibody molecules from non-human species antibody that binds the desired antigen having one or more complementarity determining regions (CDRs) from the non-human species and framework regions from a human immunoglobulin molecule.

The antibody is distinguishable from known antibodies in that it possesses different biological function(s) than those known in the art.

(1) Epitope

The antibody may immunospecifically bind to GP73 (SEQ ID NO:97), SEQ ID NO:100, a fragment thereof, or a variant thereof. The antibody may immunospecifically recognize and bind to an epitope peptide of SEQ ID NO:101 (amino acids 307-339 of SEQ ID NO:97), SEQ ID NO: 102 (amino acids 276-287 of SEQ ID NO:97), SEQ ID NO: 103 (amino acids 344-363 of SEQ ID NO:97), or SEQ ID NO: 104 (amino acids 63-96 of SEQ ID NO:97). The antibody may immunospecifically recognize and bind at least three amino acids, at least four amino acids, at least five amino acids, at least six amino acids, at least seven amino acids, at least eight amino acids, at least nine amino acids, or at least ten amino acids within the epitope peptides of SEQ ID NO: 101, SEQ ID NO: 104, SEQ ID NO: 103, or SEQ ID NO: 104. The antibody may immunospecifically recognize and bind to an epitope that has at least three contiguous amino acids, at least four contiguous amino acids, at least five contiguous amino acids, at least six contiguous amino acids, at least seven contiguous amino acids, at least eight contiguous amino acids, at least nine contiguous amino acids, or at least ten contiguous amino acids of the epitope peptides of SEQ ID NO: 101, SEQ ID NO: 104, SEQ ID NO: 103, or SEQ ID NO: 104.

(2) Antibody Binding Characteristics

The antibody may immunospecifically bind to GP73 (SEQ ID NO:97), SEQ ID NO:100, a fragment thereof, or a variant thereof and has a $K_D$ of at least $1.5 \times 10^{-12}$ M, of at least $1.6 \times 10^{-12}$ M, of at least $1.7 \times 10^{-12}$ M, of at least $1.8 \times 10^{-12}$ M, of at least $1.9 \times 10^{-12}$ M, of at least $2.0 \times 10^{-12}$ M, of at least $2.1 \times 10^{-12}$ M, of at least $2.2 \times 10^{-12}$ M, of at least $2.3 \times 10^{-12}$ M, of at least $2.4 \times 10^{-12}$ of at least $2.5 \times 10^{-12}$ of at least $5.0 \times 10^{-12}$ M, of at least $10.0 \times 10^{-12}$ M, of at least $15 \times 10^{-12}$ of at least $50 \times 10^{-12}$, of at least $100 \times 10^{-12}$ M, of at least $500 \times 10^{-12}$ M, of at least $1000 \times 10^{-12}$ M, of at least $2000 \times 10^{-12}$ M, of at least $3000 \times 10^{-12}$ M, of at least $3500 \times 10^{-12}$ M, or has a $K_d$ ranging from about $1.5 \times 10^{-12}$ M to about $3500 \times 10^{-12}$ M, from about $10.0 \times 10^{-12}$ M to about $3500 \times 10^{-12}$ M, from about $25.0 \times 10^{-12}$ M to about $3500 \times 10^{-12}$ M, from about $50.0 \times 10^{-12}$ M to about $3500 \times 10^{-12}$ M, from about $100.0 \times 10^{-12}$ M to about $3500 \times 10^{-12}$ M, from about $150.0 \times 10^{-12}$ M to about $3500 \times 10^{-12}$ M, from about $200 \times 10^{-12}$ M to about $3500 \times 10^{-12}$ M, from about $500 \times 10^{-12}$ M to about $3500 \times 10^{-12}$ M, from about $1000 \times 10^{-12}$ M to about $3500 \times 10^{-12}$ M, from about $1.5 \times 10^{-12}$ M to about $3000 \times 10^{-12}$ M, from about $10.0 \times 10^{-12}$ M to about $3000 \times 10^{-12}$ M, from about $25.0 \times 10^{-12}$ M to about $3000 \times 10^{-12}$ M, from about $50.0 \times 10^{-12}$ M to about $3000 \times 10^{-12}$ M, from about $1.5 \times 10^{-12}$ M to about $1000 \times 10^{-12}$ M, from about $25.0 \times 10^{-12}$ M to about $1000 \times 10^{-12}$ M, from about $50.0 \times 10^{-12}$ M to about $1000 \times 10^{-12}$ M, from about $100.0 \times 10^{-12}$ M to about $1000 \times 10^{-12}$ M, from about $1.5 \times 10^{-12}$ M to about $500 \times 10^{-12}$ M, from about $50 \times 10^{-12}$ M to about $500 \times 10^{-12}$ M, from about $100 \times 10^{-12}$ M to about $500 \times 10^{-12}$ M, from about $1.5 \times 10^{-12}$ M to about $100 \times 10^{-12}$ M, from about $25.0 \times 10^{-12}$ M to about $100 \times 10^{-12}$ M, from about $50.0 \times 10^{-12}$ M to about $100 \times 10^{-12}$ M, from about $1.5 \times 10^{-12}$ M to about $50 = 10^{-12}$ M, from about $10.0 \times 10^{-12}$ M to about $50.0 \times 10^{-12}$ M, or from about from about $25.0 \times 10^{-12}$ M to about $50 \times 10^{-12}$ M. The fragment may be SEQ ID NO:97 or SEQ ID NO:100.

The binding of the antibody to GP73 may be sensitive or insensitive to the presence or absence of a fucose sugar moiety on the GP73 molecule. An antibody that is sensitive to the presence or absence of a fucose sugar moiety on the GP73 molecule means that the antibody's binding affinity to GP73 changes depending on whether a fucose sugar moiety is present or absent on the GP73 molecule. For example, an antibody whose binding is sensitive to the presence or absence of a fucose sugar moiety on the GP73 molecule may have lower binding affinity to GP73 if a fucose sugar moiety is present. Alternatively, an antibody whose binding is sensitive to the presence or absence of a fucose sugar moiety on the GP73 molecule may have lower binding affinity to GP73 if a fucose sugar moiety is absent. An antibody that is insensitive to the presence or absence of a fucose sugar moiety on the GP73 molecule means that the antibody's binding affinity to GP73 does not change if a fucose moiety is present or absent on the GP73 molecule.

(3) Antibody Structure (a) Heavy Chain and Light Chain CDRs

The antibody may immunospecifically bind to GP73 (SEQ ID NO:97), SEQ ID NO:100, a fragment thereof, or a variant thereof and comprise a variable heavy chain (VH) and/or variable light chain (VL) shown in Table 1. The antibody may immunospecifically bind to GP73, a fragment thereof, or a variant thereof, and comprises one or more of the heavy chain or light chain CDR sequences also shown in Table 1. The light chain of the antibody may be a kappa chain or a lambda chain. For example, see Table 1.

TABLE 1

| PROTEIN REGION | SEQ ID NO. | SEQUENCE |
| --- | --- | --- |
| 1B-3440 (VH) | 1 | EVQLVETGGGLVQPKGSLKLSCAASGFTFNTNAMNW VRQAPGKGLEWVARIRTKRYNYTTFYADSVKDRFTIS RDDSQSMLFLQMNNLKTEDTAMYYCVTGGTGTFDY WGQGTTLTVSS |
| 1B-3440 (VH) CDR-H1 | 2 | TNAMN |
| 1B-3440 (VH) CDR-H2 | 3 | RIRTKRYNYTTFYADSVKD |
| 1B-3440 (VH) CDR-H3 | 4 | GGTGTFDY |
| 1B-3440 (VL) | 5 | EIVLTQSPTTMPASPGEKVTFTCSASSGISSNYLHWYQL KPGFSPKLLIYRTSNLASGVPARFSGGGSGTSYSLTIGT MEAEDVATYYCQQGFSIPLTFGAGTKLELKR |
| 1B-3440 (VL) CDR-L1 | 6 | SASSGISSNYLH |
| 1B-3440 (VL) CDR-L2 | 7 | RTSNLAS |
| 1B-3440 (VL) CDR-L3 | 8 | QQGFSIPLT |
| 1B-4971 (VH) | 9 | QVQLQQSGPALVKPGASVKMSCKASGYTFTNYVIHW VKQKPGQGLERIGYIWPYNDGTKFNEKFKGKATLTSD KSSSTAYMELSSLTSEDSAVYYCSSQQLAYWGQGTTL TVSS |
| 1B-4971 (VH) CDR-H1 | 10 | NYVIH |
| 1B-4971 (VH) CDR-112 | 11 | YIWPYNDGTKFNEKFKG |

TABLE 1-continued

| PROTEIN REGION | SEQ ID NO. | SEQUENCE |
|---|---|---|
| 1B-4971 (VH) CDR-H3 | 12 | QQLAY |
| 1B-4971 (VL) | 13 | DVVMTQTPLTLSVTIGQPASISCKSSQSLLYSDGKTYLI WLLQRPGQSPKRLIYLVSKLDSGVPDRFTGSGSGTDFT LRISRVEAEDLGVYYCWQGTHFPYTFGGGTKLEIKR |
| 1B-4971 (VL) CDR-L1 | 14 | KSSQSLLYSDGKTYLI |
| 1B-4971 (VL) CDR-L2 | 15 | LVSKLDS |
| 1B-4971 (VL) CDR-L3 | 16 | WQGTHFPYT |
| 1B-3246 (VH) | 17 | DVKLVESGGGLVKPGGSLKLSCAASGFTFSSYTMSWV RQTPEKRLEWVATISRGGTYIYYPDSVKGRFTISRDNA KNTLYLQMSSLKSEDTAIYYCTREYFSGDTYDYFDYW GQGTTLTVSS |
| 1B-3246 (VH) CDR-H1 | 18 | SYTMS |
| 1B-3246 (VH) CDR-H2 | 19 | TISRGGTYIYYPDSVKG |
| 1B-3246 (VH) CDR-H3 | 20 | EYFSGDTYDYFDY |
| 1B-3246 (VL) | 21 | EIVMTQAAFANPVTLGTSVSISCRSSKSLLHSNGITYLY WYLQKPGQSPQLLIYQMSNLASGVPDRFSSSGSGTDFT LRISRVEAEDVGIYYCAQNLELYTFGGGTKLEIKR |
| 1B-3246 (VL) CDR-L1 | 22 | RSSKSLLHSNGITYL |
| 1B-3246 (VL) CDR-L2 | 23 | QMSNLAS |
| 1B-3246 (VL) CDR-L3 | 24 | AQNLELYT |
| 1B-4863 (VH) | 25 | QVQLKESGPGLVAPSQSLSITCTVSGFSLTSYGVHWVR QSPGKGLEWLGVIWTGGSTNYNSALMSRLSISKDNSE SQVFLKVNSLQTDDTGMYYCARDPGTDYFDYWGQGT TLTVSS |
| 1B-4863 (VH) CDR-H1 | 26 | SYGVH |
| 1B-4863 (VH) CDR-H2 | 27 | VIWTGGSTNYNSALMS |
| 1B-4863 (VH) CDR-H3 | 28 | DPGTDYFDY |
| 1B-4863 (VL) | 29 | DIVMTQSHKFMSTSIGDRVSISCKASQDVSIDVSWYQQ KPGQSPTLLIYSASYRYIGVPDRFTGSGSGTAFTFTISSV QAEDLAIYYCQQHFTTPLTFGAGTKLELKR |
| 1B-4863 (VL) CDR-L1 | 30 | KASQDVSIDVS |
| 1B-4863 (VL) CDR-L2 | 31 | SASYRY |
| 1B-4863 (VL) CDR-L3 | 32 | QQHFTTPLT |
| 1A-3187 (VH) | 33 | QGQLQQSGAELMKPGASVKISCKATGYTIRSYWIEWV KQRPGHGLEWIGEILPGSGNTNYNEKFKGTATFTADTS SNTVYLHLSSLTSEDSAVYYCANGRGSYRYHWFAYW GQGTLVTVSP |
| 1A-3187 (VH) CDR-H1 | 34 | SYWIE |
| 1A-3187 (VH) CDR-H2 | 35 | EILPGSGNTNYNEKFKG |
| 1A-3187 (VH) CDR-H3 | 36 | GRGSYRYHWFAY |
| 1A-3187 (VL) | 37 | DIVLTQSPASLAVSLGQRATISCKASQSVDYDGDSYM NWYQQKPGQPPKVLIYAASNLESGIPARFSGSGSGTDF TLNIHPVEEEDAATYYCQQSNEDPYTFGGGTKLEMKR |
| 1A-3187 (VL) CDR-L1 | 38 | KASQSVDYDGDSYMN |
| 1A-3187 (VL) CDR-L2 | 39 | AASNLES |
| 1A-3187 (VL) CDR-L3 | 40 | QQSNEDPYT |

TABLE 1-continued

| PROTEIN REGION | SEQ ID NO. | SEQUENCE |
|---|---|---|
| 1A-4246 (VH) | 41 | EVMLVESGGGLVKPGGSLKLSCAASGFTFSSYAMSWV RLTPEKRLEWVATISSGSSYTYYPDSVKGRFTISRDNV KSTLYLQMSSLRSEDTAMYYCARNWDGELHYYAMD YWGQGTSVTVSS |
| 1A-4246 (VH) CDR-H1 | 42 | SYAMS |
| 1A-4246 (VH) CDR-H2 | 43 | TISSGSSYTYYPDSVKG |
| 1A-4246 (VH) CDR-H3 | 44 | DGELHYYAMDY |
| 1A-4246 (VL) | 45 | QIVLTQSPAIMSASLGERVTMTCTASSSVSSSYLHWYQ QKPGSSPKLWVYSTSSLASGVPARFSGSGSGTSYSLTIN NMEAEDAATYFCHQYHRSPYTFGGGTKLEIKR |
| 1A-4246 (VL) CDR-L1 | 46 | TASSSVSSSYLH |
| 1A-4246 (VL) CDR-L2 | 47 | STSSLAS |
| 1A-4246 (VL) CDR-L3 | 48 | HQYHRSPYT |

The antibody or variant or derivative thereof may contain one or more amino acid sequences that are greater than 95%, 90%, 85%, 80%, 75%, 70%, 65%, 60%, 55%, or 50% identical to one or more of SEQ ID NOs:1-48. The antibody or variant or derivative thereof may be encoded by one or more nucleic acid sequences that are greater than 95%, 90%, 85%, 80%, 75%, 70%, 65%, 60%, 55%, or 50% identical to one or more of SEQ ID NOs:49-96. Polypeptide identity and homology can be determined, for example, by the algorithm described in the report: Wilbur, W. J. and Lipman, D. J. Proc. Natl. Acad. Sci. USA 80, 726-730 (1983). The herein described antibody, variant, or derivative thereof may be encoded by a nucleic acid that hybridizes under stringent conditions with the complement of one or more of SEQ ID NOs: 17-32. The herein described antibody, variant, or derivative thereof may be encoded by a nucleic acid that hybridizes under highly stringent conditions with the complement of one or more nucleic acids that encode one or more of SEQ ID NOs:1-48.

In one aspect, the isolated antibody specifically binds GP-73 and has a CDR-H1 having the formula: CDR-H1, $X_5$-$X_6$-$X_7$-$X_8$-$X_9$ (SEQ ID NO:108), wherein: $X_5$ is S, N or T; $X_6$ is Y or N; $X_7$ is W, V, G, A or T; $X_8$ is I, V or M; and $X_9$ is E, H, S or N.

In another aspect, the isolated antibody specifically binds GP-73 and has a CDR-H2 having the formula: CDR-H2, $X_{10}$-I-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$X_{27}$ (SEQ ID NO:109), wherein: $X_{10}$ is E, Y, V, T or R; $X_{11}$ is L, W, S or R; $X_{12}$ is P, S, R or T; $X_{13}$ is absent or is K; $X_{14}$ is absent or is R; $X_{15}$ is G, T or Y; $X_{16}$ is S, G or N; $X_{17}$ is G, D, S, T or Y; $X_{18}$ is N, S, Y, G or T; $X_{19}$ is T or I; $X_{20}$ is N, K, Y or F; $X_{21}$ is Y or F; $X_{22}$ is N, P or A; $X_{23}$ is E, S or D; $X_{24}$ is K, A or S; $X_{25}$ is F, L or V; $X_{26}$ is K or M; and $X_{27}$ is G, S or D.

In yet another aspect, the isolated antibody specifically binds GP-73 and has a CDR-H3 having the formula: CDR-H3, $X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-Y (SEQ ID NO:110), wherein: $X_{28}$ is G, Q, D, E or N; $X_{29}$ is R, Q, P, Y, W or G; $X_{30}$ is G, L, F, D or T; $X_{31}$ is S, T, S or G; $X_{32}$ is Y, D, G, E or T; $X_{33}$ is R, Y, D, L or F; $X_{34}$ is Y, F, T or H; $X_{35}$ is H or Y; $X_{36}$ is W, D or Y; $X_{37}$ is F, Y or A; $X_{38}$ is absent or is F or M; and $X_{39}$ is A or D.

In yet another aspect, the isolated antibody specifically binds GP-73 and has a CDR-L1 having the formula: CDR-L1, $X_{40}$-$X_{41}$-S-$X_{42}$-$X_{43}$-$X_{44}$-$X_{45}$-$X_{46}$$X_{47}$-$X_{48}$-$X_{49}$-$X_{50}$-$X_{51}$-$X_{52}$-$X_{53}$-$X_{54}$ (SEQ ID NO:111), wherein: $X_{40}$ is K, T, R or S; $X_{41}$ is A or S; $X_{42}$ is Q, S or K; $X_{43}$ is S or G; $X_{44}$ is V or L; $X_{45}$ is D or L; $X_{46}$ is Y, D or H; $X_{47}$ is absent or S; $X_{48}$ is D, V, N or I; $X_{49}$ is G, V or S; $X_{50}$ is D, K, S or I; $X_{51}$ is S, T, I or N; $X_{52}$ is Y or D; $X_{53}$ is M, L or V; and $X_{54}$ is N, I, S, H or Y.

In still yet another aspect, the isolated antibody specifically binds GP-73 and has a CDR-L2 having the formula: CDR-L2, $X_{55}$-$X_{56}$-S-$X_{57}$-$X_{58}$-$X_{59}$-$X_{60}$ (SEQ ID NO:112), wherein: $X_{55}$ is A, L, S, Q or R; $X_{56}$ is A, V, T or M; $X_{57}$ is N, K, Y or S; $X_{58}$ is S L or R; $X_{59}$ is E, D, Y or A; and $X_{60}$ is S or I.

In yet another aspect, the isolated antibody specifically binds GP-73 and has CDR-L3 having the formula: CDR-L3, $X_{61}$-Q-$X_{62}$-$X_{63}$-$X_{64}$-$X_{65}$-P-$X_{62}$-T (SEQ ID NO:113), wherein: $X_{61}$ is Q, W, H or A; $X_{62}$ is S, G, H, Y or N; $X_{63}$ is N, T, F, H or L; $X_{64}$ is E, H, T, R or S; $X_{65}$ is D, F, T, S, L or I; and $X_{66}$ is Y or L.

In still yet another aspect, the isolated antibody specifically binds GP-73 and has a CDR-H1 having the formula: $X_5$-$X_6$-$X_7$-$X_8$-$X_9$ (SEQ ID NO:108) a CDR-H2 having the formula: $X_{10}$-I-$X_{11}$-$X_{12}$-$X_{13}$-$X_{14}$-$X_{15}$-$X_{16}$-$X_{17}$-$X_{18}$-$X_{19}$-$X_{20}$-$X_{21}$-$X_{22}$-$X_{23}$-$X_{24}$-$X_{25}$-$X_{26}$-$X_{27}$ (SEQ ID NO:109), a CDR-H3 having the formula: $X_{28}$-$X_{29}$-$X_{30}$-$X_{31}$-$X_{32}$-$X_{33}$-$X_{34}$-$X_{35}$-$X_{36}$-$X_{37}$-$X_{38}$-$X_{39}$-Y (SEQ ID NO:110), a CDR-L1 having the formula: $X_{40}$-$X_{41}$-S-$X_{42}$-$X_{43}$-$X_{44}$-$X_{45}$-$X_{46}$$X_{47}$-$X_{48}$-$X_{49}$-$X_{50}$-$X_{51}$-$X_{52}$-$X_{53}$-$X_{54}$ (SEQ ID NO:111), a CDR-L2 having the formula: $X_{55}$-$X_{56}$-S-$X_{57}$-$X_{58}$-$X_{59}$-$X_{60}$ (SEQ ID NO:112) and a CDR-L3 having the formula: $X_{61}$-Q-$X_{62}$-$X_{63}$-$X_{64}$-$X_{65}$-P-$X_{62}$-T (SEQ ID NO:113), wherein: $X_5$ is 5, N or T; $X_6$ is Y or N; $X_7$ is W, V, G, A or T; $X_8$ is I, V or M; $X_9$ is E, H, S or N; $X_{10}$ is E, Y, V, T or R; $X_{11}$ is L, W, S or R; $X_{12}$ is P, S, R or T; $X_{13}$ is absent or is K; $X_{14}$ is absent or is R; $X_{15}$ is G, T or Y; $X_{16}$ is S, G or N; $X_{17}$ is G, D, S, T or Y; $X_{18}$ is N, S, Y, G or T; $X_{19}$ is T or I; $X_{20}$ is N, K, Y or F; $X_{21}$ is Y or F; $X_{22}$ is N, P or A; $X_{23}$ is E, S or D; $X_{24}$ is K, A or S; $X_{25}$ is F, L or V; $X_{26}$ is K or M; $X_{27}$ is G, S or D; $X_{28}$ is G, Q, D, E or N; $X_{29}$ is R, Q, P, Y, W or G; $X_{30}$ is G, L, F, D or T; $X_{31}$ is 5, T, S or G; $X_{32}$ is Y, D, G, E or T; $X_{33}$ is R, Y, D, L or F; $X_{34}$ is Y, F, T or H; $X_{35}$ is H or Y; $X_{36}$ is W, D or Y; $X_{37}$ is F, Y or A; $X_{38}$ is absent or is F or M; $X_{39}$ is A or D; $X_{40}$ is K, T, R or S; $X_{41}$ is A or S; $X_{42}$ is Q, S or K; $X_{43}$ is S or G; $X_{44}$ is V or L; $X_{45}$ is D or L; $X_{46}$ is Y, D or H; $X_{47}$ is absent or S; $X_{48}$ is D, V, N or I; $X_{49}$ is G, V or S; $X_{50}$ is D, K, S or I; $X_{51}$ is S, T, I or N; $X_{52}$ is Y or D; $X_{53}$ is M, L or V; $X_{54}$ is N, I, S, H or Y; $X_{55}$ is A, L, S, Q or R; $X_{56}$ is A, V, T or M; $X_{57}$ is N, K, Y or S; $X_{58}$ is L or R; $X_{59}$ is E, D, Y or A; $X_{60}$ is S or I; $X_{61}$ is Q, W, H or A; $X_{62}$ is S, G, H, Y or N; $X_{63}$ is N, T, F, H or L; $X_{64}$ is E, H, T, R or S; $X_{65}$ is D, F, T, S, L or I; and $X_{66}$ is Y or L.

The antibody may be an IgG, IgE, IgM, IgD, IgA, and IgY molecule class (for example, IgG1, IgG2, IgG3, IgG4, IgA1 and IgA2) or subclass.

(b) Nucleotide Sequence

Provided herein is an isolated nucleic acid encoding an antibody that immunospecifically binds to GP73, a fragment thereof, or a variant thereof. The isolated nucleic acid may comprise a nucleotide sequence that hybridizes, under stringent conditions, to the nucleic acid molecule that encodes an antibody comprising the heavy chain or light chain CDR sequences shown in Table 1. The isolated nucleic acid may comprise a nucleotide sequence shown in Table 2.

TABLE 2

| NUCLEOTIDE | SEQ ID NO. | SEQUENCE |
|---|---|---|
| 1B-3440 (VH) | 49 | gaggtgcagcttgttgagactggtggaggattggtgcagcctaaagggtcattgaaactctcatgt gcagcctctggattcaccttcaataccaatgccatgaactgggtccgccaggctccaggaaaggg tttggaatgggttgctcgcataaggactaaacgttataattatacaacattttatgccgattcagtgaaa gacaggttcaccatctccagagatgattctcaaagcatgctctttctgcaaatgaacaacttgaaaac tgaggacacagccatgtattactgtgtgacaggggggactgggacgtttgactactggggccaag gcaccactctcacagtctcctca |
| 1B-3440 (VH) CDR-H1 | 50 | accaatgccatgaac |
| 1B-3440 (VH) CDR-H2 | 51 | cgcataaggactaaacgttataattatacaacattttatgccgattcagtgaaagac |
| 1B-3440 (VH) CDR-H3 | 52 | ggggggactgggacgtttgactac |
| 1B-3440 (VL) | 53 | gaaattgtactcacccagtctccaaccaccatgcctgcatctcccggggagaaggtcactttcacct gcagtgccagctcaggtataagttccaattacttgcattggtatcagctgaagcaggattctcccct aaactatgatttataggacatccaatctggcttctggagtcccagctcgcttcagtggcggtgggtc tgggacctatactctctcacaattggcaccatggaggctgaagatgttgccacttactattgccagc agggttttagtataccgctcacgttcggtgctgggaccaagctggagctgaaacgg |
| 1B-3440 (VL) CDR-L1 | 54 | agtgccagctcaggtataagttccaattacttgcat |
| 1B-3440 (VL) CDR-L2 | 55 | aggacatccaatctggcttct |
| 1B-3440 (VL) CDR-L3 | 56 | cagcagggttttagtataccgctcacg |
| 1B-4971 (VH) | 57 | caggtccagctgcagcagtctggacctgcgctggtaaagcctggggcttcagtgaagatgtcctg caaggatctggatacacattcactaactatgttatacactgggtgaaacagaagcctgggcaggg ccttgagcggattggatatatttggccttacaatgatggtactaagttcaatgagaaattcaaaggca aggccacactgacttcagacaaatcctccagcacagcctacatggagctcagcagcctgacctct gaggactctgcagtctattactgttcaagtcaacagctcgcctactggggccaaggcaccactctc acagtctcctca |
| 1B-4971 (VH) CDR-H1 | 58 | aactatgttatacac |
| 1B-4971 (VH) CDR-H2 | 59 | tatatttggccttacaatgatggtactaagttcaatgagaaattcaaaggc |
| 1B-4971 (VH) CDR-113 | 60 | caacagctcgcctac |
| 1B-4971 (VL) | 61 | gatgttgtgatgacccagactccactcactttgtcggttaccattggacaaccagcctccatctcttgc aagtcaagtcagagcctcttatatagtgatggaaagacatatttgatttggttgttacagaggccagg ccagtctccaaaagcgcctaatctatctggtgtctaaactggactctggagtccctgacaggttcactg gcagtggatcagggacagatttcacactgagaatcagcagagtggaggctgaggatttgggagtt tattattgttggcaaggtacacattttccgtacacgttcggaggggggaccaagctggaaataaaac gg |
| 1B-4971 (VL) CDR-L1 | 62 | aagtcaagtcagagcctcttatatagtgatggaaagacatatttgatt |
| 1B-4971 (VL) CDR-L2 | 63 | ctggtgtctaaactggactct |
| 1B-4971 (VL) CDR-L3 | 64 | tggcaaggtacacattttccgtacacg |

TABLE 2-continued

| NUCLEOTIDE | SEQ ID NO. | SEQUENCE |
|---|---|---|
| 1B-3246 (VH) | 65 | gacgtgaagctggtggagtctgggggaggcttagtgaagcctggagggtccctgaaactctcctg<br>tgcagcctctggattcactttcagtagctataccatgtatgggttcgccagactccggagaagaga<br>ctggagtgggtcgcaaccattagtcgtggtggtacttacatctactatccagacagtgtgaagggcc<br>gattcaccatctccagagacaatgccaagaacaccctgtacctgcaaatgagcagtctgaagtctg<br>aggacacagccatatattactgtcaagagaatatttctccggtgatacctacgactactttgactatt<br>ggggccaaggcaccactctcacagtctcctca |
| 1B-3246 (VH) CDR-H1 | 66 | agctataccatgtct |
| 1B-3246 (VH) CDR-H2 | 67 | accattagtcgtggtggtacttacatctactatccagacagtgtgaagggc |
| 1B-3246 (VH) CDR-H3 | 68 | gaatatttctccggtgatacctacgactactttgactat |
| 1B-3246 (VL) | 69 | gagattgtgatgacgcaggctgcattcgccaatccagtcactatggaacatcagtttccatctcctg<br>caggtctagtaagagtctcctacatagtaatggcatcacttatttgtactggtatctgcagaagccag<br>gccagtctcctcagctcctgatttatcagatgtccaaccttgcctcaggagtcccagacaggttcagt<br>agcagtgggtcaggaactgatttcacactgagaatcagcagagtggaggctgaggatgggtat<br>ttactactgtgctcaaaatctagaactttacacgttcggaggggggaccaagctggaaataaaacg<br>g |
| 1B-3246 (VL) CDR-L1 | 70 | aggtctagtaagagtctcctacatagtaatggcatcacttatttgtac |
| 1B-3246 (VL) CDR-L2 | 71 | cagatgtccaaccttgcctca |
| 1B-3246 (VL) CDR-L3 | 72 | gctcaaaatctagaactttacacg |
| 1B-4863 (VH) | 73 | caggtgcagctgaaggagtcaggacctggcctggtggcgccctcacagagcctgtccatcacttg<br>cactgtctctgggttttcattaaccagctatggtgtacactgggttcgccagtctccaggaaagggtc<br>tggagtggctgggagtaatatggactggtggaagcacaaattataattcggctctcatgtccagact<br>gagcattagtaaagacaactccgagagccaagttttcttaaaagtgaatagtctgcaaactgatgac<br>acaggcatgtactactgtgccagagatcctgggacggactactttgactactggggccaaggcac<br>cactctcacagtctcctca |
| 1B-4863 (VH) CDR-H1 | 74 | agctatggtgtacac |
| 1B-4863 (VH) CDR-H2 | 75 | gtaatatggactggtggaagcacaaattataattcggctctcatgtcc |
| 1B-4863 (VH) CDR-H3 | 76 | gatcctgggacggactactttgactac |
| 1B-4863 (VL) | 77 | gacattgtgatgacccagtctcacaaattcatgtccacatcaataggagacagggtcagcatctcct<br>gcaaggccagtcaggatgtgagtattgatgtgtcctggtatcaacagaaaccaggacagtctccta<br>cacttctgatttactcggcatcctaccggtacattggagtccctgatcgcttcactggcagtggatctg<br>ggacggattcactttcaccatcagcagtgtccaggctgaagacctggcaatttattactgtcagcaa<br>cattttactactcctctcacgttcggtgctgggaccaagctggagctgaaacgg |
| 1B-4863 (VL) CDR-L1 | 78 | aaggccagtcaggatgtgagtattgatgtgtcc |
| 1B-4863 (VL) CDR-L2 | 79 | tcggcatcctaccggtacatt |
| 1B-4863 (VL) CDR-L3 | 80 | cagcaacattttactactcctctcacg |
| 1A-3187 (VH) | 81 | cagggtcagctgcagcagtctggagctgaactgatgaagcctggggcctcagtgaagatatcctg<br>caaggctactggctacacaatcaggagctactggatagagtgggtaaagcagaggcctggacat<br>ggccttgagtggattggagagattttacctggaagtggtaatactaattataatgagaagttcaaggg<br>gacggccacattcactgcagatacatcctccaacacagtctatttgcacctcagcagcctgacatct<br>gaggactctgccgtctattactgcaaacgggaggggctcctataggtaccactggtttgcttact<br>ggggccaagggactctggtcactgtctctcca |
| 1A-3187 (VH) CDR-H1 | 82 | agctactggatagag |
| 1A-3187 (VH) CDR-H2 | 83 | gagattttacctggaagtggtaatactaattataatgagaagttcaagggg |

TABLE 2-continued

| NUCLEOTIDE | SEQ ID NO. | SEQUENCE |
|---|---|---|
| 1A-3187 (VH) CDR-H3 | 84 | gggaggggctcctataggtaccactggtttgcttac |
| 1A-3187 (VL) | 85 | gacattgtgctgacccaatctccagatattggctgtgtctctagggcagagggccaccatctcctg caaggccagccaaagtgttgattatgatggtgatagttatatgaactggtaccaacagaaaccagg acagccacccaaagtcctcatctatgctgcatccaatctagaatctgggatcccagccaggtttagt ggcagtgggtctgggacagacttcaccctcaacatccatcctgtggaggaggaggatgctgcaac ctattactgtcagcaaagtaatgaggatccgtacacgttcggaggggggaccaagctggaaatga aacgg |
| 1A-3187 (VL) CDR-L1 | 86 | aaggccagccaaagtgttgattatgatggtgatagttatatgaac |
| 1A-3187 (VL) CDR-L2 | 87 | gctgcatccaatctagaatct |
| 1A-3187 (VL) CDR-L3 | 88 | cagcaaagtaatgaggatccgtacacg |
| 1A-4246 (VH) | 89 | gaagtgatgctggtggagtctggggggaggcttagtgaagcctggagggtccctgaaactctcctg tgcagcctctggattcactttcagtagctatgccatgtcttgggttcgcctgactccggagaagagg ctggagtgggtcgcaaccattagtagtggtagcagttacacctactatccagacagtgtgaagggg cgattcaccatctccagagacaatgtcaagagcaccctgtacctgcaaatgagcagtctgaggtct gaggacacggccatgtattactgtgcaaggaactgggacggggaactccattactatgctatgga ctactggggtcaaggaacctcagtcaccgtctcctca |
| 1A-4246 (VH) CDR-H1 | 90 | agctatgccatgtct |
| 1A-4246 (VH) CDR-H2 | 91 | accattagtagtggtagcagttacacctactatccagacagtgtgaagggg |
| 1A-4246 (VH) CDR-H3 | 92 | aactgggacggggaactccattactatgctatggactac |
| 1A-4246 (VL) | 93 | caaattgttctcacccagtctccagcaatcatgtctgcatctctaggggaacgggtcaccatgacct gcactgccagctcaagtgtaagttccagttacttgcactggtaccagcagaagccaggatcctccc ccaaactctgggtttatagcacatccagcctggatctggagtcccagctcgcttcagtggcagtgg gtctgggacctatactctctcacaatcaacaacatggaggctgaagatgctgccacttatttctgcc accagtatcatcgttccccgtacacgttcggaggggggaccaagctggaaataaaacgg |
| 1A-4246 (VL) CDR-L1 | 94 | actgccagctcaagtgtaagttccagttacttgcac |
| 1A-4246 (VL) CDR-L2 | 95 | agcacatccagcctggcttct |
| 1A-4246 (VL) CDR-L3 | 96 | caccagtatcatcgttccccgtacacg | c. Antibody Preparation/Production

Antibodies may be prepared by any of a variety of techniques. In general, antibodies can be produced by cell culture techniques, including the generation of monoclonal antibodies via conventional techniques, or via transfection of antibody genes, heavy chains, and/or light chains into suitable bacterial or mammalian cell hosts, in order to allow for the production of antibodies, wherein the antibodies may be recombinant. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980)), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human GP73) and the other heavy and light chain are specific for an antigen other than human GP73 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

Methods of preparing monoclonal antibodies involve the preparation of immortal cell lines capable of producing antibodies having the desired specificity. Such cell lines may be produced from spleen cells obtained from an immunized animal. The animal may be immunized with GP73 or a fragment and/or variant thereof. For example, any of SEQ ID NO:97, SEQ ID NO:98, SEQ ID NO:99, SEQ ID NO:100, SEQ ID NO:101, SEQ ID NO:102, SEQ ID NO:103, SEQ ID NO:104, a fragment of SEQ ID NO:97, SEQ ID NO:98, SEQ ID NO:99, SEQ ID NO:100, SEQ ID NO:101, SEQ ID NO:102, SEQ ID NO:103, or SEQ ID NO:104, or a variant of SEQ ID NO:97, SEQ ID NO:98, SEQ ID NO:99, SEQ ID NO:100, SEQ ID NO:101, SEQ ID NO:102, SEQ ID NO:103, or SEQ ID NO:104 may be used to immunize the animal. The peptide used to immunize the animal may comprise amino acids encoding human Fc, for example the fragment crystallizable region or tail region of human antibody. The spleen cells may then be immortalized by, for example, fusion with a myeloma cell fusion partner. A variety of fusion techniques may be employed. For example, the spleen cells and myeloma cells may be combined with a nonionic detergent for a few minutes and then plated at low density on a selective medium that supports that growth of hybrid cells, but not myeloma cells. One such technique uses hypoxanthine, aminopterin, thymidine (HAT) selection. Another technique includes eletrofusion. After a sufficient time, usually about 1 to 2 weeks, colonies of hybrids are observed. Single colonies are selected and their culture supernatants tested for binding activity against the polypeptide. Hybridomas having high reactivity and specificity may be used.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. Affinity chromatography is an example of a method that can be used in a process to purify the antibodies.

The proteolytic enzyme papain preferentially cleaves IgG molecules to yield several fragments, two of which (the F(ab) fragments) each comprise a covalent heterodimer that includes an intact antigen-binding site. The enzyme pepsin is able to cleave IgG molecules to provide several fragments, including the F(ab')2 fragment, which comprises both antigen-binding sites.

The Fv fragment can be produced by preferential proteolytic cleavage of an IgM, and on rare occasions IgG or IgA immunoglobulin molecules. The Fv fragment may be derived using recombinant techniques. The Fv fragment includes a non-covalent VH::VL heterodimer including an antigen-binding site that retains much of the antigen recognition and binding capabilities of the native antibody molecule.

The antibody, antibody fragment, or derivative may comprise a heavy chain and a light chain complementarity determining region ("CDR") set, respectively interposed between a heavy chain and a light chain framework ("FR") set which provide support to the CDRs and define the spatial relationship of the CDRs relative to each other. The DR set may contain three hypervariable regions of a heavy or light chain V region. Proceeding from the N-terminus of a heavy or light chain, these regions are denoted as "CDR1," "CDR2," and "CDR3," respectively. An antigen-binding site, therefore, may include six CDRs, comprising the CDR set from each of a heavy and a light chain V region. A polypeptide comprising a single CDR, (e.g., a CDR1, CDR2, or CDR3) may be referred to as a "molecular recognition unit." Crystallographic analyses of antigen-antibody complexes have demonstrated that the amino acid residues of CDRs form extensive contact with bound antigen, wherein the most extensive antigen contact is with the heavy chain CDR3. Thus, the molecular recognition units may be primarily responsible for the specificity of an antigen-binding site. In general, the CDR residues are directly and most substantially involved in influencing antigen binding.

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, yeast or the like, display library); e.g., as available from various commercial vendors such as Cambridge Antibody Technologies (Cambridgeshire, UK), MorphoSys (Martinsried/Planegg, Del.), Biovation (Aberdeen, Scotland, UK) BioInvent (Lund, Sweden), using methods known in the art. See U.S. Pat. Nos. 4,704,692; 5,723,323; 5,763,192; 5,814,476; 5,817,483; 5,824,514; 5,976,862. Alternative methods rely upon immunization of transgenic animals (e.g., SCID mice, Nguyen et al. (1997) Microbiol. Immunol. 41:901-907; Sandhu et al. (1996) Crit. Rev. Biotechnol. 16:95-118; Eren et al. (1998) Immunol. 93:154-161) that are capable of producing a repertoire of human antibodies, as known in the art and/or as described herein. Such techniques, include, but are not limited to, ribosome display (Hanes et al. (1997) Proc. Natl. Acad. Sci. USA, 94:4937-4942; Hanes et al. (1998) Proc. Natl. Acad. Sci. USA, 95:14130-14135); single cell antibody producing technologies (e.g., selected lymphocyte antibody method ("SLAM") (U.S. Pat. No. 5,627,052, Wen et al. (1987) J. Immunol. 17:887-892; Babcook et al. (1996) Proc. Natl. Acad. Sci. USA 93:7843-7848); gel microdroplet and flow cytometry (Powell et al. (1990) Biotechnol. 8:333-337; One Cell Systems, (Cambridge, Mass.).; Gray et al. (1995) J. Imm. Meth. 182:155-163; Kenny et al. (1995) Bio/Technol. 13:787-790); B-cell selection (Steenbakkers et al. (1994) Molec. Biol. Reports 19:125-134 (1994)).

An affinity matured antibody may be produced by any one of a number of procedures that are known in the art. For example, see Marks et al., BioTechnology, 10: 779-783 (1992) describes affinity maturation by VH and VL domain shuffling. Random mutagenesis of CDR and/or framework residues is described by Barbas et al., Proc. Nat. Acad. Sci. USA, 91: 3809-3813 (1994); Schier et al., Gene, 169: 147-155 (1995); Yelton et al., J. Immunol., 155: 1994-2004 (1995); Jackson et al., J. Immunol., 154(7): 3310-3319 (1995); Hawkins et al, J. Mol. Biol., 226: 889-896 (1992). Selective mutation at selective mutagenesis positions and at contact or hypermutation positions with an activity enhancing amino acid residue is described in U.S. Pat. No. 6,914, 128 B1.

Antibody variants of the present invention can also be prepared using delivering a polynucleotide encoding an antibody of this invention to a suitable host such as to provide transgenic animals or mammals, such as goats, cows, horses, sheep, and the like, that produce such antibodies in their milk. These methods are known in the art and are described for example in U.S. Pat. Nos. 5,827,690; 5,849,992; 4,873,316; 5,849,992; 5,994,616; 5,565,362; and 5,304,489.

Antibody variants also can be prepared by delivering a polynucleotide of this invention to provide transgenic plants and cultured plant cells (e.g., but not limited to tobacco, maize, and duckweed) that produce such antibodies, specified portions or variants in the plant parts or in cells cultured therefrom. For example, Cramer et al. (1999) Curr. Top. Microbol. Immunol. 240:95-118 and references cited therein, describe the production of transgenic tobacco leaves expressing large amounts of recombinant proteins, e.g., using an inducible promoter. Transgenic maize have been used to express mammalian proteins at commercial production levels, with biological activities equivalent to those produced in other recombinant systems or purified from natural sources. See, e.g., Hood et al., Adv. Exp. Med. Biol. (1999) 464:127-147 and references cited therein. Antibody variants have also been produced in large amounts from transgenic plant seeds including antibody fragments, such as single chain antibodies (scFv's), including tobacco seeds and potato tubers. See, e.g., Conrad et al. (1998) Plant Mol. Biol. 38:101-109 and reference cited therein. Thus, antibodies of the present invention can also be produced using transgenic plants, according to known methods.

Antibody derivatives can be produced, for example, by adding exogenous sequences to modify immunogenicity or reduce, enhance or modify binding, affinity, on-rate, off-rate, avidity, specificity, half-life, or any other suitable characteristic. Generally, part or all of the non-human or human CDR sequences are maintained while the non-human sequences of the variable and constant regions are replaced with human or other amino acids.

Small antibody fragments may be diabodies having two antigen-binding sites, wherein fragments comprise a heavy chain variable domain (VH) connected to a light chain variable domain (VL) in the same polypeptide chain (VH VL). See for example, EP 404,097; WO 93/11161; and Hollinger et al., (1993) Proc. Natl. Acad. Sci. USA 90:6444-6448. By using a linker that is too short to allow pairing between the two domains on the same chain, the domains are forced to pair with the complementary domains of another chain and create two antigen-binding sites. See also, U.S. Pat. No. 6,632,926 to Chen et al. which is hereby incorporated by reference in its entirety and discloses antibody variants that have one or more amino acids inserted into a hypervariable region of the parent antibody and a binding affinity for a target antigen which is at least about two fold stronger than the binding affinity of the parent antibody for the antigen.

The antibody may be a linear antibody. The procedure for making a linear antibody is known in the art and described in Zapata et al. (1995) Protein Eng. 8(10):1057-1062. Briefly, these antibodies comprise a pair of tandem Fd segments (VH-CH1-VH-CH1) which form a pair of antigen binding regions. Linear antibodies can be bispecific or monospecific.

The antibodies may be recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

It may be useful to detectably or therapeutically label the antibody. Methods for conjugating antibodies to these agents are known in the art. For the purpose of illustration only, antibodies can be labeled with a detectable moiety such as a radioactive atom, a chromophore, a fluorophore, or the like. Such labeled antibodies can be used for diagnostic techniques, either in vivo, or in an isolated test sample. Antibodies can also be conjugated, for example, to a pharmaceutical agent, such as chemotherapeutic drug or a toxin. They can be linked to a cytokine, to a ligand, to another antibody. Suitable agents for coupling to antibodies to achieve an anti-tumor effect include cytokines, such as interleukin 2 (IL-2) and Tumor Necrosis Factor (TNF); photosensitizers, for use in photodynamic therapy, including aluminum (III) phthalocyanine tetrasulfonate, hematoporphyrin, and phthalocyanine; radionuclides, such as iodine-131 (131I), yttrium-90 (90Y), bismuth-212 (212Bi), bismuth-213 (213Bi), technetium-99m (99mTc), rhenium-186 (186Re), and rhenium-188 (188Re); antibiotics, such as doxorubicin, adriamycin, daunorubicin, methotrexate, daunomycin, neocarzinostatin, and carboplatin; bacterial, plant, and other toxins, such as diphtheria toxin, pseudomonas exotoxin A, staphylococcal enterotoxin A, abrin-A toxin, ricin A (deglycosylated ricin A and native ricin A), TGF-alpha toxin, cytotoxin from chinese cobra (naja naja atra), and gelonin (a plant toxin); ribosome inactivating proteins from plants, bacteria and fungi, such as restrictocin (a ribosome inactivating protein produced by Aspergillus restrictus), saporin (a ribosome inactivating protein from Saponaria officinalis), and RNase; tyrosine kinase inhibitors; ly207702 (a difluorinated purine nucleoside); liposomes containing anti cystic agents (e.g., antisense oligonucleotides, plasmids which encode for toxins, methotrexate, etc.); and other antibodies or antibody fragments, such as F(ab).

The antibodies can be sequenced and replicated by recombinant or synthetic means. They also can be further sequenced down to the linear sequence of nucleotides that encode them. Accordingly, this invention provides these polynucleotides, alone or in combination with a carrier, vector or host cell as described above, that encode a sequence of an antibody of this invention.

Antibody production via the use of hybridoma technology, the selected lymphocyte antibody method (SLAM), transgenic animals, and recombinant antibody libraries is described in more detail below.

(1) Anti-GP73 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, second edition, (Cold Spring Harbor Laboratory Press, Cold Spring Harbor, 1988); Hammerling, et al., In Monoclonal Antibodies and T-Cell Hybridomas, (Elsevier, N.Y., 1981). It is also noted that the term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

In an embodiment, the present invention provides methods of generating monoclonal antibodies as well as antibodies produced by the method. The method may comprise culturing a hybridoma cell secreting an antibody of the invention wherein, preferably, the hybridoma is generated by fusing splenocytes isolated from an animal, e.g., a rat or a mouse, immunized with GP73 with myeloma cells and then screening the hybridomas resulting from the fusion for hybridoma clones that secrete an antibody able to bind a polypeptide of the invention. Briefly, rats can be immunized with a GP73 antigen. In a preferred embodiment, the GP73 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks; however, a single administration of the polypeptide may also be used.

After immunization of an animal with a GP73 antigen, antibodies and/or antibody-producing cells may be obtained from the animal. An anti-GP73 antibody-containing serum is obtained from the animal by bleeding or sacrificing the animal. The serum may be used as it is obtained from the animal, an immunoglobulin fraction may be obtained from the serum, or the anti-GP73 antibodies may be purified from the serum. Serum or immunoglobulins obtained in this manner are polyclonal, thus having a heterogeneous array of properties.

Once an immune response is detected, e.g., antibodies specific for the antigen GP73 are detected in the rat serum, the rat spleen is harvested and splenocytes isolated. The splenocytes are then fused by well-known techniques to any suitable myeloma cells, for example, cells from cell line SP20 available from the American Type Culture Collection (ATCC, Manassas, Va., US). Hybridomas are selected and cloned by limited dilution. The hybridoma clones are then assayed by methods known in the art for cells that secrete antibodies capable of binding GP73. Ascites fluid, which generally contains high levels of antibodies, can be generated by immunizing rats with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using GP73, or a portion thereof, or a cell expressing GP73. In a preferred embodiment, the initial screening is performed using an enzyme-linked immunosorbent assay (ELISA) or a radioimmunoassay (RIA), preferably an ELISA. An example of ELISA screening is provided in PCT Publication No. WO 00/37504.

Anti-GP73 antibody-producing hybridomas are selected, cloned, and further screened for desirable characteristics, including robust hybridoma growth, high antibody production, and desirable antibody characteristics. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, hybridomas are rat hybridomas. In another embodiment, hybridomas are produced in a non-human, non-rat species such as mice, sheep, pigs, goats, cattle, or horses. In yet another preferred embodiment, the hybridomas are human hybridomas, in which a human non-secretory myeloma is fused with a human cell expressing an anti-GP73 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce two identical Fab fragments) or pepsin (to produce an $F(ab')_2$ fragment). A F(ab')2 fragment of an IgG molecule retains the two antigen-binding sites of the larger ("parent") IgG molecule, including both light chains (containing the variable light chain and constant light chain regions), the CH1 domains of the heavy chains, and a disulfide-forming hinge region of the parent IgG molecule. Accordingly, an F(ab')2 fragment is still capable of crosslinking antigen molecules like the parent IgG molecule.

(2) Anti-GP73 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052; PCT Publication No. WO 92/02551; and Babcook et al., Proc. Natl. Acad. Sci. USA, 93: 7843-7848 (1996). In this method, single cells secreting antibodies of interest, e.g., lymphocytes derived from any one of the immunized animals are screened using an antigen-specific hemolytic plaque assay, wherein the antigen GP73, a subunit of GP73, or a fragment thereof, is coupled to sheep red blood cells using a linker, such as biotin, and used to identify single cells that secrete antibodies with specificity for GP73. Following identification of antibody-secreting cells of interest, heavy- and light-chain variable region cDNAs are rescued from the cells by reverse transcriptase-PCR (RT-PCR) and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example, by panning the transfected cells to isolate cells expressing antibodies to GP73. The amplified immunoglobulin sequences further can be manipulated in vitro, such as by in vitro affinity maturation method. See, for example, PCT Publication No. WO 97/29131 and PCT Publication No. WO 00/56772.

(3) Anti-GP73 Monoclonal Antibodies Using Transgenic Animals

In another embodiment of the invention, antibodies are produced by immunizing a non-human animal comprising some, or all, of the human immunoglobulin locus with a GP73 antigen. In an embodiment, the non-human animal is a XENOMOUSE® transgenic mouse, an engineered mouse strain that comprises large fragments of the human immunoglobulin loci and is deficient in mouse antibody production. See, e.g., Green et al., Nature Genetics, 7: 13-21 (1994) and U.S. Pat. Nos. 5,916,771; 5,939,598; 5,985,615; 5,998, 209; 6,075,181; 6,091,001; 6,114,598; and 6,130,364. See also PCT Publication Nos. WO 91/10741; WO 94/02602; WO 96/34096; WO 96/33735; WO 98/16654; WO 98/24893; WO 98/50433; WO 99/45031; WO 99/53049; WO 00/09560; and WO 00/37504. The XENOMOUSE® transgenic mouse produces an adult-like human repertoire of fully human antibodies, and generates antigen-specific human monoclonal antibodies. The XENOMOUSE® transgenic mouse contains approximately 80% of the human antibody repertoire through introduction of megabase sized, germline configuration YAC fragments of the human heavy chain loci and x light chain loci. See Mendez et al., Nature Genetics, 15: 146-156 (1997), Green and Jakobovits, J. Exp. Med., 188: 483-495 (1998), the disclosures of which are hereby incorporated by reference.

(4) Anti-GP73 Monoclonal Antibodies Using Recombinant Antibody Libraries

In vitro methods also can be used to make the antibodies of the invention, wherein an antibody library is screened to identify an antibody having the desired GP73-binding specificity. Methods for such screening of recombinant antibody libraries are well known in the art and include methods described in, for example, U.S. Pat. No. 5,223,409 (Ladner et al.); PCT Publication No. WO 92/18619 (Kang et al.); PCT Publication No. WO 91/17271 (Dower et al.); PCT Publication No. WO 92/20791 (Winter et al.); PCT Publication No. WO 92/15679 (Markland et al.); PCT Publication No. WO 93/01288 (Breitling et al.); PCT Publication No. WO 92/01047 (McCafferty et al.); PCT Publication No. WO 92/09690 (Garrard et al.); Fuchs et al., Bio/Technology, 9: 1369-1372 (1991); Hay et al., Hum. Antibod. Hybridomas, 3: 81-85 (1992); Huse et al., Science, 246: 1275-1281 (1989); McCafferty et al., Nature, 348: 552-554 (1990); Griffiths et al., EMBO J., 12: 725-734 (1993); Hawkins et al., J. Mol. Biol., 226: 889-896 (1992); Clackson et al., Nature, 352: 624-628 (1991); Gram et al., Proc. Natl. Acad. Sci. USA, 89: 3576-3580 (1992); Garrard et al., Bio/Technology, 9: 1373-1377 (1991); Hoogenboom et al., Nucl. Acids Res., 19: 4133-4137 (1991); Barbas et al., Proc. Natl. Acad. Sci. USA, 88: 7978-7982 (1991); US Patent Application Publication No. 2003/0186374; and PCT Publication No. WO 97/29131, the contents of each of which are incorporated herein by reference.

The recombinant antibody library may be from a subject immunized with GP73, or a portion of GP73. Alternatively, the recombinant antibody library may be from a naive subject, i.e., one who has not been immunized with GP73, such as a human antibody library from a human subject who has not been immunized with human GP73. Antibodies of the invention are selected by screening the recombinant antibody library with the peptide comprising human GP73 to thereby select those antibodies that recognize GP73. Methods for conducting such screening and selection are well known in the art, such as described in the references in the preceding paragraph. To select antibodies of the invention having particular binding affinities for GP73, such as those that dissociate from human GP73 with a particular $K_{off}$ rate constant, the art-known method of surface plasmon resonance can be used to select antibodies having the desired $K_{off}$ rate constant. To select antibodies of the invention having a particular neutralizing activity for hGP73, such as those with a particular $IC_{50}$, standard methods known in the art for assessing the inhibition of GP73 activity may be used.

In one aspect, the invention pertains to an isolated antibody, or an antigen-binding portion thereof, that binds human GP73. Preferably, the antibody is a neutralizing antibody. In various embodiments, the antibody is a recombinant antibody or a monoclonal antibody.

For example, antibodies of the present invention can also be generated using various phage display methods known in the art. In phage display methods, functional antibody domains are displayed on the surface of phage particles which carry the polynucleotide sequences encoding them. Such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv, or disulfide stabilized Fv antibody domains recombinantly fused to either the phage gene III or gene VIII protein. Examples of phage display methods that can be used to make the antibodies of the present invention include those disclosed in Brinkmann et al., J. Immunol. Methods, 182: 41-50 (1995); Ames et al., J. Immunol. Methods, 184:177-186 (1995); Kettleborough et al., Eur. J. Immunol., 24: 952-958 (1994); Persic et al., Gene, 187: 9-18 (1997); Burton et al., Advances in Immunology, 57: 191-280 (1994); PCT Publication No. WO 92/01047; PCT Publication Nos. WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; and 5,969,108.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab', and F(ab')$_2$ fragments can also be employed using methods known in the art such as those disclosed in PCT publication No. WO 92/22324; Mullinax et al., BioTechniques, 12(6): 864-869 (1992); Sawai et al., Am. J. Reprod. Immunol., 34: 26-34 (1995); and Better et al., Science, 240: 1041-1043 (1988). Examples of techniques which can be used to produce single-chain Fvs and antibodies include those described in U.S. Pat. Nos. 4,946,778 and 5,258,498; Huston et al., Methods in Enzymology, 203: 46-88 (1991); Shu et al., Proc. Natl. Acad. Sci. USA, 90: 7995-7999 (1993); and Skerra et al., Science, 240: 1038-1041 (1988).

Alternative to screening of recombinant antibody libraries by phage display, other methodologies known in the art for screening large combinatorial libraries can be applied to the identification of antibodies of the invention. One type of alternative expression system is one in which the recombinant antibody library is expressed as RNA-protein fusions, as described in PCT Publication No. WO 98/31700 (Szostak and Roberts), and in Roberts and Szostak, Proc. Natl. Acad. Sci. USA, 94: 12297-12302 (1997). In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence (s), or by other methods for affinity maturation in vitro of recombinant antibodies, as described above. A preferred example of this methodology, is PROfusion display technology.

In another approach, the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed in U.S. Pat. No. 6,699,658 (Wittrup et al.) incorporated herein by reference.

d. Production of Recombinant GP73 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection, and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Exemplary mammalian host cells for expressing the recombinant antibodies of the invention include Chinese Hamster Ovary (CHO cells) (including dhfr-CHO cells, described in Urlaub and Chasin, Proc. Natl. Acad. Sci. USA, 77: 4216-4220 (1980), used with a DHFR selectable marker, e.g., as described in Kaufman and Sharp, J. Mol. Biol., 159: 601-621 (1982), NS0 myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention (i.e., binds human GP73) and the other heavy and light chain are specific for an antigen other than human GP73 by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells, and recover the antibody from the culture medium. Still further, the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

(1) Humanized Antibody

The humanized antibody may be an antibody or a variant, derivative, analog or portion thereof which immunospecifically binds to an antigen of interest and which comprises a framework (FR) region having substantially the amino acid sequence of a human antibody and a complementary determining region (CDR) having substantially the amino acid sequence of a non-human antibody. The humanized antibody may be from a non-human species antibody that binds the desired antigen having one or more complementarity determining regions (CDRs) from the non-human species and framework regions from a human immunoglobulin molecule.

As used herein, the term "substantially" in the context of a CDR refers to a CDR having an amino acid sequence at least 90%, at least 95%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. According to one aspect, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or of a heavy chain.

The humanized antibody can be selected from any class of immunoglobulins, including IgM, IgG, IgD, IgA and IgE, and any isotype, including without limitation IgG 1, IgG2, IgG3, and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In one embodiment, such mutations, however, will not be extensive. Usually, at least 90%, at least 95%, at least 98%, or at least 99% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

The humanized antibody may be designed to minimize unwanted immunological response toward rodent anti-human antibodies, which limits the duration and effectiveness of therapeutic applications of those moieties in human recipients. The humanized antibody may have one or more amino acid residues introduced into it from a source that is non-human. These non-human residues are often referred to as "import" residues, which are typically taken from a variable domain. Humanization may be performed by substituting hypervariable region sequences for the corresponding sequences of a human antibody. Accordingly, such "humanized" antibodies are chimeric antibodies wherein substantially less than an intact human variable domain has been substituted by the corresponding sequence from a non-human species. For example, see U.S. Pat. No. 4,816,567, the contents of which are herein incorporated by reference. The humanized antibody may be a human antibody in which some hypervariable region residues, and possibly some FR residues are substituted by residues from analogous sites in rodent antibodies. Humanization or engineering of antibodies of the present invention can be performed using any known method, such as but not limited to those described in U.S. Pat. Nos. 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; and 4,816,567.

The humanized antibody may retain high affinity for GP73 and other favorable biological properties. The humanized antibody may be prepared by a process of analysis of the parental sequences and various conceptual humanized products using three-dimensional models of the parental and humanized sequences. Three-dimensional immunoglobulin models are commonly available. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristics, such as increased affinity for GP73, is achieved. In general, the hypervariable region residues may be directly and most substantially involved in influencing antigen binding.

As an alternative to humanization, human antibodies (also referred to herein as "fully human antibodies") can be generated. For example, it is possible to isolate human antibodies from libraries via PROfusion and/or yeast related technologies. It is also possible to produce transgenic animals (e.g. mice that are capable, upon immunization, of producing a full repertoire of human antibodies in the absence of endogenous immunoglobulin production. For example, the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. The humanized or fully human antibodies may be prepared according to the methods described in U.S. Pat. Nos. 5,770,429; 5,833,985; 5,837,243; 5,922,845; 6,017,517; 6,096,311; 6,111,166; 6,270,765; 6,303,755; 6,365,116; 6,410,690; 6,682,928; and 6,984,720, the contents each of which are herein incorporated by reference.

e. Anti-GP73 Antibodies

Anti-GP73 antibodies may be generated using the techniques described above. The anti-GP73 antibody may be a 1B-3440 monoclonal antibody, a 1B-4971 monoclonal antibody, a 1B-3246 monoclonal antibody, a 1B-4863 monoclonal antibody, a 1A-3187 monoclonal antibody, a 1A-4246 monoclonal antibody, or antibody fragments thereof.

(1) 1B-3440

As used herein, "1B-3440" or "mAb 1B-3440" refers to a monoclonal antibody produced by hybridoma cell line that was made using RBF/DnJ mice strain that was immunized with recombinant GP73. The spleen cells of the mice were fused with mouse myeloma cell line NS/0 myeloma cells.

1B-3440 binds to an epitope on GP73 that is different from the epitopes that 1B-4971, 1B-3246, 1B-4863, 1A-3187, and 1A-4246 bind. 1B-3440 recognizes the epitope peptide of SEQ ID NO: 67. 1B-3440 has a binding affinity ($K_D$) for GP73 of $9.1 \times 10^{-11}$ M. 1B-3440 has a heavy chain amino acid sequence of SEQ ID NO: 1, which is encoded by a nucleotide sequence of SEQ ID NO: 49, and a light chain amino acid sequence of SEQ ID NO: 5, which is encoded by a nucleotide sequence of SEQ ID NO: 53. 1B-3440 includes CDR-H1 (SEQ ID NO: 2), CDR-H2 (SEQ ID NO: 3), and CDR-H3 (SEQ ID NO: 4) and CDR-L1 (SEQ ID NO: 6), CDR-L2 (SEQ ID NO: 7), and CDR-L3 (SEQ ID NO: 8), which are encoded by nucleotide sequences of SEQ ID NOs: 50-52 and 54-56, respectively.

(2) 1B-4971

As used herein, "1B-4971" or "mAb 1B-4971" refers to a monoclonal antibody produced by hybridoma cell line that was made using RBF/DnJ mice strain that was immunized with recombinant GP73. The spleen cells of the mice were fused with mouse myeloma cell line NS/0 myeloma cells.

1B-4971 binds to an epitope on GP73 that is different from the epitopes that 1B-3440, 1B-3246, 1B-4863, 1A-3187, and 1A-4246 bind. 1B-4971 recognizes the epitope peptide of SEQ ID NO: 65. 1B-4971 has a binding affinity ($K_D$) for GP73 of $2.0 \times 10^{-12}$ M. 1B-4971 has a heavy chain amino acid sequence of SEQ ID NO: 9, which is encoded by a nucleotide sequence of SEQ ID NO: 57, and a light chain amino acid sequence of SEQ ID NO: 13, which is encoded by a nucleotide sequence of SEQ ID NO: 61. 1B-3440 includes CDR-H1 (SEQ ID NO: 10), CDR-H2 (SEQ ID NO: 11), and CDR-H3 (SEQ ID NO: 12) and CDR-L1 (SEQ ID NO: 14), CDR-L2 (SEQ ID NO: 15), and CDR-L3 (SEQ ID NO: 16), which are encoded by nucleotide sequences of SEQ ID NOs: 58-60 and 62-64, respectively.

(3) 1B-3246

As used herein, "1B-3246" or "mAb 1B-3246" refers to a monoclonal antibody produced by hybridoma cell line that was made using RBF/DnJ mice strain that was immunized with recombinant GP73. The spleen cells of the mice were fused with mouse myeloma cell line NS/0 myeloma cells.

1B-3246 binds to an epitope on GP73 that is different from the epitopes that 1B-3440, 1B-4971, 1B-4863, 1A-3187, and 1A-4246 bind. 1B-3246 recognizes the epitope peptide of SEQ ID NO: 66. 1B-3246 has a binding affinity ($K_D$) for GP73 of $7.9 \times 10^{-11}$ M. 1B-3246 has a heavy chain amino acid sequence of SEQ ID NO: 17, which is encoded by a nucleotide sequence of SEQ ID NO: 65, and a light chain amino acid sequence of SEQ ID NO: 21, which is encoded by a nucleotide sequence of SEQ ID NO: 69. 1B-3246 includes CDR-H1 (SEQ ID NO: 18), CDR-H2 (SEQ ID NO: 19), and CDR-H3 (SEQ ID NO: 20) and CDR-L1 (SEQ ID NO: 22), CDR-L2 (SEQ ID NO: 23), and CDR-L3 (SEQ ID NO: 24), which are encoded by nucleotide sequences of SEQ ID NOs: 66-68 and 70-72, respectively.

(4) 1B-4863

As used herein, "1B-4863" or "mAb 1B-4863" refers to a monoclonal antibody produced by hybridoma cell line that was made using RBF/DnJ mice strain that was immunized with recombinant GP73. The spleen cells of the mice were fused with mouse myeloma cell line NS/0 myeloma cells.

1B-4863 binds to an epitope on GP73 that is different from the epitopes that 1B-3440, 1B-4971, 1B-3246, 1A-3187, and 1A-4246 bind. 1B-4863 has a binding affinity ($K_D$) for GP73 of $1.2 \times 10^{-10}$ M. 1B-4863 has a heavy chain amino acid sequence of SEQ ID NO: 25, which is encoded by a nucleotide sequence of SEQ ID NO: 73, and a light chain amino acid sequence of SEQ ID NO: 29, which is encoded by a nucleotide sequence of SEQ ID NO: 77. 1B-4863 includes CDR-H1 (SEQ ID NO: 26), CDR-H2 (SEQ ID NO: 27), and CDR-H3 (SEQ ID NO: 28) and CDR-L1 (SEQ ID NO: 30), CDR-L2 (SEQ ID NO: 31), and CDR-L3 (SEQ ID NO: 32), which are encoded by nucleotide sequences of SEQ ID NOs: 74-76 and 78-80, respectively.

(5) 1A-3187

As used herein, "1A-3187" or "mAb 1A-3187" refers to a monoclonal antibody produced by hybridoma cell line that was made using CAF1/J mice strain that was immunized with recombinant GP73. The spleen cells of the mice were fused with mouse myeloma cell line NS/0 myeloma cells.

1A-3187 binds to an epitope on GP73 that is different from the epitopes that 1B-3440, 1B-4971, 1B-3246, 1B-4863, and 1A-4246 bind. 1A-3187 recognizes the epitope peptide of SEQ ID NO: 68. 1A-3187 has a binding affinity ($K_D$) for GP73 of $2.0 \times 10^{-9}$ M. 1A-3187 has a heavy chain amino acid sequence of SEQ ID NO: 33, which is encoded by a nucleotide sequence of SEQ ID NO: 81, and a light chain amino acid sequence of SEQ ID NO: 37, which is encoded by a nucleotide sequence of SEQ ID NO: 85. 1A-3187 includes CDR-H1 (SEQ ID NO: 34), CDR-H2 (SEQ ID NO: 35), and CDR-H3 (SEQ ID NO: 36) and CDR-L1 (SEQ ID NO: 38), CDR-L2 (SEQ ID NO: 39), and CDR-L3 (SEQ ID NO: 40), which are encoded by nucleotide sequences of SEQ ID NOs: 82-84 and 86-88, respectively.

(6) 1A-4246

As used herein, "1A-4246" or "mAB 1A-4246" refers to a monoclonal antibody produced by hybridoma cell line that was made using CAF1/J mice strain that was immunized with recombinant GP73. The spleen cells of the mice were fused with mouse myeloma cell line NS/0 myeloma cells.

1A-4246 binds to an epitope on GP73 that is different from the epitopes that 1B-3440, 1B-4971, 1B-3246, 1B-4863, and 1A-3187 bind. 1A-4246 recognizes the epitope peptide of SEQ ID NO: 67. 1A-4246 has a binding affinity ($K_D$) for GP73 of $3.8 \times 10^{-9}$ M. 1A-4246 has a heavy chain amino acid sequence of SEQ ID NO: 41, which is encoded by a nucleotide sequence of SEQ ID NO: 89, and a light chain amino acid sequence of SEQ ID NO: 45, which is encoded by a nucleotide sequence of SEQ ID NO: 93. 1A-4246 includes CDR-H1 (SEQ ID NO: 42), CDR-H2 (SEQ ID NO: 43), and CDR-H3 (SEQ ID NO: 44) and CDR-L1 (SEQ ID NO: 46), CDR-L2 (SEQ ID NO: 47), and CDR-L3 (SEQ ID NO: 48), which are encoded by nucleotide sequences of SEQ ID NOs: 90-92 and 94-96, respectively.

3. PHARMACEUTICAL COMPOSITIONS

The antibody may be a component in a pharmaceutical composition. The pharmaceutical composition may also contain a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which activity of a targeted GP73 is detrimental. In a further embodiment, the prophylactic or therapeutic agents are known to be useful for, or have been, or are currently being used in the prevention, treatment, management, or amelioration of a disorder, or one or more symptoms thereof. In accordance with these embodiments, the composition may further comprise of a carrier, diluent, or excipient.

The antibodies of the invention can be incorporated into pharmaceutical compositions suitable for administration to a subject. Typically, the pharmaceutical composition comprises an antibody of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives, or buffers, which enhance the shelf life or effectiveness of the antibody.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidurala administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO97/32572; WO97/44013; WO98/31346; and WO99/66903, each of which is incorporated herein by reference in their entireties. In one embodiment, an antibody of the invention or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention is administered locally to the affected area to a subject to prevent, treat, manage, and/or ameliorate a disorder or a symptom thereof.

In another embodiment, the antibody can be delivered in a controlled release or sustained release system. In one embodiment, a pump may be used to achieve controlled or sustained release (see Langer, supra; Sefton, 1987, CRC Crit. Ref Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of the therapies of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. Nos. 5,679,377; 5,916,597; 5,912,015; 5,989,463; 5,128,326; PCT Publication No. WO99/15154; and PCT Publication No. WO99/20253. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a particular embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in Medical Applications of Controlled Release, supra, vol. 2, pp. 115-138 (1984)).

Controlled release systems are discussed in the review by Langer (1990, Science 249:1527-1533). Any technique known to one of skill in the art can be used to produce sustained release formulations comprising one or more antibodies of the invention. See, e.g., U. S. Pat. No. 4,526,938, PCT publication WO91/05548, PCT publication WO96/20698, Ning et al., 1996, "Intratumoral Radioimmunotheraphy of a Human Colon Cancer Xenograft Using a Sustained-Release Gel," Radiotherapy & Oncology 39:179-189; Song et al., 1995, "Antibody Mediated Lung Targeting of Long-Circulating Emulsions," PDA Journal of Pharmaceutical Science & Technology 50:372-397; Cleek et al., 1997, "Biodegradable Polymeric Carriers for a bFGF Antibody for Cardiovascular Application," Pro. Intl. Symp. Control. Rel. Bioact. Mater. 24:853-854; and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entireties.

In a specific embodiment, where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle. Moisturizers or humectants can also be added to pharmaceutical compositions and dosage forms if desired. Examples of such additional ingredients are well-known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebuliser, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985, 320; 5, 985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, an antibody of the invention and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the antibodies, or pharmaceutical compositions, of the invention is packaged in a hermetically sealed container such as an ampoule or sachette indicating the quantity of the antibody. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies of the invention can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies of the invention prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions. (See International Appln. Publication No. WO 04/078140 and U.S. Patent Appln. Publication No. US2006104968, incorporated herein by reference.)

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Compositions can be in the form of injectable or infusible solutions, such as compositions similar to those used for passive immunization of humans with other antibodies. In one embodiment, the antibody is administered by intravenous infusion or injection. In another embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., a binding protein, e.g. an antibody, of the present invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, methods of preparation comprise vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies of the present invention can be administered by a variety of methods known in the art. For many therapeutic applications, the route/mode of administration may be subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

In certain embodiments, an antibody of the invention may be orally administered, for example, with an inert diluent or an assimilable edible carrier. The antibody (and other ingredients, if desired) may also be enclosed in a hard or soft shell gelatin capsule, compressed into tablets, or incorporated directly into the subject's diet. For oral therapeutic administration, the antibody may be incorporated with excipients and used in the form of ingestible tablets, buccal tablets, troches, capsules, elixirs, suspensions, syrups, wafers, and the like. To administer an antibody of the invention by other than parenteral administration, it may be necessary to coat the antibody with, or co-administer the antibody with, a material to prevent its inactivation.

In certain embodiments, an antibody of the invention is linked to a half-life extending vehicle known in the art. Such vehicles include, but are not limited to, the Fc domain, polyethylene glycol, and dextran. Such vehicles are described, e.g., in U.S. Application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody of the invention that mediates a prophylactic or therapeutic effect.

Any of the methods for gene therapy available in the art can be used according to the present invention. For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, Science 260:926-932 (1993); and Morgan and Anderson, 1993, Ann. Rev. Biochem. 62:191-217; May, 1993, TIBTECH 11(5):155-215. Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990). Detailed description of various methods of gene therapy are disclosed in US20050042664 A1 which is incorporated herein by reference.

Antibodies of the invention can be used alone or in combination to treat diseases or conditions associated with liver disease and/or cancers, or any other disease or condition associated with GP73. It should further be understood that the combinations are those combinations useful for their intended purpose.

The pharmaceutical compositions may include a "therapeutically effective amount" or a "prophylactically effective amount" of an antibody. A "therapeutically effective amount" refers to an amount effective, at dosages and for periods of time necessary, to achieve the desired therapeutic result. A therapeutically effective amount of the antibody may be determined by a person skilled in the art and may vary according to factors such as the disease state, age, sex, and weight of the individual, and the ability of the antibody to elicit a desired response in the individual. A therapeutically effective amount is also one in which toxic or detrimental effects, if any, of the antibody are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of the antibody is a dose of between 0.1 and 200 mg/kg, for example between 0.1 and 10 mg/kg. The therapeutically or prophylactically effective amount of the antibody may be between 1 and 200 mg/kg, 10 and 200 mg/kg, 20 and 200 mg/kg, 50 and 200 mg/kg, 75 and 200 mg/kg, 100 and 200 mg/kg, 150 and 200 mg/kg, 50 and 100 mg/kg, 5 and 10 mg/kg, or 1 and 10 mg/kg. It is to be noted that dosage values may vary with the type and severity of the condition to be alleviated. Further, the antibody dose may be determined by a person skilled in the art and may vary according to factors such as the disease state, age, sex, and weight of the individual, and the ability of the antibody to elicit a desired response in the individual. The dose is also one in which toxic or detrimental effects, if any, of the antibody are outweighed by the therapeutically beneficial effects. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

4. GP73 DETECTION

The present invention also is directed to a method of detecting and measuring GP73 or fucosylated GP73 in a sample from a subject using the GP73 antibodies described above to bind to different GP73 or fucosylated GP73 epitopes. The method includes (a) obtaining a biological sample from a subject, (b) contacting the biological sample with a capture antibody, which binds to an epitope on GP73

(or GP73 fragment) or fucosylated GP73 (or fucosylated GP73 fragment) to form a capture antibody-GP73 antigen complex, (c) contacting the capture antibody-GP73 or or fucosylated GP73 antigen complex with a detection antibody which includes a detectable label and binds to an epitope on GP73 or fucosylated GP73 that is not bound by the capture antibody, to form a capture antibody-GP73 or fucosylated GP73 antigen-detection antibody, and (d) determining the presence, amount or concentration of GP73 or fucosylated GP73 in the biological sample based on the signal generated by the detectable label in the capture antibody-GP73 or fucosylated GP73 antigen-detection antibody complex.

The present invention is further directed to a method of detecting and measuring fucosylated GP73 or fucosylated GP73 in a sample from a subject using the GP73 antibodies describe above. The binding of the GP73 antibodies may or may not be sensitive to fucosylation of GP73. The method includes (a) contacting the test sample with at least one capture binding protein, wherein the capture binding protein binds to a region of GP73 (or a fragment of GP73) or fucosylated GP73 (or a fragment of fucosylated GP73) to form a capture binding protein-GP73 or fucosylated GP73 complex; (b) contacting the capture binding protein-GP73 or fucosylated GP73 complex with at least one detection binding protein comprising a detectable label, wherein the detection binding protein binds to a region of GP73 or fucosylated GP73 that is not bound by the capture binding protein and forms a capture binding protein-GP73 or fucosylated GP73-detection binding protein complex; and (c) determining the GP73 or fucosylated GP73 concentration in the test sample based on the signal generated by the detectable label in the capture binding protein-GP73 or fucosylated GP73-detection binding protein complex formed in (b). The capture binding protein comprises a protein, antibody or antibody fragment whose binding to GP73 or fucosylated GP73 is sensitive to the presence or absence of a fucose sugar moiety on GP73 or fucosylated GP73 and the detection binding protein comprises a protein, antibody or antibody fragment whose binding to GP73 or fucosylated GP73 is insensitive to the presence or absence of a fucose sugar moiety on GP73 or fucosylated GP73. Alternatively, the capture binding protein comprises a protein, antibody or antibody fragment whose binding to GP73 or fucosylated GP73 is insensitive to the presence or absence of a fucose sugar moiety on GP73 or fucosylated GP73 and the detection binding protein comprises a protein, antibody or antibody fragment whose binding to GP73 or fucosylated GP73 is sensitive to the presence or absence of a fucose sugar moiety on GP73 or fucosylated GP73.

The present invention is further directed to a method for diagnosing a disease in a subject based on the GP73 (or GP73 fragment) levels or fucosylated GP73 (or fucosylated GP73 fragment) levels in a sample from the subject. The method includes the steps of (a) obtaining a biological sample from a subject, (b) determining the level of GP73 or fucosylated GP73 in the biological sample, (c) comparing the level of GP73 or fucosylated GP73 in the biological sample to a reference level of GP73 or fucosylated GP73, (d) identifying the subject as having a disease if the level of GP73 or fucosylated GP73 in the biological sample is greater than the reference level of GP73 or fucosylated GP73, and (e) administering a treatment regimen to the subject identified as having disease.

Levels of at least 0.05 ng/mL, 0.06 ng/mL, 0.07 ng/mL, 0.08 ng/mL, 0.09 ng/mL, 0.10 ng/mL, 0.11 ng/mL, 0.12 ng/mL, 0.13 ng/mL, 0.14 ng/mL, 0.15 ng/mL, 0.16 ng/mL, 0.17 ng/mL, 0.18 ng/mL, 0.19 ng/mL, 0.20 ng/mL, 0.25 ng/mL, 0.30 ng/mL, 0.35 ng/mL, 0.40 ng/mL, 0.45 ng/mL, 0.50 ng/mL, 0.55 ng/mL, 1 ng/mL, 5 ng/mL, 10 ng/mL, 15 ng/mL, 20 ng/mL, 21 ng/mL, 22 ng/mL, 23 ng/mL, 24 ng/mL, 25 ng/mL, 26 ng/mL, 27 ng/mL, 28 ng/mL, 29 ng/mL, or 30 ng/mL of GP73 (or GP73 fragment) or fucosylated GP73 (or fucosylated GP73 fragment) in a biological sample may be detected.

Ranges of GP73 and fucosylated GP73 detection have at least 5%, 10%, 25%, 50%, 75%, 100%, 110%, 120%, 130%, 140%, 150%, 160%, 170%, 180%, 190%, 200%, 210%, 220%, 230%, 240%, 250%, 260%, 270%, 280%, 290%, 300%, 400%, or 500% improved range size compared to other commercially available GP73 or fucosylated GP73 immunoassays.

Ranges of about 0 ng/mL to about 30 ng/mL, about 0.05 ng/mL to about 30 ng/mL, about 0.06 ng/mL to about 30 ng/mL, about 0.07 ng/mL to about 30 ng/mL, about 0.08 ng/mL to about 30 ng/mL, about 0.09 ng/mL to about 30 ng/mL, about 0.095 ng/mL to about 30 ng/mL, about 0.10 ng/mL to about 30 ng/mL, about 0.105 ng/mL to about 30 ng/mL, about 0.11 ng/mL to about 30 ng/mL, about 0.12 ng/mL to about 30 ng/mL, about 0.13 ng/mL to about 30 ng/mL, about 0.14 ng/mL to about 30 ng/mL, about 0.15 ng/mL to about 30 ng/mL, about 0.20 ng/mL to about 30 ng/mL, about 1.00 ng/mL to about 30, about 0 ng/mL to about 27.5 ng/mL, 0.05 ng/mL to about 27.5 ng/mL, 0.06 ng/mL to about 27.5 ng/mL, 0.07 ng/mL to about 27.5 ng/mL, 0.08 ng/mL to about 27.5 ng/mL, 0.09 ng/mL to about 27.5 ng/mL, 0.095 ng/mL to about 27.5 ng/mL, 0.10 ng/mL to about 27.5 ng/mL, 0.105 ng/mL to about 27.5 ng/mL, 0.11 ng/mL to about 27.5 ng/mL, 0.12 ng/mL to about 27.5 ng/mL, 0.13 ng/mL to about 27.5 ng/mL, 0.14 ng/mL to about 27.5 ng/mL, 0.15 ng/mL to about 27.5 ng/mL, 0.20 ng/mL to about 27.5 ng/mL, 1.00 ng/mL to about 27.5 ng/mL, about 0 ng/mL to about 26 ng/mL, about 0.05 ng/mL to about 26 ng/mL, 0.06 ng/mL to about 26 ng/mL, 0.07 ng/mL to about 26 ng/mL, 0.08 ng/mL to about 26 ng/mL, 0.09 ng/mL to about 26 ng/mL, 0.095 ng/mL to about 26 ng/mL, 0.10 ng/mL to about 26 ng/mL, 0.105 ng/mL to about 26 ng/mL, 0.11 ng/mL to about 26 ng/mL, 0.12 ng/mL to about 26 ng/mL, 0.13 ng/mL to about 26 ng/mL, 0.14 ng/mL to about 26 ng/mL, 0.15 ng/mL to about 26 ng/mL, 0.20 ng/mL to about 26 ng/mL, 1.00 ng/mL to about 26 ng/mL, about 0 ng/mL to about 25 ng/mL, 0.05 ng/mL to about 25 ng/mL, 0.06 ng/mL to about 25 ng/mL, 0.07 ng/mL to about 25 ng/mL, 0.08 ng/mL to about 25 ng/mL, 0.09 ng/mL to about 25 ng/mL, 0.095 ng/mL to about 25 ng/mL, 0.10 ng/mL to about 25 ng/mL, 0.105 ng/mL to about 25 ng/mL, 0.11 ng/mL to about 25 ng/mL, 0.12 ng/mL to about 25 ng/mL, 0.13 ng/mL to about 25 ng/mL, 0.14 ng/mL to about 25 ng/mL, 0.15 ng/mL to about 25 ng/mL, 0.20 ng/mL to about 25 ng/mL, 1.00 ng/mL to about 25 ng/mL, about 0 ng/mL to about 24 ng/mL, 0.05 ng/mL to about 24 ng/mL, 0.06 ng/mL to about 24 ng/mL, 0.07 ng/mL to about 24 ng/mL, 0.08 ng/mL to about 24 ng/mL, 0.09 ng/mL to about 24 ng/mL, 0.095 ng/mL to about 24 ng/mL, 0.10 ng/mL to about 24 ng/mL, 0.105 ng/mL to about 24 ng/mL, 0.11 ng/mL to about 24 ng/mL, 0.12 ng/mL to about 24 ng/mL, 0.13 ng/mL to about 24 ng/mL, 0.14 ng/mL to about 24 ng/mL, 0.15 ng/mL to about 24 ng/mL, 0.20 ng/mL to about 24 ng/mL, 1.00 ng/mL to about 24 ng/mL, about 0 ng/mL to about 22.5 ng/mL, 0.05 ng/mL to about 22.5 ng/mL, 0.06 ng/mL to about 22.5 ng/mL, 0.07 ng/mL to about 22.5 ng/mL, 0.08 ng/mL to about 22.5 ng/mL, 0.09 ng/mL to about 22.5 ng/mL, 0.095 0 ng/mL to about 22.5 ng/mL, 0.10 ng/mL to about 22.5 ng/mL, 0.105 ng/mL to about 22.5 ng/mL, 0.11 ng/mL to about 22.5 ng/mL, 0.12 ng/mL to about 22.5 ng/mL, 0.13 ng/mL to about 22.5 ng/mL, 0.14 ng/mL to about 22.5 ng/mL, 0.15 ng/mL to about 22.5 ng/mL, 0.20 ng/mL to about 22.5 ng/mL, 1.00 ng/mL to about 22.5 ng/Ml, about 0 ng/mL to about 20 ng/mL, 0.05 ng/mL to about 20 ng/mL, 0.06 ng/mL to about 20 ng/mL, 0.07 ng/mL to about 20 ng/mL, 0.08 ng/mL to about 20 ng/mL, 0.09 ng/mL to about 20 ng/mL, 0.095 ng/mL to about 20 ng/mL, 0.10 ng/mL to about 20 ng/mL, 0.105 ng/mL to about 20 ng/mL, 0.11 ng/mL to about 20 ng/mL, 0.12 ng/mL to about 20 ng/mL, 0.13 ng/mL to about 20 ng/mL, 0.14 ng/mL to about 20 ng/mL, 0.15 ng/mL to about 20 ng/mL, 0.20 ng/mL to about 20 ng/mL, 1.00 ng/mL to about 20 ng/mL, about 0 ng/mL to about 15 ng/mL, 0.05 ng/mL to about 15 ng/mL, 0.06 ng/mL to about 15 ng/mL, 0.07 ng/mL to about 15 ng/mL, 0.08 ng/mL to about 15 ng/mL, 0.09 ng/mL to about 15 ng/mL, 0.095 ng/mL to about 15 ng/mL, 0.10 ng/mL to about 15 ng/mL, 0.105 ng/mL to about 15 ng/mL, 0.11 ng/mL to about 15 ng/mL, 0.12 ng/mL to about 15 ng/mL, 0.13 ng/mL to about 15 ng/mL, 0.14 ng/mL to about 15 ng/mL, 0.15 ng/mL to about 15 ng/mL, 0.20 ng/mL to about 15 ng/mL, or 1.00 ng/mL to about 15 ng/mL of GP73 or fucosylated GP73 may be detected.

a. Immunoassay

GP73 and fucosylated GP73, and/or peptides or fragments thereof, i.e., GP73 and fucosylated GP73 fragments, may be analyzed using the antibodies described above in an immunoassay. The presence or amount of GP73 or fucosylated GP73 can be determined using antibodies and detecting specific binding to GP73 or fucosylated GP73. For example, the antibody, or antibody fragment thereof, may specifically bind to GP73 or fucosylated GP73. If desired, one or more of the antibodies can be used in combination with one or more commercially available monoclonal/polyclonal antibodies. Such antibodies are available from companies such as R&D Systems, Inc. (Minneapolis, Minn.) and Enzo Life Sciences International, Inc. (Plymouth Meeting, Pa.).

The presence or amount of GP73 or fucosylated GP73 present in a body sample may be readily determined using an immunoassay, such as sandwich immunoassay (e.g., monoclonal-polyclonal sandwich immunoassays, including radioisotope detection (radioimmunoassay (RIA)) and enzyme detection (enzyme immunoassay (EIA) or enzyme-linked immunosorbent assay (ELISA) (e.g., Quantikine ELISA assays, R&D Systems, Minneapolis, Minn.)). A chemiluminescent microparticle immunoassay, in particular one employing the ARCHITECT® automated analyzer (Abbott Laboratories, Abbott Park, Ill.), is an example of a preferred immunoassay. Other methods include, for example, mass spectrometry and immunohistochemistry (e.g. with sections from tissue biopsies) using GP73 antibodies (monoclonal, polyclonal, chimeric, humanized, human etc) or antibody fragments thereof against GP73. Other methods of detection include those described in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792, each of which is hereby incorporated by reference in its entirety. Specific immunological binding of the antibody to the GP73 can be detected via direct labels, such as fluorescent or luminescent tags, metals and radionuclides attached to the antibody or via indirect labels, such as alkaline phosphatase or horseradish peroxidase.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and processed quickly through washes and detection steps to generate a measurable signal, such as a colored spot.

A heterogeneous format may be used. For example, after the test sample is obtained from a subject, a first mixture is prepared. The mixture contains the test sample being assessed for GP73 or fucosylated GP73 and a first specific binding partner, wherein the first specific binding partner and any GP73 or fucosylated GP73 contained in the test sample form a first specific binding partner-GP73 or fucosylated GP73 antigen complex. The first specific binding partner may be an anti-GP73 antibody that binds to an epitope having an amino acid sequence comprising at least three contiguous (3) amino acids of SEQ ID NO: 97. The order in which the test sample and the first specific binding partner are added to form the mixture is not critical. The first specific binding partner may be immobilized on a solid phase. The solid phase used in the immunoassay (for the first specific binding partner and, optionally, the second specific binding partner) can be any solid phase known in the art, such as, but not limited to, a magnetic particle, a bead, a test tube, a microtiter plate, a cuvette, a membrane, a scaffolding molecule, a film, a filter paper, a disc, and a chip.

After the mixture containing the first specific binding partner-GP73 or fucosylated GP73 antigen complex is formed, any unbound GP73 or fucosylated GP73 is removed from the complex using any technique known in the art. For example, the unbound GP73 or fucosylated GP73 can be removed by washing. Desirably, however, the first specific binding partner is present in excess of any GP73 or fucosylated GP73 present in the test sample, such that all GP73 or fucosylated GP73 that is present in the test sample is bound by the first specific binding partner.

After any unbound GP73 or fucosylated GP73 is removed, a second specific binding partner is added to the mixture to form a first specific binding partner-GP73 or fucosylated GP73 antigen-second specific binding partner complex. The second specific binding partner may be an anti-GP73 or fucosylated GP73 antibody that binds to an epitope having an amino acid sequence comprising at least three contiguous (3) amino acids of SEQ ID NO: 33. Moreover, the second specific binding partner is labeled with or contains a detectable label as described above.

The use of immobilized antibodies or antibody fragments thereof may be incorporated into the immunoassay. The antibodies may be immobilized onto a variety of supports, such as magnetic or chromatographic matrix particles, the surface of an assay plate (such as microtiter wells), pieces of a solid substrate material, and the like. An assay strip can be prepared by coating the antibody or plurality of antibodies in an array on a solid support. This strip can then be dipped into the test biological sample and processed quickly through washes and detection steps to generate a measurable signal, such as a colored spot.

(1) Sandwich ELISA

The Sandwich ELISA measures the amount of antigen between two layers of antibodies (i.e., at least one capture antibody) and a detection antibody (i.e. at least one detection antibody). The capture antibody and the detection antibody bind to different epitopes on the antigen, e.g., GP73 or fucosylated GP73. Desirably, binding of the capture antibody to an epitope does not interfere with binding of the detection antibody to an epitope. Either monoclonal or polyclonal antibodies may be used as the capture and detection antibodies in the sandwich ELISA.

Generally, at least two antibodies are employed to separate and quantify GP73 or fucosylated GP73 in a test sample. More specifically, the at least two antibodies bind to certain epitopes of GP73 or fucosylated GP73 forming an immune complex which is referred to as a "sandwich". One or more antibodies can be used to capture the GP73 or fucosylated GP73 in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, the binding of an antibody to its epitope desirably is not diminished by the binding of any other antibody in the assay to its respective epitope. Antibodies are selected so that the one or more first antibodies brought into contact with a test sample suspected of containing GP73 or fucosylated GP73 do not bind to all or part of an epitope recognized by the second or subsequent antibodies, thereby interfering with the ability of the one or more second detection antibodies to bind to the GP73 or fucosylated GP73.

The antibodies may be used as a first antibody in said immunoassay. The antibody immunospecifically binds to epitopes on GP73 or fucosylated GP73. In addition to the antibodies of the present invention, said immunoassay may comprise a second antibody that immunospecifically binds to epitopes that are not recognized or bound by the first antibody.

A test sample suspected of containing GP73 or fucosylated GP73 can be contacted with at least one first capture antibody (or antibodies) and at least one second detection antibodies either simultaneously or sequentially. In the sandwich assay format, a test sample suspected of containing GP73 or fucosylated GP73 is first brought into contact with the at least one first capture antibody that specifically binds to a particular epitope under conditions which allow the formation of a first antibody-GP73 or fucosylated GP73 antigen complex. If more than one capture antibody is used, a first multiple capture antibody-GP73 or fucosylated GP73 antigen complex is formed. In a sandwich assay, the antibodies, preferably, the at least one capture antibody, are used in molar excess amounts of the maximum amount of GP73 or fucosylated GP73 expected in the test sample. For example, from about 5 µg/ml to about 1 mg/ml of antibody per ml of microparticle coating buffer may be used.

(a) Anti-GP73 Capture Antibody

Optionally, prior to contacting the test sample with the at least one first capture antibody, the at least one first capture antibody can be bound to a solid support which facilitates the separation the first antibody-GP73 or fucosylated GP73 antigen complex from the test sample. Any solid support known in the art can be used, including but not limited to, solid supports made out of polymeric materials in the forms of wells, tubes, or beads. The antibody (or antibodies) can be bound to the solid support by adsorption, by covalent bonding using a chemical coupling agent or by other means known in the art, provided that such binding does not interfere with the ability of the antibody to bind GP73 or fucosylated GP73. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing GP73 or GP73 or fucosylated GP73 is incubated in order to allow for the formation of a first capture antibody (or multiple antibody)-GP73 or fucosylated GP73 antigen complex. The incubation can be carried out at a pH of from about 4.5 to about 10.0, at a temperature of from about 2° C. to about 45° C., and for a period from at least about one (1) minute to about eighteen (18) hours, from about 2-6 minutes, or from about 3-4 minutes.

(b) Detection Antibody

After formation of the first/multiple capture antibody-GP73 or fucosylated GP73 antigen complex, the complex is then contacted with at least one second detection antibody (under conditions that allow for the formation of a first/multiple antibody-GP73 or fucosylated GP73 antigen-second antibody complex). If the first antibody-GP73 or fucosylated GP73 or fucosylated GP73 antigen complex is contacted with more than one detection antibody, then a first/multiple capture antibody-GP73 or fucosylated GP73 antigen-multiple antibody detection complex is formed. As with first antibody, when the at least second (and subsequent) antibody is brought into contact with the first antibody-GP73 or fucosylated GP73 antigen complex, a period of incubation under conditions similar to those described above is required for the formation of the first/multiple antibody-GP73 or fucosylated GP73 antigen-second/multiple antibody complex. Preferably, at least one second antibody contains a detectable label. The detectable label can be bound to the at least one second antibody prior to, simultaneously with or after the formation of the first/multiple antibody-GP73 or fucosylated GP73 antigen-second/multiple antibody complex. Any detectable label known in the art can be used.

Chemiluminescent assays can be performed in accordance with the methods described in Adamczyk et al., Anal. Chim. Acta 579(1): 61-67 (2006). While any suitable assay format can be used, a microplate chemiluminometer (Mithras LB-940, Berthold Technologies U.S.A., LLC, Oak Ridge, Tenn.) enables the assay of multiple samples of small volumes rapidly. The chemiluminometer can be equipped with multiple reagent injectors using 96-well black polystyrene microplates (Costar #3792). Each sample can be added into a separate well, followed by the simultaneous/sequential addition of other reagents as determined by the type of assay employed. Desirably, the formation of pseudobases in neutral or basic solutions employing an acridinium aryl ester is avoided, such as by acidification. The chemiluminescent response is then recorded well-by-well. In this regard, the time for recording the chemiluminescent response will depend, in part, on the delay between the addition of the reagents and the particular acridinium employed.

The order in which the test sample and the specific binding partner(s) are added to form the mixture for chemiluminescent assay is not critical. If the first specific binding partner is detectably labeled with an acridinium compound, detectably labeled first specific binding partner-GP73 or fucosylated GP73 antigen complexes form. Alternatively, if a second specific binding partner is used and the second specific binding partner is detectably labeled with an acridinium compound, detectably labeled first specific binding partner-GP73 or fucosylated GP73 antigen-second specific binding partner complexes form. Any unbound specific binding partner, whether labeled or unlabeled, can be removed from the mixture using any technique known in the art, such as washing.

Hydrogen peroxide can be generated in situ in the mixture or provided or supplied to the mixture before, simultaneously with, or after the addition of an above-described acridinium compound. Hydrogen peroxide can be generated in situ in a number of ways such as would be apparent to one skilled in the art.

Alternatively, a source of hydrogen peroxide can be simply added to the mixture. For example, the source of the hydrogen peroxide can be one or more buffers or other solutions that are known to contain hydrogen peroxide. In this regard, a solution of hydrogen peroxide can simply be added.

Upon the simultaneous or subsequent addition of at least one basic solution to the sample, a detectable signal, namely, a chemiluminescent signal, indicative of the presence of GP73 or fucosylated GP73 is generated. The basic solution contains at least one base and has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate, and calcium bicarbonate. The amount of basic solution added to the sample depends on the concentration of the basic solution. Based on the concentration of the basic solution used, one skilled in the art can easily determine the amount of basic solution to add to the sample.

The chemiluminescent signal that is generated can be detected using routine techniques known to those skilled in the art. Based on the intensity of the signal generated, the amount of GP73 or fucosylated GP73 in the sample can be quantified. Specifically, the amount of GP73 in the sample is proportional to the intensity of the signal generated. The amount of GP73 or fucosylated GP73 present can be quantified by comparing the amount of light generated to a standard curve for GP73 or fucosylated GP73 or by comparison to a reference standard. The standard curve can be generated using serial dilutions or solutions of known concentrations of GP73 or fucosylated GP73 by mass spectroscopy, gravimetric methods, and other techniques known in the art.

In a chemiluminescent microparticle assay employing the ARCHITECT® (or its successor) analyzer, the conjugate diluent pH should be about 6.0+/−0.2, the microparticle coating buffer should be maintained at room temperature (i.e., at about 17 to about 27° C.), the microparticle coating buffer pH should be about 6.5+/−0.2, and the microparticle diluent pH should be about 7.8+/−0.2. Solids preferably are less than about 0.2%, such as less than about 0.15%, less than about 0.14%, less than about 0.13%, less than about 0.12%, or less than about 0.11%, such as about 0.10%.

(2) Methods of Using Anti-GP73 Antibodies

The present invention is directed to a method for determining the presence, amount, or concentration of GP73 or GP73 fragment in a test sample using the disclosed anti-GP73 antibodies, or antibody fragments thereof. The method includes the steps of (a) contacting the test sample with a capture antibody, which binds to an epitope on GP73 or GP73 fragment, so as to form a capture antibody-GP73 or GP73 fragment antigen complex; (b) contacting the capture antibody-GP73 or GP73 fragment antigen complex with at least one detection antibody, which comprises a detectable label and binds to an epitope on GP73 or GP73 fragment that is not bound by the capture antibody, to form a capture antibody-GP73 or GP73 fragment antigen-detection antibody complex; and (c) determining the presence, amount or concentration of GP73 or GP73 fragment in the test sample based on the signal generated by the detectable label in the capture antibody-GP73 or GP73 fragment antigen-detection antibody complex whereupon the present, amount, or concentration of GP73 or GP73 fragment in the test sample is determined.

The capture antibody and detection antibody may be an anti-GP73 antibody described above. For example, the capture antibody may include the 1A-4246 antibody or a domain or region of: a variable heavy domain comprising the amino acid sequence of SEQ ID NO:1; a variable light domain comprising the amino acid sequence of SEQ ID NO:5; a variable heavy domain comprising the amino acid sequence of SEQ ID NO:1 and a variable light domain comprising the amino acid sequence of SEQ ID NO:5; a variable heavy chain comprising a complementarity determining region (CDR)1 comprising the amino acid sequence of SEQ ID NO:2, a CDR2 comprising the amino acid sequence of SEQ ID NO:3, and a CDR3 comprising the amino acid sequence of SEQ ID NO:4; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; or a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8. The detection antibody may include a 1B-4863 antibody or a domain or region of: a variable heavy domain comprising the amino acid sequence of SEQ ID NO:9; a variable light domain comprising the amino acid sequence of SEQ ID NO:13; a variable heavy domain comprising the amino acid sequence of SEQ ID NO:9 and a variable light domain comprising the amino acid sequence of SEQ ID NO:13; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; or a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12 and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16.

The present invention is also directed to a method for determining the presence, amount, or concentration of fucosylated GP73 or fucosylated GP73 fragment in a test sample using the disclosed anti-GP73 antibodies, or antibody fragments thereof. The method includes the steps of (a) contacting the test sample with a capture antibody, which binds to an epitope on fucosylated GP73 or fucosylated GP73 fragment, so as to form a capture antibody-fucosylated GP73 or fucosylated GP73 fragment antigen complex; (b) contacting the capture antibody-fucosylated GP73 or fucosylated GP73 fragment antigen complex with at least one detection antibody, which comprises a detectable label and binds to an epitope on fucosylated GP73 or fucosylated GP73 fragment that is not bound by the capture antibody, to form a capture antibody-fucosylated GP73 or fucosylated GP73 fragment antigen-detection antibody complex; and (c) determining the presence, amount or concentration of fucosylated GP73 or fucosylated GP73 fragment in the test sample based on the signal generated by the detectable label in the capture antibody-fucosylated GP73 or fucosylated GP73 fragment antigen-detection antibody complex whereupon the present, amount, or concentration of fucosylated GP73 or fucosylated GP73 fragment in the test sample is determined, wherein the capture binding protein comprises a protein, antibody or antibody fragment whose binding to fucosylated GP73 or fucosylated GP73 fragment is sensitive to the presence or absence of a fucose moiety on GP73 and the detection binding protein comprises a protein, antibody or antibody fragment whose binding to fucosylated GP73 or fucosylated GP73 fragment is insensitive to the presence or absence of a fucose moiety on GP73.

The protein, antibody or antibody fragment whose binding to fucosylated GP73 or fucosylated GP73 fragment is sensitive to the presence or absence of a fucose sugar moiety on fucosylated GP73 or fucosylated GP73 fragment may include Aleuria aurantia lectin (AAL) or a fragment thereof; a variable heavy domain region comprising the amino acid sequence of SEQ ID NO:25 or SEQ ID NO:33; a variable light domain region comprising the amino acid sequence of SEQ ID NO:29 or SEQ ID NO:37; a variable heavy domain comprising the amino acid sequence of SEQ ID NO:25 and a variable light domain region comprising the amino acid sequence of SEQ ID NO:29; a variable heavy domain comprising the amino acid sequence of SEQ ID NO:33 and a variable light domain region comprising the amino acid sequence of SEQ ID NO:37; a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28; a variable heavy chain comprising a CDR1 comprising the amino acid sequence of SEQ ID NO:34, a CDR2 comprising the amino acid sequence of SEQ ID NO:35, and a CDR3 comprising the amino acid sequence of SEQ ID NO:36; a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40; a variable heavy chain comprising a CDR 1 comprising the amino acid sequence of SEQ ID NO:26, a CDR2 comprising the amino acid sequence of SEQ ID NO:27, and a CDR3 comprising the amino acid sequence of SEQ ID NO:28, and a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32; or a variable heavy chain comprising a CDR 1 comprising the amino acid sequence of SEQ ID NO:34, a CDR2 comprising the amino acid sequence of SEQ ID NO:35, and a CDR3 comprising the amino acid sequence of SEQ ID NO:36, and a variable light chain comprising a CDR1 comprising the amino acid sequence of SEQ ID NO:38, a CDR2 comprising the amino acid sequence of SEQ ID NO:39, and a CDR3 comprising the amino acid sequence of SEQ ID NO:40.

The protein, antibody or antibody fragment whose binding to fucosylated GP73 or fucosylated GP73 fragment is insensitive to the presence or absence of a fucose sugar moiety on fucosylated GP73 or fucosylated GP73 fragment may include a variable heavy domain region comprising the amino acid sequence of SEQ ID NO:1, SEQ ID NO:9, SEQ ID NO:17, or SEQ ID NO:41; a variable light domain region comprising the amino acid sequence of SEQ ID NO:5, SEQ ID NO:13, SEQ ID NO:21, or SEQ ID NO:45; a variable heavy domain comprising the amino acid sequence of SEQ ID NO:1 and a variable light domain region comprising the amino acid sequence of SEQ ID NO:5; a variable heavy domain comprising the amino acid sequence of SEQ ID NO:9 and a variable light domain region comprising the amino acid sequence of SEQ ID NO:13; a variable heavy domain comprising the amino acid sequence of SEQ ID NO:17 and a variable light domain region comprising the amino acid sequence of SEQ ID NO:21; a variable heavy domain comprising the amino acid sequence of SEQ ID NO:41 and a variable light domain region comprising the amino acid sequence of SEQ ID NO:45; a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable heavy chain comprising a CDR1 comprising the amino acid sequence of SEQ ID NO:18, a CDR2 comprising the amino acid sequence of SEQ ID NO:19, and a CDR3 comprising the amino acid sequence of SEQ ID NO:20; a variable heavy chain comprising a CDR1 comprising the amino acid sequence of SEQ ID NO:42, a CDR2 comprising the amino acid sequence of SEQ ID NO:43, and a CDR3 comprising the amino acid sequence of SEQ ID NO:44; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48; a variable heavy chain comprising a CDR 1 comprising the amino acid sequence of SEQ ID NO:2, a CDR2 comprising the amino acid sequence of SEQ ID NO:3, and a CDR3 comprising the amino acid sequence of SEQ ID NO:4, and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; a variable heavy chain comprising a CDR 1 comprising the amino acid sequence of SEQ ID NO:10, a CDR2 comprising the amino acid sequence of SEQ ID NO:11, and a CDR3 comprising the amino acid sequence of SEQ ID NO:12, and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; a variable heavy chain comprising a CDR 1 comprising the amino acid sequence of SEQ ID NO:18, a CDR2 comprising the amino acid sequence of SEQ ID NO:19, and a CDR3 comprising the amino acid sequence of SEQ ID NO:20, and a variable light chain comprising a CDR1 comprising the amino acid sequence of SEQ ID NO:22, a CDR2 comprising the amino acid sequence of SEQ ID NO:23, and a CDR3 comprising the amino acid sequence of SEQ ID NO:24; or a variable heavy chain comprising a CDR 1 comprising the amino acid sequence of SEQ ID NO:42, a CDR2 comprising the amino acid sequence of SEQ ID NO:43, and a CDR3 comprising the amino acid sequence of SEQ ID NO:44, and a variable light chain comprising a CDR1 comprising the amino acid sequence of SEQ ID NO:46, a CDR2 comprising the amino acid sequence of SEQ ID NO:47, and a CDR3 comprising the amino acid sequence of SEQ ID NO:48.

The capture antibody and detection antibody may be an anti-GP73 antibody described above. For example, the capture antibody may include the 1A-4246 antibody or a domain or region of: a variable heavy domain comprising the amino acid sequence of SEQ ID NO:1; a variable light domain comprising the amino acid sequence of SEQ ID NO:5; a variable heavy domain comprising the amino acid sequence of SEQ ID NO:1 and a variable light domain comprising the amino acid sequence of SEQ ID NO:5; a variable heavy chain comprising a complementarity determining region (CDR)1 comprising the amino acid sequence of SEQ ID NO:2, a CDR2 comprising the amino acid sequence of SEQ ID NO:3, and a CDR3 comprising the amino acid sequence of SEQ ID NO:4; a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8; or a variable heavy chain comprising a CDR1 comprising the amino acid sequence of SEQ ID NO:2, a CDR2 comprising the amino acid sequence of SEQ ID NO:3, and a CDR3 comprising the amino acid sequence of SEQ ID NO:4 and a variable light chain comprising a CDR1 comprising the amino acid sequence of SEQ ID NO:6, a CDR2 comprising the amino acid sequence of SEQ ID NO:7, and a CDR3 comprising the amino acid sequence of SEQ ID NO:8. The detection antibody may include a 1B-4863 antibody or a domain or region of: a variable heavy domain comprising the amino acid sequence of SEQ ID NO:9; a variable light domain comprising the amino acid sequence of SEQ ID NO:13; a variable heavy domain comprising the amino acid sequence of SEQ ID NO:9 and a variable light domain comprising the amino acid sequence of SEQ ID NO:13; a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12; a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16; or a variable heavy chain comprising a CDR1 comprising the amino acid sequence of SEQ ID NO:10, a CDR2 comprising the amino acid sequence of SEQ ID NO:11, and a CDR3 comprising the amino acid sequence of SEQ ID NO:12 and a variable light chain comprising a CDR1 comprising the amino acid sequence of SEQ ID NO:14, a CDR2 comprising the amino acid sequence of SEQ ID NO:15, and a CDR3 comprising the amino acid sequence of SEQ ID NO:16.

b. Controls

It may be desirable to include a control sample. The control sample may be analyzed concurrently with the sample from the subject as described above. The results obtained from the subject sample can be compared to the results obtained from the control sample. Standard curves may be provided, with which assay results for the biological sample may be compared. Such standard curves present levels of marker as a function of assay units, i.e. fluorescent signal intensity, if a fluorescent label is used. Using samples taken from multiple donors, standard curves can be provided for control levels of the GP73 or fucosylated GP73 in normal healthy tissue, as well as for "at-risk" levels of the GP73 or fucosylated GP73 in tissue taken from donors, who may have one or more of the characteristics set forth above.

Thus, in view of the above, a method for determining the presence, amount, or concentration of GP73 or fucosylated GP73 in a test sample is provided. The method comprises assaying the test sample for GP73 or fucosylated GP73 by an immunoassay, for example, employing at least one capture antibody that binds to an epitope on GP73 or fucosylated GP73 or or fucosylated GP73 and at least one detection antibody that binds to an epitope on GP73 or fucosylated GP73 which is different from the epitope for the capture antibody and optionally includes a detectable label, and comprising comparing a signal generated by the detectable label as a direct or indirect indication of the presence, amount or concentration of GP73 or fucosylated GP73 in the test sample to a signal generated as a direct or indirect indication of the presence, amount or concentration of GP73 or fucosylated GP73 in a calibrator. The calibrator is optionally, and is preferably, part of a series of calibrators in which each of the calibrators differs from the other calibrators in the series by the concentration of GP73 or fucosylated GP73.

5. METHODS OF DIAGNOSING, PROGNOSTICATING, OR ASSESSING THE EFFICACY OF A THERAPEUTIC/PROPHYLACTIC TREATMENT

The method can further comprise diagnosing, prognosticating, or assessing the efficacy of a therapeutic/prophylactic treatment of a patient from whom the test sample was obtained. If the method further comprises assessing the efficacy of a therapeutic/prophylactic treatment of the patient from whom the test sample was obtained, the method optionally further comprises modifying the therapeutic/prophylactic treatment of the patient as needed to improve efficacy. By measuring and detecting GP73 and fucosylated GP73, the method allows for more diseases to be more accurately diagnosed and subsequently treated more successfully, compared to other commercially available GP73 immunoassays. The method can be adapted for use in an automated system or a semi-automated system.

Generally, a predetermined level can be employed as a benchmark against which to assess results obtained upon assaying a test sample for GP73 or fucosylated GP73. Generally, in making such a comparison, the predetermined level is obtained by running a particular assay a sufficient number of times and under appropriate conditions such that a linkage or association of analyte presence, amount or concentration with a particular stage or endpoint of a disease, disorder or condition (e.g., liver disease or cancer) or with particular indicia can be made. Typically, the predetermined level is obtained with assays of reference subjects (or populations of subjects). The GP73 measured can include GP73 fragments thereof, degradation products thereof, and/or enzymatic cleavage products thereof. The fucosylated GP73 can include glycosylated GP73 fragments thereof, degradation products thereof, and/or enzymatic cleavage products thereof.

In particular, with respect to a predetermined level as employed for monitoring disease progression and/or treatment, the amount or concentration of GP73 or GP73 fragment or fucosylated GP73 or fucosylated GP73 fragment may be "unchanged," "favorable" (or "favorably altered"), or "unfavorable" (or "unfavorably altered"). "Elevated" or "increased" refers to an amount or a concentration in a test sample that is higher or greater than a typical or normal level or range (e.g., predetermined level), or is higher or greater than another reference level or range (e.g., earlier or baseline sample). The term "lowered" or "reduced" refers to an amount or a concentration in a test sample that is lower or less than a typical or normal level or range (e.g., predetermined level), or is lower or less than another reference level or range (e.g., earlier or baseline sample). The term "altered" refers to an amount or a concentration in a sample that is altered (increased or decreased) over a typical or normal level or range (e.g., predetermined level), or over another reference level or range (e.g., earlier or baseline sample).

The typical or normal level or range for GP73 or fucosylated GP73 is defined in accordance with standard practice. A so-called altered level or alteration can be considered to have occurred when there is any net change as compared to the typical or normal level or range, or reference level or range that cannot be explained by experimental error or sample variation. Thus, the level measured in a particular sample will be compared with the level or range of levels determined in similar samples from a so-called normal subject. In this context, a "normal subject" is an individual with no detectable disease or disorder, and a "normal" (sometimes termed "control") patient or population is/are one(s) that exhibit(s) no detectable disease or disorder, respectively, for example. An "apparently normal subject" is one in which GP73 or fucosylated GP73 or fucosylated GP73 has not been or is being assessed. The level of an analyte is said to be "elevated" when the analyte is normally undetectable (e.g., the normal level is zero, or within a range of from about 25 to about 75 percentiles of normal populations), but is detected in a test sample, as well as when the analyte is present in the test sample at a higher than normal level. Thus, inter alia, the disclosure provides a method of screening for a subject having, or at risk of having, liver disease or cancer.

a. Methods of Providing a Diagnosis of a Subject Having Disease

The method described herein can be used to provide a diagnosis of a subject having disease by determining the levels of GP73 or fucosylated GP73 in a subject. The method may be used to detect disease in a subject using the anti-GP73 antibodies described above, or antibody fragments thereof. The method includes the steps of (a) obtaining a biological sample from a subject, (b) determining the level of GP73 or fucosylated GP73 in the biological sample using anti-GP73 antibodies, or antibody fragments thereof, (c) comparing the level of GP73 or fucosylated GP73 in the biological sample to a reference level of GP73 or fucosylated GP73, (d) identifying the subject as having disease if the level of GP73 or fucosylated GP73 in the biological sample is greater than the reference level of GP73 or fucosylated GP73, and (e) administering a treatment regimen to the subject identified as having disease. The anti-GP73 antibodies used in the method may be the 1A-4246 antibody and 1B-4863 antibody, or antibody fragments thereof.

(1) Liver Disease

The method described herein can be used to provide a diagnosis of a subject having liver disease by determining the levels of GP73 or fucosylated GP73 in a subject. The method may be used to detect liver disease in a subject using the anti-GP73 antibodies described above, or antibody fragments thereof. The method includes the steps of (a) obtaining a biological sample from a subject, (b) determining the level of GP73 or fucosylated GP73 in the biological sample using anti-GP73 antibodies, or antibody fragments thereof, (c) comparing the level of GP73 or fucosylated GP73 in the biological sample to a reference level of GP73 or fucosylated GP73, (d) identifying the subject as having liver disease if the level of GP73 or fucosylated GP73 in the biological sample is greater than the reference level of GP73 or fucosylated GP73, and (e) administering a treatment regimen to the subject identified as having liver disease. The anti-GP73 antibodies used in the method may be the 1A-4246 antibody and 1B-4863 antibody, or antibody fragments thereof.

The reference level in this method can be the level of GP73 or fucosylated GP73 in a patient having liver disease. Levels higher than or equal to 0.30 ng/mL, 0.31 ng/mL, 0.32 ng/mL, 0.33 ng/mL, 0.34 ng/mL, 0.35 ng/mL, 0.36 ng/mL, 0.37 ng/mL, 0.38 ng/mL, 0.39 ng/mL, 0.40 ng/mL, 0.41 ng/mL, 0.42 ng/mL, 0.43 ng/mL, 0.44 ng/mL, 0.45 ng/mL, 0.46 ng/mL, 0.47 ng/mL, 0.48 ng/mL, 0.49 ng/mL, 0.50 ng/mL, 0.51 ng/mL, 0.52 ng/mL, 0.53 ng/mL, 0.54 ng/mL, 0.55 ng/mL, 0.56 ng/mL, 0.57 ng/mL, 0.58 ng/mL, 0.59 ng/mL, 0.60 ng/mL, 0.61 ng/mL, 0.62 ng/mL, 0.63 ng/mL, 0.64 ng/mL, 0.65 ng/mL, 0.66 ng/mL, 0.67 ng/mL, 0.68 ng/mL, 0.69 ng/mL, 0.70 ng/mL, 0.71 ng/mL, 0.72 ng/mL, 0.73 ng/mL, 0.74 ng/mL, 0.75 ng/mL, 0.76 ng/mL, 0.77 ng/mL, 0.78 ng/mL, 0.79 ng/mL, 0.80 ng/mL, 0.81 ng/mL, 0.82 ng/mL, 0.83 ng/mL, 0.84 ng/mL, 0.85 ng/mL, 0.86 ng/mL, 0.87 ng/mL, 0.88 ng/mL, 0.89 ng/mL, 0.90 ng/mL, 0.91 ng/mL, or 0.92 ng/mL in serum of GP73 or fucosylated GP73 identify the subject as having liver disease.

(a) Liver Cirrhosis

The method described herein can be used to provide a diagnosis of a subject having liver cirrhosis by determining the levels of GP73 or fucosylated GP73 in a subject. The method may be used to detect liver cirrhosis in a subject using the anti-GP73 antibodies described above, or antibody fragments thereof. The method includes the steps of (a) obtaining a biological sample from a subject, (b) determining the level of GP73 or fucosylated GP73 in the biological sample using anti-GP73 antibodies, or antibody fragments thereof, (c) comparing the level of GP73 or fucosylated GP73 in the biological sample to a reference level of GP73 or fucosylated GP73, (d) identifying the subject as having liver cirrhosis if the level of GP73 or fucosylated GP73 in the biological sample is greater than the reference level of GP73 or fucosylated GP73, and (e) administering a treatment regimen to the subject identified as having liver cirrhosis. The anti-GP73 antibodies used in the method may be the 1A-4246 antibody and 1B-4863 antibody, or antibody fragments thereof.

The reference level in this method can be the level of GP73 or fucosylated GP73 in a patient having liver cirrhosis. Levels higher than or equal to 0.68 ng/mL, 0.69 ng/mL, 0.70 ng/mL, 0.71 ng/mL, 0.72 ng/mL, 0.73 ng/mL, 0.74 ng/mL, 0.75 ng/mL, 0.76 ng/mL, 0.77 ng/mL, 0.78 ng/mL, 0.79 ng/mL, 0.80 ng/mL, 0.81 ng/mL, 0.82 ng/mL, 0.83 ng/mL, 0.84 ng/mL, 0.85 ng/mL, 0.86 ng/mL, 0.87 ng/mL, 0.88 ng/mL, 0.89 ng/mL, 0.90 ng/mL, 0.91 ng/mL, or 0.92 ng/mL in serum of GP73 or fucosylated GP73 identify the subject as having liver cirrhosis.

(b) Liver Cancer

The method described herein can be used to provide a diagnosis of a subject having liver cancer by determining the levels of GP73 or fucosylated GP73 in a subject. The method may be used to detect liver cancer in a subject using the anti-GP73 antibodies described above, or antibody fragments thereof. The method includes the steps of (a) obtaining a biological sample from a subject, (b) determining the level of GP73 or fucosylated GP73 in the biological sample using the anti-GP73 antibodies described above, or antibody fragments thereof, (c) comparing the level of GP73 or fucosylated GP73 in the biological sample to a reference level of GP73 or fucosylated GP73, (d) identifying the subject as having liver cancer if the level of GP73 or fucosylated GP73 in the biological sample is greater than the reference level of GP73 or fucosylated GP73, and (e) administering a treatment regimen to the subject identified as having liver cancer. The anti-GP73 antibodies used in the method may be the 1A-4246 antibody and 1B-4863 antibody, or antibody fragments thereof.

The reference level in this method can be the level of GP73 or fucosylated GP73 in a patient having liver cancer. Levels higher than or equal to 0.30 ng/mL, 0.31 ng/mL, 0.32 ng/mL, 0.33 ng/mL, 0.34 ng/mL, 0.35 ng/mL, 0.36 ng/mL, 0.37 ng/mL, 0.38 ng/mL, 0.39 ng/mL, 0.40 ng/mL, 0.45 ng/mL, 0.50 ng/mL, 0.55 ng/mL, 0.58 ng/mL, 0.59 ng/mL, 0.60 ng/mL, 0.61 ng/mL, 0.62 ng/mL, 0.63 ng/mL, 0.64 ng/mL, 0.65 ng/mL, 0.66 ng/mL, 0.67 ng/mL, or 0.68 ng/mL in serum of GP73 or fucosylated GP73 identify the subject as having liver cancer.

(2) Cancer

The method described herein can be used to provide a diagnosis of a subject having cancer by determining the levels of GP73 or fucosylated GP73 in a subject. The method may be used to detect cancer in a subject using the anti-GP73 antibodies described above, or antibody fragments thereof. The method includes the steps of (a) obtaining a biological sample from a subject, (b) determining the level of GP73 or fucosylated GP73 in the biological sample using anti-GP73 antibodies, or antibody fragments thereof, (c) comparing the level of GP73 or fucosylated GP73 in the biological sample to a reference level of GP73 or fucosylated GP73, (d) identifying the subject as having cancer if the level of GP73 or fucosylated GP73 in the biological sample is greater than the reference level of GP73 or fucosylated GP73, and (e) administering a treatment regimen to the subject identified as having cancer. The anti-GP73 antibodies used in the method may be the 1A-4246 antibody and 1B-4863 antibody, or antibody fragments thereof.

The reference level in this method can be the level of GP73 or fucosylated GP73 in a patient having cancer. Levels higher than or equal to 0.29 ng/mL, 0.30 ng/mL, 0.31 ng/mL, 0.32 ng/mL, 0.33 ng/mL, 0.34 ng/mL, 0.35 ng/mL, 0.36 ng/mL, 0.37 ng/mL, 0.38 ng/mL, 0.39 ng/mL, 0.40 ng/mL, 0.41 ng/mL, 0.42 ng/mL, 0.43 ng/mL, 0.44 ng/mL, 0.45 ng/mL, 0.46 ng/mL, 0.47 ng/mL, 0.48 ng/mL, 0.49 ng/mL, 0.50 ng/mL, 0.51 ng/mL, 0.52 ng/mL, 0.53 ng/mL, 0.54 ng/mL, 0.55 ng/mL, 0.56 ng/mL, 0.57 ng/mL, 0.58 ng/mL, 0.59 ng/mL, 0.60 ng/mL, 0.61 ng/mL, 0.62 ng/mL, 0.63 ng/mL, 0.64 ng/mL, 0.65 ng/mL, 0.66 ng/mL, 0.67 ng/mL, 0.68 ng/mL, 0.69 ng/mL, 0.70 ng/mL, 0.71 ng/mL, 0.72 ng/mL, 0.73 ng/mL, 0.74 ng/mL, 0.75 ng/mL, 0.76 ng/mL, 0.77 ng/mL, 0.78 ng/mL, 0.79 ng/mL, 0.80 ng/mL, 0.81 ng/mL, 0.82 ng/mL, 0.83 ng/mL, 0.84 ng/mL, 0.85 ng/mL, 0.86 ng/mL, 0.87 ng/mL, 0.88 ng/mL, 0.89 ng/mL, 0.90 ng/mL, 0.91 ng/mL, 0.92 ng/mL, 0.93 ng/mL, 0.94 ng/mL, 0.95 ng/mL, 0.96 ng/mL, 0.97 ng/mL, 0.98 ng/mL, 0.99 ng/mL, 1.00 ng/mL, 1.01 ng/mL, 1.02 ng/mL, 1.03 ng/mL, 1.04 ng/mL, 1.05 ng/mL, 1.06 ng/mL, 1.07 ng/mL, 1.08 ng/mL, 1.09 ng/mL, or 1.10 ng/mL in serum of GP73 or fucosylated GP73 identify the subject as having cancer.

b. Methods for Determining the Risk of a Subject of Developing Liver Disease

The methods described herein also can be used to determine whether or not a subject has or is at risk of developing liver disease by determining the levels of GP73 or fucosylated GP73 in a subject using the anti-GP73 antibodies described above, or antibody fragments thereof. Thus, in particular embodiments, the disclosure also provides a method for determining whether a subject having, or at risk for, liver diseases, discussed herein and known in the art, is a candidate for therapy or treatment. Generally, the subject is one who has experienced some symptom of the disease or who has actually been diagnosed as having, or being at risk for, such a disease, and/or who demonstrates an unfavorable concentration or amount of GP73 or GP73 fragment, as described herein.

Specifically, such a method can comprise the steps of: (a) determining the concentration or amount in a test sample from a subject of GP73 or fucosylated GP73 using the methods described herein, or methods known in the art); and (b) comparing the concentration or amount of GP73 or fucosylated GP73 determined in step (a) with a predetermined level, wherein, if the concentration or amount of GP73 or fucosylated GP73 determined in step (a) is favorable with respect to a predetermined level, then the subject is determined not to have or be at risk for liver disease as discussed herein and known in the art. However, if the concentration or amount of GP73 or fucosylated GP73 determined in step (a) is unfavorable with respect to the predetermined level, then the subject is determined to have or be at risk for liver disease as discussed herein and known in the art. The liver disease may be liver cirrhosis or liver cancer.

c. Methods for Determining the Risk of a Subject Developing Cancer

The methods described herein also can be used to determine whether or not a subject has or is at risk of developing cancer, by determining the levels of GP73 or fucosylated GP73 in a subject using the anti-GP73 antibodies described above, or antibody fragments thereof. Thus, in particular embodiments, the disclosure also provides a method for determining whether a subject having, or at risk for, cancer, as discussed herein and known in the art, is a candidate for therapy or treatment. Generally, the subject is one who has experienced some symptom of the disease or who has actually been diagnosed as having, or being at risk for, such a disease, and/or who demonstrates an unfavorable concentration or amount of GP73 or fucosylated GP73, as described herein.

Specifically, such a method can comprise the steps of: (a) determining the concentration or amount in a test sample from a subject of GP73 or fucosylated GP73 using the methods described herein, or methods known in the art), and (b) comparing the concentration or amount of GP73 or fucosylated GP73 determined in step (a) with a predetermined level, wherein, if the concentration or amount of GP73 or fucosylated GP73 determined in step (a) is favorable with respect to a predetermined level, then the subject is determined not to have or be at risk for cancer as discussed herein and known in the art. However, if the concentration or amount of GP73 determined in step (a) is unfavorable with respect to the predetermined level, then the subject is determined to have or be at risk for cancer as discussed herein and known in the art. The cancer may be colon cancer, gastric cancer, breast cancer, prostate cancer or liver cancer.

d. Methods of Monitoring the Progression of Disease in a Subject

The methods described herein also can be used to monitor the progression of disease, such as liver disease or cancer, in a subject by determining the levels of GP73 or fucosylated GP73 in a subject using the anti-GP73 antibodies described above, or antibody fragments thereof. Optimally, the method includes the steps of (a) determining the concentration or amount of GP73 or fucosylated GP73 in a test sample from a subject using the anti-GP73 antibodies described above, or antibody fragments thereof, (b) determining the concentration or amount of GP73 or fucosylated GP73 in a later test sample from a subject using the anti-GP73 antibodies described above, or antibody fragments thereof, and (c) comparing the concentration or amount of GP73 or fucosylated GP73 as determined in step (b) with the concentration or amount of GP73 or fucosylated GP73 determined in step (a), wherein if the concentration or amount determined in step (b) is unchanged or is unfavorable when compared to the concentration or amount of GP73 or fucosylated GP73 determined in step (a), then the disease in the subject is determined to have continued, progressed or worsened. By comparison, if the concentration or amount of GP73 or fucosylated GP73 as determined in step (b) is favorable when compared to the concentration or amount of GP73 or fucosylated GP73 as determined in step (a), then the disease in the subject is determined to have discontinued, regressed or improved.

Optionally, the method further comprises comparing the concentration or amount of GP73 or fucosylated GP73 as determined in step (b), for example, with a predetermined level. Further, optionally the method comprises treating the subject with one or more pharmaceutical compositions for a period of time if the comparison shows that the concentration or amount of GP73 or fucosylated GP73 as determined in step (b), for example, is unfavorably altered with respect to the predetermined level.

Still further, the methods can be used to monitor treatment in a subject receiving treatment with one or more pharmaceutical compositions. Specifically, such methods involve providing a first test sample from a subject before the subject has been administered one or more pharmaceutical compositions. Next, the concentration or amount in a first test sample from a subject of GP73 or fucosylated GP73 is determined (e.g., using the methods described herein or as known in the art). After the concentration or amount of GP73 or fucosylated GP73 is determined, optionally the concentration or amount of GP73 or fucosylated GP73 is then compared with a predetermined level. If the concentration or amount of GP73 or fucosylated GP73 as determined in the first test sample is lower than the predetermined level, then the subject is not treated with one or more pharmaceutical compositions or alternatively, the subject may be treated with one or more pharmaceutical compositions. If the concentration or amount of GP73 or fucosylated GP73 as determined in the first test sample is higher than the predetermined level, then the subject is treated with one or more pharmaceutical compositions for a period of time or alternatively, the subject is not treated with one or more pharmaceutical compositions. The period of time that the subject is treated with the one or more pharmaceutical compositions can be determined by one skilled in the art (for example, the period of time can be from about seven (7) days to about two years, preferably from about fourteen (14) days to about one (1) year).

During the course of treatment with the one or more pharmaceutical compositions, second and subsequent test samples are then obtained from the subject. The number of test samples and the time in which said test samples are obtained from the subject are not critical. For example, a second test sample could be obtained seven (7) days after the subject is first administered the one or more pharmaceutical compositions, a third test sample could be obtained two (2) weeks after the subject is first administered the one or more pharmaceutical compositions, a fourth test sample could be obtained three (3) weeks after the subject is first administered the one or more pharmaceutical compositions, a fifth test sample could be obtained four (4) weeks after the subject is first administered the one or more pharmaceutical compositions, etc.

After each second or subsequent test sample is obtained from the subject, the concentration or amount of GP73 or fucosylated GP73 is determined in the second or subsequent test sample is determined (e.g., using the methods described herein or as known in the art). The concentration or amount of GP73 or fucosylated GP73 as determined in each of the second and subsequent test samples is then compared with the concentration or amount of GP73 or fucosylated GP73 as determined in the first test sample (e.g., the test sample that was originally optionally compared to the predetermined level). If the concentration or amount of GP73 or fucosylated GP73 as determined in step (c) is favorable when compared to the concentration or amount of GP73 or fucosylated GP73 as determined in step (a), then the disease in the subject is determined to have discontinued, regressed, or improved, and the subject should continue to be administered the one or pharmaceutical compositions of step (b). However, if the concentration or amount determined in step (c) is unchanged or is unfavorable when compared to the concentration or amount of GP73 or fucosylated GP73 as determined in step (a), then the disease in the subject is determined to have continued, progressed or worsened, and the subject should be treated with a higher concentration of the one or more pharmaceutical compositions administered to the subject in step (b) or the subject should be treated with one or more pharmaceutical compositions that are different from the one or more pharmaceutical compositions administered to the subject in step (b). Specifically, the subject can be treated with one or more pharmaceutical compositions that are different from the one or more pharmaceutical compositions that the subject had previously received to decrease or lower said subject's GP73 or fucosylated GP73 level.

Generally, for assays in which repeat testing may be done (e.g., monitoring disease progression and/or response to treatment), a second or subsequent test sample is obtained at a period in time after the first test sample has been obtained from the subject. Specifically, a second test sample from the subject can be obtained minutes, hours, days, weeks or years after the first test sample has been obtained from the subject. For example, the second test sample can be obtained from the subject at a time period of about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5, years, about 6.0 years, about 6.5 years, about 7.0 years, about 7.5 years, about 8.0 years, about 8.5 years, about 9.0 years, about 9.5 years or about 10.0 years after the first test sample from the subject is obtained. When used to monitor disease progression, the above assay can be used to monitor the progression of disease in subjects suffering from acute conditions. Acute conditions, also known as critical care conditions, refer to acute, life-threatening diseases or other critical medical conditions involving, for example, the cardiovascular system or excretory system. Typically, critical care conditions refer to those conditions requiring acute medical intervention in a hospital-based setting (including, but not limited to, the emergency room, intensive care unit, trauma center, or other emergent care setting) or administration by a paramedic or other field-based medical personnel. For critical care conditions, repeat monitoring is generally done within a shorter time frame, namely, minutes, hours or days (e.g., about 1 minute, about 5 minutes, about 10 minutes, about 15 minutes, about 30 minutes, about 45 minutes, about 60 minutes, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days or about 7 days), and the initial assay likewise is generally done within a shorter timeframe, e.g., about minutes, hours or days of the onset of the disease or condition.

The assays also can be used to monitor the progression of disease in subjects suffering from chronic or non-acute conditions. Non-critical care conditions or non-acute conditions, refers to conditions other than acute, life-threatening disease or other critical medical conditions involving, for example, the cardiovascular system and/or excretory system. Typically, non-acute conditions include those of longer-term or chronic duration. For non-acute conditions, repeat monitoring generally is done with a longer timeframe, e.g., hours, days, weeks, months or years (e.g., about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 2 days, about 3 days, about 4 days, about 5 days, about 6 days, about 7 days, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 16 weeks, about 17 weeks, about 18 weeks, about 19 weeks, about 20 weeks, about 21 weeks, about 22 weeks, about 23 weeks, about 24 weeks, about 25 weeks, about 26 weeks, about 27 weeks, about 28 weeks, about 29 weeks, about 30 weeks, about 31 weeks, about 32 weeks, about 33 weeks, about 34 weeks, about 35 weeks, about 36 weeks, about 37 weeks, about 38 weeks, about 39 weeks, about 40 weeks, about 41 weeks, about 42 weeks, about 43 weeks, about 44 weeks, about 45 weeks, about 46 weeks, about 47 weeks, about 48 weeks, about 49 weeks, about 50 weeks, about 51 weeks, about 52 weeks, about 1.5 years, about 2 years, about 2.5 years, about 3.0 years, about 3.5 years, about 4.0 years, about 4.5 years, about 5.0 years, about 5.5, years, about 6.0 years, about 6.5 years, about 7.0 years, about 7.5 years, about 8.0 years, about 8.5 years, about 9.0 years, about 9.5 years or about 10.0 years), and the initial assay likewise generally is done within a longer time frame, e.g., about hours, days, months or years of the onset of the disease or condition.

Furthermore, the above assays can be performed using a first test sample obtained from a subject where the first test sample is obtained from one source, such as urine, serum, or plasma. Optionally the above assays can then be repeated using a second test sample obtained from the subject where the second test sample is obtained from another source. For example, if the first test sample was obtained from urine, the second test sample can be obtained from serum or plasma. The results obtained from the assays using the first test sample and the second test sample can be compared. The comparison can be used to assess the status of a disease or condition in the subject.

e. Methods for Determining if a Subject is Predisposed to or Suffering from a Disease Moreover, the methods described herein also can be used to determine whether a subject predisposed to or suffering from a disease (e.g., liver disease or cancer, as discussed herein and known in the art) will benefit from treatment. In particular, the disclosure relates to GP73 companion diagnostic methods and products. Thus, the method of "monitoring the treatment of disease in a subject" as described herein further optimally also can encompass selecting or identifying candidates for liver disease treatments, such as liver resection and liver transplant, or for cancer treatments, such as surgery, radiation therapy, targeted therapy, and chemotherapy.

f. Methods for Determining if a Subject is Responding to the Administration of a Pharmaceutical Composition The methods described herein also can be used to determine if a subject is responding to the administration of one or more pharmaceutical compositions by determining the levels of GP73 or fucosylated GP73 in the subject using the anti-GP73 antibodies described above, or antibody fragments thereof. The method optionally comprises an assay as described herein, where the level of GP73 or fucosylated GP73 is assessed before and following treatment of the subject with one or more pharmaceutical compositions (e.g., particularly with a pharmaceutical related to a mechanism of action involving GP73 or fucosylated GP73), or where the level of GP73 is assessed following such treatment and the concentration or the level of GP73 or fucosylated GP73 is compared against a predetermined level. An unfavorable concentration of amount of GP73 or fucosylated GP73 observed following treatment confirms that the subject will not benefit from receiving further or continued treatment, whereas a favorable concentration or amount of GP73 or fucosylated GP73 observed following treatment confirms that the subject will benefit from receiving further or continued treatment. This confirmation assists with management of clinical studies, and provision of improved patient care.

The method includes the steps of (a) obtaining a biological sample from a subject, (b) determining the level of GP73 or fucosylated GP73 in the biological sample using the anti-GP73 antibodies described above, or antibody fragments thereof, (c) comparing the level of GP73 or fucosylated GP73 in the biological sample to a reference level of GP73 or fucosylated GP73, wherein an altered concentration of GP73 or fucosylated GP73 indicates that the subject is not responding to the administration of one or more pharmaceutical compositions, and (d) adjusting the treatment of the subject if the subject is not responding to the administration of one or more pharmaceutical compositions.

6. COMBINATION OF BIOMARKERS

The antibodies and methods described above may be used to detect and measure levels and concentrations of GP73 or fucosylated GP73 in combination with one or more biomarkers or immunoassays specific for disease. The combination of GP73 or fucosylated GP73 with one or more biomarkers or immunoassays specific for disease may provide a greater discrimination between healthy controls and individuals with disease compared to measuring GP73 or fucosylated GP73 alone. For example, measure a panel of GP73 or fucosylated GP73 and additional liver disease biomarkers may provide a greater discrimination between healthy controls and individuals with disease compared to a panel of GP73 or fucosylated GP73 alone. The combination of GP73 or fucosylated GP73 with at least one or more biomarkers may provide greater discrimination between healthy controls and individuals who have liver disease and/or individuals who have cancer.

Examples of the one or more biomarker include protein induced by the absence of vitamin K or antagonist-II (PIVKA-II), α-fetoprotein (AFP), AFP-L3, hemopexin (HPX), fucosylated hemopexin (Fuc-HPX), fucosylated kininogen (Fc-Kin), and fucosylated a-1-antitrypsin (F-AT).

a. PIVKA-II

Protein induced by the absence of vitamin K or antagonist-II (PIVKA-II), also known as des-g-carboxy prothrombin (DCP), is an abnormal form of the coagulation protein, prothrombin and is widely used with AFP in Japan during and after HCC treatment to predict adverse outcomes, and to detect early recurrence and potential malignancy. PIVKA-II is the least sensitive to risk factors for HCC (such as cirrhosis), and hence the most useful in predicting HCC. It differentiates HCC from non-malignant liver diseases, however, false increases of PIVKA-II concentrations are found in patients with severe obstructive jaundice due to intrahepatic cholestasis, or under conditions in which the action of vitamin K is impaired in individuals with long standing vitamin K deficiency, and in those who have ingested Warfarin or wide spectrum antibiotics.

b. AFP

Alpha-Fetal Protein (AFP), also known as α-fetoprotein, alpha-1-fetoprotein and alpha-fetoglobulin, is a protein that in humans is encoded by the AFP gene. AFP is widely used in clinical practice worldwide for screening patients at high-risk for HCC, for the diagnosis and monitoring of HCC patients in conjunction with ultrasound to detect early recurrence, for monitoring the response to therapy, and for detecting early relapse. However, AFP can be produced under many circumstances, including other liver diseases, leading to false positives and is not present in all patients with HCC.

The *Lens culinaris* hemagglutinin reactive fraction of AFP (AFP-L3) is a fucosylated glycoform of AFP, which may be used as a marker to represent the degree of biological malignancy of HCC. An AFP-L3 assay has also been approved by the US Food and Drug Administration for diagnosis of HCC because of its higher specificity than AFP.

c. HPX

Hemopexin (HPX), also known as beta-1B-glycoprotein, is encoded by the HPX gene. HPX is expressed primarily in the liver and is an abundant and acute phase protein in human serum. HPX binds heme with the highest affinity of any known protein. Its function is to scavenge the heme released or lost by the turnover of heme proteins such as hemoglobin and thus protects the body from the oxidative damage that free heme can cause. In addition, HPX releases its bound ligand for internalisation upon interacting with a specific receptor situated on the surface of liver cells. This function of HPX is to preserve the body's iron. This protein has five glucosamine oligosaccharides that are N-linked to the acceptor sequence, Asn-X-Ser/Thr. Fucosylated HPX (Fuc-HPX) has two core fucosylation sites of HPX in human serum, which were identified using a proteomics approach. Fucosylated hemopexin (Fuc-HPX) may be a potential biomarker for HCC as levels of Fuc-HPX in the *Lens culinaris* hemagglutinin lectin bound serum fraction showed good diagnostic accuracy for HCC in a study using a small sample set.

d. Serum Glycoproteins

Changes in glycosylation have been associated with the development of cirrhosis and HCC has been reported. The altered glycosylation of serum glycoproteins, such as fucosylated kininogen (Fc-kin) and fucosylated al-antitrypsin (F-AT), may be potential biomarkers when used independently or in combination with other HCC markers.

7. TREATMENT OF SUBJECTS SUFFERING FROM LIVER DISEASE

The subject identified in the methods described above having levels of GP73 greater than or equal to the values discussed above is identified as a patient suffering from liver disease. The subject is then treated for the liver disease. Treatment of liver disease may include small molecule GP73 or fucosylated GP73 inhibitors and anti-GP73 neutralizing antibodies.

a. Liver Cirrhosis

The subject identified in the methods described above having levels of GP73 or fucosylated GP73 greater than or equal to the values discussed above is identified as a patient suffering from liver cirrhosis. The subject is then treated for liver cirrhosis. Treatment may include a low-sodium diet, medications, surgery, such as liver transplant, paracentesis with or without a protein (albumin) infusion, endoscopic variceal banding or sclerotherapy, balloon tamponade, transjugular intrahepatic portosystemic shunt (TIPS), avoiding alcohol, avoiding sedative medicines, such as sleeping pills, anti-anxiety medicines and narcotics, and avoiding nonsteroidal anti-inflammatory drugs (NSAIDs), such as aspirin, ibuprofen and naproxen. Examples of medications may include GP73 inhibitors, diuretic medicines, such s spironolactone and furosemide, antibiotics, such as ciprofloxacin, neomycin or metronidazole (Flagy1), and cefotaxime, beta-blocker medicines, such as propranolol and nadolol, vasoconstrictor medicines, such as octreotide, lactulose, immunosuppressors, such as prednisone and azathioprine, ursodeoxycholic acid (UDCA; ursodiol (Actigall), colchicine, methotrexate, erythropoietin and epoetin alfa (Epogen, Procrit).

b. Liver Cancer

The subject identified in the methods described above having levels of GP73 or fucosylated GP73 greater than or equal to the values discussed above is identified as a patient suffering from liver cancer. The subject is then treated for liver cancer. Treatment may include surgical removal of the cancer (liver resection) with or without liver transplant, chemotherapy, such as doxorubicin (Adriamycin), 5-fluorouracil (5 FU), tamoxifen (Nolvadex), Octreotide (Sandostatin), gemcitabine, cisplatin, and oxaliplatin, biotherapy, such as bevacizumab, chemoembolization (trans-arterial chemoembolization or TACE), radioembolization (selective internal radiotherapy; "SIRT"), ablation, such as radiofrequency ablation (RFA) therapy, percutaneous ethanol (alcohol) injection, and cryoablation, stereotactic radiosurgery, and proton beam therapy. Treatment may also include drugs that block components of the angiogenesis pathway, such as sorafenib (Nexavar). Treatment may also include GP73 inhibitors. The drugs may be delivered via the hepatic artery or portal vein.

8. TREATMENT OF SUBJECTS SUFFERING FROM CANCER

The subject identified in the methods described above having levels of GP73 or fucosylated GP73 greater than or equal to the values discussed above is identified as a patient suffering from cancer. The subject is then treated for the cancer. Treatment of cancer may include surgery, chemotherapy, radiation therapy, small molecule GP73 or fucosylated GP73 inhibitors and/or GP73 or fucosylated GP73 inhibitors.

9. KIT

Provided herein is a kit, which may be used for assaying a test sample for GP73 or GP73 fragment or fucosylated GP73 or fucosylated GP73 fragment. The kit comprises at least one component for assaying the test sample for GP73 or fucosylated GP73 and instructions for assaying the test sample for GP73 or fucosylated GP73. For example, the kit can comprise instructions for assaying the test sample for GP73 or fucosylated GP73 by immunoassay, e.g., chemiluminescent microparticle immunoassay. Instructions included in kits can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

The at least one component may include at least one composition comprising one or more isolated antibodies or antibody fragments thereof that specifically bind to GP73 or fucosylated GP73. The antibody may be a GP73 or fucosylated GP73 capture antibody and/or a GP73 or fucosylated GP73 detection antibody. The antibody may include the 1A-4246 antibody, 1B-4863 antibody, or antibody fragments thereof. The antibody is optionally detectably labeled.

Alternatively or additionally, the kit can comprise a calibrator or control, e.g., purified, and optionally lyophilized, GP73 or fucosylated GP73, and/or at least one container (e.g., tube, microtiter plates or strips, which can be already coated with an anti-GP73 monoclonal antibody) for conducting the assay, and/or a buffer, such as an assay buffer or a wash buffer, either one of which can be provided as a concentrated solution, a substrate solution for the detectable label (e.g., an enzymatic label), or a stop solution. Preferably, the kit comprises all components, i.e., reagents, standards, buffers, diluents, etc., which are necessary to perform the assay. The instructions also can include instructions for generating a standard curve.

The kit may further comprise reference standards for quantifying GP73 or fucosylated GP73. The reference standards may be employed to establish standard curves for interpolation and/or extrapolation of GP73 or fucosylated GP73 concentrations. The reference standards may include a high GP73 or fucosylated GP73 concentration level, for example, about 100 ng/mL, about 125 ng/mL, about 150 ng/mL, about 175 ng/mL, about 200 ng/mL, about 225 ng/mL, about 250 ng/mL, about 275 ng/mL, or about 300 ng/mL; a medium GP73 concentration level, for example, about 25 ng/mL, about 40 ng/mL, about 45 ng/mL, about 50 ng/mL, about 55 ng/mL, about 60 ng/mL, about 75 ng/mL or about 100 ng/mL; and/or a low GP73 concentration level, for example, about 1 ng/mL, about 5 ng/mL, about 10 ng/mL, about 12.5 ng/mL, about 15 ng/mL, about 20 ng/mL, or about 25 ng/mL.

Any antibodies, which are provided in the kit, such as recombinant antibodies specific for GP73, can incorporate a detectable label, such as a fluorophore, radioactive moiety, enzyme, biotin/avidin label, chromophore, chemiluminescent label, or the like, or the kit can include reagents for labeling the antibodies or reagents for detecting the antibodies (e.g., detection antibodies) and/or for labeling the analytes or reagents for detecting the analyte. The antibodies, calibrators, and/or controls can be provided in separate containers or pre-dispensed into an appropriate assay format, for example, into microtiter plates, Optionally, the kit includes quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and further optionally are useful indicators of the integrity of the immunoassay kit reagents, and the standardization of assays, The kit can also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit can additionally include one or more other controls. One or more of the components of the kit can be lyophilized, in which case the kit can further comprise reagents suitable for the reconstitution of the lyophilized components.

The various components of the kit optionally are provided in suitable containers as necessary, e.g., a microtiter plate. The kit can further include containers for holding or storing a sample (e.g., a container or cartridge for a urine, plasma, or serum sample). Where appropriate, the kit optionally also can contain reaction vessels, mixing vessels, and other components that facilitate the preparation of reagents or the test sample. The kit can also include one or more instrument for assisting with obtaining a test sample, such as a syringe, pipette, forceps, measured spoon, or the like.

If the detectable label is at least one acridinium compound, the kit can comprise at least one acridinium-9-carboxamide, at least one acridinium-9-carboxylate aryl ester, or any combination thereof. If the detectable label is at least one acridinium compound, the kit also can comprise a source of hydrogen peroxide, such as a buffer, solution, and/or at least one basic solution. If desired, the kit can contain a solid phase, such as a magnetic particle, bead, test tube, microtiter plate, cuvette, membrane, scaffolding molecule, film, filter paper, disc, or chip.

If desired, the kit can further comprise one or more components, alone or in further combination with instructions, for assaying the test sample for another analyte, which can be a biomarker, such as a biomarker of liver disease or disorder.

a. Adaptation of Kit and Method

The kit (or components thereof), as well as the method for determining the concentration of GP73 or fucosylated GP73 in a test sample by an immunoassay as described herein, can be adapted for use in a variety of automated and semi-automated systems (including those wherein the solid phase comprises a microparticle), as described, e.g., in U.S. Pat. Nos. 5,089,424 and 5,006,309, and as commercially marketed, e.g., by Abbott Laboratories (Abbott Park, Ill.) as ARCHITECT®.

Some of the differences between an automated or semi-automated system as compared to a non-automated system (e.g., ELISA) include the substrate to which the first specific binding partner (e.g., analyte antibody or capture antibody) is attached (which can affect sandwich formation and analyte reactivity), and the length and timing of the capture, detection, and/or any optional wash steps. Whereas a non-automated format such as an ELISA may require a relatively longer incubation time with sample and capture reagent (e.g., about 2 hours), an automated or semi-automated format (e.g., ARCHITECT® and any successor platform, Abbott Laboratories) may have a relatively shorter incubation time (e.g., approximately 18 minutes for ARCHITECT®). Similarly, whereas a non-automated format such as an ELISA may incubate a detection antibody such as the conjugate reagent for a relatively longer incubation time (e.g., about 2 hours), an automated or semi-automated format (e.g., ARCHITECT® and any successor platform) may have a relatively shorter incubation time (e.g., approximately 4 minutes for the ARCHITECT® and any successor platform).

Other platforms available from Abbott Laboratories include, but are not limited to, AxSYM®, IMx® (see, e.g., U.S. Pat. No. 5,294,404, which is hereby incorporated by reference in its entirety), PRISM®, EIA (bead), and Quantum™ II, as well as other platforms. Additionally, the assays, kits, and kit components can be employed in other formats, for example, on electrochemical or other hand-held or point-of-care assay systems. The present disclosure is, for example, applicable to the commercial Abbott Point of Care (i-STATS, Abbott Laboratories) electrochemical immunoassay system that performs sandwich immunoassays. Immunosensors and their methods of manufacture and operation in single-use test devices are described, for example in, U.S. Pat. No. 5,063,081, U.S. Pat. App. Pub. No. 2003/0170881, U.S. Pat. App. Pub. No. 2004/0018577, U.S. Pat. App. Pub. No. 2005/0054078, and U.S. Pat. App. Pub. No. 2006/0160164, which are incorporated in their entireties by reference for their teachings regarding same.

In particular, with regard to the adaptation of an assay to the I-STAT® system, the following configuration is preferred. A microfabricated silicon chip is manufactured with a pair of gold amperometric working electrodes and a silver-silver chloride reference electrode. On one of the working electrodes, polystyrene beads (0.2 mm diameter) with immobilized capture antibody are adhered to a polymer coating of patterned polyvinyl alcohol over the electrode. This chip is assembled into an I-STAT® cartridge with a fluidics format suitable for immunoassay. On a portion of the wall of the sample-holding chamber of the cartridge there is a layer comprising the detection antibody labeled with alkaline phosphatase (or other label). Within the fluid pouch of the cartridge is an aqueous reagent that includes p-aminophenol phosphate.

In operation, a sample suspected of containing GP73 or fucosylated GP73 is added to the holding chamber of the test cartridge and the cartridge is inserted into the I-STAT® reader. After the second antibody (detection antibody) has dissolved into the sample, a pump element within the cartridge forces the sample into a conduit containing the chip. Here it is oscillated to promote formation of the sandwich between the first capture antibody, GP73 or fucosylated GP73, and the labeled second detection antibody. In the penultimate step of the assay, fluid is forced out of the pouch and into the conduit to wash the sample off the chip and into a waste chamber. In the final step of the assay, the alkaline phosphatase label reacts with p-aminophenol phosphate to cleave the phosphate group and permit the liberated p-aminophenol to be electrochemically oxidized at the working electrode. Based on the measured current, the reader is able to calculate the amount of analyte GP73 or fucosylated GP73 in the sample by means of an embedded algorithm and factory-determined calibration curve.

The methods and kits as described herein necessarily encompass other reagents and methods for carrying out the immunoassay. For instance, encompassed are various buffers such as are known in the art and/or which can be readily prepared or optimized to be employed, e.g., for washing, as a conjugate diluent, and/or as a calibrator diluent. An exemplary conjugate diluent is ARCHITECT® conjugate diluent employed in certain kits (Abbott Laboratories, Abbott Park, Ill.) and containing 2-(N-morpholino)ethanesulfonic acid (MES), a salt, a protein blocker, an antimicrobial agent, and a detergent. An exemplary calibrator diluent is ARCHITECT® human calibrator diluent employed in certain kits (Abbott Laboratories, Abbott Park, Ill.), which comprises a buffer containing MES, other salt, a protein blocker, and an antimicrobial agent. Additionally, as described in U.S. Pat. Application No. 61/142,048 filed Dec. 31, 2008, improved signal generation may be obtained, e.g., in an I-STAT® cartridge format, using a nucleic acid sequence linked to the signal antibody as a signal amplifier.

While certain embodiments herein are advantageous when employed to assess disease, such as liver disease or cancer, the assays and kits also optionally can be employed to assess GP73 in other diseases, disorders, and conditions as appropriate.

The method of assay also can be used to identify a compound that ameliorates diseases, such as liver disease or cancer. For example, a cell that expresses GP73 can be contacted with a candidate compound. The level of expression of GP73 or fucosylated GP73 in the cell contacted with the compound can be compared to that in a control cell using the method of assay described herein.

The present invention has multiple aspects, illustrated by the following non-limiting examples.

10. EXAMPLES

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present invention has multiple aspects, illustrated by the following non-limiting examples.

Example 1

Human GP73 Gene Expression

Human GP73 protein (aka GOLM1, GOLPH2) is a 400 amino acid (45.2 kDa) integral protein of the cis-Golgi membrane. The human GP73 (amino acids 63 to 400 based on GenBank sequence AAF44663.1 (SEQ ID NO:97) was synthesized and cloned into a pET vector (Novagen) for expression. A 6× His Tag was fused at the C-terminal for purification. The final plasmid pET-GP73 (SEQ ID NO:98, see FIG. 1) was transformed into BL21(DE3) cell and induced by 1 mM IPTG at 30° C. for 4 hrs. The induced *E. coli* cells were centrifuged for 20 min at 3,900 rpm and washed once with PBS. The washed cell pellet was re-suspended with about 5 mL BugBuster® Protein Extraction reagent (Novagen) per gram cell pellet. Cell suspensions were incubated for 30 min at room temperature with gentle shaking. The lysates were centrifuged at 14,000 rpm for 20 min at 4° C. The supernatant was purified using nickel affinity column chromatography per manufacturer instruction (Novagen).

In addition, the washed cell pellet was dissolved in 1× His-bind binding buffer (Novagen) with protease inhibitors (Sigma) and sonicated in ice bath for 5×10 seconds pulse with 30 seconds rest between pulses. The lysates were centrifuged at 14,000 rpm for 20 min at 4° C. The supernatant was purified using nickel affinity column chromatography per manufacturer instruction (Novagen).

The human GP73 (amino acids 63 to 400) was also cloned into the pFuse-hIgG1-Fc vector (InvivoGen). A human Fc region was fused at C-terminal to generate GP73-hFc (GP73 linked to the fragment crystalline region of human IgG; SEQ ID NO:99, see FIG. 2). The final plasmid DNA pFuse-GP73-Fc was transfected with linear polyethyleneimine (PEI, MW 25 kDa) (Polysciences, Inc.) into HEK293F, CHO or HepG2 cells. After 5 days of culture, the supernatant was harvested by centrifugation at 1,000 rpm for 20 min and followed by filtration (0.2 micron filter). The harvested supernatant was purified by Protein G column chromatography per manufacturer instruction (GE healthcare).

Example 2

Animal Immunizations

Female CAF1a and RBF/DnJ mice (both from The Jackson Laboratory, Bar Harbor, Me.) were immunized twice, every seven weeks, with 20 µg purified GP73-hFc (described in Example 1) emulsified in Complete or Incomplete Adjulite Freund's Adjuvant (Pacific Immunology, Ramona, Calif.). Complete Freund's adjuvant was used for the primary immunization and Incomplete Freund's adjuvant was used for the second immunization. Each inoculum was prepared by first diluting the GP73-hFc to the appropriate concentration in sterile saline (0.9% sodium chloride, Abbott Laboratories), adding an equal volume of adjuvant and then mixing by passing back and forth between two syringes via a 3-way stopcock until a thick, stable emulsion was formed. Sera samples were taken 10-14 days following the second immunization. On the fourth and third days prior to B cell harvest, a RBF/DnJ mouse was administered 35 µg GP73-hFc diluted in sterile saline. This inoculum was delivered into the body cavity near the spleen. On the third day prior to B cell harvest, a CAF1/J mouse was administered 50 µg GP73-hFc diluted in sterile saline. This inoculum was also delivered into the body cavity near the spleen.

Example 3

Screening of Mouse Sera for Antigen Reactivity

Sera samples were tested in a 96-well micro titer enzyme immunoassay (EIA) for reactivity to solution phase GP73-hFc. Assay plates (NUNC Corporation, Naperville, Ill.) were coated with 100 µL/well of sheep anti-mouse IgG Fc specific antibody (Jackson ImmunoResearch, West Grove, Pa.) diluted to 2 µg/mL in phosphate-buffered saline (PBS, Abbott Laboratories). Plates were incubated overnight, the capture antibody was removed, and 200 µL/well of blocking solution was added (3% w/v [weight/volume] bovine serum albumin (BSA) and 0.5% v/v [volume/volume] polysorbate-20 diluted in PBS (all Abbott Laboratories)). The plates were incubated for about 30 min and then washed with distilled water (dH$_2$O, Abbott Laboratories). Serial dilutions (in block solution) of the mouse sera or a positive control were added to the assay plates (100 µL/well), incubated for about 60 min and then washed with dH$_2$O. 100 µL/well of normal serum solution (NSS; block solution containing 2% v/v normal mouse serum) was added for additional blocking. This solution helps to prevent non-specific binding in the assay well. The plates were incubated for about 30 min and then washed with dH$_2$O. Subsequently, 100 µL/well of a 500 ng/mL solution of GP73-hFc was added to the assay wells for a brief incubation, after which the plates were washed with dH$_2$O. Rabbit anti-GP73 antibody (Drexel University) diluted to 500 ng/mL in NSS was added to all assay wells (100 µL/well), which were incubated for 30 min and then washed with dH$_2$O. Next, 100 µL horseradish peroxidase labeled goat anti-rabbit (Jackson ImmunoResearch) diluted to 200 ng/mL in NSS was added, allowed to incubate for about 30 min and then the plates washed. o-Phenylenediamine (OPD) substrate (Abbott Laboratories) was used as the chromagen to generate signal, and the reaction was quenched using 1 N sulfuric acid (Abbott Laboratories). Signal was read at a wavelength of 492 nm.

Example 4

Screening of Mouse Sera for Relative Affinity

Samples were tested for reactivity to limiting concentrations of antigen to determine the relative affinity of each sera sample for the GP73-hFc antigen. The assay format was identical to that described above, except that instead of preparing serial dilutions of mouse sera test samples, each sample was prepared at a single dilution, in block. Additionally, the GP73-hFc antigen was tested at varying concentrations, beginning with 2000 ng/mL in NSS, followed by ten log 3 dilutions, also in NSS. Binding curves were generate and used to determine relative affinity. Based on these results, a CAF1/J mouse ("mouse #458") and a RBF/DnJ mouse ("mouse #501") were chosen for B cell fusion.

Example 5

Mouse Splenocyte Fusion

On the day of fusion, the mice were euthanized and their spleens containing anti-GP73 splenocytes were harvested and placed into Hybridoma Serum Free Medium (HSFM) supplemented with Pen Strep (Invitrogen Corporation). A cell fusion was performed as described by Kohler and Milstein (Nature (1975) 256:495-7). Each mouse spleen was placed into a separate petri dish containing HSFM. The splenocytes were perfused out of each spleen using a syringe containing HSFM and cell scraper, then counted using a hemocytometer. Approximately $3.9 \times 10^7$ splenocytes from mouse #458 was isolated in a 50 mL centrifuge tube for fusion 1A, and $3.8 \times 10^7$ splenocytes from mouse #501 was isolated in a 50 mL centrifuge tube for fusion 1B. Splenocytes from each mouse were washed by centrifugation into a cell pellet and re-suspended in HSFM. These splenocytes were mixed with an equal number of NS/0 myeloma cells (American Type Culture Collection) and centrifuged into a pellet. The fusion was accomplished by exposing the splenocytes and NS/0 cells to 50% Polyethylene glycol (PEG) (MW 1300-1600) in HSFM. One mL of the PEG solution was added to each cell pellet over 30 seconds, followed by one additional minute of incubation. The PEG and cell pellet were diluted by slowly adding 30 mL of HSFM over 30 seconds. The fused cells were then removed from suspension by centrifugation and decanting the supernatant. The cell pellet from each fusion was re-suspended into approximately 300 mL of HSFM supplemented with approximately 10% fetal bovine serum (FBS) (Hyclone Laboratories), HAT (Hypoxanthine, Aminopterin, Thymidine) (Sigma Laboratories), HT Supplement (Invitrogen Corporation), BM Condimed H1 (Roche Applied Science), Cholesterol and L-Glutamine (Invitrogen Corporation) to select for hybridomas. The fused cells were seeded into T162 culture flasks at an approximate density of $2.5 \times 10^5$ cells/mL and cultured in bulk for approximately 48 hrs at 37° C. with 5% CO2. Following 48 hrs of HAT selection, the bulk culture was centrifuged and the pellet was re-suspended into semi-solid tissue culture medium. The semi-solid tissue culture medium consisted of a 50% mixture of 2×IMDM (Invitrogen) with CloneMatrix (Molecular Devices) supplemented with 10% FBS, HT Supplement, Penn/Strep, L-Glutamine, and a 5 µg/mL solution of CloneDetect (Molecular Devices). The semi-solid culture plates were allowed to incubate for 7-10 days before colony selection on the ClonepixFL (Molecular Devices). A colony grown in the semi-solid medium was considered a clone because the single cell initiating it had not been allowed to move and mix with other cells during growth. All cell lines of interest were subcloned to ensure clonality. An immunoprecipitation reaction occurs between the antibody being produced by the colony and the goat anti-mouse IgG Fc-FITC that fluoresces. The brighter the fluorescence signal observed, the more antibody being produced. Colonies were analyzed for fluorescence on the ClonepixFL and the ones with the brightest fluorescent signal were selected for automated transfer to 96 well tissue culture plates containing HSFM with 10% FBS and L-Glutamine. The 96 well tissue culture plates were allowed to grow for 3 to 5 days at 37° C. prior to supernatant screening for antibody production.

Example 6

Hybridoma Screening and Selection

Cell supernatant samples were analyzed for anti-GP73 antibodies by EIA. Sheep anti-mouse IgG Fc (Jackson Immunoresearch) was coated on 96 well micro-titer EIA plates at 1 µg/mL. After the capture reagent was coated on the solid phase, it was removed and the plates were blocked using a BSA/PBS block solution. The wells were washed with distilled water and cell supernatants were added to the blocked plates and allowed to incubate at room temperature for at least one hour. A mouse monoclonal antibody 14H4-23 (Drexel University) was used a positive control. The anti-mouse IgG Fc captured the anti-GP73 mouse antibody from the supernatant. Following the incubation, the supernatants were washed off using distilled water. An irrelevant mouse-human chimeric antibody was added to all wells and incubated at room temperature for 30 min to block any captured mouse antibodies that react with the human IgG Fc fusion protein linked to the GP73 antigen. The wells were washed with distilled water and GP73-hFc was added to the plates at 200 ng/mL and incubated for 30 min. Following this incubation, the antigen was washed from the plates using distilled water. Biotin labeled goat anti-GP73 was added to the plates at 200 ng/mL and incubated for 30 min at room temperature. The plates were washed and streptavidin-HRPO (Jackson Immunoresearch) (diluted to approximately 200 ng/mL) was added to the plates and allowed to incubate for 30 min. The plates were washed with distilled water and OPD substrate was used as the chromagen to generate signal. Plates were read at 492 nm and the results were analyzed. Hybrids were considered positive if they had an EIA signal at least 3 times greater than background. See Table 3.

TABLE 3

| Sample | OD (A492) |
| --- | --- |
| Background | 0.06 |
| PC (14H4-23) | 1.57 |
| 1A-3187 | 1.34 |
| 1A-4246 | 1.92 |
| 1B-3246 | 1.48 |
| 1B-3440 | 1.46 |
| 1B-4863 | 1.44 |
| 1B-4971 | 1.79 |

Positive clones were expanded to 24 well plates in IMDM supplemented with 10% FBS and HT supplement. Following 5-14 days growth, the 24 well cultures were evaluated by EIA in the same manner as previously described, except the supernatant samples were titrated against GP73-hFc and BSA to eliminate non-specific protein binders. Once again the clones generating signal at least 3 times greater than background were considered positive and selected for further evaluation. See Table 4.

TABLE 4

| Sample | Dilution | BSA Background OD (A492) | GP73-hFc OD (A492) |
|---|---|---|---|
| NC mAb | 400 ng/mL | 0.05 | 0.05 |
| PC (14H4-23) | 400 ng/mL | 0.06 | 1.49 |
| 1A-3187 | 1:25 | 0.11 | 1.30 |
| 1A-4246 | 1:25 | 0.04 | 1.35 |
| 1B-3246 | 1:16 | 0.06 | 1.64 |
| 1B-3440 | 1:25 | 0.09 | 1.51 |
| 1B-4863 | 1:25 | 0.06 | 1.61 |
| 1B-4971 | 1:25 | 0.10 | 2.10 |

The 24 well cultures were then evaluated by EIA for their ability to form a sandwich with the rabbit anti-GP73 used as a capture reagent coated directly on the solid phase. The same EIA protocol previously described was used, except rabbit anti-GP73 antibody was coated at 1 µg/mL, the GP73-hFc was tested at 200 ng/mL, and a HRP labeled goat anti-mouse IgG FC antibody was used as the conjugate reagent to generate signal. See Table 5.

TABLE 5

| Sample | Dilution | BSA Background OD (A492) | GP73-hFc OD (A492) |
|---|---|---|---|
| NC mAb | 400 ng/mL | 0.10 | 0.10 |
| PC (14H4-23) | 400 ng/mL | 0.10 | 1.34 |
| 1A-3187 | 1:125 | 0.09 | 0.97 |
| 1A-4246 | 1:25 | 0.12 | 0.85 |
| 1B-3246 | 1:125 | 0.10 | 0.79 |
| 1B-3440 | 1:125 | 0.12 | 0.76 |
| 1B-4863 | 1:125 | 0.10 | 1.41 |
| 1B-4971 | 1:125 | 0.10 | 1.60 |

The clones that were identified as positive at the 24 well stage were expanded for cryopreservation followed by generation of high-density cell supernatant. Supernatant from these clones were tested for mouse antibody isotype using a Southern Biotech Clonotyping Kit in an EIA format. See Table 6.

TABLE 6

| Sample | Isotype |
|---|---|
| 1A-3187 | IgG1k |
| 1A-4246 | IgG1k |
| 1B-3246 | IgG1k |
| 1B-3440 | IgG1k |
| 1B-4863 | IgG1k |
| 1B-4971 | IgG1k |

Example 7

Hybridoma Scale Up, Antibody Purification, and Antibody Labeling

The cell lines were expanded in IMDM (Invitrogen Corporation) supplemented with L-glutamine and 10% Ultra Low IgG FBS (Invitrogen Corporation) and seeded into roller bottles at approximately $0.5 \times 10^5$ cells/mL. The cultures were incubated at 37° C. while rotating at approximately 1 revolution per minute for 10-14 days, or until a terminal end culture was obtained. The terminal roller bottle supernatant was harvested and clarified with a 0.45 micron filter. The clarified supernatant was diluted with an equal volume of 1.5 M glycine/3 N NaCl buffer at pH 8.9 (Abbott Laboratories), then loaded onto a pre-equilibrated 5 mL Protein A column using the AKTA automated purification system (Amersham/Pharmacia/GE). The column was then washed with approximately 5 column volumes of binding buffer and when a stable baseline was achieved, the mAb was eluted with a pH 3.0 citrate buffer (Abbott Laboratories). The mAb was then transferred to a desalting column for an exchange into PBS, and then further dialyzed in PBS using 10,000 molecular weight cut-off dialysis membrane (Pierce Chemical). The purified antibodies were biotin labeled for use as secondary screening reagents. Sulfo-NHS-LC-Biotin (Pierce) was added to purified antibody at a 20 molar excess and allowed to incubate for 30 min. Unbound biotin was removed through dialysis in PBS and the mAbs were tested by EIA to confirm they were successfully labeled.

Example 8

Purified Antibody Characterization

1. Sensitivity to Fucose—Competitive Inhibition Assay with Aleuria Aurantia Lectin (AAL)

The biotin labeled anti-GP73 mAbs were tested to determine if they were sensitive to the presence of fucose on the GP73-hFc antigen by EIA. Aleuria Aurantia Lectin (AAL) (Vector Laboratories) binds fucose with a high degree of specificity. Donkey anti-human IgG Fc (Jackson Immunoresearch) that was pretreated with periodate to oxidize any glycosylation/fucosylation sites was coated on 96 well micro titer EIA plates at approximately 1 µg/mL. Periodate treatment was done to prevent nonspecific binding of AAL to the capture reagent. After the capture reagent was coated on the solid phase, the capture reagent was removed and the plates were blocked for 30 min using Protein-Free T20 (TBS) Blocking Buffer (Thermo Scientific). The wells were washed with distilled water and a 200 ng/mL solution of GP73-hFc antigen was added to the blocked plates and allowed to incubate at room temperature for at least 30 min. The anti-human IgG Fc captures the human IgG fusion protein on the GP73 antigen. The wells were washed with distilled water and AAL was added to the wells in serial dilutions from 0-200 ng/mL and incubated for at least 30 min. Following this incubation, the antigen was washed from the plates using distilled water. Biotin labeled anti-GP73 mAbs were added to the plates at predetermined concentrations for each mAb ranging from 50 to 2000 ng/mL and incubated for 15 min at room temperature. Biotin labeled AAL was used as a positive control for the assay and a biotin labeled irrelevant mAb was used as the negative control. The plates were washed and streptavidin-HRPO (diluted to approximately 200 ng/mL) was added to the plates and allowed to incubate for 30 min. The plates were washed with distilled water and OPD substrate was used as the chromagen to generate signal. Plates were read at 492 nm and the results were analyzed. See FIG. 3. As shown in FIG. 3, biotin labeled anti-GP73 mAbs 1A-3187 and 1B-4863 demonstrate some competitive inhibition from free AAL at the higher concentrations tested in this assay. All other biotin labeled mAbs exhibit no inhibition even at 200 ng/mL.

2. Reactivity with IgG, GP73, and GP73-hFc

Figure 4:
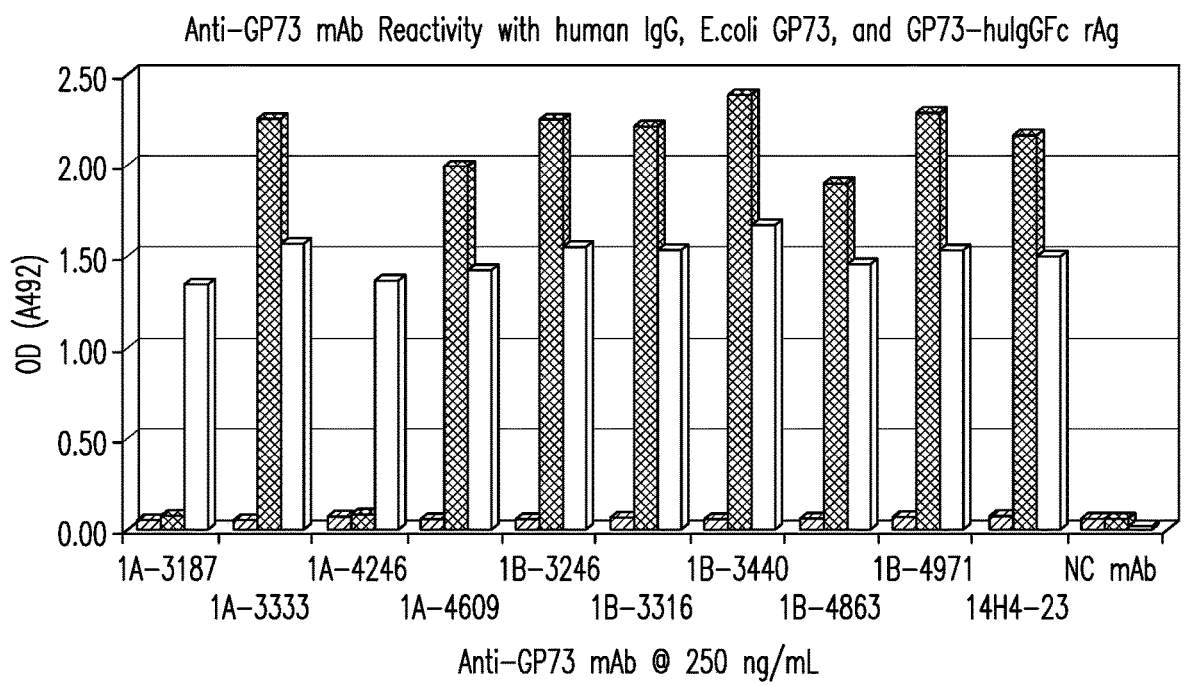
FIG. 4 shows the reactivity of anti-GP73 mAb with mouse-human chimeric IgG, GP73 expressed in *E. coli*, and GP73-hFc recombinant antigen expressed in HEK cells.

The purified anti-GP73 mAbs were tested for EIA reactivity to human IgG, GP73 produced in E. coli, and GP73-hFc produced in HEK 293 cells. A mouse-human chimeric antibody, GP73 produced in E. coli, and GP73-hFc produced in HEK 293 cells were coated on micro titer plates at approximately 1000 ng/mL and allowed to incubate over night at 4-8° C. After the capture reagent was coated on the solid phase, it was removed and blocked using a BSA/PBS block solution. The wells were washed with distilled water. Purified anti-GP73 and negative control mAbs were added to the blocked plates in serial dilutions starting at 1000 ng/mL and allowed to incubate at room temperature for approximately 30 min. The wells were washed with distilled water. Goat anti-mouse IgG-HRP (Jackson Immunoresearch) was added to the wells at approximately 250 ng/mL and allowed to incubate for approximately 30 min at room temperature. The plates were washed with distilled water and OPD substrate was used as the chromogen to generate signal. Plates were read at 492 nm and the results were analyzed. See FIG. 4. As shown in FIG. 4, none of the mAbs tested react with the human IgGFc on the mouse-human chimeric and all mAbs tested demonstrate reactivity with GP73-hFc. The 1A-3187 and 1A-4246 demonstrate no reactivity with the *E. coli* produced GP73 without the human IgG Fc fusion protein suggesting this was structurally different than the GP73-hFc, possibly due to the lack of glycosylation from the *E. coli* production organism.

3. Fucose Sensitivity—Free Fucose Inhibition

Figure 5:
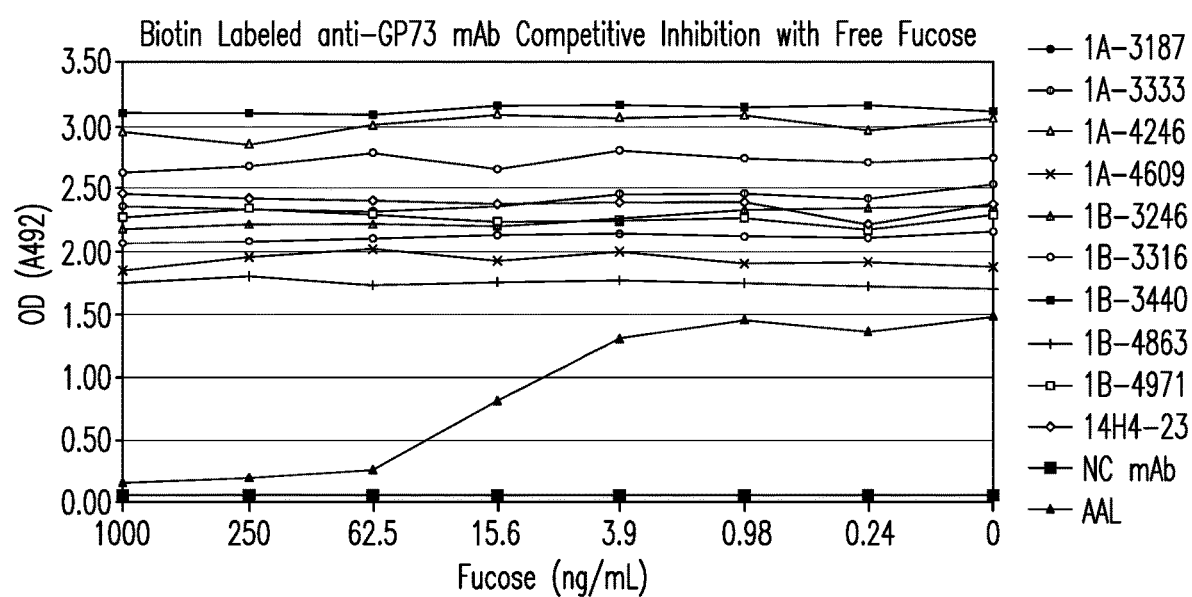
FIG. 5 shows a competitive inhibition assay of the biotin labeled anti-GP73 mAb with free fucose.
Figure 6:
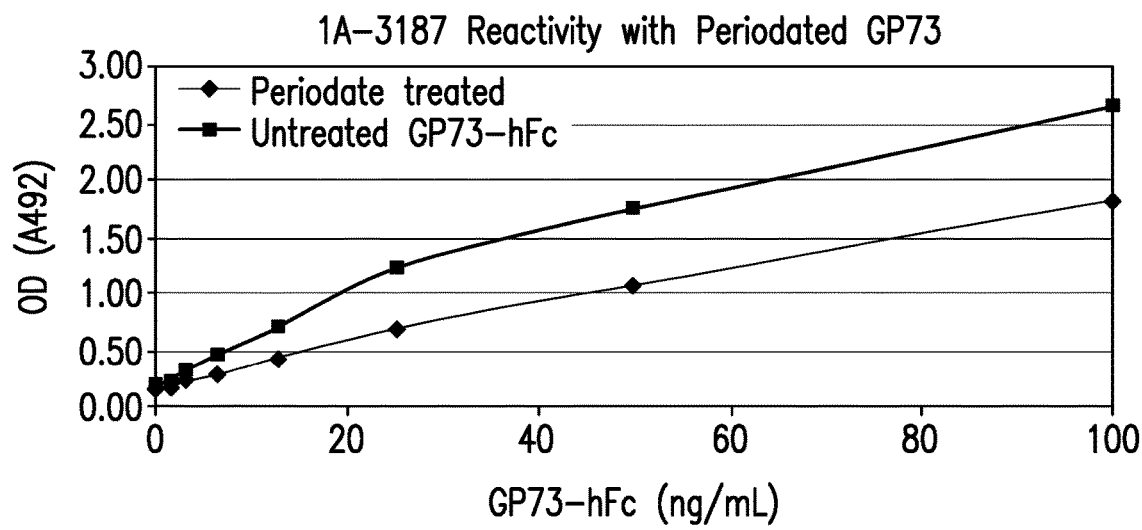
FIG. 6 shows the mAb 1A-3187 reactivity with periodated GP73.
Figure 7:
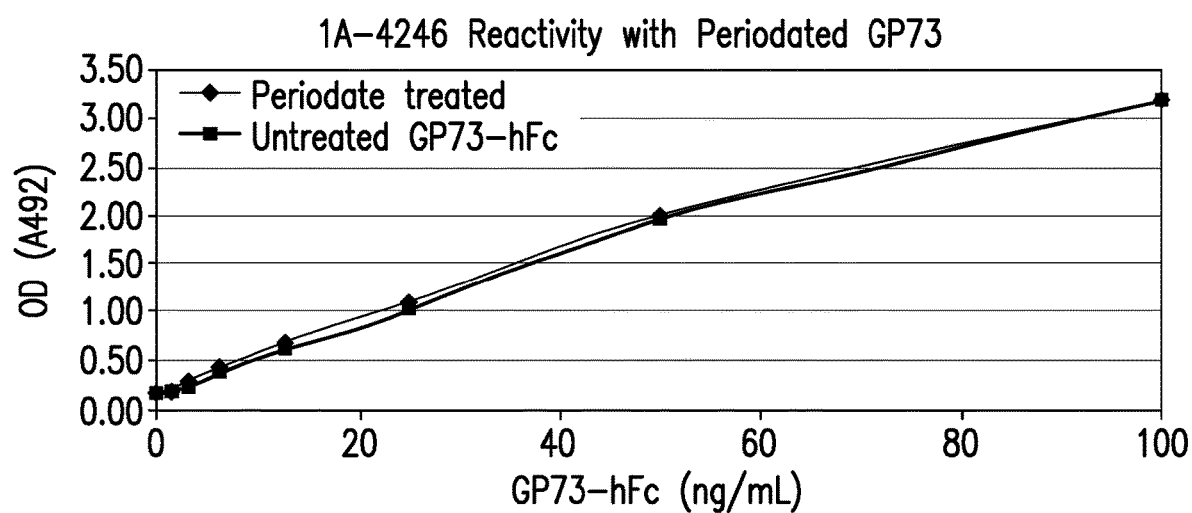
FIG. 7 shows the mAb 1A-4246 reactivity with periodated GP73.
Figure 8:
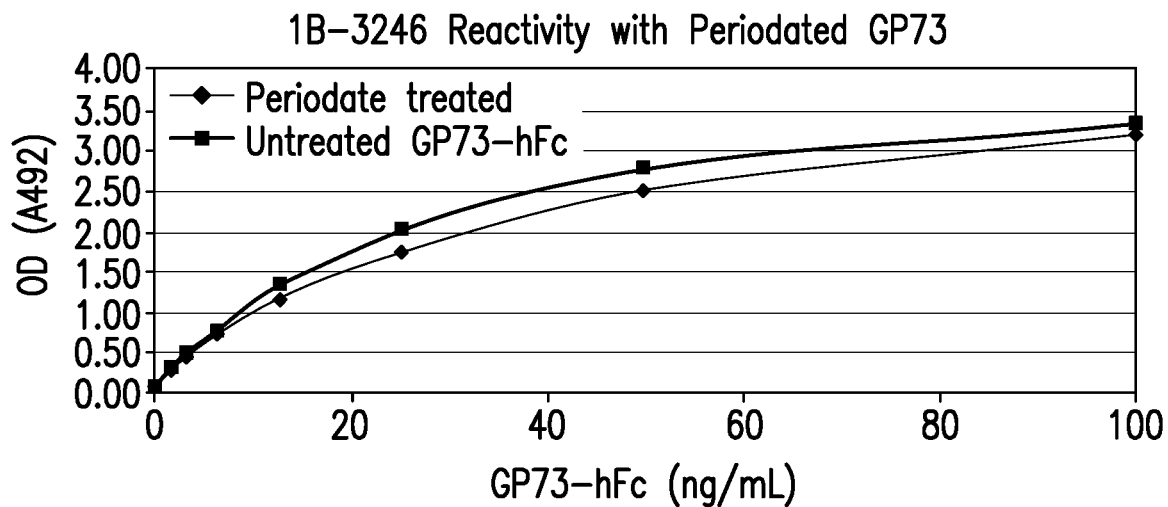
FIG. 8 shows the mAb 1B-3246 reactivity with periodated GP73.
Figure 9:
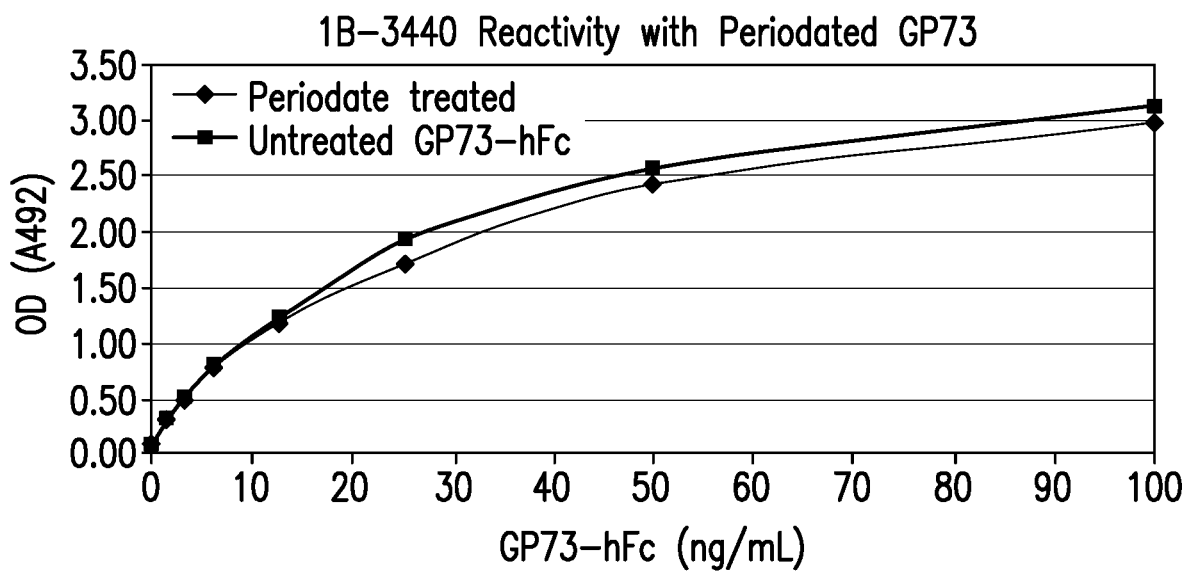
FIG. 9 shows the mAb 1B-3440 reactivity with periodated GP73.
Figure 10:
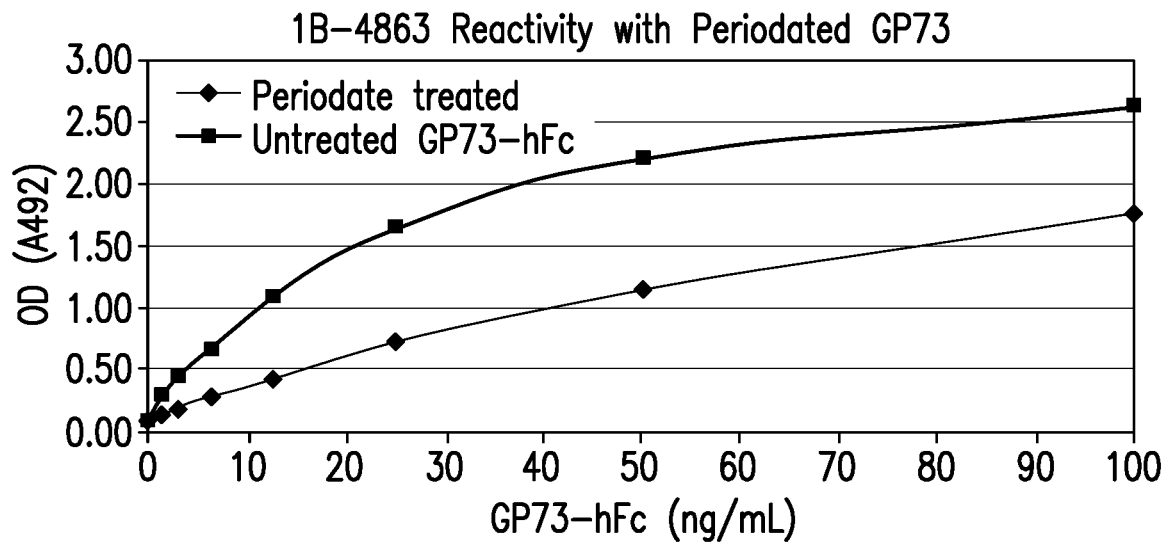
FIG. 10 shows the mAb 1B-4863 reactivity with periodated GP73.
Figure 11:
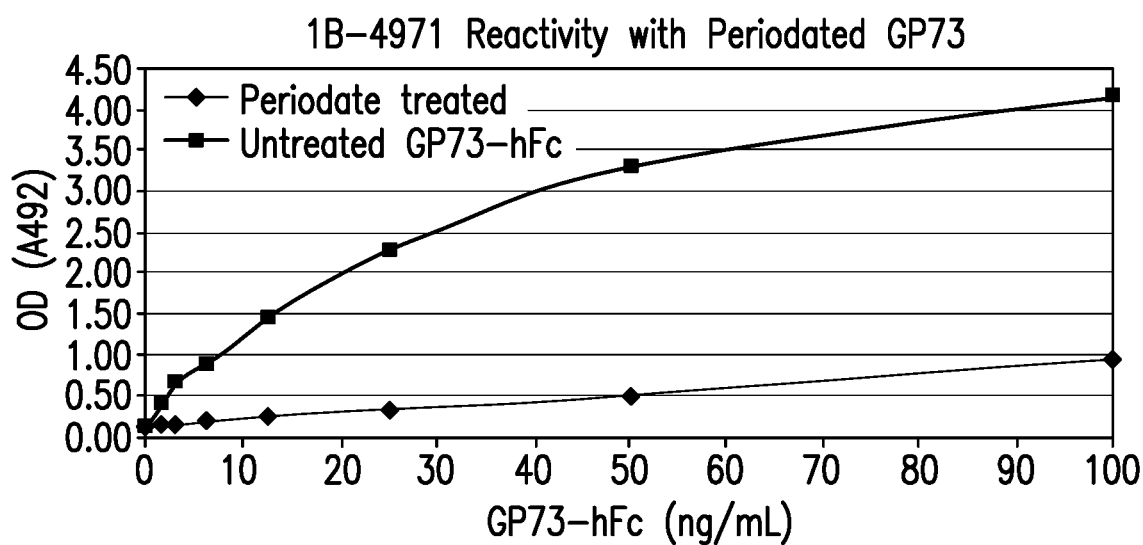
FIG. 11 shows the mAb 1B-4971 reactivity with periodated GP73.

The biotin labeled anti-GP73 mAbs were tested to determine if they were sensitive to the presence of fucose on the GP73-hFc antigen by EIA. Aleuria Aurantia Lectin (AAL) (Vector Laboratories) binds fucose with a high degree of specificity. Donkey anti-human IgG Fc (Jackson Immunoresearch) was coated on 96 well micro titer EIA plates at approximately 1 µg/mL. After the capture reagent was coated on the solid phase, the capture reagent was removed and the plates were blocked for 30 min using Protein-Free T20 (TBS) Blocking Buffer (Thermo Scientific). The wells were washed with distilled water. A 200 ng/mL solution of GP73-hFc antigen was added to the blocked plates and allowed to incubate at room temperature for at least 45 min then washed with distilled water. Fucose was added to the wells of a separate non-absorbing microtiter plate in serial dilutions starting from 1000 µg/mL. Biotin labeled anti-GP73 mAbs were added to the plates at predetermined concentrations for each mAb ranging from 50 to 2000 ng/mL and incubated for 45 min at room temperature. The mixture was added to the microtiter plates with the captured GP73-hFc and allowed to incubate for 15-20 min at room temperature. Biotin labeled AAL was used as a positive control for the assay and a biotin labeled irrelevant mAb was used as the negative control. The plates were washed. Streptavidin-HRPO (diluted to approximately 200 ng/mL) was added to the plates and allowed to incubate for 30 min. The plates were washed with distilled water and OPD substrate was used as the chromogen to generate signal. Plates were read at 492 nm and the results were analyzed. See FIG. 5. FIG. 5 indicates that biotin labeled AAL binding was inhibited by free fucose, but none of the biotin labeled anti-GP73 mAbs demonstrated any inhibition from free AAL. These results indicate that none of the GP73 mAbs bind specifically to fucose alone in solution.

4. Reactivity to Periodate and No-Periodate Treated GP73-hFc

The biotin labeled mAbs were further evaluated to compare their reactivity to periodate and non-periodate treated GP73-hFc antigen. Periodate treatment should oxidize the glycosylation/fucosylation sites on the antigen so an antibody reactive with fucose should not be as reactive with the periodate treated material. Donkey anti-human IgG Fc (Jackson Immunoresearch) that was pretreated with periodate to oxidize any glycosylation/fucosylation sites was coated on 96 well micro titer EIA plates at approximately 1 µg/mL. Periodate treatment was done to prevent nonspecific binding of fucose reactive antibodies with the capture reagent. After the capture reagent was coated on the solid phase, it was removed and the plates were blocked for 30 min at room temperature using Protein-Free T20 (TBS) Blocking Buffer (Thermo Scientific). The wells were washed with distilled water. Serial dilutions of both the periodate treated and non-periodate treated GP73-hFc antigen starting at 100 ng/mL were added to the blocked plates and allowed to incubate at room temperature for at least 30 min. The plates were washed. Streptavidin-HRPO (diluted to approximately 200 ng/mL) was added to the plates and allowed to incubate for 30 min at room temperature. The plates were washed with distilled water and OPD substrate was used as the chromogen to generate signal. As shown in FIGS. 6-11, antibodies 1A-3187, 1B-4863, and 1B-4971 exhibited reduced binding to periodate treated GP73-hFc compared to the non-periodate treated material.

5. Binding Pairs

The purified anti-GP73 mAbs were tested for their ability to form binding pairs with GP73-hFc antigen by EIA. Anti-GP73 produced antibodies were coated on micro titer plates at approximately 1000 ng/mL and allowed to incubate over night at 4-8° C. After the capture reagent was coated on the solid phase, the plates were blocked using a BSA/PBS block solution. The wells were washed with distilled water and purified GP73-hFc was added to the blocked plates in serial dilutions from 0-100 ng/mL diluted in BSA block and allowed to incubate at room temperature for approximately 30 min. The wells were washed with distilled water and biotin labeled anti-GP73 mAbs were added to the plates at concentrations predetermined for each mAb ranging from 50 to 5000 ng/mL and incubated for 30 min at room temperature. The plates were washed. Streptavidin-HRPO (diluted to approximately 200 ng/mL) was added to the plates and allowed to incubate for 30 min at room temperature. The plates were washed with distilled water and OPD substrate was used as the chromogen to generate signal. Plates were read at 492 nm and the results were analyzed. Table 7 summarizes the assay signal for each antibody pair combination, which indicates whether or not each binding pair was capable of forming a sandwich. These antibodies were grouped into 6 different epitopes based on their sandwich formation pattern. Antibodies that did not form a sandwich, or formed a weak sandwich, were assigned to the same epitope group. It was assumed that antibodies binding to the same or similar epitope could not form a GP73 sandwich together because they competed for the same binding site. There were exceptions to this for cases like antibody 1B-4863, which was capable of forming a sandwich with all antibodies, including the biotin labeled version of itself. Because there were two GP73 molecules attached to one human IgG Fc it was possible for an antibody to sandwich with itself, but for most of these mAbs, binding of the first antibody seemed to block the second epitope present on the same GP73-hFc molecule and prevent another antibody directed against the same epitope from binding.

TABLE 7

| Coated | 1B-3246-Bt | 1B-3440-Bt | 1A-4246-Bt | 1B-4971-Bt | 1A-3187-Bt | 1B-4863-Bt | NC-Bt |
|---|---|---|---|---|---|---|---|
| 1B-3246 | 0.47 | 3.20 | 2.52 | 3.04 | 3.06 | 2.94 | 0.06 |
| 1B-3440 | 3.12 | 0.42 | 3.10 | 3.45 | 3.47 | 3.09 | 0.07 |
| 1A-4246 | 3.32 | 3.68 | 0.10 | 4.65 | 4.08 | 3.50 | 0.08 |
| 1B-4971 | 1.78 | 1.62 | 1.18 | 0.63 | 1.57 | 1.42 | 0.06 |
| 1A-3187 | 1.03 | 0.85 | 0.52 | 0.86 | 0.29 | 1.08 | 0.06 |
| 1B-4863 | 2.61 | 2.85 | 2.52 | 3.27 | 2.90 | 2.41 | 0.06 |
| NC | 0.05 | 0.05 | 0.05 | 0.06 | 0.09 | 0.05 | 0.06 |

6. Western Blot Analysis Using Anti-GP73 Antibody

The mammalian cell (HEK and CHO) expressed GP73-hFc or E. coli expressed GP73, as described above, were electrophoresed in a 4-20% SDS-PAGE gel. The GP73 Proteins were transferred to nitrocellulose membranes at 100 volts for 1-2 hrs in a standard transfer buffer (25 mM Tris, 192 mM glycine, and 20% methanol, pH 8.3). The nitrocellulose membrane was blocked with PBS buffer containing 5% non-fat dry milk and 0.05% Tween 20 for about 1 hr. The nitrocellulose membrane was incubated with an appropriate amount of anti-GP73 monoclonal antibody in 10 mL of 2.5% non-fat dry milk and 0.05% Tween 20 PBS buffer, pH 7.2. The nitrocellulose membranes were washed with 0.05% Tween 20/PBS, pH 7.2, incubated with goat anti-mouse IgG antibody conjugated with HRP for 1 hr at room temperature, and washed with 0.05% Tween 20/PBS buffer. Antibody bound to the GP73 protein was visualized by the addition of freshly prepared metal enhanced 3,3'-Diaminobenzidine in stable peroxide buffer (Pierce, Ill.). See Table 8.

TABLE 8

| Antibody | Western blot on HEK expressed GP73-hFc antigen | Western blot on CHO expressed GP73-hFc antigen | Western blot on E. coli expressed GP73 antigen |
|---|---|---|---|
| anti-GP73 1B-3246 | Positive | Positive | Positive |
| anti-GP73 1A-4246 | Positive | Positive | Negative |
| anti-GP73 1A-3187 | Positive | Positive | Negative |
| anti-GP73 1B-4863 | Positive | Positive | Positive |
| anti-GP73 1B-3440 | Positive | Positive | Not done |
| anti-GP73 1B-3263 | Positive | Positive | Not done |
| GP73 14H4-23-288 | Positive | Not done | Positive |

Summary of the antibody characterization is shown in Tables 9 and 10.

TABLE 9

| Clone # | Isotype | W. Blot CHO GP73 | W. Blot HEK GP73 |
|---|---|---|---|
| 1A-3187 | IgG1k | + | + |
| 1A-4246 | IgG1k | + | + |
| 1B-3246 | IgG1k | + | + |
| 1B-3440 | IgG1k | + | + |
| 1B-4863 | IgG1k | + | + |
| 1B-4971 | IgG1k | + | + |
| 14H4-23 | N/A | + | + |

TABLE 10

| Clone # | Free AAL Displacement | Binds E. coli GP73 | Binds Hu IgG | Free Fucose Displacement | Periodated GP73 reactivity |
|---|---|---|---|---|---|
| 1A-3187 | Yes | No | No | No | Reduced |
| 1A-4246 | No | No | No | No | Strong |
| 1B-3246 | No | Yes | No | No | Strong |
| 1B-3440 | No | Yes | No | No | Strong |
| 1B-4863 | Yes | Yes | No | No | Reduced |
| 1B-4971 | No | Yes | No | No | Reduced |
| 14H4-23 | No | Yes | No | No | Strong |

Example 9

Anti-GP73 Monoclonal Antibody Gene Sequencing

The mRNA was extracted from appropriate hybridoma cell cultures using commercially available reagents (Oligotex direct mRNA kit, Qiagen) following the manufacturer's recommendations. The heavy chain and kappa light chain cDNA was generated from the extracted mRNA using Superscript III (Life Technologies) and oligo dT primers (Novagen) following standard protocols. Amplicons were cloned into a commercially available vector (Life technologies) per the manufacturer's directions and transformed into E. coli. Sequence analysis using M13 forward and reverse primers was performed using BigDye Terminator v3.1 cycle sequencing kit (Applied Biosystems, Foster City, Calif.) on plasmids isolated from multiple transformed E. coli colonies to identify the heavy and light chain coding sequences. See Tables 1 and 2. FIGS. 12-17 show a diagram and the amino acid and nucleotide sequence of the variable heavy and light regions with the CDR sequences identified.

The 1A-3187 variable light (VL) sequence uses a V segment of the IGKV21 subgroup. The 1A-4246 and 1B-3440 VL sequences use a V segment of the IGKV4/5 subgroup. The 1B-4863 VL sequence uses a V segment of the IGKV19/28 subgroup. The 1B-3246 VL sequence uses a V segment of the IGKV24/25 subgroup. The 1B-4971 VL sequence uses a V segment of the IGKV2 subgroup.

The 1A-3187 variable heavy (VH) sequence uses a V segment of the Igh-VJ558 VH1 family. The first amino acid after CDR-H2 varies from the typical antibody sequences near CDRs having a T instead of K/R. The 1B-4971 VH sequence also uses a V segment of the Igh-VJ558 VH1 family. The 1B-3440 VH sequence uses a V segment of the IgH-V10 VH10 family. The 1B-4863 VH sequence uses a V segment of the Igh-VQ52 VH2 family. The 1A-4246 and 1B-3246 VH sequences use a V segment of the Igh-V7183 VH5 family.

Example 10

GP73 Epitope Mapping with Anti-GP73 MAb

Epitope mapping of GP73 with anti-GP73 MAb was completed using epitope excision followed by LC/MS/MS method. The samples used were GP73-hFc antigen and anti-GP73 MAb 1. Immobilization of anti-GP73 MAb to the CNBr-Activated Sepharose resin: 20 mg of CNBr-Activated Sepharose resin was weighted into a compact reaction column with frit. The resin was washed three times with 200 µL of 1 mM HCl. The resin was washed three times with 200 µL of 100 mM NaHCO$_3$ pH 8/500 mM NaCl buffer. Anti-GP73 MAb was added to the column. The reaction column was placed on a rotator at room temperature for 4 hrs. The resin was washed three times with 200 µL of 100 mM NaHCO$_3$ pH 8/500 mM NaCl buffer. 200 µL of 100 mM Tris-HCl pH 8/500 mM NaCl was added to the column and the column was rotated at room temperature for 1 hr. The resin was washed three times with 200 µL of 100 mM sodium acetate pH 4/500 mM NaCl buffer and 100 mM Tris-HCl pH 8/500 mM NaCl buffer. The resin was washed three times with 200 µL of 100 mM NaHCO$_3$ pH 8/100 mM NaCl buffer. 200 µL of 100 mM NaHCO$_3$ pH 8/100 mM NaCl buffer was added and the top cap on the column was secured.

2. Antigen Binding: The reaction column was washed three times with 200 µL of 100 mM NaHCO$_3$ pH 8/500 mM NaCl buffer. 50 µL antibody resin prepared in step 1 was transfer to the new reaction column. The resin was washed three times with 200 µL of 100 mM NaHCO$_3$ pH 8/100 mM NaCl buffer. GP73-hFc antigen sample was added to the column. The reaction column was placed on a rotator at room temperature for 4 hrs. The resin was washed three times with 200 µl of 100 mM NaHCO$_3$ pH 8/100 mM NaCl buffer.

3. Proteolysis: 200 µL of 100 mM NaHCO$_3$ pH 8/100 mM NaCl buffer was added to the column. Trypsin was added to the column and the reaction column was placed on a rotator at room temperature overnight.

4. Elution: Solution was flushed through and collected as flow-through fraction. The resin was washed three times with 200 µL of 100 mM NaHCO$_3$ pH 8/100 mM NaCl buffer twice. The resin was washed three times with 200 µL of 100 mM NaHCO$_3$ pH 8/500 mM NaCl buffer. The resin was washed three times with 200 µL of 100 mM NaHCO$_3$ pH 8/100 mM NaCl buffer. 200 µL of 2% formic acid was added for elution. The eluted fraction and other fractions were dried with an Eppendorf Vacufuge.

5. C18 ziptip desalting of samples before LC/MS/MS injection: The eluted fractions were reconstituted in 10 µL 0.1% trifluoroacetic acid (TFA). The C18 ziptip was wet three times with 50% ACN/H$_2$O. The C18 ziptip was wet three times with 0.1% TFA. The samples were aspirated and dispensed 15 times for binding. The tip was washed 7 times with 0.1% TFA. The samples were eluted with 10 µL 50% ACN/H$_2$O, 0.1% TFA.

6. The eluted fraction was analyzed by LC/MS/MS using AB Sciex Q-Star Elite MS instrument coupled with Agilent 1200 HPLC. See Table 11 and FIG. 18.

TABLE 11

| Anti-GP73 MAb | Epitope Peptide |
|---|---|
| 1A-3187 | ELKKNEFQGELEKQREQLDKIQSSHNFQLESVNK (SEQ ID NO: 104) |
| 1B-4971 | VSQENPEMEGPERDQLVIPDGQEEEQEAAGEGR (SEQ ID NO: 101) |
| 1B-3246 | EQVVEDRPVGGR (SEQ ID NO: 102) |
| 1B-3440 | LRGEDDYNMDENEAESETDK (SEQ ID NO: 103) |
| 1A-4246 | Inconclusive |
| 1B-4863 | Inconclusive |

Example 11

GP73 mAb Binding Kinetics

The affinities/kinetics of anti-human GP73 monoclonal antibodies 1A-3187, 1A-4246, 1B-3246, 1B-3440, 1B-4863, and 1B-4971 for HEK expressed recombinant GP73-hFc (Abbott, Ill., USA) were determined using a Biacore 2000 instrument (GE Healthcare, Piscataway, N.J.). First, an approximately 13,000-15,000 RU rabbit anti-mouse IgG Capture Biosensor was created by amine-coupling rabbit anti-mouse IgG antibody (GE Healthcare) to a CM5 biosensor chip (GE Healthcare) via EDC/NHS/ethanolamine chemistry provided in an Amine Coupling Kit (GE Healthcare) after pre-treating the biosensor with duplicate injections of 100 mM HCl, 50 mM NaOH, and 0.1% SDS. Purified GP73 antibody and antigen (HEK GP73-hFc) were diluted into a running buffer (hereinafter "running buffer") composed of HBS-EP buffer (GE Healthcare) supplemented with 0.1% BSA and 0.1% CM-Dextran. Each GP73 antibody was diluted to 1 µg/mL. The GP73-hFc antigen was diluted to concentrations of 0.412 to 100 nM using a 3-fold dilution series assuming an oligomeric molecular weight of 490 kDa (Abbott Laboratories).

The GP73-hFc antigen program was as follows. After equilibrating the rabbit anti-mouse IgG Capture Biosensor for 3 min at 5 µL/minute with running buffer, GP73 antibody (7-14 µL) was injected over individual flow cells with one flow cell being left blank as a reference flow cell. The flow cells were washed with running buffer for 3 min at a flow rate of 60 µL/min. 150 µL of HEK293 expressed GP73-hFc antigen at a random concentration was injected across the biosensor. The biosensor was subsequently re-equilibrated with running buffer for 5 min at a flow rate of 60 µL/minute. All biosensor surfaces were regenerated with one 30 µL injection of 10 mM glycine, pH 1.7 (GE Healthcare), at a flow rate of 10 µL/minute. All concentrations of HEK293 expressed antigen were tested in duplicate. The binding kinetics (association and dissociation) were monitored via sensorgrams during antigen injection and running buffer re-equilibration. The sensorgrams were double-referenced and fit to a 1:1 binding model using Scrubber 2.0 software (BioLogic Software Pty Ltd., Australia) to determine association and dissociation rates, as well as overall $K_D$. The results are shown in Table 12. Standard errors of determined values are reported in parentheses with respect to the smallest number place value.

TABLE 12

| GP73 monoclonal antibody | HEK Expressed GP73-hFc | | |
|---|---|---|---|
| | $k_{on}$ (M$^{-1}$s$^{-1}$) | $k_{off}$ (s$^{-1}$) | $K_D$ (M) |
| 1A-3187 | 1.228(5) × 10$^5$ | 2.5(1) × 10$^{-4}$ | 2.00(8) × 10$^{-9}$ |
| 1A-4246 | 3.29(1) × 10$^5$ | 1.26(2) × 10$^{-3}$ | 3.83(5) × 10$^{-9}$ |
| 1B-3246 | 3.18(1) × 10$^6$ | 2.5(2) × 10$^{-4}$ | 7.9(5) × 10$^{-11}$ |
| 1B-3440 | 1.984(6) × 10$^6$ | 1.8(1) × 10$^{-4}$ | 9.1(5) × 10$^{-11}$ |
| 1B-4863 | 2.058(6) × 10$^6$ | 2.5(1) × 10$^{-4}$ | 1.20(6) × 10$^{-10}$ |
| 1B-4971 | 3.90(2) × 10$^6$ | 1(2) × 10$^{-5}$ | 2(5) × 10$^{-12}$ |

Example 12

ARCHITECT® GP73 Data

Figure 19:
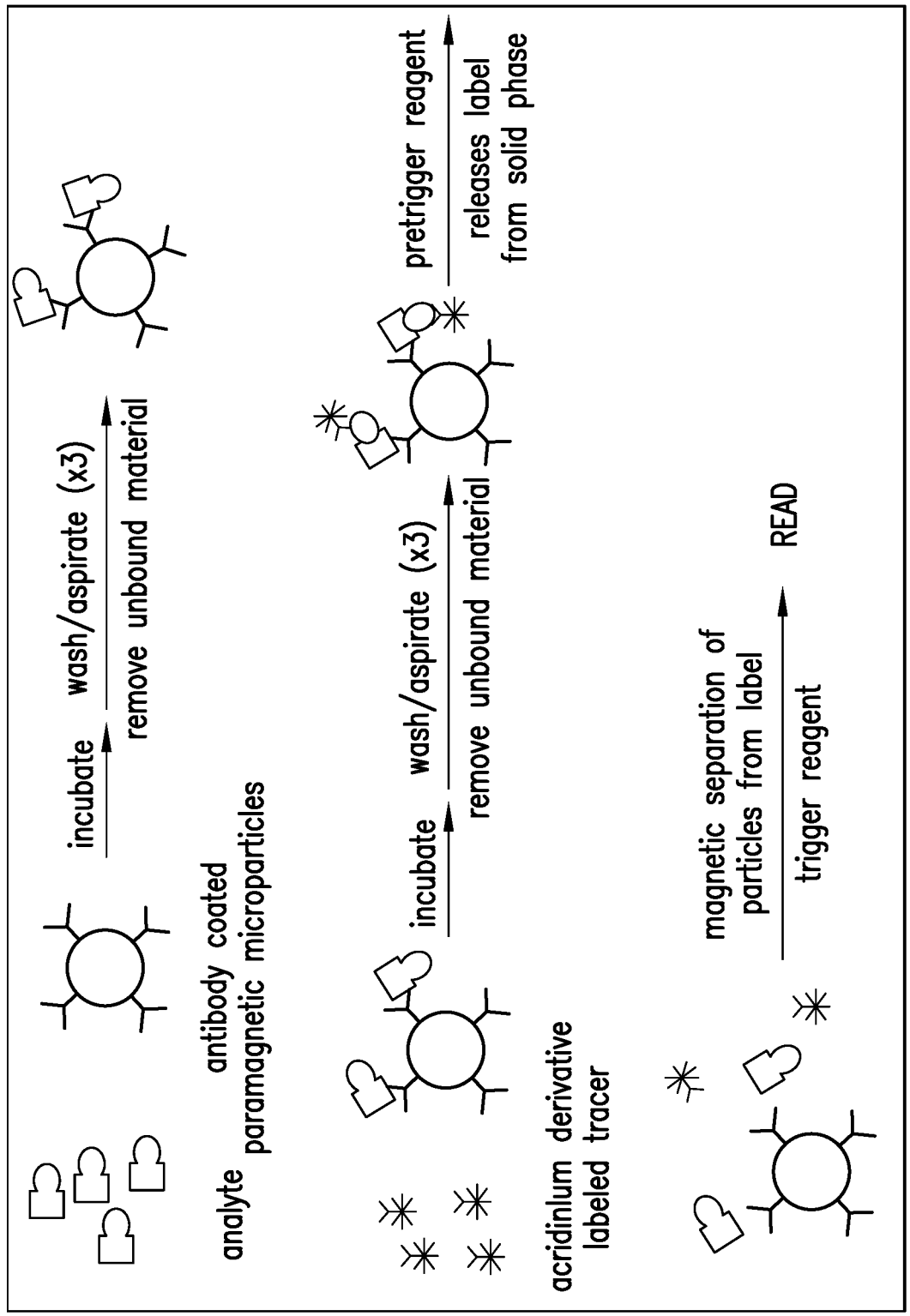
FIG. 19 shows an example of ARCHITECT® sandwich immunoassay principle.

The ARCHITECT® sandwich immunoassay principle is shown in FIG. 19. Briefly, an antibody coated on a microparticle captures the analyte of interest, then a second antibody conjugated to acridinium binds to a second epitope on the analyte, then a separation of the particles from the label and subsequent read is performed to determine the relative light units (RLU) from the chemiluminescence reaction.

Figure 20:
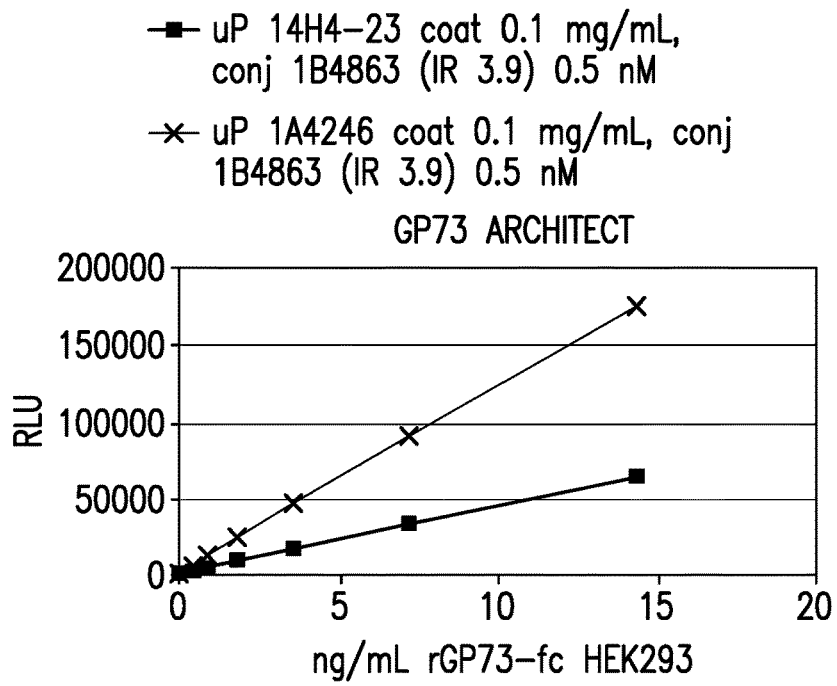
FIG. 20 shows the GP73 ARCHITECT® assay using mAb 14H4-23 or 1A-4246 as the capture antibody (0.1 mg/mL) and 1B-4863 as the detection antibody (0.5 nM).

Monoclonal antibody pairs, such as 1A-4246 as a capture monoclonal antibody and 1B-4863 as a detection monoclonal antibody, were tested by ELISA to mimic the same epitopes of GP73 that bind to the Drexel University mouse monoclonal antibody 14H4-23 used as a capture antibody and the rabbit polyclonal antibody used as a detection antibody. The initial ARCHITECT® experiment compared the Drexel capture antibody 14H4-23 to the capture antibody 1A-4246. Each capture antibody was paired with detection antibody 1-B4863, which was diluted to 0.5 nM. The incorporation ratio of acridinium to antibody for 1B-4863 was 3.9. As shown in FIG. 20, the capture antibody 1A-4246 outperformed the Drexel capture antibody 14H4-23 by approximately three-fold based on the standard curve using recombinant GP73-hFc fusion protein produced in HEK293 transient transfection with a range of 0-14.4 ng/mL. See Table 13.

TABLE 13

| ARCHITECT ® GP73 | | | | | | | | | |
|---|---|---|---|---|---|---|---|---|---|
| Sample ID | ng/mL | Mean | Std. Dev. | % CV | Count | Ratio to CAL A | Span to CAL A | Data Replicates | | |
| uP 14H4-23 coat 0.1 mg/mL, conj 1B4863 (IR 3.9) 0.5 nM | | | | | | | | | | |
| calA(ru) | 0 | 291.3 | 25.1 | 8.6 | 3 | | | 281 | 320 | 273 |
| calB(ru) | 0.056 | 580.7 | 53.2 | 9.2 | 3 | 2.0 | 289.3 | 530 | 576 | 636 |
| calC(ru) | 0.113 | 808.7 | 34.1 | 4.2 | 3 | 2.8 | 517.3 | 790 | 788 | 848 |
| calD(ru) | 0.225 | 1436.7 | 104.5 | 7.3 | 3 | 4.9 | 1145.3 | 1453 | 1532 | 1325 |
| calE(ru) | 0.45 | 2493.0 | 115.6 | 4.6 | 3 | 8.6 | 2201.7 | 2521 | 2366 | 2592 |
| calF(ru) | 0.9 | 4522.0 | 235.3 | 5.2 | 3 | 15.5 | 4230.7 | 4254 | 4617 | 4695 |
| calG(ru) | 1.8 | 8555.7 | 259.4 | 3.0 | 3 | 29.4 | 8264.3 | 8507 | 8324 | 8836 |
| calH(ru) | 3.6 | 16995.3 | 376.4 | 2.2 | 3 | 58.3 | 16704.0 | 17403 | 16922 | 16661 |
| calI(du) | 7.2 | 33256.3 | 1752.1 | 5.3 | 3 | 114.2 | 32965.0 | 31916 | 32614 | 35239 |
| calJ(ru) | 14.4 | 63405.0 | 1124.1 | 1.8 | 3 | 217.6 | 63113.7 | 62593 | 64688 | 62934 |
| uP 1A4246 coat 0.1 m9/mL, conj 1B4863 (IR 3.9) 0.5 nM | | | | | | | | | | |
| Cal A | 0 | 322 | 16.3 | 5.1 | 3 | | | 333 | 310 | |
| Cal B | 0.056 | 1032 | 84.0 | 8.1 | 3 | 3.2 | 710.2 | 1033 | 1115 | 947 |
| Cal C | 0.113 | 1855 | 166.8 | 9.0 | 3 | 5.8 | 1533.2 | 1823 | 1706 | 2035 |
| Cal D | 0.225 | 3376 | 247.6 | 7.3 | 3 | 10.5 | 3054.2 | 3217 | 3661 | 3249 |
| Cal E | 0.45 | 6546 | 629.7 | 9.6 | 3 | 20.4 | 6224.5 | 6825 | 5825 | 6988 |
| Cal F | 0.9 | 12558 | 656.9 | 5.2 | 3 | 39.1 | 12236.2 | 11921 | 13233 | 12519 |
| Cal G | 1.8 | 24117 | 926.2 | 3.8 | 3 | 75.0 | 23795.2 | 23329 | 23884 | 25137 |
| Cal H | 3.6 | 46080 | 777.4 | 1.7 | 3 | 143.3 | 45758.8 | 45635 | 46978 | 45628 |
| Cal I | 7.2 | 89539 | 4212.5 | 4.7 | 3 | 278.5 | 89217.5 | 91530 | 84700 | 92387 |
| Cal J | 14.4 | 173701 | 3197.5 | 1.8 | 3 | 540.3 | 173379.5 | 176903 | 173692 | 170508 |

Figure 21:
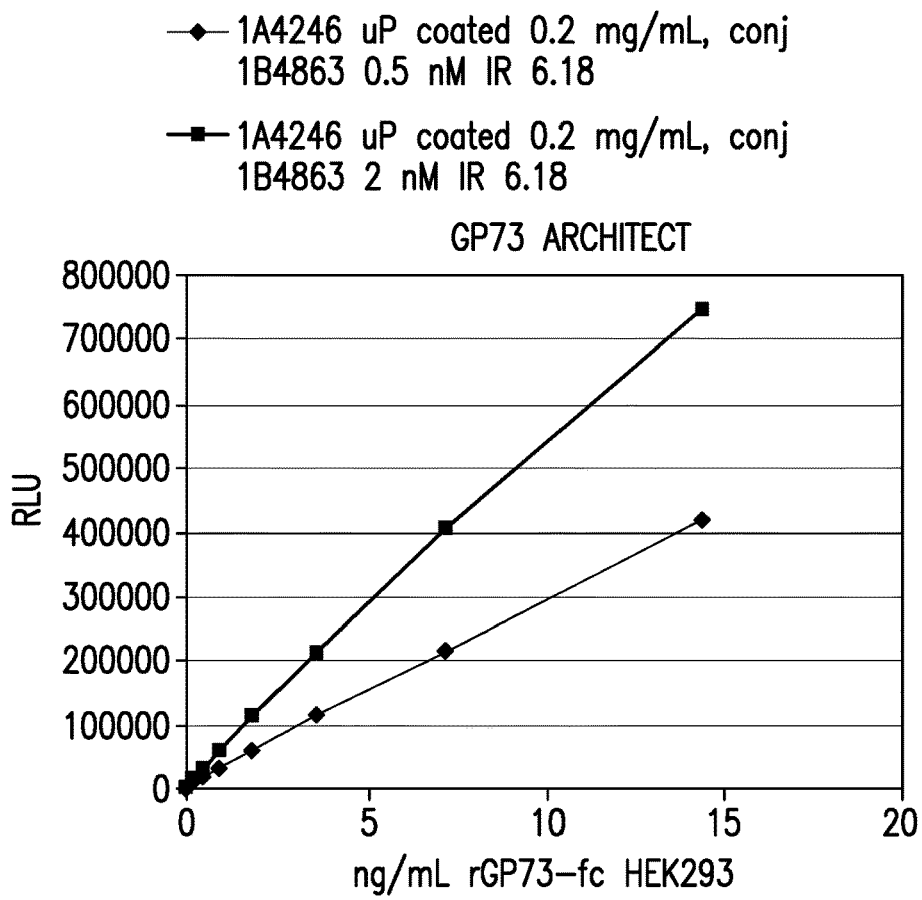
FIG. 21 shows the GP73 ARCHITECT® assay using mAb 1A-4246 (0.2 mg/mL) as the capture antibody and 1B-4863 as the detection antibody (0.5 or 2 nM).

In the follow up ARCHITECT® experiment, 1A-4246 was used as the capture antibody at a concentration of 0.2 mg/mL with 1B-4863 used as the detection antibody at a concentration of 0.5 nM or 2 nM. The incorporation ratio of acridinium to antibody for 1B-4863 was 6.18. The higher conjugate concentration of 2 nM produces a greater signal as expected (see FIG. 21), but there was higher background in Cal A (see Table 14). This GP73 ARCHITECT® data shows a very linear response to the recombinant GP73-hFc antigen for both monoclonal antibody pairs.

TABLE 14

| ARCHITECT ® GP73 | | | | | | | | | | |
|---|---|---|---|---|---|---|---|---|---|---|
| Sample ID: | ng/mL | Mean | Std. Dev. | % CV | Count | Ratio to CAL A | Span to CAL A | Data Replicates | | |
| 1A4246 uP coated 0.2 mg/mL, conj 1B4863 0.5 nM IR 6.18 | | | | | | | | | | |
| Cal A | 0 | 546 | 57.3 | 10.5 | 3 | | | 606 | 539 | 492 |
| Cal B | 0.056 | 2599 | 147.5 | 5.7 | 3 | 4.8 | 2053.3 | 2757 | 2465 | 2575 |
| Cal C | 0.113 | 4630 | 192.6 | 4.2 | 3 | 8.5 | 4084.0 | 4638 | 4818 | 4433 |
| Cal D | 0.225 | 8221 | 148.3 | 1.8 | 3 | 15.1 | 7675.7 | 8063 | 8357 | 8244 |

TABLE 14-continued

| ARCHITECT® GP73 | | | | | | | | | | |
|---|---|---|---|---|---|---|---|---|---|---|
| Sample ID: | ng/mL | Mean | Std. Dev. | % CV | Count | Ratio to CAL A | Span to CAL A | Data Replicates | | |
| Cal E | 0.45 | 16146 | 697.1 | 4.3 | 3 | 29.6 | 15600.7 | 16849 | 16135 | 15455 |
| Cal F | 0.9 | 30829 | 247.0 | 0.8 | 3 | 56.5 | 30283.3 | 31001 | 30546 | 30940 |
| Cal G | 1.8 | 60219 | 1095.7 | 1.8 | 3 | 110.4 | 59673.0 | 59211 | 61385 | 60060 |
| Cal H | 3.6 | 116737 | 2887.4 | 2.5 | 3 | 213.9 | 116191.3 | 117598 | 113517 | 119096 |
| Cal I | 7.2 | 213371 | 6890.7 | 3.2 | 3 | 391.0 | 212825.7 | 205710 | 215342 | 219062 |
| Cal J | 14.4 | 420567 | 9171.0 | 2.2 | 3 | 770.7 | 420021.7 | 427394 | 410143 | 424165 |
| 1A4246 uP coated 0.2 mg/mL, conj 1B4863 2 nM IR 6.18 | | | | | | | | | | |
| Cal A | 0 | 2489 | 593.3 | 23.8 | 3 | | | 1878 | 2525 | 3063 |
| Cal B | 0.056 | 5569 | 328.8 | 5.9 | 3 | 2.2 | 3080.7 | 5334 | 5945 | 5429 |
| Cal C | 0.113 | 9942 | 656.4 | 6.6 | 3 | 4.0 | 7453.7 | 10155 | 9206 | 10466 |
| Cal D | 0.225 | 16465 | 921.9 | 5.6 | 3 | 6.6 | 13976.7 | 15896 | 15971 | 17529 |
| Cal E | 0.45 | 30421 | 972.2 | 3.2 | 3 | 12.2 | 27932.7 | 29460 | 31404 | 30400 |
| Cal F | 0.9 | 58437 | 603.1 | 1.0 | 3 | 23.5 | 55948.3 | 58869 | 58694 | 57748 |
| Cal G | 1.8 | 113539 | 2427.9 | 2.1 | 3 | 45.6 | 111050.3 | 116218 | 112915 | 111484 |
| Cal H | 3.6 | 209923 | 1191.0 | 0.6 | 3 | 84.4 | 207434.7 | 209531 | 211261 | 208978 |
| Cal I | 7.2 | 404976 | 5626.5 | 1.4 | 3 | 162.7 | 402487.0 | 409800 | 398795 | 406332 |
| Cal J | 14.4 | 742497 | 19168.7 | 2.6 | 3 | 298.4 | 740008.3 | 747483 | 758680 | 721328 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for determining GP73 concentration in a test sample, the method comprising:
   (a) contacting the test sample with at least one capture antibody comprising (i) a variable heavy chain comprising a CDR1 comprising the amino acid sequence of SEQ ID NO: 42, a CDR2 comprising the amino acid sequence of SEQ ID NO: 43, and a CDR3 comprising the amino acid sequence of SEQ ID NO: 44, and (ii) a variable light chain comprising a CDR1 comprising the amino acid sequence of SEQ ID NO: 46, a CDR2 comprising the amino acid sequence of SEQ ID NO: 47, and a CDR3 comprising the amino acid sequence of SEQ ID NO: 48, which binds to an epitope on GP73 comprising the amino acid sequence of SEQ ID NO: 102 to form a capture antibody-GP73 antigen complex;
   (b) contacting the capture antibody-GP73 antigen complex with at least one detection antibody comprising a detectable label, wherein the detection antibody comprises (i) a variable heavy chain comprising a CDR1 comprising the amino acid sequence of SEQ ID NO:26, a CDR2 comprising the amino acid sequence of SEQ ID NO:27, and a CDR3 comprising the amino acid sequence of SEQ ID NO:28, and (ii) a variable light chain comprising a CDR1 comprising the amino acid sequence of SEQ ID NO:30, a CDR2 comprising the amino acid sequence of SEQ ID NO:31, and a CDR3 comprising the amino acid sequence of SEQ ID NO:32 which binds to an epitope on GP73 that is not bound by the capture antibody and forms a capture antibody-GP73 antigen-detection antibody complex; and
   (c) determining the GP73 concentration in the test sample based on the signal generated by the detectable label in the capture antibody-GP73 antigen-detection antibody complex formed in (b).

2. The method of claim 1, further comprising comparing the signal generated by the detectable label as a direct or indirect indication of the GP73 concentration in the test sample to a signal generated as a direct or indirect indication of the GP73 concentration in a control or calibrator.

3. The method of claim 2, wherein the GP73 concentration in the test sample is used to determine or assess whether a subject has or is at risk of developing liver disease.

4. The method of claim 1, wherein the capture antibody comprises a variable heavy chain domain comprising the amino acid sequence of SEQ ID NO: 41 and a variable light chain domain region comprising the amino acid sequence of SEQ ID NO: 45.

5. The method of claim 1, wherein the detection antibody comprises a variable heavy chain domain comprising the amino acid sequence of SEQ ID NO: 25 and a variable light chain domain region comprising the amino acid sequence of SEQ ID NO: 29.

* * * * *